United States Patent
Carlson et al.

(10) Patent No.: US 9,049,848 B1
(45) Date of Patent: Jun. 9, 2015

(54) INCREASED RESISTANCE TO ENTEROBACTERIACEAE IN BOVINES

(71) Applicant: PSR DAIRY GENETICS, LLC, Gilbert, IA (US)

(72) Inventors: Steve Carlson, Story City, IA (US); Tim Day, Gilbert, IA (US)

(73) Assignee: PSR DAIRY GENETICS LLC, Gilbert, IA (US)

( * ) Notice: Subject to any disclaimer, the term of this patent is extended or adjusted under 35 U.S.C. 154(b) by 0 days.

(21) Appl. No.: 14/010,809

(22) Filed: Aug. 27, 2013

Related U.S. Application Data

(60) Provisional application No. 61/695,842, filed on Aug. 31, 2012.

(51) Int. Cl.
   *A01K 67/027* (2006.01)
   *C12N 15/85* (2006.01)
   *C12Q 1/68* (2006.01)

(52) U.S. Cl.
   CPC ............ *A01K 67/0275* (2013.01); *C12N 15/85* (2013.01); *C12Q 1/6888* (2013.01)

(58) Field of Classification Search
   None
   See application file for complete search history.

(56) References Cited

U.S. PATENT DOCUMENTS

2002/0151698 A1    10/2002  Lal et al.

*Primary Examiner* — Doug Schultz
(74) *Attorney, Agent, or Firm* — McKee, Voorhees & Sease, PLC

(57) ABSTRACT

A mechanism for increasing resistance to Enterobacteriaceae infection is described. Additionally genetic markers for identifying traits associated with resistance to Enterobacteriaceae are also described. Thus the invention provides methods and compositions for the production of animals which exhibit increased resistance to Enterobacteriaceae infection. The invention further provides methods and compositions for marker assisted breeding to identify animals resistant to Enterobacteriaceae infection. The invention allows for cattle production with lower susceptibility to Enterobacteriaceae infection.

11 Claims, 46 Drawing Sheets

Figure 4:
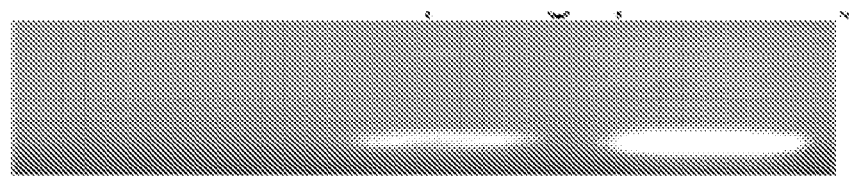

>chromosome:UMD3.1:1:2108619:2196714:1   (SEQ ID NO:4)
GGCTTGGGCTTGTGCGGCTTCTCTTCACCGCCGCTCCCCGCCCCGGGAGCTCCTGTGGTG
TCGGATAATCCTTTCCCTTCTCTCACTCCTAAGGAGCTTTGAATCAGCCCTGTTCACCTT
CCTTCCCACCTTCGTCTCCTCCCCCGCGCCCCCCAGCCCAGGGGATCGGTTTGAAGTTTC
CGAATCGTTTTCCCTTTCAAACGGCAGTGAGAAATCCCGAAGCAGAAAGCTGATAAACCA
CTCCCGAGCGAAAATAGACTCATTTTTTTTTTCCTTTTGGTAAACAGAAAGGGGAAAC
TCATCTTAACCAAACCGTTCTTGGAACTTGGAGTGATATGAGAACCCTGTCTTGCCTTGC
TGTGAGACCACTTTCCCTCTTGCTTTTCGGTAAAAAATTAAGTGACGACTTATCTTTTGG
AATAAACCATTCTGTCCCCGAGCTCTCTCCGCACCCCCTCCGCTCCACCCCCACCCCCCC
CCCCCATCAAAACCTAGCAGGGGAGGACTTCGGGGTGGCTTGCAGTCCTTGCTGCAGAAG
GAAACATTAGCTGTATTTGCTTTGCTTGATTTTCACAGGGCTGCCTCCGAAGAAAGGAGA
ATGGCGTTCAGCAAAGGATTTCGGATCTATCACAAATTGGATCCCCCACCTTTCAGCCTC
ATAGTGGAAACCAGGCATAAGGAAGAATGTCTCATGTTCGAGTCTGGGGCTGTAGCGGTG
CTCTGTAAGTCTTCTCTCTCAACCCAGCTGATCAGGATCTGTTTGCTTGCAATAATTCAG
ATTCAACCTTTTTTTTTTTTTTTTCTTTTTTTCAAAAGAAGATTCTGATAACCCCCTCA
TTGTATTTCACCTCACAGGTCATGCTTTTATTTCCTTTTAACCAGACCTTATTGTTTTTC
AAAGTTTTCTTTGCCTGCTGCAGGTTTTGATGAGGGTGGGGAGAGATGCCAGTTTGGGT
ACAGATTTTTGCTTTCTTGGGTTCTGCTGCTGCTTCTAAAAGTAAATCTTTCTTTCCAAA
AAAATACAGTTGCAATGTATAGCATATCATGTAAACTTGTAAAACAGCTTGCTTGACATT
TTTGCAGAATGAACAGAATTTCTTATACCTGATATTTGTTTAATATTTTTGGAATATATT
ATGATGAGGCTCTTATATTTTCATTAAGAAAATTTTAAACAACCTTTAAAATTTCATGTA
AGGTAGGTGCTTGATTTCATATTGGTTAAGAAATTATTTTGATAGTTTATTTAAAGAAA
AGGACTACTGCAGCACAGGAAAAATAATAGATTAGTAAGGTTTGGGTTATTTTGTGGGCA
GATGGATGAGATTAAAAATATAAATATTAATTTGAATATTACATTTTTTAGTATAAGATT
TTGACAGGTAACTTCAGTTTGGGATTATTTCAAATGTGATTATTGTTAGAGGCTTTCTTG
TGATAACTACTTGTTCTATATTATGTTTTTGCTATGTAGGATCAATTTGGATATTGGTCA
TATTTTTAAAAGTTAAAAATAACATTTGAAAGGCATACTTACAACTATAAACCCATGAGC
ATTAAAGTTTCTCCAGATTTGGTAGGGAAAGGCTGAAGACTGTAATATTTATATACAGAA
TATTAACATGCAGAATATTATGATCAGTTAAACCTGATCTTAATACTCAAAAATAATAAA
ATTTTACCCTGATTGTGGACATAGTGACATAATGGAAAATCTTAAGCAAAGAACAAAGTA
TAAGAAATACGTATTTTTTGGTAAATACAGTAACATGGTTTTAGTGAACAGGAAGAGGTT
ATATGTTTTCTAAGAAACAATTAGTAGCATGTGTTACAATCAGTCAGGACTTAGTTCGTT
TACATTGTTATTTATACTTAAATCAACCAAACTGTTGCTTGCTACAGTGTTAATTTGCAA
AGTATGTTTCTTTGTACTACAAGTCTCATACTGATGAATTCTATCTAGATCAAAGACTGT
CTATGGGGAAAAGGTTTGTCTTAGCATATGAAACACTTTTCAGCTGCTTGTGTTTTGGTG
GTTTCCTAATTTGTCTAAATTCTAAATGTTTCTTTAACGGTGATTGTTAGTAATACTAGG
AAGTCGAATTCTGGCTGCAAAGTATTTATTACCTATAGGTCAGGAAGCCTAAGGATAAT
CTTAATTCCAAACCTCCAGCAGTCCTCTTTTATGCCAAATAATGGTTTAAAAAAAAAAGT
TAACTCCCCAGCTATCCATTTTGGCATTGCTGGCAGTGTGCTCAGTTGTGAATGACTCTT
TTGTGACCCCTTGGACTAGAGCACCCCAGGCTCTTCTGTCCTTGTAATTCTCCAGGCAAA
AATACTAGAGTGGGTTGCCATTTCCTACTCCAGGGGATCTTCCCCACCCAGGAATTAAAC
CTGCATGTCTTGTGTCTCCTGCATTGGCAGGCTTATTCTTTACCACTGCGTCATCCAGGA
AGCCCATTTTTAAGTTAGCGTTCATATTAAGAAAAGAATATTAAAAACATTGTCTTTA
CTACTTATTAACTCTCTTTATTTTCATTAGCTTTAGACTGTATATATAAGTAATGGTTTT
CAGGAGAAGAAAACTTCGAATGTTGCCTCTCTCTATAGAGCTCACATAAATGGATATTTA
ATTTTCTGAGTATGTCATTAGCTTTTCTATTGTAAAATTTAATATTTAAATATTAATAT
TTAAGAGCTAACAGACCTTTTTATAAATCATTTGACTTGTAAAATTGACATTCTAGTCTG
AATGCTACCAAGATGTGTACTGTGCTGTAGAATGTTCATTTTTAAAACCTTCACTTTTTT
TTGAATACAAAAAAAAAAATGTACCCAGGGAATTGTGCTGGGAAAATACTGACTTGTTCT ----- Start Codon

FIG. 1A

```
ATTTATCTTCATCTTTCTTAGCCCTTTGAATTTCAGTGCATCTTGCATGTTAATCTACCA
GAAGAATCTTCTAAAATCATTTTTGATATTTAACGAAAATGTTACCCCATTTTTCAGTAA
GAGTAAGTTCAAACTCCTCAGCCTGTCAATTGAGGCCTTCCATCATTTGGCCCCACCCCA
TAATTCACTGTTGACCTCCTTTAAGGGAGACTGGTGTTACCTTAGCACCCTCCCAAAGTA
TTGTTCTTTTTCCAGCCCTCATCATCCTTTCTTCCTGGAATGATGGAATGCTTTTTTCTA
TCTTTCCAGTCAAAGCCAGTCAGTTCCAGCTTCAGGAGTCTTCTTCCTTCCAGAAGAATC
TGCCCCACCCACCCCCTCCTTCTTATTCTTGTCTCTTCCTTCCCTGAATCTTGTGAACTT
TAGTCTTTATCACAAGGTGAATGCTTTTTTTGTGCTGCCTTCATTGCTCTCTGTATGCTT
GTATACAGTGGTGGAAGTGATCCTAGCAGGACTCAGCCTTCTGGTACCCAAAGTTTATGA
CTTCTATTGGCTCCAGTTGTCCAGCTCTAAAGTTTAAACAGTTAGACATCTTAGGCCATA
CATATCGTTAAAGATTAGTCACTTACTTTTCTTGGCATAGGCCAGAAGTGCCATGAGATA
CCCACCATGAAATGTCGTCTTTCCAATTACTGGCATACGTTAAAAAATAGGGTGCGAGTG
AAAATCAGTTCCTGGATCCTCTTAGGGCTTGGGTATCCACTAATCAGTCCAGTCCTGTCT
TCATGTTGATAAAAATGTTAAATCAGTCCTGATACTACGACTTAATCAGTCAGTGAACCA
GTGTCTTTCAGCTCTGGATGCACATTACAATTTACAAATAGTGATGCCTGGGCTCCAGCC
AGAGGTTCTGATATAATTAGATTGCGATGACTGTTTCTGAGCATGGTTTATGTAGGCTTT
CTTATGATAGATTATGGCATAACTTTTCTGGCTTGCAGATTTTATCCAAAAATGACCATG
TTTCCAGAATTTTAACGCTGTCGTTGTCTACTGTGGGGTCAGAATGGCACCCCACTCCAG
TACTCTTGCCTGGAAAATCCCATGGTGGGCTACAGTCCATGGGGTCGCAAAGAGTTGGAC
ACAACTGAGCACACACACGTACATGGCGTCAGTAATGAATTTTCTTAGAACTCAGCCTGA
ACCAAGTGCCGATGTTCCCGTAGCACTTTCAGTCTACGGGAACATCACAGAACGGGAAAC
TTGAAGTTTCTGTGTCTCAGTGCTGCACTCCTTGAGGGAAAGGCCCAGATCTCATTGTAA
TGTTTGTATCCCTAGTGTTTAGTTCAGTATCTTACCTGTATTGCAGAATAAATGATTATT
AAATAAGTGGCATGGGGGAAGACTTACCTAAACTATATTATAGTATTCTGTGTTGAAAGT
GTTGTACCTTTTCGTATAAAATTGATTCTGTATCTTTTAAAGAACTGCTGGTTGACCAAA
TTGCTGATTTAAAACACATATATTAACATGTTGTTTGGATTTGTTACTGAAAAATTCTGT
TGGAAGTTTTAACTATTAGCATTAACTATTAACCACATCATTAAGGTTTTTCTGAAATGC
CAGTTAAAATCTGTGATGAATGTTGTTTATAACTTCATAAGTACGATTAACAGTTTGTTT
TAAAATTACTTTTCTATTTAGGTAGAAAAACATTTTGTTATTTCTTTCATTGCATGTATT
TAACAACCTTCTGAAACATTCTTAGATAATAGTTAATATGCTTTTTAGTAGCATGCTCAT
TTTTAGTGTTAGTCGTTTTTTAAAATTACCAGTTCAGAAAAATATTCAGTTGAACTGAAA
ATTTGGTGTCTGTGGAGCAGTGACCCAGGGTATCAGCTGTGACTAGTATACTGTGCTGAA
ACAGCATAAGCAGCAAGTGTGATGGTCAACAAGTTATAACACTACATATTTCTTCTTGGA
ACTAATGTAATGTAGTAAGAGATAAAAGAAGACATCTGTCAGTTTTGTGTGGAGTTCAGT
TTTTCTCCTCTTTATACGGTTAGACACATGAAAAGACCATCACGAGGGAAGGACAAGTAG
CCAGTCAGACAGACAGATGCATAAAATGCACAGGCTATCTTGTTGTTTTTCAGCCCATCT
CATGTTTCTGTAAAGGGAAATAATTTGCTTTATAATTGTATCCTAAATAGAAGATGGAGT
AAAGAGAAGGTCAGCCCAGAGGAAATGGAGGATGATGCTCAAAATAGAATTTATGAATCA
CCTGTTTAAAAGATGGGATGTAAATTGTTGATATAAATTCCTGACTCTTAAAAGGAGAG
CTTCTGTTCTTTGGTATCACATGCTGATGTGGTAGGAAGGATTAATTGCTTTATCTGCC
TAGTGGCAAGATTATTTTCAGGCCTTAACTCTGGACATAGTTTTACCCCAGGCTGTTAGT
CTAAGTTTTTGTCTACCTCATTTTTTTCCCTCTCTTTTGTCTTATCATGGAAACATGA
GCCATAAAACTTTAGGACAGTATTCTCCAGATCTCTGTCACAGAACGTGAAGTGAAACTG
CATACTGTGAAGGAGTCATAATTGCCATTTACTGAAAGTTACTCTGCTAGTCCAACATTA
AGCTAGAGGTGCCTAAACTCTCTTGTCTCATGGCATCTTGGGGTCTCATTAAGTTTTTAA
CAGCACCCTTAAGTCACTGTTATGTTCATTAAGTAGTTAGGTCCAAATAATAAACATTTA
CATCCCAACAACTTTAGTAGCTGTTTGGAAAAAATGATGCCAAGAAATTGAAAATAATTT
ACTTTGTTCGTAAATAACCACAATTATTTACTCAAAGTTTGGGGTGCCTGCTAAGCACTG
AACAGCTTTTCAAACCTTGGCACCAGATTGAACTGAACAGCACCACCCTCATTGCCTGTT
CCGCATTGACTTTGGAGTGGAAGTGTTTTGTTTTGTTTGTTTTTAGTCAGAGAAACCA
CTGAAAACTCAGCTGCCCAAAGATATGATGTCATAAAGGAATGTACTGCAATCAAATGTT
```

FIG. 1B

```
AAAAACTCTAAACCACCCTAGTGTAATAGTTTGGGCAGTTCTTAGCATGTAGTGAGTATT
TCCGTGTTTCCTTCCATTTAAAATATCCTTCATCTCTCCTGGGAGTTTGCTGAAGTGTCC
TGGACCTTCTCAGCATAGAGTTTAGACTGTGGCACTAGACTTGCTTTATTTCATTAAATT
CTGTGGGTTGTACTTTTATCCCCATTTCGAAAAAGTGGAAACTGAGGCTTGGAGAGATTA
AATAACTACTCCAATGACATAGTCTTAGCATTTGCTTTTTCACCGTAATTATTATTTGGG
CTGCTGTTAGGGTGGTGGTTATTGTTTGGGGGGTTGAGGAATGAATAGCAAAAAGACAAG
AATGCCTATAGAATTTTAAAGTTGAGTGAAATGGGCAGCATTTTCTAACGAGGGAAGTGT
TAAACCTGCTGTGTTTGCCTACAAATTATTACTATATAAGGGAAAAAACATGGTTTGAT
TTAGCATTAGGTCATTAAAAAACCAGGTTTCTTTGCCAGGCCAAGTTAAATGTCAGCTTT
TAGAATTTTGGATGACAACTGTGGTAGGTGGTGATAAAAAGCAGTATCCGTAGTTTTTC
TTTTTTTTTAATTGCCACATGCTACCAGTCACCATGATTGCCCTTTAGATAAGTTACAGT
GCTTTATCTTTTTTTAAGAAAAAATTTCAAGCTGAAAGAAGTGACTTTTTTATAGTTGAC
TTTTGCTGCACAGAAAAATGAATTTTAGACTTGTTAGATACGACTTTATGTTAGGGTTGC
AAAATTTCACTTTTTTTCTGTAAATAATTTTTGGAATGTTCATATTTAATAAAAAAGAAA
GTAAATAGCAACTTTTAAATATCAATGCTTAAAAAAAGAAAATTACCCTTCCTCCTCCAT
CCTGGGCAGCAGGGTTGTTCAGTGGCTCAGTCGTGTCTGACTCTTTGCGACCCCATGGAC
TGCAGCACACCAGGCCTCCCTGTCCTTCACTAACTCCCGGAGTTTGCTCAAACTCGTGTT
CATCAAGTCAGTGATGCCATCCAACTGTTTTGTCCTCTGTTGTCCCCTTCTCTTCCTGCC
TTCAGTCTTTCCCATCGTCAGGGACTTTTCCAATGATTCATTTCTTCTCATCAGATGGCC
AAAGTATTGGAGCTGTAGCTTCAGCATCAGTCCTTTCAATGAACATTCAAGACTGATTTC
CTTTACTAGCGACTGCTTTGGTCTCCTTGCCGTCCAAGGGACTCTCAAGAGTCTTCTCCA
ATACCACAGTTCAAAAGCATCAGTTCTTTTTTTTTTTTTTTTTTAAAGCATCAGTTCTT
TGGTGCTCAGCTTTCTTTATAGTCCAACTCTCACATCCATACATGACTACTGGAAAAACC
ATAGCTTTGACTAGATGGACCTTTGTTGGCAAAGTAATGTCTCTGCTTTTTAAAGTGCTG
TCTAGGTTTGTCATAGCTTTTCTTCCAGGGAGCAAGCATCTTAATTTCACGGCTGCAGTC
ACCATCAGCAGTGATTTTGGAACCCAAGAAAATAAAGTCTGTCACTATTTCCCTTGTTTC
CCCATCTATTTGCCATGAAGTGATGGGACCAGATGCCATGATCTTAATTTTGTAAATGTT
GAGTTTTAAGCCAGCTTTTTCACTATCTTTTTACCTTCATCAAGAAGCCCTTTAGTTCCT
CTTTGCTTTCTGCCATAAGGGTGGTATCATCTGCCTATCTGAGATTATTGATATTTCTCC
CTGCAATCTGGATTCCAGCTGTACTTCATTCAGTGCAGCATTTCACATGATGTATTCTGC
ATATAAGTTAAATAAGCAGGGTGACTATATACAACCCTGATATACTCCTTTTCCAAGTTG
GAACCAGTCCGTTGTTCCATATCCAGTTCTAACTGTTACTTCTTGACCTCTATACAGATT
TCTCAGGAGGCAGATGAGGTGGTCTGGTTTTCCATTCTCTTTAAGAATTTTCCACAGTTT
GTTGTGATCCACACAGGCAAAGACTTTAGCAGTCAATAAAGCAGAAGTAGATGTTTTTCT
GGAATTCTCTTACCTTTCCTATGGTCTAGTGGATGTTGGCAGTTTGAACTCTGGTTCCTC
TGCCTTTTCTAAATCCAACTTGCACATCTGGAAGTTCTTGGTCCACATACTGATGAAGCC
TAGGTTATCCTGTTGTTATAACATAGGGCTCATAGTAGTTCCTGGGCTTCCCAGGTGGCT
CAGTGGTAAAGAACCCGCCTCCCAGTACTGGAAACTCATGCTTGATTGCTGGGTCAGGAA
AATCTCTTGGAGAAGGAAATGGCAGCCCACTCCAGTATTCTTGCATGGGAAATCCCATGG
GCTTAGGGGCCTGGAGGGCTATAGTACATGGGTTTGCAAAGAGTCAGATACCACTGAGCA
ACTAAACAACAATAGTAGGTCCTAAGTGCTTTCATTTTTTGCCACTTAAGTTTGCTATAA
GAAAATTAAGGGTGAAGGCAAAATTTCTGTCTCACTGAATAGTAAAGCCTAATTATGTGA
CCTTTTAAAAGAATATTTATTTATTTATTTATTTGACTGCACCAGTTCTTAGTTATAGCA
TGTGGAATCTAGTTTCCCGACCAGGGATTGAACCTGGGTCCCCTGCATTGGGAGTTCAGT
TTTAGCCGCTGGACTACCAGAGAAATCCTATGTCTCAGATTTTCTAAATTGTCCTTAAAA
TATAGCTTAATGGTATAACAGGATCTAGATTTGTCCTCCCACTTTATATAATAACAACAA
AACAAACAAAAAATGTGAAACAGTTGTCAGCTCTTGAACCATAGGCAGCACAAGACACTG
ATCCCTGAGAGAAGGGAAACAAATGAGGTGATTCTTGTTTGTGGGTTGCTGCCTTGAGAG
TTTCCAGGCTACAATAGCATCAGGAGGAACCCAGACAAAGCCTGGCAGTCTCCCCGAATT
GAGACAGAGTAGGGACTTTGGGGAAACTGGGGCATCTAGAGTTCTCAGGACTGAGTACCA
GCATAAGGATATCTGCACAGAGCTCCTGAGATGCATGGTGGGTTCCACGTGGTCCCTCAG
```

FIG. 1C

```
CTGAGTTCTGTTTGGTACCAGTGTGAGAGGAAGCTACCAAGACTGGGAAAGAAGCACCCA
AAAGGAGCCAGCAGAAAAATTCCTGGTGCTCACCCAGGTCTGGGAATAGGTCATGGTCCA
AACAGCCAGAATTGAGAAAGCTGTTTGGTTTGAGCACCCCGAGAGGGGTATATATTGGTT
CATTAGTGGGCCCAAGTTGCTCTCAACCACATGCTGCTCTGGTCCTGCCCAACAGGCTTC
AAAGCAACACCCAAAGGGATCAAACTGTTTGCAACTAGTTTCCAAATAGCTCAACTGTAT
CACAGAACACAGTTTAGCACTGTTCACAGGAACACAAAGTGTATATACATATATCCAGCA
TTCAACCCTGTAAATTTCACAGTGTCTGGCATTCAATTAAAAATTACCATGCATGCAAAG
AAGCAAGAAAATATGCCACATAACGAGAAAAGTCAATCTGTAGAAACAGATGCTCAAATT
AATAAGAACATTAAAACAGCTATTATAAATATACTCCGTATGTTCAGGAACACAAGAAAG
AATGAGCATGTTAAGGAGAGGTATACAAAATGTGAAAGACCCAAATCAGACTTCTAGAAA
TGAAAACAGCAATGTCTGAAATGAAAAAAATACACTGATAGGGATTAATAGATTAGACTG
CAGAATAAATGAATGACAAATTTGAAGATGCAATAATAGACAACTCAAATGAAACATGGG
GAAAAAGACTTAAATAGATAAACAGAACATCAGAGGGCTGTGGGAAAATCTCAAGTGGCC
AGATATATACACATGGGCTTCCCTGATGGCTCAGCTGGTTAAGAACCTGCCTGCCAATGC
AGGAGACACAAGAGGTACAGGTTTGATCCCTGGGTTGGGAACATCCCCTGGAGGAGGGAT
TGGCAATCCACTCCAGTATTCTTGCCTGGAGAATCACATGGACAGAGGAGCATGGCAGGC
TACAGTCCATGGGGTCGCAAAGAATCGGATATGAATGAAGTGACTGAGCACACACACATG
TATATATAGTTGGAATCCTAAAAGGGAGGGGTGGAGCCGGGAAATATTTGAAGAAATTGT
GGCTGATAATTTTCCAAAGTTGATGAAAACTATAAATCCACAGATCCTAGAAGCTAAATG
AACCATAAGCAGAAGAAACATGAAGAGAAAGAACTACACATGGTCAAATTGCTTAAAACC
AGTGACAGAAAAATTCTAAAAATAATCCAAGAAAGAAAAAAGACATATGTGTAGAGGAAT
GAAGACACGAATCATGATAGACATTTCTTTAGAAGCAATTTAACCTGGGACTTCCCTGGT
GGTCCAGTGGTTAAGACGCCACACTTCCAGTGCCGGGAATGTGGATTAGATCCCTGGATG
AGCGGCTAAGATCCCACATGCTGTGCAGCATGACTCAAAAAAAGAAAAAAGAAACAGTCC
AACCCAGAGGAGAAAGAGCTAGGTCTTTAATGAGCTGAAATGGAAAAAAAACAGAAGAAT
AATGAAAAAAAAAAAAACAAAACAAAACCCAAAACCTGTCCATCTAGAATTCTGTACTCC
ATCACAAAGAAAGGTGATGTAAAGACTTTTTAGATGTTCAAAAGCCAAAACAAAATGAGC
TAATTATATGAATAGCGATTTAGATTAGTATTGCTTTTCTTTATATCTAGTGCCAGTATT
TTCAGAAATTCTGAGTTTATAAAGACTGAGTCAGTTTTGTTAATTGTGTATATGTGTGTG
TGTGTTATTTGCTTAGTTGTGTCCGATTCTTTGTGACCCCATGTACTGTAGCCCTCCAGG
CTCCTCTGTCTGGAATTTTCCAGGCAAGAATACTGGAGTGGGTTGCCATTTCCTTCAACG
TGGGAATCTTCCCGACCCAGGGATCAAACCCAGGTCTCCTGAATTGCAGGCAGATTATTT
GCCACCTGAGCCTCCAGGGAAGCCCATTTTGTTACTTAGTTATGTTTAAACTCTAAACTT
GAAAGATGCAGAAAGAGTGGAATGGACTTATGCAGTTGGGGTTAGCTTTGTAAGTAGAGT
GCCAGAAGGAGGTTTATCTGTAAAAAATTGTGTCTTATGTTTTGATGGTGACACAGTTGC
TTGAGATTTTTAATAGTTGTTAATAAGAATTTGTGTTTTATCTTTTTCCACTAAAATAGG
TTTTGCCTGTTTGCCTATAATGTAAGCCATTGTTATCCCTCTGTAATGTTCTACAGTATG
AGCAGAGCATTCATGTTGGCATACATTTCGTAGCCACTGAACTAATAGAATTACTGTGAG
TGCATTTGGAGAGATGCATTAACTCTCCCTCGTCAACTGGACACTATTTAATTACTCCCA
CATTTCAGGTTGAAAGACTGTATGTGCCCTTTACACTCCTAGATGATTCTGAGATAACTT
AAGTCAGTTAAAAGTAAAAGAGGGACTTCCCTGGTAGTCCAGTGGTTAAGAATTTGTCT
ACCAATGCAGGGGATGAGGGTTTGATTCCTGGTCAGGGAACTAAAATCCCACATGCAGTA
GGGCAAGTAAGCCTGTGCACCGAGACTGGAGAGCCAGCCACTCTAGAGCCCAGCCCATGC
ACCGTAACAAGAGCAGCCTGGCGCCCTGCAGGCCATGGGGTTGCACAGAGCCGGACGCGA
CTGAGCCACTGAACTGCGCTGAAGACCATAGGATGGGGTTCCCAGGTGGCTCAGTGGTAA
AGAATCCGCCTGCCAAGCAGCAGACGTGGGTTCGATCCCTAGGTCTGGAAGATCCCCTGA
GAAGGAAATGGCAACCCATTCCAGTATTCTTGCCTGCAAAATCCTGTGGACAGAGAAGCC
TGGTGGGCTACAGTCCATGGGTCACCAAAGGGTTGTGGACACAACTTAGCAACTAAACA
ACAGCAACAGACCATAGGATTACTGTAGTCTGTTGACTACCTTACTGAAATGTAGATAAA
CAAAGTCTTTTAATATCCTGTGGTTCATATTCTAAGCATAGGCAGGATGAATCATACTAT
TAAGTAAATTCCTAGCTGCTGGTACATTAGTGCTCGTTAGTGGTCTGTCTTGGTCAGCGC
```

*FIG. 1D*

```
TAGGGAAGTGACGTTGGAGAATGGGGTAGAAATGTAGTTACCAGATGTGTAGATGTTACA
ACACTGTGTGGGACTGACACAGAGCTGGGTAAAATAATTACTGATTGTGGACGGCACAGT
TGAGATCCAACTTTTTTAGACTGAGAAAATGGATTAGAACCTGAAACATGAAAAATGCAC
TTTCCCCTTGTTTAATTTTTGTGTCCATTCCTGAACCACGTGCTGTGTGTAGGGCCAG
CAGGACTGCTTGGGTTGGACAGATGATTGGCAACAGGAGACAACTTTGTGTAGTTGTCTG
AGTTCCCATAAAGCCGCTACCAGCAGGATGCTACATAGTAAGGAAGGGTTGATGGCCACC
TTGACCACTGTGTTCCTTCAAACCTGCTCTTCCTTCAGTCTTCTTTACTCGGGGAGTTGC
CCTCCATCCCCTGGCTGTTTAAACCAGAACTTAAGAATCACCCTCTACCCCTCCTTCAC
TCTGGTTTTACACATTCACTCCATTACCAAATCCAGTCAACTCAACCTCCTAATTTCATT
GAGAATCCATGCAGTTTACCATTTCAGCTGGTTTTGCATCAGTAATGCCACTGCATTCTT
TTTCATGGACCATTGTAATTGCCTCAACTGGTCTCCCTGCTTCCACTCTCCCCACCCAAC
TCTGCAGTGTTTTAAATATGCAGTTTACTTTTTAATGTTTTAAAAGTTTGTTTATTTT
GACTGCGCTGTGTCTTTGTTGCTGCGCCTGGGTTTCCTCTAGTTATAGCGAGCAGGGCCT
ATTTTGTTGCGGGGCATGGGCTCTAGGCGTGCAGGCCCAGTGGGCATGGTGCATGGGTTT
AGCTGTCCTGTGGCACTTGGAATCTTCCTAGCACAGGGAACTTTTGACCCCTGCATTGGC
AGGTGGATTCTTAGCCACTGGACCACCAGGAAAGTCCTAAATACACAATTGAGATCTTAT
TCGCCTGCTCAATACCCTTCAGTGGTTGGCCACTGAACTTAAAATGCAGAGTCTTTAAAA
TGGCCTGCAGTGAAGTGGAGCCCTGCCCCCCTCCTCACTCTTACACTGTACTGTCTCTTG
GTTTCTGTGTTCCAGCCACATTGGCCCTTTTTTAAGTTATGAATGTCTCAAATTCTTTCT
GGTCTCAGGGTCTTCACATATGCTGTTGCTTCTGCTCAAGATTTTATTTTTAAAAATAAA
CTTGTTCACACATGTGGAAAAGTACATAAACCATAAATGTTCAACTTGATGACTTATTAC
AGAGTGAACATATTAATGTTGCCACTACCAGGTTGAGAACTAGAACATTATTGCTGGCTC
TCCTTTCCAATTATTATCTCCATCATGATATGCAGAGATCATAACTGCACGATTGCTTGC
ATCATAGATTAGTTCTGTCTGGTTTCCAACTTAACATAAATGAAATCATTCAGTAAGTAT
TCTCTTGCACCCAGCTTCTTTCATTCAGTGTTAAATATGGGAGATCTTGCTTGTGATAGC
GTATAGCAGTAGTTTATTCATTTTCATTGCTATGTAGTATTCCATTGTATGAACGTTCTG
GTGTTCTGTTGACATTGGCTTTATTTTCAATTTTTTCTATTACAGATGATTCTAGTATGA
ACATCCTTCTACATGTCTTTCGGTGCACATACTTTAATTTCTCTGTTGGATATTCTTAGG
AATGAAATTTCTGGTTTTAGGGTATATGGATGTTCCTGGAACACTCTTAACCTTTACTCT
TCAGATACCAACTAAAAGGTCACTTCCACAGGCAGGCAGGCAGGCAGGCCTGCCTCCAAC
AAACAATTTTAAATTAGGTTCTCTTGCTGCAGTCTATTGGAACTCCATCATTGTGCTTAA
TATAATTTTGCACTTGTGTGATTATATAATGCCTGTCTTCCCAATGGAAGGTATTAGGGC
ACTGACTTTTTTATTCCTGGAATAGACATTCAGTACAGACTTATTGCACCAATGAGTGA
AAGGTTATTTTGAAATGTTACTAAGATTGGGGTGTATAATTTATATAGAACACTAATTTG
GACAGTGGGTTATCTTTCAGCTAAAAGTTTAGTTATTAATAGTACAAAGAAAACCATTT
TCTTTTCAAATAATTTTTTTCTTTATGTATGATAAAATTGAAAGAGGCTTTCTTGCCAGC
TGCTTACATGATCTTAAATGAATCACTTAACCTCTAGTCTTTTTCTTCTGGAAATGAGTA
GCTTGGCCTGTAGACCTCGAGGATCCTCTGACTTGAGGCTCTCTACATGCAAATAAGCCA
ACCACAAAGTGCGGTGCATGCAACCTCAGGCAAATTGTGATTCTAGGCAGGGTATGCCGA
TTTGTCATCTTGTTTTCATATTCTTACCGGCTTTTTTCAGCTTGGTCTTCTGAATCAGCT
AAGGAAAGGTGTCTGTTCCCACCTGGAAGGCTTGAGCCACAGTAGAAGGTTGACCTTGGA
TGGCAGGATCTTAACTGAGTAATGTAATTATTTAGCTTGAAGTATTGTAATTCATCAGAA
GTTAGAGGAATCTACATTTAAATTTAATTCAGAAATACCATGGACGTTTTAAAGAAATG
ACATTTTTTTTTATTACTCAAAAATGCTTCATTTTTATTTAGTTTTCTGACTCTGT
GCTTGTGCTTTCAACACTTTCACAACGATCTTCTGCTCCTCTTTAAGGAAAGCGTGCTTG
ATCCTGTCACGGACACATTTAGCACACATGGAACCACCATAGGCTTGGCTGACATGCTTA
TTCATTTTAGACAATCTCATGAGAACTTTAGGTTTCACAGCACGAACACCTCTAAGTCAG
CCTGGGCACACACCACATGCAGATTTTGGTTTTTTCCCAATCTCCTTGGTATAAAGGTAA
ACAACTGTATTACCAGGGGTTCGGGACAGCCTGGTTTTGTTAGAGGCTGTATTGTAGGAC
AGCCTACGATGGTATGTCAGACGTTGCACCATCCTGAATGCCTGTAGCTGCCATCCCCAC
AAGAGGAAAAGGAAGTCCTTGCAGGTTCAAGAAATGACATTTTAAATTATCTGATGATC
```

*FIG. 1E*

```
TTAGATCATAAGATCTAATTTTGCTTCTTTGGGTTCAGATGGTGGGGTTATTAGCAAGGC
GGGTATGACCACCATGTCACAGTTATCCTGTTTATTAAGCCTCTATTTAGATTCATAACT
CAGGAAAGTCAATAAATAGGTATATGATTGTTTTCATCTGAATTTCTGTACCTGATCTTT
TTTTAAAATTTGTTTATTTTCAATTGACAGATAATTGCTTTACAGTATTATATTGGTTTC
TATCAAACATCAGCCTGAATGAGCCATAGGTTTACCCATGTCCCCTCCCACTTGAGCATC
TCTCCCACCTCCCTCCCCCTGCCACCCTTCTAGGTTGGTACTGAGCCCCAGTTTCAGTTC
CTGAGTCATACAGCAAATTCCCATTGGCTCTCTATTTTGCATATGGTAACATATGTTCCA
TGTTACTCTCTCCATATATCTCAACCTCTCCTTCCTCCCCACAGCCATGTCCACCAGTCT
GTTCTCAATGTCTGTGTCTCCATTGCTGCTCTGCAAATAGGTTCATCAGTACTACCTTTC
TAGATCCCATATATATGTGTTAGTATACAATATCTCCAAATAGGAAAAGGAGTATGTCAA
GGCTGTATATTGTCACCCTGCTTATTTAACTTATATGCAGAGTACATCATGAGAAACGCT
GGACTGGCAGAAACACAAGCTGGAATCAAGATTGCCGGGAGAAATATCAATAACCTCAGA
TATGCAGATGACACCACCCTTATGGCAGAAAGTGAAGAGGAACTAAAAAGTCTCTTGATG
AAAGTGAAAGAGGAGAGTGAAAAAGTTGGCTTAAAGCTCAGCATTCAGAAAACGAAGATC
ATGGCACCCAGTCCCATCACTTCATGGCAAATAGATGGGAAAACAGTGGAAACAGTGTCA
CTTTATTTTTGGGGCTCCAAAATCACTACAGATGGTGACTGCAGCAATGAAATTAAAAG
ATGCTTACTCCTTGGAAGGAAAGTTTTGTCCAACCTAGATAGCATATTCAAAAGCAGAGA
CATTACTTTGCCAACAAAGGTCCGTCTAGGCAAGGCTATGGTTTTTCCAGTGGTCATGTA
TGGATGTGAGAGTTGGACTGTGAAGAAGGCTGAATGCTGAAGAATTGATGCTTTTGGAAT
GTAGTGTTGGAGAAGACTCTTGAGAGTCCCTTGGACTGCAAGGATAGCCAACCAGTCCAT
TCTGAAGGAGATCAGCCCTGGGATTTCTTTGGAAGGAATGATGCTAAAGCTGAAACTCCA
GTACTTTGGCCACCTCATGTGAAGAGTTTTCTCATTGGAAGAGACCCTGATGCTGGGAGG
GATTGGGGCAGGAGGAGAAGGGGGATGACAGAGGATGAGATGGCTGGATGGCATCACTG
ACTCGATGGACGTGAGTCTGAGTGAACTCCGGGAGTTGGTGATGGACAGGGAGGCCTGGT
GTGCTGTGATTCATGGGTCACAAAGAGTCAGACAGGACTGAGCGACTGAACTGAACTGA
ACTGAACTGATACAATATTTGTTTTTCTGTGTACCTGATACTATGTTTCATTATTTGCCA
TAAATTCTCATTTGAAAAGAGAGGTATAACACCAGCAATGCTGAGTAATGCCAGTCACGT
CATATGACATAGTACCATAAAAGTAAGCCAGTCGAACAGAAAAGGTGTTGAATATTGTGA
TAGAGAACAATTGGTAGGTTAAATTTTGATAGAGAACAATTGATCTATTTATACACTGAG
TGTTTTCTGTAGTCTATAAAGAGATCAAAGAGTTTATAAAGCTATATATAGGTTTATAGC
TTCTATTTTCATTATTTTCCTGTAGCTTAAATAGGAAATGTAGATTAGGCCTACCTTCAG
ACATTAATTTGTTCAATTCAAAAACTGTGAAACACCCTCAGAGCTAAAATAATGACTAAA
ATTGTAGGATATCACTAGCTCATGGCTTTGGTAGTTTTAAATACTTATTAACTACTTCTC
CGATGGTAGGTGAAGGCAACCTTATGATCTTCCAACTATAACTTTGACAGGGGGCTCCCC
TGGTAGCTCAGTGATAAAGAATTTGCCTGCCAATACAGGGGACACAAGTTACATCCCCGG
TCCAGGAAGATCCCACATGCTGTGGGACAACTAAGTCCATGTGCCACAACTACGAGGCCA
CAACCACTAAGTCACCTGGGAAGCCCCATCAGCATAAGAAGGACTATTTTCTATGAGAAA
TATGCAAAAGATTTATGACAGAATACTAGCAATATATTTCATCCTTAAATATTTTTTGGA
GAGTATGTGCTTATAGCACATATTTATTTTGCTTTAAATTCTTTTCTGTGACCTGATTC
CTGTTCATATATTCAGTAGGAGTAGAATCCTAGGGCCTTCAGATAATCAATCCTAATGAT
ATGAGATTATACTTAAAAATGTAACTAAAATTATAAATTTACACTGAAGGTAGCTCAGTG
TTCTCTGGAAATGCACATTTGTATTTAGAGTGAAGACTAAGATTTAAAGCATGAATGAAA
GATAGTTTCAAACATGAGAAGAAAAGTTTTGCCTTTAAAAAAAAAATTATTTATTTATG
GCCACATGGCTTGTGGAATCTTAGTTCCCTGACCTGGGATTGAACCCATGCCCCGCTGCA
TTGGAAGCACAGAATCTTAACCACTGGACCACCAGGGAAGTCCCAAGTTTTTCCTTTTAA
AATAAGGAAAATAAGAGTGGAGTTAACATACTGTTGACGTCTGAAGTGTAATAGCAGTAA
CTTCAGAAGCCGGGCTCTGACTTGACTTCCGTGCTTAAAGTGTGAGCTGAAGAGGTGGGG
CCTTCTTACTTCAGCTGAACTGCTCAAGATCCTGGCTCAGAAGGACTTGGAAAACAATGG
GCTTCTTGGCCATTCATTCATACCTACTGGTGTTTAGAAACCAGTCACTTGTAAAAAGGA
AGGCTTGACTTTCCTAGCATTTCATTTGTTAAATAGCAACAACATGAAGAGGAAAGGGGA
GAAAAAAATACCTCTTACAAAAATCAGTCCGTTCCCCTCATGGAAAGCACAGTGGAGAAC
```

*FIG. 1F*

```
CTTTTTATCAGCAAGGCAGCACTTAGGGGAGAATGAGCGGCCTGAGCTTCCGCACAGCCA
GGCTTCCTGGACTTTGAGCTCTGCTCCTCCTCTCACTCTGTGTCCTCCGAGCTCTCCGCC
CCTGCTGCCATTTCCTGTGCTCCATAGCGTGGATCCTGGTTTGCAGTCACCTAATGGTGC
CCATCTTCCCCATCTCTACTTCACCCCTCACCACAGACATCACATTCGAAAATTGCCTCC
TTTACTGTGAGGAATTGTTAAACTTCAACGATGAGGGTTTTCAAATGCTGTCAGTGGTAA
GATGTAATGTTTATCTTCTTTGCATATTTTTTAAAACTAACAAACCATTCCCTTTTATG
CCCAAACCTCTTTTTTTTTTTTGGAGTTAAGTTTTATTTGGTTCAAAATAAGGACTGCA
GCCCAGGACACAGTGCCTCATATAGTTCAGAAGAAATGTTCCTCTCAATTTATTATTTTT
TTTTCTGTTAGATGAAAATCTAGTCAGCAGCTGCAGTGTTCAGAGGCTTGGGTTAGGTGG
GTATCGTGTTGAGATATAAGTAAGTAAAACCTAGTTTCTATTGCTATTAGTAGACAAGAG
ATTTCCTTCCAGCCAGAGTACTCAGGGAAAACTTTAGGAAGAAAGCAGCATTTTTGGTTA
GGTATTGAAAGGTGATGGCTTCCCTGGTGGCTCAGTGGTAAAGACTGCCTGCCAGCGTG
GGAGACCGGTTTTGAGCCCCGATCTGGGAAGATCGCACATGCTGAGGAACAGCTAAGCCT
GTGCGCCACGTCTGCTGAGCCTGTGCTTTGGAGCCTGCGGGTCGCAGCTACTGAGCCAGT
GCACCTGGAGCCTGTGCTCCACAGCAAGAGAAGTCACCTCGATAGAAGCCTGCGCACCGC
AACTGCAGAGTGGCCCCACTCACCCCAACTAGAGGAAAGCCTTCACAGCAACGAAGACCC
AGCACAGCCAGATAGATCAATGACTAACAAATATTCAGGATGGAAAGAACGCTGTGAATA
AGGAAAGGGAGGTGGGGGTGAAGAACACGGAGCCTGTAGGAGGCAAGCACATTCTGGTTT
TGGCTGAAGCTGGGATGCGAGGGTAGAGTGTTAAGGGGACAAGAAAGATGGGGATGGACT
GAGTAAATTCGTGACAAATGCTGCGTTTTATCTAAAGGTTATACACGTTATTTTAAAGCG
TTATGGCTTTCCTATTTTAAGTGATCTCTTTATAGTAGAGATTCTCAAATTGTTTTCTAG
AAATTAAATTATCAGAGAAATGGAACAATAATTTAGTCAGGTCCCTCCTAATTATATATT
TCTCAGTATTTCATGGAGTTTCATAAAATACGGGAGTCTTTTTTTCCCCTCAGTTAAAA
AAATACACATATGGGAAGGAAATAAAATTGAATTATAAGTAATTATCTTAATGCCATTTA
GAGATACAGACTTCTTAATTTAGGAATATGCACATGTATTTCTAACAGCTATTTTGCTG
GCTACATTAAAATGAAAAAAAAAACACATTAAATAATGTTACATGTATGGAAAAGTTGAA
GTTCAGCACAAAAGAATTTTCTTTTTCTGAACTATTTGACACTATTAAGTTGCTAACATG
AGGTAAACAGGGTTTATCTGTTTCCCCTAAATGCTTTATTATAATATTTCCTAGAAAGGC
ATTCTTCTGCATAACTACCAGATAACCGTCAAAAAATGAACATGGTACCAGCTGTCCAAT
TCTCAGACTCTATTTTAGTTCATTAGCTGTCCGAACAATATCTTTCATAGCAAAAAGATC
GAGTTGAATTGTGTATATTATATTTAGTTATCATGTCTCTTTAGTATCCTTAGATGTGGA
GAAGTTTCCCAGTCTTTGACATTTATGACTATAAAGTGTTATGGCTTTTGAAGGCGAGGG
CCAGTTGTTTGGTAGAAATGTCCCTCACTCAGAATTTGTCTGATGGTTCTTCCTGTTCAG
AGTCATGTGGTGTTGGCAGGAATATTACAGAACAGTGTGCTTTTCATGGTATCCTGTCAG
CTGACACAGTGTTGACTTGTCCCATTTACTGTTGGTGTTCACTCTGATAACTTGTGTTGA
TGTGGTATCTGCCAGGCGTCACTGGCCAGCTCTTTTTTCCTTTATAATTAATAAGTGTTT
GAAGGTGAGGTACTTTGAGACTGTGTATGATCCCATTGCTCTTCAAACTTTAAGTTTATG
GGTTTATTCAGGGATTTATAATCTTTTACTCTTAAAATTTGTCTTAAAATTGTCCCAAAT
TTTGCCAGAAGAAGAAGCCCCTTTAAGGCTGGCTTCTGTATTTTGTGACGTGCCTTAAT
TGTTCTTTGAACACTTGTTTACTTTCTGGCACAAAAATTTGTTCTAGCCTTGTCTTGCCC
CTGCTGTTCTCCTGGAATCAGCCATTTCTCCGTGGAGTCCTAGTTCCTTTTAGTGGAGAA
TGTATTAGAAAGCAAGATCTGAGTGCTGGCTGTGTTGTCTGTTATTGAGCATTGCTGATC
ACAGGTCCTGTCAATTGATAGAGTGAAGGAAAATGTATAAGCGTGTATGTATATGCAAGG
GTCTCCCCCTGGCTCAGTGGTGAATAATCCGCCTGCAGGGCAGGAGACACAGGAAGTGAG
GATTCGATCCCTGGAAAATCCCCTAGAGGAGGAAATGTCAACCCACTCCAGTACTCTTAG
CAGAAAATCCTGTGGACAACGGAGCCTGGTGGGCTATAGTTCATGGGTTGCAAAGAGTCG
GACACGACTGAGCACAAGTGGGTCTATGTATTTGAAAGTATAATTATGCCCACCCATTTC
TGTCTTTGTCTGTCTCTAGAAAACTGAGTTCACAGTGGTAACTCCAGTTCCGATCAGC
ACCACAGCATCTTTTCTGGTTTTCTCTCTGTGTTTGTACTGCCCTTTTCCGACAGTGAGA
AACCTGCTCCGTGGTTCTTGGTCGTCCCCTGTGTATAACCAACCACTCTCCTGTTGCCA
CTACAGCCTCATCCACCCCACGGGTGGCTTCCTTGCCCCACTGGGCTCTAGCACCCTGC
```

*FIG. 1G*

```
TTGGAGCCTCCGTCCAACGCACCGTGCCTTCTCTACTCTTTCAAGCTCCAGCATCCTTTT
GCAGGCCATTCCCACCATTCCTGGGTGGACACCACCCTTCTTACTCCGCTCAGACTTCAT
CACCTCCTGCCCGCTGCCCCTCCCCTCAAATGGAGTCTTTCTTTCCCCACCTGTGGCTTC
AACTCCATGAGCAGGGACACCTTCTTACTCTCCCTGGACTCACAGCCTGCGAAGGACCTC
CTTCCATTCTACCCCACACCTTTGAAGCATAAATGAAACAACAGTTAATCATCTACTGTC
CTTTAGAGTAAAGATATTTAAGAAGGAAACACTAGGTTTTCTTTTATAAAATTGGAAGGA
TCTAGAGGTAAATGTTCATATGGTTCTGAAATCGCCTTCACCAGTTCACTGAACATAAAT
TACTGAACTCCTCCTGGGTGCCAGGCACTGAGCTAGCCCACCGGGGACAGGCCAGTGGAT
TAGACAAAGCCGCTTCCCTCAAGAAGCTGCCTTCTCTGACTGTTGGAGTGTAGCCAGGGT
AGTAAATTAGTAACCTCCCTAAGCCTGTTCCCTCCTGTCAAATATTTGTCACTCTAAAAA
ATAATTTAAAATTTCATTTAATATTTTGAGAAGAAACCAAAAAATTCCTGGCAGGGAAAA
TGACATCTCATCTATTCTTTGAATCATTTTTCTTTCCTTTAGCATTATTTTAGTTAAGAA
TATACACTTTAATTTAAATTGTGTATGTTTGTGTGTGTGTCCTGTTCCCTGAGTCTCAGA
ATATAATACAAAAGCACAAATAACTAAACAGTATGACATTTGTTCACCTGTTTGAATCAG
GTGACAGTCTAATAGATGGGTCTTCTTTGGGCCTGAAAAACATGGTAGATTCATATATTT
GGAGCACAGTTATTGAAAAGGTAATTATTATGCATTATTAGAAGAGAGAAGATTTGTTG
CATGGTAATTTAAGTTATAAAATGACTTTGTCTTTTCTAAGGGAAGGTGTATGTTAGTTG
CTTAGGCATGTCTGACTCTTTGCGACCCCATGAACTATAGCCTACCAGGCTCCTGTGTCC
ATGCGACTTTCCAGGCAAAAATACTGAAGTGGGTGGCCATTTCCTTCTCCAGAGGGAAAG
TGACAACTTAACACTAAAAATATATTTTCTTTTTAACCCTATTACTGGTATTTGAACCTA
AATGGTTGGTGCTAAAACTGATAGATATATCTGGTAATTTCTATATTACTGTACTAGTGG
TAGTGTTTGAAATGCATATAACGTGTAAACTCTAGAATAGAATTTGCCCTGGAAACCATG
CCTTCTATCATCAGAGAGATAACAAGCCTCTCTAAGGTTTGCTTTTGTACATTTTGTACT
TACAAGGCAAGATGTGGGAGAAGGGGTTCCTCTATTACTTTAAAATTAAAAATTGTGTTG
TGATATTTTCTAACTTGGAGAAGGCGATGGCACCCCACTCCAGTACTCTTGCCTGGAAAA
TCCCATGGACGGAGGAGCCTGGTAGGCTGCAGTCCATGGGGTCACTAAGAGTCGGACACG
ACTGAGCGACTTCCCTTTCACTTTTCACTTTCATGCATTGGAGAAGGAAATGGCAACCCA
CTCCAGTGTTCTTGCCTGGAGAATCCCAGGGAGCGGGGAGCCTGGTGGGCTGCTGTCTAT
GGGGTCATACAGAGTCGGACACGACTGAAGTGACTTAGCAGCAGCAGCATTTTCTAACTC
TGTTCCTTGTCATTGAATGTTAGGAGTAACTTCTATAAATATATAGTGTAACAAATAATA
ATGATAGGAACTCTAGGAATGAAGAATGAAATTCACATCGCCATAACTTTAATGGCTTGG
TGAAATCGTCCTCACTCCCTAACTTCATACAGGTGGTTTGATAAAAATAAAGGCCCACCG
CAGTAAAGAGCATGCTAAAGAAGTGTGACATCATCAGGTGGCTGAGTGAGTGACTCAGTC
TTTTTTTAATATTTATTTATTTATTTGGCTGCATGGGGTCTTAGTTGCAGCATTCCAGAT
CTTTAGTTGCGGCACGTGAACTTCTGGTTGCCCCACGTGGGATCTAGTTCTCTGACCAGG
AATCGAATGCCGGCCCTCTGCATTGGGAGCTTAGGAGTCTTAGCCACTGGACCACCGTTC
AGTCTTAGCCTCTGCTGCCAACTAGCAGAGCACAGCTCATTCGACAGCAGAAGTGGGATA
ATCAGGAAGAAGTCTAAAAGTCAGTGGTCTGAAAAGAGGTGAGGCAGGCAGGGAAGATGA
GCTGTCTGGAGAACCCTGGAGACGAGCTTCGAGACAAAGGAAAGAGCTTTAATGCAGAAT
ACTATGGGATATTAGGCAAAGCAGTAGACTGAGACTATGGCCGTTTTGTTGGCAATAGAG
ATCAACAGAGAAGACTGTAAGAATCTGCTTACAAGCGTTTGTAAGGTGGAACACATGCAT
ATTGTCAAAACATATTCAATACTGTGATTCTGTATCAGAATGTAATTTATTAGAATATTT
ATTAGACTTTGTAATATACTGTATTTTATGTGCAAATCTTTGAGAAATGAGAGAAGGGAA
AAGTACAAGAGATAAGAGATAAATAAGGAGTGAGCCAGTCATCTAAGAGGTGAACTGGGA
GCTGTGGGGTAGGCTGTGGATTAGGGAGGGCAGTGAAGAAGGAAAGAACTGGAAAGGAAA
GGATGGAATGAAAAGAGGCTCCTGTCTTTCCAGATTTGTAGGCCTTAGAAGGTCATATT
TGCTATTGTACATTGAGATACTAGCTGTGGTTTATGTTTCTTTGGTTCTGTGTCCAGTTT
TCAATAAGTGTGTTTGCTAAGAACTCGGAAGGTTTTCCTTTAAAGCTTCAGGATTTGTTT
TTGTTTTTTCTCAATAGAATGACCATCACAGCCTGTCTAAGGGAATTGTTCTGTAGGTT
GTATTCATTAGTGGATGACATTAACTTCATAGCAGAAGAAATAAATCCAGACGAAGGCCA
GACTGACAATTTCCCTGTCCCTGTGCTTGACTCATGTGGTCAAGCATTACCATTAACTTT
```

*FIG. 1H*

```
CATAATTTAAGCGTTAGTAGTCTTCCATGCGTCAAGCTCTGTTCTAAGTGTCAACGATTA
AAGAATGAATAAGACAAGAGTTCCACCTTCAGGGAACAGGTTGGCTAATGAGAAAGACAA
GTGATGAATATATTTTAAATGTTTTGGCAACATGAAGAGGGAGCTCTGTGAAATTCTTGT
GCTTAGATAAATAAAGGTTTCAAGAAAGTGACTTTATGTCTTTGTTTTTCTAAGGTGAGT
TCAGTTTTGGCCAGAGGCAAAAGTTGGGTCAAGCCTTGCAGGCAGAAAGCCAGATCACTG
TGCAAAGGCACAGAGATGTAGAAAGTGTGTTTGGGCAACAGTGAGCGTCTCATGTGACTG
GGGCATAAGGTGCATGGGCTGTGGAGGGAAGGGGAGCAATGAGGACTGAAGCAGAAACGG
TGGGTTGAGGCTAAAGTCTGGAAGAGTCTTTGTTAAGGGGTTGGGTGTTGTCCCGTAGGG
ATATCAGGACGCAGTGTGTTCCTGGTATTAAGATTAGCTAAACAGATCAGGGGACAGCG
AAGAAAATTCAAAAGCAACCTCCAAAAGATAGGAATATTATTAAAGATAGTAAGTACTTC
AGGATCATTAGGCGAGGATGGATTCATGAATTGATGGTGCTGGAATAACTTGTTACTTCT
TTGGGAAAAACTATTAAAGTTACTGGTTCAAAAAAAGATTTTATGCAGTACATTTATGTT
AAGAATATCAGACTTAGATTCAGACTTTAGATTTTTGGTTGAAACTCTGGCTTTATAGCT
AAAGCAATCTGGTGTTTCAGGTCCTTTTTCTTATACTAAAGCTTTTTTTTTTTTTTGT
AGCATCAGCAGAAAAAGAGGCAATCAAGGGTACATACTCCAAAGTTCTAGATGCCTATGG
ACTTTTAGGTGTTTTACGATTAAATCTTGGTAAGTATTCAATATAATTCAATCTGTTTTT
TCATTTCTGTTTTTGTAACTTTGAAGATTTGATAGACATTATTTCATAGACTCTGTATTT
GATCTGTGAGTATAATCATCTCTTAACCTTGAGATGGTTGTTGCCTGAAAAGCCATGCTA
CATGCTCATGCTCTCATGATTCTAAATTCCAGAGACAGCATCCTGTCTGAACACTTTAAG
AGATAGTAACATTGTTAGAAGAGAAAATAAGGGCATTGCCCCCTTTTTTTTTCTTGCT
TCAGTGCACTTAAGGAAAGATGTCTTAGAACCACACACTGTTTCCCCTGGTTTGTGGTGG
AAAAGATACCTGTTTTCTACTCAAAACATCTCAGCTTGAGCCTGTATGCCATTCAGTGTC
ATCATGGGCTGCAAAGTAACATTTGTGATCACCAGTTCTACAACAGTGTGACTCAGAGTG
TGGCCCACGGACAGGTTACACTCCATGAACTGTTTTGTTAGTGGTCTGGATGAGAAAAGA
AGCTGGTGCGGTCATGCAAATCAACACATGGCTTCCTTCATTGATAAAGTCTTACTGTGG
AGAAAAAAAAGAAGTCAGCTAAACCAAATAGAGAACTTAGTGAGGCAGTTTTCTCTTCT
GGAGCAAGCACCTGTTCTCACTAAACTGGTAACTGAACTAGTCCATGGATAGTACTTTGA
GGAGCACTGGTCTTGTCAAATGGAGATATGCCATTCGTTATGAGTCTGTCACACGTAAAG
CACTGTGTGTGCGTGCGTGCTCACTCACTCAGTCATGTCCGACTCTTTGTGACCATGTGG
ACTGTAGCCCACCAGGCTCTAGTGTCCATAGGATTTCAGGCAAGAACACTGGAGTGGCTT
GCCATTTCCTCCTCCAGGGTATCTTCCCGACTCAGGGGTCAAACCTGATTCTCTTGCATC
TCCTGCATTGGCAGGCAGATTCTTTACCACTGTGCCACCTGGGAGCACTTAACTAGTATT
GCCCTGGATCATCCTCACAGTCCAATGAGATTTGCTTAATCTCATTTTCTTTTTTTATT
TATTTTTTGGCCACCCCTCATGGCAGGTGGGATCTTAGTTCCCTGACCAAGGATCAAACT
TGGATCCCTGCATTGGAAGCAGAGTCTTAACCATTGGACCGCCAGGGAAGTCCCTTAATC
TTATTTTCTAAAGGCAGGATATCTCATGTTGCATATGTTAACACATGAAGTTGGTTGATG
TAATAAGTAGTGGAGAAGCCAAGATGCAGGGCACTTCTGCCTATGTCAAGCCCCCACATG
CTCAAAGTATACCACTGCTGAATTCCACCTTCATACTCACTGCACAGGATTTTTGTCAAA
ATTAGATGAAAAAAATTGCTATGAAAGTTTTTGTCAGCCAAATCACTTTATAAATTGTTA
CCAAAGACTTTTTCTTCACATAGCAGCAACAGCAGCAGCAGTTCACATTTAAATGCCATT
TTTTCAACCTTACTGTTTATGAAAAACTCTCAATTCATTGTCTTGTCTGAACTTCTTACA
ATCATAAAGGAAAGGTAGGGAAGATAACACCTACATTTTAAAAATTTGATAAATCTCACA
TACTTTTAAGTAGAGGAATAATTTCATAAATGTAAGATTATTCTGTTAATGTTTAAATGC
TTCATCATACTAAATGTATTTAACAAGGATTTTTTCTCCCAACTTCTGCCAAAATCTTGT
TGTGAACTTAAATGTGTCTATGATAAATTTAAAATAACCACACTGTCAGATTTTAAAAGA
CAGAGACACTAGAAGAAAGTTGGAAGAAATTTTGAATAGCTTGTAGAATATTGGCACTTC
CCATCCCATTAAGTCTTTGGTTTTTGCAGGTGATATTATGTTACATTATCTGGTCCTAGT
CACTGGATGTATGTCTGTTGGAAAAATTCAAGAATCTGAAGTTTTCCGAGTTACTTCCAC
TGAATTTATATCACTGCGAGTTGATTCTTCGGATGAGGATCGCATTTCGGAAGTGCGAAA
AGTTTTAAATTCAGGAAACTTTTATTTTGCATGGTCTGCATCCGGAGTCAGTTTGGATCT
GAGTCTTAATGCCCACCGTAGCTTGCAAGAACACACAACTGACAATAGATTTTTCTGGTG
```

*FIG. 1I*

```
AGTTTGTATTACGTTTTCCCTTGTGATCACGTGCAGTGCAGCCACTGGTGAGCTGGAACA
TGGAAGGCATAACAGTTATTTCTAGAGTGGGCAACGGTGGGCACGGCCAGTTGAGCACAC
CACTCTTTACTGTTGCGGGATCCTCAGTGGAGCATAGCAGATATCTGCCATCGTTTTATT
AAAGTAGTCCTGTGACGTGAAACCCATTTACTCTTCCTGATCTAGACAGACCTTCCATTG
CAGACATATATTTAAAATATTTATTTTTAAATCAGGAAGGAATTAATCATAATAGAATTG
TGTTATTCATATGTATGGTTCTTAGTTTGAGATCTCATCTCTGGCCACATTTGCCTTTCT
AAGCCTACATTCCCTTATTGTTTTAATTGGAAGGTTGTAAGTAAATGATTTTTTTTTAT
TCAAGAGCAGCCGACTACAGGGAAGTAGTATGCTGGAATCAAGTTTAGTACTGTAATAAA
ATGGGACTTAAGTAGGTAACTGCCACATATTTCGGGATTATGCATGAAGGTGCTGTATGG
TAAGTATGCGTTAATGGGGCAGCAGGACCCACATGACTGTAATTGGTATCGCTTTATTGG
AACAGACCAGATTTCCAGTATAGTCGTTCTCTTGTCCACAGTCAGCATTGCTGTTGACTT
TTTTCCTTAACACAATGGACAAATTGTATTTCAGTTGTTTACTTACGTTATAAGGCCAAA
GTCCAGGACTATGCTCACAGCTTCCCTCAGTAATTCAGACTCGGGGGTTCCCCACTGTAT
ACTTTCTCTCTCCCACTTCCACTATCTGCCTGAATGGTCCTGGAGAAAGGCCCTGGGG
ATCAGAGGGCTCAAAGTCAGCAATGCTAGGACTGGAAACTACATTTAGAGCAATAACTTG
GTAGCTTGTAGCTCCCATAGAAGTGTCTTGGCCCAGAGTGGCATTGGGGAGCCAAGAAGG
CAGAGGGAAAAGGGGCTTTGGAGCGCTGTATCTGGAGACTTGGAGCCTAGCGGAGGGCGA
AAGGATGGCGGTGGGGAAGGGAGGGCATAGGAGAGATGAGTCGGCAGTCCCATCTGCTCA
TGTCAACCCGGCACTTCTCTGATGGAAGAGACACTGATGTTTCTGAAGAAGCTGATGGCG
TTGCAGCTGGTCTTAGGGCAGCTCTCCTTACCTTTCTTCCCTCTGCTCTTTCTAACCCCA
CATTTCTTAGATTGAGAGAGAAAAGTTTCTCTGCCGTAATCAAGTCCAGGCAAATGCAGA
TGCATTGGCTAAATGGCCAGCAGTTAAGAATATCACAAAGTTTAATCCGTGGGAATAATT
CTTTTATCTTTTCATTCAGTTATGGGTAGAAGTGGGGCCAATTTAGATAACAGATTGAG
GAGGTTTATGAGCTGGAAACAGGCTGAGCAAAGAGGAGGCTGAAATGCTAAAGGTGAGTT
TTGCTCACTTTATAGTCTTTAAAGCTTTGCTAAGGATTAGAGTCTGGAGCTTCACTTTGC
ATAGAAAAGGAAAGCTTTTAGAATTCATTATGCCAACCCTTGCAGCTTTGTAGAAATAT
TTCCCAAGATACAGCCAAGTAAGTTCTGTAGCCAGAGAGTGGCAAACACCTATCCCAAAA
GCCCATGTAGTTTTAATCCATTGGGGATTTGAGGCTGCTGCCAGTTGAGAGTCAAGTGTA
AACTTAAATAGAATTAAAACAGCAAGGCATTGACTGTGAAGAAAAACGAAAACTGACAGC
AGAGGGAGAAATTCTATCTGAACAAATACACGGCTCCCACTGCTATTTAAATGGGGACA
ATCAGTCTGTCCTACCTCTGCTATGATCTGGGCCTCAGCTTTGGTATCTGGATGAACTGG
GTCACAGCCAGTTTGAGCTTTGCCAGTTCAGATCAAGGTAGATATTAAGTAAAGTGTGGA
AACTGAAGTCACGTTTTAAATTAGTAATATTCATCGGATTTAACGTTATCCCAAGAGTA
AGCCTACTACTCACTGACTTTCCAGTCTGCTTTCTTCAGTGGATAAGAGAGGCTGGGGTT
ATATCTGGTTTATCAGGATTACAAGTGGCCACTACCTGTTTACTGTCCCCTGCAGCGTAG
CCTGAAGTGGTGGGGACTGGAAAGACTGCTCCAACAGCATTGATGTAGATTCTTAACAAC
TCTAAGCTTTCAAGAAATGCTGTCACATTGTTTTTATACCTCTTTAAGAAACAAGATAG
TGCAAAGCACTTAAGATTTCCTCTTAAACTGGTAGTTTGAAAACTCAGAGAACCAAGCTT
CAATAATTCTAGCAACTTCCCTTTTGTAAGGCGCCTTTATTATCTGCAAGTCCCAGAGAG
GAAGTTTTCTGCACAACAGCATATTTACTTGGTGGTGGTTTGGTGAGGCGTTTTGGAG
GCCTGTGTTTCCAACCTCCAGCCTTCCTTTGGAGAAGGAAATGGCAACCCACTCCAGTAC
TCTTGCCTGGAAAATCCCATGGACGGAGGAGCCTGGTAGGCTTCAGTCCATGGGGTCGCG
AAGAGTCGGACACGACTGAGCGACTTCACTTTCACCTTTCACTTTGATGCATTGGAGAAG
GAAATGGCAACCCACTCCAGTGTTCTTGCCTAGAGAATCCCAGGGATGGGGAGCCTGGT
GGGCTTCCGTCTATGGGTCGCACAGAGTCGGACACGACTGAAGCGGCTTAGCAGCAGCA
GTGGTTCCAGCAGAGCCCCTGAGGCAAGCAGAGGGATGTGAAGATGGCCAGTGTAGCAGG
TCCCCAGCCCCATCCCAACGTTAGCCATGACAACTCCACTTTTAATATGTTTTCTGATC
ATCAGGTTTCTGTGTGTTCATTTAAACAGAACTCTCTGCCCTAAAAAGGATTGAAAAGTA
GGCCCTCTCTGTTACCTAGAGTATAGAAGTATTTGGAGCGCTGGGAAAACCCTAGACAGG
CATTAATATGGTAATTACTAGCTCATGTAACTATTTAAATTTAATTAAAATGGAGCCTTA
TAAAAGTCAAGCCTTAAGAAAATCCATATATATATGAATTCCCTGGAGTTGGGTGTGGAA
```

*FIG. 1J*

```
ACGCTTTTGGAACAAGTGGTAAATACATTATGAAGAAAGACATAACAAATGGGGCCCAAA
TTCTAAAAACGTAGAATATGTGCTGCTTTTGCATGGCCCACCGATCACACGTCCAAGGGT
CTCTCTGTCTAGCCCTATCCTCCAGTCCCTGGCACAATGAATGTAAGTGGGTTGATTTCC
CTCTGGCGCCTCTGAAGTCCCAGGGGCGCTGTCTTAGAATGCATGTTGTGTTGTGCAGTG
TGCTGCCTGTGCTCATCGCTCAGTCACATCCAACTCTTTGTGACCCAATGGACTGCAGTC
CATCAAGCTCCTATGTCCATGGAATTTTCCAGGCAAGAATACTGGAGCGTGTTGGGGAGT
GCTCATCACGCTAATGCAGTTCTTTCTTTTTCTGTTAGGAATCAGTCTTTGCACTTGCAT
CTCAAGCACTACGGTGTGAATTGTGACGACTGGTTATTACGCCTCATGTGTGGGGGAGTA
GAAATCAGAACAATTTATGCTGCTCATAAACAGGCAAAGGCTTGCCTCATTTCCAGACTA
AGCTGTGAACGAGCTGGGACCAGGTTTAACGTCCGGGGAACAAATGATGATGGTCACGTT
GCCAATTTTGTAGAAACAGAACAGGTATATAGTGTTTTATCTTGCTTAATCACAAAGAAC
AATTGCAAAGCAGATTTTTATTTGATTCAGAACTCATTTTGACATCTGTAATGCCATTTT
ATGGTTGCTCTTGGCTACTTGTGAGCCTTAAGAAAGGATCCTCAAAAACAAGCTTATTTA
GGTATGGCTCTTTGAGTAAGTAACAATTTGTTACTAATCAGCATGACATCATCAGTGCCC
TATGTTTAGTATTGAATTGAAAATCTTCAGTTACAGAGCTAGACAACTTAAGAAAAGTG
GGTTTTAATGAAATTAAGTCAAACTCAACTCTTAAAGGTAGGTTGTGTACCATCTGAAAG
GAGAAGTTACATTATTTTTGGCTATAACTATGTAATTATAAATTCAGGCCTTGCCCTCAA
TCCAGTTCAAGTCTTCAGATTAGTTTTTAAAAATTAGAAAAAGCTAAAGAAAAATAACAA
AATGAATTCAAAAGGAATTTCTTTTTTAAAAGTTGTAATGCTTATGCTTATATTTTCACT
ATCGGTTAATGTTTGTAGAACTATCACTAGTTGAAAAAAATTCGGCTTATTTATGGCCTA
TTTTGACTATTTTGTTAGGATAATTTGTTTATGAGAGACTGGTCAAGAGATATAACTGTT
AGTAGATTTGTCTTCTGATGTAGAGGTAACAACTTTGTGGAAGTATTTTACCCAGTATTT
TTCTCTGTAGGTTGTGTACTTAGATGACTCTGTTTCTTCCTTCATACAAATCCGGGGATC
TGTCCCATTGTTCTGGGAGCAGCCAGGATTGCAGGTATGTGTTTTGACATTTAGTTTTCT
TTCTTTTTCTCTTCAGAACTTTTCATATTTTTTAAACTTTCAGGTTAGCTTATTAGTTCC
TCGGATAATTTTGTTACTCAGTCTAATAATGTTACCTGGATTTATAAATAAATAGTATAC
AGAAATTGTTTACAAATCCTGGAATTGTCTTAGTTATTCTTTCCTTCAGTGTTCTTTCAA
ATATCCATAGGAGTGCAGCTCCCATATTTCATATTAAAATTTCAATGTTTTCATGGCGTG
TTGATTTTCAAAGTGTTTCTGTATTTACTATCTTCGTATATAACAATTTAGCATCTGTAG
GCAGAAAATGTAGTAGTTAAAACAAAGCTTCTGAAACTAAGCCTCTCAATTTGAATCCT
TATACTGCTAGGCTGTGTGATCTCAGGCAAGTGATTTAACCCCTTAGTGTCCATTTTCTT
ATCTGTAACATGGTAATATTAGTAGTTCCTACTTCTTAGTTTCTTACAACCCTTACCTAG
TTCTGACCGCCAGAACTAGGTAAGGGTTAGCTGAAATGGCACCCCACTCCAGTATTCTTG
TGGGGAGAATCCCAGTCCATGAGGTTGCAAAGAGTTGGACACAGCTGAATGTCTGAGCAC
GTTTGTTGTTATTAATATATCTAGGAATTTCCTGGCATGGCAGTCAGTGGTTAGGACTCC
ATACTTTCACTACTGAGGGCCCAGGCTAGATCCCTGGTAGGGGAACTAAGATTCTGCAAG
CCATGCAGTGTGGCCAAAAAAAAAGAGGAACATATCTGCTGATGAAATTTTACTTTGCA
GTTTGTAATGACTTGGGACTTGTCATCTTGAACATTGTTCTCTGTTTTGCTTTCTGATCT
TTTCCCCCCCAAACTTTCCTTTTGTTTAGTAAATGTCTAATCTTTAAAATGTAAGATGTT
TTTTTCACGTTAGTTCATAATATTGGATTGCCCATACTAGTGTGATTTTGCATTTTATTT
TTATTCAAACATGTTTAGTCCCTAAAGTATAAGTTACATTCATTTTGGGCTTCTGATATA
TACTGCCTAGTAAATTCTGTGCCTCAGTCTATACTATTGAAAAAAATATACAGGAAAAAG
AAAATTTTGCCTTCATTTACTTTCATTTAGTTCACAGCTGGGTCTCTCTTACACTCTAGG
ATGGTTATTGTGGAGAAAAATTGCACACCACTTGAATCTTTTCAATAAGGGAGTTTATTC
AAGACAGGCTAAGAATTAACAAGGATTAACACTGGTGCTGCTTTGCTAAAATTCTTGAGT
TCTTGTCAACACCAGTTTGAGTCATGTGGGTTTCATCTTTGGCATTTTGGCGTAACTTAT
ATAGATATATTTCTTCCTGTGTCTCCCTTAGGAAAGAATACCAACCCTACCCCATTTCTA
TTTTTGTGACCAGAGAAGGGTGTTTGGAATATTTGCTCTAAGAAATTTCTAAAACCCTGC
TTTGATGGGAGGTAAACGCTTTTGGTTTAGAGACAGGCTAGTGTAAGAGATTCTTCTAGT
CTATTTATAGGCCCTCTGTTTTACTGCTTTCTGTGTTATTTTCTTAAGTTCAGAATTACA
GTGTTTGATTATTCAGTAATGTTGGGTCCTGAGTAGTTACATGGAGGGATCCTCCTTGGA
```

FIG. 1K

```
TGGGACTTCCTTTCGACGTCCTTCTTTGTTCTGTGGCCTGTCCACACAGATAATCTGACT
GGATAATGTCATTTGATTATGGGCCGACAACTGTAGATTTGAAAATTGTGCCTTTCTTGA
TAGAGATAGTAATTTTTGAGACCTCAAGACAGTCCAACAGTTCTGCCAAATCATCACTGA
GCTGGCCTGTCATCTTGGGTTGGGTTGAGGGTTGGGTCAGTGGTTCTGAGGTATTTAGCT
TAGTAGTTTTTAAAGCCAACCTTTCTTTGACCAGAGATGGATTAGTTTCATGAGTATCTT
TTATCATTTTCCCCACCACTCTAAAAGAGCAGTTAATAGAGGAATGAAAATAATAGATAC
TGACTTTTTGAAATAAAAATACCAAGGCCCTAAGTTCATTTTTGACTTCAAGCGGTTGTT
GGGTGTCCTGAGTGTTCTTAGGGCTGGAATTTATTTTCAGGGCTCCTTCAAGTTAGTCAC
TTAGTGAGCTGTTTCACTTCAGTGGTCACGGACAGTGAGTCCTTCCTTGGCAGTTGTCCC
TTGTTCTCTCTCTTTTCCTCCATGATACATTCTTCTCAGGTCTTGAGCTATTTTAAAGG
AATCTTTGAGAGTGATTTAAAATGCAGATTCATGGCCTCAACTTCCCATCAACTGAAGT
AGAATTTGTTGGAGTAGGGCCAAGGAATCTGCATTTCAACCAGGTACCCCACCACTCAGA
TTAGAGAGCTTGGCGGTAGTGGATCCTGCTCAGCTGCTTTTGCAGCGCATCCAGACTGCC
TGCTCCAGCGGCCAACCCTGAGCCAAGCAAGGCAGCCCTGTGATGCTTAATCCCAGTGCT
GTCTGAGGTCTTGGACTTTTCTTTTCATTCCCACTTCTGTCATCTTGGTTAAGGTCTTCA
TAGTTTTTTCTTGCCTGAAAGATTCTCAGATTTCTAACTGGTCTCCTCCCATCTTTCTGT
TGTCTAACCAACGTATTGCTGTAAGAATTGTGAATTGTAGGTAGTTTTATATATGTGTTG
GGGAGCAAGTAATAGGGAACAACTACAGCCATTACCAAAAAACAAATATGAGAAAGCTTG
TATTTTTTTCACCTTCTTGACAGTTAAGAGTACTAGTGCAAGATGAATGTTAATGAATA
AACAAAATGCAAAGTATTGGACTTTTAGAGAGTTAGAGGGCAACTACCTGAGATGACTCC
AGAGAAAAGTATGAACTTTGTCTGACGTTTCTGCCGCCTAAAATGCACAAACGTGTCTT
GGAGCACACACCTTTCAAAGCTTAAGATTTTATACAGTCTATTGTGTACTAAAAGTAAAA
TGAAATAAAGATGTGACATTTGGCTAATCAGTTTCTTACTAAGAAGGAAAAGCTCTAAAG
AGAGTCCACTGATTTCTCAGGACAGTCATTCAGTCATCTCGGCAGGAGAGGGAATGCTGA
ATGAATGATAATACTGTTAATTCAGTTTGGGACATGGATGAGCATTTAGAGCTTATTTTC
TGGTTTTATTTGTCCAATTGCATGACTGATCTGGCACTTCTCCTCCATGCCACCTTTAAA
GTCACATTATTCACAGATGAGCCAGGATGAATTCTGGGGAACCTTGGGCCCACAGTCTCA
GGGAGGTATTTACAAGTGAAACTCAGGGAAATAATCTGGTCTCACTGTTGTATTTCTTCT
TGGCATCTTTTGTATCTCTTGATTCTGCCTCATCTCTCTCCCACTTTTCCTATATGAGAA
AAGAAAAACTGTAGCAACACACAGTAGGTAGTTATTTTCCATCTTGTTTAATTCTTATAA
CCCAAATTTCAAAATATGCTGTTGTTTTAGTTGTGTGCCTGAGAGATTGACTTGGAAAGT
CTTTTTCCAGGAATGGTTATGGGATCTTTGGGTGAGAGTGGAGTGAATAGGGTATTTAGC
ATAACAGAGAAAAAAATATGTAGCCATTGCACTTGTCGGCAGTCTGAAAGAGTAGATGT
TTTGGTCAGGAGGCCTGTACTGTCATGGGAATCATTTTTCGGAATGAATGATGTTGCTGT
AAGAGGACAGGTTTCTTCACTTGACTGGGTTTGTTCTTTTGTTGCACGAATGACAATATC
TGTTGACTTACAAAGGGCACATATTTAGAACGTAAGACAAGGTAATGTATATGAAAGCAC
TCTTAAAAATATCTTACATAAATAAAAATTCCTGTTTTTACAGTTTACCAGTTTACCAGT
GTTGCATAATGCTCTAACTTCTAGTTTTTTTTTTTTTTAATGAGGTTGTATTTTAAAGA
TAAAAAGGAGAAACCCCTAGAACTTATTTTTTAAGAGAATATCACAAATGACAATTACT
GAGCTTACTACTGTGTGCTTAGCAAATGAATTATTACATAGAGTAAACAATGCTATTTCT
TTCGTCTGCATGTTGGCTTTTGGTACGATTAAGCATATTTTTCTTATCTTAGGTGGGATC
TCATCGTGTCCGTATGTCAAGGGGATTTGAAGCCAATGCACCTGCTTTTGACAGGTAAGA
CTGATGACTTTTATATATTGCTGTGAGTTTTGATGTTGCTAAGCAGTGAGATTAGTTGTA
TTTACTGCTTCATTTCACCTTTTGGGCTCTTAAGTAAAATTTCTTCTTGACTCTGATTTA
AGTGGAAGACAGTGACACTCTTAGGAATTCTAGGAGTGATGGCAGTAAGTGGGTAGGTCT
TGATGTCTTGGCCTTAAAACTACCTCTGATGGGTGTGTTATCCAATATGGTGGCTATTAG
CTACGTGAAGCTAGCTCTTGGGCATTTGAAATTGACTAGTCCAGATTGAAATATGTTGTA
GGTATATAATAGGTCCTGGATTTCAGACCTAGTGCAAAAAAATGCAAATGCCAATATT
TGTTTTATATATCAATTACATGAACTAAAAAGCCTCTTGATGAAAGTGAAAGTGGAGAGT
GAAAAGTTGGCTTAAAGCTCAACATTCAGAAAACAAAGATCATGGCATCCAGTCTCATC
ACTTCATGGGAAATAGATGGGGAAACAGTGGAAACAGTGTCAGACTTTATTTTTTTGGGC
```

*FIG. 1L*

```
TCCAAAATCACTGCAGATGGTGACTGCAGCCATGAAATTAAAAGACGCTTACTCCTTGGA
AGGAAAGTTATGACCAACCTAGATAGCATATTGAAAGCAGAGACATTACTTTGCTAACA
AAAGTCTGTCTAGTCAAGGCTATGGTTTTTTCTCTGGTCATGTATGGATGTGAAAGTTGG
ACTGTGAAGAAGGCTGAGTGCTGAAGAATTGATGCTTTTGAACTGTGGTGTTGGAGAAGA
CTCTTGAGAGTCCCTTGGACTGCAAGGAGATCCAACCAGTCCATTCTGAAGGAGATCAGC
CCTGGGATTTCTTTGGAAGGAATGATGCTAAAGCTGAAACTCCAGTACTTTGGCCCCCTC
ATGCGAAGAGTTGACTCATTGGAAAAGACTCTGATGCTGGGAGGGATTGAGGGCAGGAGG
AGAAGGGGACGACAGAGGATGAGATGGCTGGATGGCATCACTGACTCAATGGACGTGAGT
CTGAGTGAACTCCAGGAGTTGGTGATAGACAGGGAAGCCTGGCGTGCTGTGATTCATGAG
GTCGCAAAGAGTCGGACACGACTGAGCGACTGAACTGAACATGTAGAAATGATAC
TTTAGTTGTATTGGATTAAATAAAATATATGTAAATTAATTTGACCTTTTGGTTTTTACC
TTTTTAAGTTGCCTTCTGGAAAATTTTAAATTATATCTGTGACTTACGTTATATTTCCTG
TGGATGACATTGCTCTCTAGCCTCTGGACTGATTAGAAGCTGGAGAGACTAAAGGATCCT
CTGTGGGGCCTATTTATCTTAAGGCTGGAGCTGTTCAGGAGCTCTGAATCCACACGGAGT
AGGCAGTGTCCTCACATGTGAGGTGCAGCCTAGTGCCCTCTACCCTCATTGCCTTGCCAA
CCTAGCTGCATGGCTCCTGGTTTCCATGTCCACCCAGCATTAGCCTCAGGGTGGAGAGGG
GGCCAGATGACTCTGAAAGCCCTAGCATCAGCTCAGTGCAGTTCAGTTGCTCAGTCGTGT
CCGACTCTTTGCGACTGCATGGACTGCAGCACGCCAGGCCTCCCTGTTCATCACTAACTC
CTGGAGCTTATTCAAACTCATGTCCGTTGAGTCGGTAATGCCATCAAACCATCTCATCTT
CTGTTGTCCCCTTCTGCTCCTACCTTCAATCATTCCCCACATCAGGATCTTTTCCAGTGA
GTCAGTTCTTTGCATCAGGTGGCCAAAGTACAAGGAGTTTCAGCTTCAGCATCAGTCCTT
CCAATGAATATTCAGGACTGATCTCCTTTAGGATGGACTGGTTGGATCTCCTTGCAGTCC
AAGGGACTCTCAAGAGACTAATGGAAAAACCAAAGCTTTGACTAGACGGACTTTTGTTGG
CAAAGTAATGTCTCTGCTTTTAATATACTGTCTAGGTTGGTCATAACTTTTCTTCCAAG
GAGGAAGCATCTTTTAATTTCATGGCTGCAGTCAAAGTCTGTCACTGTTTCCATTGTTTT
CCCATCTATTTGCCATGAAGTGATGGCAAATAGATGATAAGTTGATAAGTCAGAGAGAAA
ATTGCATTAACTGACTTTTCACAAATTCAGAGTTTTGATTCCACGTGAAATGGATTTGTA
TATAGTTTTGCCAATCCTATGAGTTTAAAATACTGCCATGTAGGTCCTGGTTAAAAGTGG
GTTCCTGTTTATTGAAAAAAGTTTTTGACTTATCACTTGACATACGCTTACTGCCTTTCT
ACCTTTAACAGGCATTTTAGGACACTTAAGAATTTGTATGGTAAACAAATAATAGTAAAT
CTGCTTGGATCTAAGGAAGGTGAACATATGCTAAGTAAGGCTTTCCAGGTAAGTGATCAT
TTTTTTCCTTCTGTTCTGGCCCATGGACACCTAGGATAGTATTTTAAAAATAATAGTCAA
ATTCTTCCAGGAATAAGTTCTTCCTGGAAGAAGATTGAATACTTGTTGGAACCATTAGTT
CTTTGAAGGCAGGTAGGCAACAATTTAGGGTAATCTTGCTGAAATTGGGATTATAGAACG
CTTTTAAGGCATTGACCCTGTTTTCTAATCTGCTTATTTATGTAGTGGAGAAGCAGAAGA
ATACCCTCCTCCTAAAAAATGTTCATCAGTCACTGGCAGAAAGATACCAGGCAGTTTCCC
CCTTCATCTCTTCATTGCTTTGGCTAGTTCCTACAAACCATAGTCACTGTTTTAAATCTA
TGAAATTGTGAATAAAGCATTTGTATACACACAGGACTTCTTGTACCAATGAAAGAAAAT
TTGAGAATTTCACATAAGTAAGAACCTAAAGAAATGTCTGACTTCTAAAGAAAACATACT
TTTCATAAATATTTATTGGATCAATAATGAATTGATATAAATTATAGTGTTATATAAGGT
TATAACCTTAAACAAAATGGCTAGAAAACATTTTCTCACGTTAATGAAGTCCAGGATTAA
TTATTTGGCTATTTTGTTTGAATATCATTAATAAACAAGTTATACTTTAGAGAGTGACTT
TTTATTATAAGCTTTTAAAACATTTGTATATATTGAATGAAGGTATAAAAATGAATTCTT
CAAATTTTGATGAGCTTTTCCTTAGAAGTCAATTACTTTGTTTTGAGATTCTATAATAGA
TATAGTCATTATATTTTATGGTAAAAAATGAAATGCTGGTTGTTGGAAATAACTTTTCA
TTTTCTAAACCAAATGAAAATGTGAAGTTCCCTGATATTAATTATGTAAGACCTAACTAA
TCTATCTGGAATAGTATAGGAGGTTTTAGGAAAGGATGCTGTAAGATATTAGCAAGTAA
TTTTTCATTTTACTGCCAATGGCAATGAAAGAAAGCTTTGTGAAATTAGTAAGATTTCAA
GAACCTGCTTAGATTTTCATTTAAAATAAAAGTTCCATTTATAACATTGTGTTGATACAA
TCATATTTGGTTAACATTTAAATGAATATTTCCATGGTGGCTCAAACGGTAAAGAGTTCA
CCTGCAGTGCAGGAGACCTGGTTCAATCCCTGGATCGGAAAGTTCCCCTGGAGAAGGGAA
```

*FIG. 1M*

```
TGGCTACCCACTTCAGTATTCTTTTCTGGAGAATTCCATAGACGGGAGCCTGGCGGGCTA
CAGTCTATGGGGCCGCAAAGAGTCAGACACAACTGAGTGACTAACACTTTCACTTTCCTT
GGCAGTCCAGTGAGTGGTTAAGAATCTGCAGTTTCACTGCAAGGGGCGTGGGTTTGATCC
CTGATTGAGGATAGGGGAGATAGGGGATCCTGCCTGCCGGATCTGTGATTTGCAGCCAAA
AAAAAAAAACCGAAGAAGAATTAAATGAATATTTTATTTTTATTTTCAGAGTCATCTGAA
AGCTTCTGAACATGCTGCTGATATCCAGATGGTGAATTTTGACTATCATCAAATGGTTAA
AGGAGGAAAGGCAGAAAAATTACATAGTGTTCTTAAACCTCAAGTCCAGAAGTTTCTGGA
TTATGGAATTTTTCATTTTGATGGAAGTGAAGTTCAAAGGTTTGACTTCTCTGTTTTTCC
TTTTTTTAAATTGGAACTTTTCTGTAGTTATTTAATTTCTTTATTATACTTGATTTTAA
GCTTGTTGTTCTTCTTTCTAATAGTAGCTTACATTACTGGGCACGTGCTATGTGTGGGTC
AGGTAGTGCACTTAGTCTTTACAATTATTAATAACAACTGTAGGGATGGGTCACACTGGA
GGAAGTGGGGGGCTGAAAGCTGTCATCTTCCCACGTCACGTAAGTAGAAAGTGTTAGAG
CTCGAATTCATCTAGCTCCAAATCTCATGCTGCTCTTTCGGAGGCTGTTCCATTTCTCTC
GTAAAATTAATGTCATAATATTTCTTGGCCTCAGTAAAGATTATTTAATGCAAATAAAAG
ACATGGGTTATTGTCTGTTCTGCTATAGAACTGCGTGGTTATAAATCTGAATGTGTGTTT
AGCTCCTGACTACTGGCCTCATTAAAAATAAGTGGATGTGGTTGACTGGAGAGCTAGTAA
TAGAGAGTGGACGGCAAAATGTTAACGCTTATAGAATCTGGATGGTGGGTATATGGATGA
TCACTGTAAAATTCTTTCATCTTTTTTGTGTGTTTGAGAATTATACTAGAGAATTGAAGT
GGGGAGAAAGTAGATGCTACATTTTAATCAGCTTAATTTTTCTCAGTTTGTTTTAGCTTT
TGTTATTTTGGTTTTAAATTGCCCATTTAGTTTCACTGAATTTGTTTCAGGTGCCAGAGT
GGTACAGTTCGAACAAACTGCTTGGATTGTCTTGACAGAACAAATAGTGTGCAGGCATTC
CTTGGTTTAGAGGTAAAAAAATATGTGTATGTAACTTAACGTCAAATTCCTTTTTCAGTG
CTTTTGTGATATTTATGTTTGGCATTAATTATTTTTCACAAAATGAAGTTAAGCTTCATT
TTCACAAATAAAGTTTGACTTCTCTTCTAGTTTTTTTTTTCAAGTAGTGTCCCTTTTCA
TTTAAATGTTTCCTTTATCTGTTCTAAATACTTTCTTTAGATAGCTTCTGTTTCCTTTTA
TTGTTCATTAACTTTGCCTCCAAAAAAAAAAGCCTGCTGTTTATACTGTTTTAGTAATT
GTCTCGCCTGCCTGTCTTTTGGATAGGCAAAATATATAATATATATATATATATATAT
ATTATTCTCAGTATTGTAATTTTAAAAAATAATTTTATTTATCTATTTTTGGCTGTGCT
GTGTTTTCATTGCTGCGTGGGCTCTTTTCTAGTTGTGGCAAGCAGGGGCCACTCTGCTG
TTGCGGTGCTGGGCTTCTCATTGCAGTGGCCTCTTGTTGCGGAACATGGGTTCCAGCGTG
CTCGGGCATCAGCAGTCGCAGCTCCCGGGCTCTAGAGCACAGGCTCAATAGTTGTGGCCC
ACCAGCTTAGTTGCTCCGCAGCATGTGGGCTCCTCCCAGACCAGGGGTTGAACCCGTGCT
TCCTGCGTTGGCAGGTGGATTCTCTAGCACTGAGCCACCAGGGAAACCCTTGATACTGTC
TTTTTAAGACCTTTTGGAATTAAGGAGGATCTATTTTCACATGTACAACCCTATAGAATT
ATATTTTAACAATCTAAACCAGTACAGTTTACATAGCATTTTTTAAAAATTGCTACAA
AAACCAGGATCAGTTGAAAAATGTCATTGTTAGAATAAAACTGAATGAGAGCCAACTTCT
CTAACACACTCTTTGTTTAAATTTTGTCTTTAGTACTTACCTATCAAACTCAGTCTAAT
TTAGGCATAATCTCAACTATGTGACAGACTGTGTAGCAATACTTAGATTTCCCAATCTTG
CCCCTTATGCAGCTGTCAGGGTCATAAGACTATGGTGGGTCTTCATTAGTTCTGTAGGA
ACTTAGCATAGTTCTCCAATACTGTAAAACCAGGAATAGAAAGTAAAAGGTTCTTATTTC
CTCTAGCAAATGATCTTAAATTTGGCTAGAATATTGGTTAATTAGTTACTCTGCAGCTGA
GATTCATTCAGTCTCAAAAGGAAAGTACCATGTATAGAATTTCCTACTAGAAAATGTAT
TTTTGATGTAACTAGATTTTACTGCTTTGCCTTTTTGAAATCTGTTGTTGAGGATTATC
ATTATAATTTAGAAAATATGACAGAAGAAAGTGAAAGCAGGCATTTGATTACTGTGGAT
TGAGTTTTATGAGATATCTTGGGTTTATGTTGAGTTCTCTTAAGTGGCTAAAGACATTTA
GTTAGAGTAAGCTTGTGAAACACTTGAACATCTTCACTGAACATAGAACAAGTGTTAGTT
TTCAGAATCTGTCTTAGTGGACTACCCACTGTTTGTTATTAATATTAGGTGTGAGAGTAC
TTACTCCCCTAGTAGCTTGACTGGTTACAAAATATACTGCAAGTGTAAGTAAAAGCAAAC
TGCTTGTAGTGAAAACCAGTTTTGCCCAGTTCTTTGAAGAAAGAGGAGATGATAAAGGAG
AACCTGGAGGCTTGTTTGCTTTATTCTACATGCCAGCAAAGAACAGCCCTGGTGTAAGT
CTAGGCAATAGGATTAGACCCAGTATAGAGTTTTTAATATTATTTTAGTTTTTGATCCCT
```

*FIG. 1N*

```
GTGTAATTATGGATAATCTCCATAATATCTTTATCTTATAGATAAGATAAAAGGAAACAC
AAGTGGGAAGGAGTTAAGTAAAACTACAGGGGCATAGACTATGACTGGATTCCAAATAAG
AGAAATAGACTGGGTAAGGATTATACATTGCTTTGACTTTGCCAGACTTTAAGGCTAAGA
GTCATTCAGAGTAAAGACTTCTAAACACATATACTGTGATGAAGGAACTGTGGTAGCCCC
AAGATCCTCTCATTCTTCGAATACTGTGTTCCCCCTAGTTCTCCCTTATGTACTTTACTG
ATACGAATTCAGTACATTCAGAGCTGTCATGACTTTATTCAGAAATATGACTTATTTAAA
AATTTTGATATCAATTCAAGAGCAGCTCTGCTTTTTCATAATCTCCTGACCTTAATTAC
CCAAACATATAGAACCAAATGCAAAAATTAAAGAAAGTTATTTCTATACATTTTTAAATA
AAGTATGTATATTCCTCTGCTCCAGTGGGTGCTGTTGCATAATTATTCTTTTAGGTGAAC
AAGATAAACTAGTCTGATTTATAGGAACTTTTTTTTTTTTTTTTCTTATTTTGGCCC
CACAGCTTGTGGGATCTTAGATCCCCAACCAGGAATTAAACTCAGGCCTTCGGCAGTGAA
AGCAGGGAGTCCTAACCACTGGACTGCCAGGGAATTCCCTAAAGGTTTGGGACATTTTAA
AAAGCTTAATATCATTTAACCAGAAAAAGTTCTTGTTACTACAAGGATTGAATACTGTAG
GTGGCATTGATGTGATAGTTACTTTAGAAATTGGCATGGGGGGGAATAACAAAGCCTAGT
AAACTTGAATTTTCAGAATCCAGACCCACAACATCCTGTAACGATAAATTTTTGGTTTGA
TTCTGGTAGTTCTTAAAAGGTCACATCTTAATGGATGTATTTATATACTTATAAAAGTTT
CTTTTCTGCTATTTTAGATGCTGACTAAACAGTTGGAAGCTCTTGGTTTAGCTGAAAAGC
CTCAGTTGGTGACTCGCTTTCAAGAAGTTTTTCGATCAATGTGGTCTGTGAATGGTGATT
CAATCAGTAAGATTTATGCAGGAACTGGAGCCCTTGAAGGAAAGGCTAAGGTAGATCTAG
ATTATAAAGATCCTCTTTTTTCTTCTTTAATAAAGCTTTAAATGAACTCTTTTAAGTT
AGTAGTTTTTTTAAGGTATCTATTTTAGAATTCTGTTTCATCATGTTTTTATGTCCTGT
TTATTACCTCCTTCTCTAGTGGATACTAATGACTGAATGGATAGTTATTTCCCTAGGTTT
GAGAGGTATATTATATATGTATGACATATTTAGTTGTTTAGTGATAATCTACTAGGCTTA
CATACGTATTACTTACGATTTTTTAATGATTTTTCACTTGCATATGTGTTTTAATTTTT
ATACTGTTTATTTTAATCAGAAATATGTTTTTTTTTAAGCCTTTGCTTTGCCTTTTTTAT
TTATTTTTTTGGTCACACAAGGCAGCATGTGGACCTTAGTTCCTTGGATCAGGGATCAA
ACCCAGGCCCCTGCAGTGAAAGTGCAGAGTCTTAACCACCAGACTGCTATGGAATTACCC
AAAATATGTTTGTGTTTTTTAAATTAGGGCCGTCTTTGGTGGCCCAGTGGTTAAGATTC
CACGCTTCTAGTGCAGGGGGCGTGGATTCGATCCTTAGTTGGGGAACTAAGATCCCACAG
GCTGCGCAGCACAACCATAATTAAAACAAAAGTTCCCGCCTCCCCAAATGTTACTCTTGC
CAAGAAAGGGTCTTACCTTACTTGCCTTTGTGTCCCAGTGCTTGCCGCAGCACATACAG
TTGGATAGATGGGTGACAAGCGCCGGATGGACAGATAAATCAGTGGGTACTTTATGCAAC
ACCACCTATGAACCCAGTGCTATCAGGGCTGAAGTTTTTATTCTTTTTCTTATCTTACCT
TGACAAGGAGGCTATCAAAATGTGCCTTTGCAAGTGTGAGGTGTGGACGTAATTATGTAT
CTGTATGTCATCATTACTTTAATTTGTTGGTATTATCTACAGACTGCTTCTGCTTTAGTG
TTTGTCCCTTACTGAGGGACTTTGGGTACATACTTGAAATATTTTCATTATATCCTTAA
ATATTGACCTTTTATGGCTTCTGGATTCAGCTGAATTTATTAATGTACTACAACCCTACA
ATTTCTCAAATTACCCCAGGAATAGAAACAGAGACATTTACTACTTGTATAGTTTCTTAC
TTAGTCTCTTCAGTATAGCAGCTGAATTTCATCATCTCAAGTCTTCTGTTTTCCACTTCT
TCCTCTTCTGTGTCTCATAAAACGCCATGCCTCTGTTCAGAAGTATTGGCCTTAGCTGCA
AAGTTCCTTTTGTTCAACTCAGAAATAATTTGTATTGACATTTACAAATATTTACTTCTT
AAATGGTCCCTGTTTTGAAAAACCTGATGTTGTTAAACTTTCATGTATTCTTTTTTAAAT
AAACAACATAATTCTTGCTTTTAAACCTGATTCTCTACAACTATTGCTTAAAATATTCTT
TTATGTTCTGCCTCTTTGTTTCTGCAATTGACTGTCTATGTACAGAGGTTACATATATTT
TCAGTGATCTTTTCTAACAAACTAGATATGAAATTTATGTATTAAATATACTAGTCTGA
ATTGACCTGAAATCTAACATCTGAACTGCTCTTTCTTTTCCTTTCTCTGGGTTCCTTTTG
ATTAATTGCCTGATAATGTGAATGGTGAGTCCCCTTTTTAAAATAATGTTATTTACATTT
GTTTTATGGAAGGAAATAACATTTTTAAGCCTCAAATCCTTGTTATTTCTTTGAGGAATA
AAAATTACATATTGCAAACTAAAGTTTTTTTTAACTTTTTTTAAACAGTCATCAAAAT
CTGTAAGATTAAAATATCTTTATGGTAACTAACACACCTGAGTGAAGTAAACGTTCACTA
GAAGTTATAATCAGCTCTCTCACTGTAGGAATTGGCATGCAGTTTATATTTTTATATTTA
```

*FIG. 10*

```
CATAGGCAAAATGAGCTAAAATAGAAAACTGTAGTTTCTATGTTACAGGCTAGACCTTCA
CTCTCATGCTCAGTTTTGTTTCTAACTAATATCAGTTACTTGGGAGCAATCTCAGTTTTA
TTCTCTGCTGTTCGTGTGCTTTGGAGTTTTTCTGAGAGTGCGGACGTGCAGTGTGTCCTC
CTCTATCTCCTCTGCTTCTCCCCACCCGCCCCGTCCACCCCAGGCCTGACAGTCACAATG
GGAGAAGTGATCTCCTTGCCTTGAGTAAGCACATTTCAGTCTGTTTCCTCTCCAGTAAAC
AGTTACACAGGTTTACTGCTCTGGATGTCATCAGTGGATGCAGCTGTGGCACTGAGCCCC
TTCTGTCTCCCTGCAGTGCTGTGATCCAAAAGAGGAAAGGAAACAGTGACACCTTAATGT
GACATTTTAATGTGACAGTTTGATATTCAGAATGGAATGATGAGGTCCTTTTACTACAGT
GAAGTCGTATACAACTTATCTAAAGTTTCAGAATACCTATTGAGTGAAAACAATGTAGAA
TGAAAGTCCATGCTTTTTTCCCCAACAGGCTGGAAAGTTAAAAGATGGTGCTCGTTCAGT
TAGTAGAACAATTCAGAATAACTTCTTTGACAGCTCCAAGCAAGAAGCAATTGATGTTTT
GCTCCTGGGAAATACTCTAAATAGTGATTTAGCTGACAAAGCTCGAGCCCTTTTAACTAC
TGGAAGTTTGCGTGGTAGGCGTACTTTATATTTTACTTTATGTTGTCTGTATTCCTTCTA
AAAGTCCAAGAGGTGAATGTAAACTTATTTACATATATACTTTCTAGTTTGAATTGATTA
AATAGTTTTTTGAAAGAATTTCTATCATTGTAATTTTCTAAAATTCCATTCTCCAAAGG
AAGTTTGATTCTCCTAAAATATTTATAGCATTAGCAGAATTATTAAGCTGTAAACTGAAG
CCCATGCATGTTTTCTTTTATAGATTATGATTGAGGGGCAAATGATTTAAATATTGCTA
ACTTTATTTAAGGCAAGATTTCATAAAATATTCAACTAGTACTTTCAGTATTCAGTAACC
TAGTTATGTAGAAAGCATTGCTTTATTGAAAAAAAACAATACCTGTTCTGGTTATTTTAC
TAATCACAACCCCAGACGTTTCTATAACTTGGTCTTACTTTTTAAGTGCTGCTGTTTGAA
TAAGCTTTAAATCATATTAATAATTTTAAAATGTTGCTTATTATTGGACACTGTCATCCC
CAATTTTAATATTTGACATAAAATATATGCCAGGCTTTCAGAATAGCTGTTGATTTTTCA
CTGTGTTTCTTTAAAACCAAAAGAATTTGAGCTCATGTCAGTGAGCATATTAAGCAGGAT
CATGGGAAAACTCAGTATACATTGTATAACTTATTAAATTAGACTCCCTTAATTTTTTT
TTTTTTCTATTTTAGCTTTCCAGCACTCTGAACATTTTTTTTACTTCTGTTATCCCCCA
AAAGAACCCTTTCAGTTTTCCCTGTTCAACTAGGAGAAATTGTTCCTCAAATAACCTCCT
CATGGGTTATCACTTGTTATCATGGATTCTTTCAGAATTCTGCGTGGTGCTGAAGGTAGT
TAATTACATGTCAGCTCCTCAGGGATCTGTGAGTAGACTGGGGGACTGAAATCTACTAAA
GCTCTGAACACCAGAATCTGATCATAGCTACTGCTTTTAACTTCAGGCTTTCTTCCAGCA
GTAGACACTGACTCATTTGCGTCTTATCACCTCTTTCCACCCGTGCCTTCTTTGATATGG
AGGCATTAATCAGCAACCACTGAAAGTAAGCTATTAAAGGAAAGAGAAGTGAGGGACCTG
AATAATTCCCAGACTTGATCATTAGTTTTTTAGTTTCCTGCACATTTTACTATGTGAAGA
ACGTACCCTTAAAAAAACAGTACAGTCAATTCTGCTATAGCTCTTATTTTAAGAATGAGA
ATTTATTCCAACGGGGATGCTATGTCAGGAAAAATTGTGAGTATAACGCCAATTCTGTAG
TAGTTCATGCATATTTCACTGGTGGTAGTAGTGCTAGAGAAATGCAGAAAGCTGTACTCA
GCGGAACTGAGGTGGATAGAAATATACAAAACACACATATACATGTGCATGGACCTCTCC
CTCCCTCTGTTCACCAACTGTGTGATGAGCCAGATCCTCCCATATCTGGTGTCACAGCTT
ACTATCTAGTTTCGGAGAAGCCTTCTTCCAGCATTCACAATTGCTCACAAGCACAGGCAT
CTTCCTGCTCATTTATAAGCAAACCTCAAGTCTTTTTCAAGATAAAGTACCATATGTTAG
ACGTATTTGTCCATTCCTTAACCGTTTAACATGTGTAGGGTTCTGCTACTGTTTTTATAG
CAGGTTCCTATCTTGGCACATCATTGCTGAAGTGTTTGAATGTTGTGCCCAAACCCAAAT
ATTTTTGCCATAAACCCCATGCCTGTGGGAATTTATACCATCTTGCATAGCTGGTCATTG
TGTTGGAATGTATGTGTTTTTTAATAACTGAACTGATTGTACCTGTCAGCTGGTGAGTC
CCAAAAAATACTCCAAGGTGTGCATTAGGGCAGTATCTGCAATATTTCAGTGTCCTCCAG
CCTCTTAGGTTTTCAGGTTCGTATTCTCAGAAGTATGTGCACTTGCACACTCAACAGACA
TACATATGGGACCGGCCTGGAAAGCAGGCCTAGAACCTTCTGATTGTGAAACTCTGCACA
TCACTATGTCCCCGTAGGATTTTTCTTAGATACAGTGGGTTTACATCAGTTATTGTCATT
TATTTTATCTTTGGTATCCTTCAGCCATCAGAAAAATGTCATCAAACTAAATCAAAAGA
AAAAAATGAAGCTGTCTGAGAAGGTTTTGTCATAACACTCGACTTCAACTGTAACTTACT
GTGTTACTAATGACTCTTTGTTTTCTTCTTGATGCATCCGTAGTTTCTGAACAGACGTTA
CAGTCAGGTACAGTATAGAAAATCAACCTGTCAATAAATGCAACTTTTTCTCAAATTTTT
```

FIG. 1P

```
TTTAAAAAGCGGATGTTGTATATAAATAGAGCCACAAATAAATGGAAACTTTATTTTTCC
CTCTGATTCTGACAGGATAAATTGATGCTTTGTTTTAATCTAAGAAAAAGAATTTTAAGT
TTGAGAAAACAGACTACTTCATTTAGAAGGAGCTATGCCAAGCTCTTTGTCTTCTTGTAG
CAAGTGCTTAATTTCAATTAAATATGGGTCATCTAGTTTTAATTTTACTTTTACATTTCA
GTGAACAAACATTATTAGTGTTATATTTTACCCTTTATTGTTGTTTAGTCACTAAGTCAT
GTCTGACTCCTTTGCGACCCCATGGACCATAGCCCACCACGTTCTTCTGTCCATGGAATT
TCTCAGGCAAGAATATTGGAGTGTGTTGCCATGTCCTCCTCCAGGGGATTTCCCAGCTCG
GGGGTTGAACCTGCATATCCTGCGTTGTCAGGAGGATTCTTTACCACTGAGCCAACAGGG
AAGTCCTGAAAAAAACCTAGATGTGACTCTTACAGATTAATGGGAAATACTACCTATGAT
GTTTACAACTACTCAATAGCACTTGTCACACACATAACATTTTAAAAAAGACATTGACTC
ATTTTCTCATATGGTGTGTGAAATATTTTCTGAAACTGGAAGACCTGCACTAAAATATGA
TCTGAAATCTTTTAAAAAGCATTAAGATTGCTAGCAAAGTTAGAAGAGCCAAGTGTGTAA
GACCTAAAGGTCTTATTTTTCTTGTCATTCCAGTTCTTAAAAATCTCATACCTTCATTCT
CTGGACAAGGTTTATGATCTTGTCTTTAAACTTGAGTCTGTGGCAAAAGGAACTCTTGCC
AGAAACTTTGCTGAAAAGACATCTTTTCTTCCCTTCACTTAAGATTTGGTATCACTTAAG
ATTTTTGTTTCACTTAGTTATTTTTCTGAGTGTTTTAAGACACTGTAGGTAAGTTTTTGA
GAAGATGGAGGAAGAGAGCACTTGTATTTATTTTTGAATTAACATCATGAAATCCGTTTT
CTGAAATGATATGATATTTAGGAATGGACATCTGTTTGAACAGAGACACATTTCTTTCTG
CACATTAAGGTGCCAACCAGTTTTTTTAAAAAAGAATAAACTAGGAATTTTAAAACTTTT
TATTCCCATTTATAAACTGACTTTAGTAGCTTACTCAATGTGGTACATGGTTTTCTTCAC
ACAATTCATTGTATGTCTTGCTGCATATTTTAAGCCATTAAATAATTATAGAGCTTGTGT
TTTCATGTAGAAAGGATTGTAGAAGCTGTTTTCATAGTAGTAACACTGTCAGTGACTTCG
ATTAGAAAGACCAGTGTTGATCAGTAGTAATAGAGAAGGATTCTTTATCCAAGTTCAGCC
AACATTCAGTTAACCATATCAACAGGCCAGAAAAACAATCTGCTTTCATTCCCCCCAGAC
TCGGTGCAAGTAATCAGATAACAGACTCAGAGATGTATACATGTGCCCTAGGAACAGTGA
GGATGTGCTTGTCACCTGAACCTGCAGTTCTTTTGTAGGATTCACAAGTCAGACTGTTTT
CATTCTAATCCAAAAATGTTATCAGCCTTTTTCACTCATTCTTTCACAAGCTTGCTTGCT
GTACCTTGGTATCCATTCCAAAAATAATAATTAATATCATAATAAAATAAGATCACCTGG
TGAGAGGTGAAGATCATTTTGATTTCCGTCTCCTCTTGGCAGTTAACCACCCTTTTAAGG
GCATATTCTTTATCATTATTAATGGATTGAAGTCCTAGGAAGTTTCTATTCACTTTAAGT
GCCAGGATTTGACTTAATCTAAGTGAAATGTGGTTTAGAAGGCAGAAAGTTAGGTGGAAG
CCAAAAAGTAGGTGGAGAAGAGAGATTGAGGATTCAAAATGTATTTCATGTTTATTCATT
TAACCATTGTTTACTGAACGCTCAGTATGTACCGGGAGAAGGCAGTGGCACCCCACTCCA
GTACTCTTGCCTGGAAAATCCCATGGACAGAGGAGCCTGGTAGGCTGCAGTCCGTGGGGT
TGCTAAGAGTCGGACACAACTGAGCGACTTCCCTTTCACTTTTCACTTTCATGCATTGGA
GGAGGAAATGGCAACCCACTCCAGTGTTCTTGCCTGGAGAATCCCAGGGACGGTGGGGCC
TGGTGGGCTGCCGTCTATGGGGTCACAGAGTCGGACATGACTGAAGTGACTTAGCAGCAA
GCAGCAGCAGTATGTACCAGGTGCTCTTCTAGTCTGGAGATATTGGAGCAAATAAAATAG
ACCAAAACTTCTATATAGCACAGGGAACTTGACTTAATGATCTGTGGTGGCTCAAATGGG
AAGGAAATCCAAAAAGAGGGGATGTATGTATACATGTAGCCGATTCCCTTTGCTGTAGA
GCAGAAACGGACACAACATTATATAGCGACTATCGGGGCTTCCTGTGTGGTGCAGCAGTA
AAGAATTCACCTGCCATTGCAGGGGGCACAAGAGACACGGGTTCGATCCCTAGGTGAGAA
GATCCCCTGGAGGAGTAAGTGGCAATGCGCTCCAGTATTCTGCCTGGAAAATTCCATGGG
CAGAGGATCCTGGTGGGCTATGGTTGAAAAGAGTCAGACGTGACTGAGCACATACACTCA
CACATCCCAATAAATAAATAAAATGAAAGGATATTCATTCTGTATGTGTTAGTCACTCAG
TCATGTTCTACTTTGTGCCCCATGGACTGTAGCCCTCCAGGCTCCTCTGTCTGTGGAATT
CTCCAGGCAAGAATACTAGAGTGAGTTGCCATTTCCTACTCCAGGGGATTTTCATGACCT
AGGGATTGTACCCGGGTCTCCTACATCGCAGGCAGATTCTTTACTGTCTGAGCCACAGAA
CTATCATATTATCAAGCATATCTACTTCTGGATATATATTTGCATACTGAAGTGGGTAGC
CATTCCCTTTTCCAGGGGATCTTCTTGATCCAGGGATCAAACCCAGGTCTCCTGCATTGC
AAGCAGATTCTTTTACCATCTGAGCTACCAGGGAAGCTCCATTCATTCTGGTTCCCCTGC
```

*FIG. 1Q*

```
ACAAAAAATGAAAATGAGATCAACCAACATTTCTGCCCTTGTGGAACTTCCATTTTCGGT
GAGGGGTGACAGTTAACAGGATAAATAAATAAAATGCATAGTTTGTACATGGTAATAAAT
AAACACCATAGAGAAAAGTAAAGCAGGGAGGTGATATGGACAGTAAGAGACAGAATGCAC
ATTTTAATAAGCTGATCAGGAAAAGCCTCACGGCAGAGTTGATGCCTGCAAGCGGTGAGG
GAATAGTGTTGCGAGCAGTGGAAGCAGCCAGTGCAGAGGGGTCCAGGGCCAGAGCGGTG
AGCGAACAAGGTGGGATGGCAGCTGAGGGTAGAGAGGCAGGGCAGGTTGTCTGGGGTCTT
GTAGAACATTGGTGAAGACGGTGTCGCCTGTGATCGGGAGGCTTTTAGTAATGGCTTCA
TTCTCCAGCATCTCATTATTGTCCATGATTTGCGTTTGTGTCAGGGAGCTGTTTTTCATC
AAGCTACCTGTGAGTAGTTAGAGTCCTATATGTCATGGTTCTTGAACATCTTTCTTTGGG
GAAAAATAACTTATTTTTACTAGCTTCCGAATGAAAGTTGTCTGTAAGTCAGTTGCTATA
TTCCTTAAAATTTGCAGTCTCTGATTTTGTGTATCATAAAATGATGTACTACTTCACTGA
AACAGAACTGTTTTGCATGTTTTATGTTGCTGAATTAATTTTGTAATAGTTTTTTTTACT
TGGGCTGTTGTACTTCACGTAGTTGATATTTTCAAAGTGTGTTGGTTACTTGCATTGTGT
TGGGCTCTGTGTTCAAGGCTTATCTCTTTTGTGCCTGTGCATGTATTTGATGCTTGTTTG
TGCCAATGATGGTAATTGTACTTTCTAGCCATCATCTCTCAGTTATGAAGATCAATTTTT
GTAAATGTTTTCACGCACCCAAAATTTTGTTGTATTTTGTTTTTACCAGCATCTTCTAAA
GTACTAAAGAGTATGTGTGAGAATTTCTACAAGTATTCAAAGCCCAAGAAAATTCGAGTA
TGTGTGGGCACATGGAACGTGAATGGCGGGAAGCAGTTTCGCAGCATAGCTTTTAAGAAT
CAGACCCTTACGGACTGGCTTCTTGATGCCCCAAGTTAGCTGGCATCCAGGAGTTTCAA
GGTTGGCTTCTTACAATATGGATTAATTAACCCTGACTCTGATGTATTAACCTAGAAAAC
AAATGCGGCGCTTCACAATATGCAGTACTTTATAAAAGAAACTTCTATATATACATTTGA
AGCCCAGCATTCTTCTTAGAGATCAAATCTCTTCAAATCTTAGGTCTTCTGTATTCATAG
ACCTTTCTCTACTACTTCATAGGAACCTATGGTAAAGTGAGAAATCTTTTGTTATTTGA
TTCTCAGACAATGTAATCCATACATGAGTAGATAACTCTTTTGTGTGTGGGTTTGTGTAT
TTATTTTTTTAAGATGTGATTTTTTTTCTCCTGTTTTTATTCTTTAAACTGATGCATAGC
AAATTTATTTTGTGATTAAGAATTTTTCAAACCTAATGTATTTTGTTTTTCAAATAGAGC
CCTTTATTTGCTAAGATAAGAAATAGGGTAGGTCATGAGTAGGTTTACAAAACTCATTTT
GACATTTATTGTCCCTGTAACAGAACAATACTGATTCATCCTTGTAAAAACTCATCACTG
AGTTTGGGTACTCTACCACCAAGCTCTTAATAGCCAGTACTTAAGCTGAGGATGCTTGTA
TTAAGATTTTTAACTAGAATCATGGATTTGAGGACTGTTTGCTTCAACTTGAATTCCTTT
TTAAAATGGTACACATTTACCAAGTGTTATTTATGAAGGAGATATGTATAGGAAATACTG
TGAGATACAGATTTTTCTTTTTAGTTGCCTTTAATCAGTCACACCTTAAACCCTGGGAA
TTTCCCTAAACTTTTACTAAAATGCTGCTTTTCATTTTACATTGAACCTAACTTGAAATT
GTAGCTGTAGTATTAATAGTAATAACAATAATAAAGTAACAGCTAACACTACTATTATGA
GTACTTGACATCTATTCATTTAATCATTATAACAGACCTAATACATAGCCACTCTTAGTA
TTTCAGTTTTTAGATGAGGAAACTGAGACACAGGAAGAGAAGTGACACGCCCAACGTCAT
GCAGCTGGCAGTGACAGAGCCAGGATTTAGGGATGGACATCTGGCAGTTTGATTCTGGAG
TTGTGCCGCACTGCACTTTGTGTGTGAACTTGGGCAAGTTGCTTAGATTTTCCAGAGCCT
CAGTTTCCTGTCTGTAAATAACAGGCAGATGTAATCTGTCTCGTAAGGTGTCTGTAGTAA
AAGAGAAGATTCACAGGTAAGCCTTGCACACAATAGCAGTCAGTGAATACTTTACATTTT
TTATTCCTCAGTATTTGTTCATAGTATTTATATAAGCTCTTTCTCTTAGCTATTTGTCCC
GTTTCTGAATGCTTGGGCCACCCAGGCTACCCTGGGCTTGCTTATCTAAAGCAGTTCTGT
TCTCTTTTGGTAAGCCATGGGAGAGCTAATGGCTAGAAGAGAGGGGTCTGAAGCCCTGAC
TTCCCATTTTCCTGGATTGCTTCCACCTAGGAATTTCCAAATTAAAGTGTAAAATTCCCT
CTCAGCTGTTTGCTCTAATTTGAGTTGGTTACTCGCCCACCTTATTGTTTGTGCTCTTTC
TGAAAAATTTCTTGGTGGCTAAAAAAGGAGGGGATTTATGTATACTTAGGGTTGATTCAT
GTTGTTGTACAGCAGAAACCAATACAACATTGTAAAGCAATTATCCTCCAATTAAAAATA
AATAATTTAAAAAAATTTTAAGTAATTACTTATCCATTTGGATTCATCTTTTAGCCTCTG
AGAAGCGGCTTGTTTCTGCTGTCCATGGTTCAAACCATAACAACAGTTCTTTCAAAAA
TGATTTCTGAAAGGACTTATCTTCAAGAATAATAGTCTTCAAGAAAAGCAAACTTAGGTC
ACCTAAATAGAAATTGAAAGTAATTTTGTCCCCCTCATGGTTTTTTGCCTTTAATTTGCT
```

FIG. 1R

```
TTTGGTTAAACTTGGAACACAAAAATGGACTTGTATGAGATCTGATGTTCGTCTTAGTTC
TGTTGGGGTAGGGAAGTTGCCGTTTAACTAAGGCCATCTTTTAAAAGGCTTTCTTGGATG
CTTAATTTTAGATAAAAGAAGTAAACCAATGGATATATTTGCAATTGGTTTTGAGGAAAT
GGTAGAGCTGAATGCTGGAAACATTGTGAATGCAAGGTAAGCCAGCCAGGTAACACACAG
GGAAACTTTCTAGTTGATGAACATGGGGGACAGGTAACTAAGTACTTACTACAAGCATAG
ATAGAGATAATATATGTGAAGGTGCTTTTTAAACTGTAATTCAATAATAGTTCTCAAAC
TTTTTGGTTTCAGGTCTTTCTACACTCTTAAAAATGTTGAAGATCTTAAAGAACTTTTAT
TTATGTGGTTTATCTCTTGATACGTATCACATTAGAAATTAGAGACAAAAATTTTTAAG
CATTCAGTTCATTTAAAAATAATAACTCATTACATGTTAACATAAGTAACACATTTTTTT
TCTGAAAAGTAACTATTTTCCAAAACAAAAATTTACTAAGAAGGATGGCATCAATTGATA
GCTTGCAAATCTGTTTAGTCTGGTTTAAGATGGCTGGGTTCTCACATCTACCTCTGCATT
AGTCTGTGTAGTGTGTTGTTTTGATTGAAATATATGAAGAAAATCACATAAATACGTAGT
TGGAAACCAAAATATTTTAGTAGCCTTTTTAGATTTTTTCTTCTCTGATAATACTCAGCA
AATAGTCATTTTTGGTGGTTAGTTACAGTGTGGAATCTGAAACCATAGTGATGAACTTTT
TGTGCTCAATTATACCAAAACATCGGTCTGTCTTTTACCCGTGCGTGATTTTGACACGTC
ATTCATTAGGCATTTGGAACATAGTAGTAGTAAACTAATTATGTAGATCTTTCAGAATTA
TGTAGATCTTTCAGATTTTGATACATGTCATTGTATAATATCAAAACATAATATTGGTTA
ATTTCATCACCAAATTAATTTAATCTCTTCAGCAAATTCTTCAACTATTGGGAAGCTGTC
AAGATCATAGTAGCAAATACAGGTTTATCAAAATTCCCCCTTTTCTTTCAAAATGTAAAT
TTTATTATTAGAAATATACACCATAGGTCATGTCCTTTGAAAACACAGGCATGGTTGAAA
ACATGTTTGCCGGATAGTCTAAATTTGAATAATCATAGTGTGTCTGTCACTAGTTCTTCC
AAGTAAAAATTGTATTCTATAAAAAAAGTGGCATTTCAGCTCTGACCTCAGACTTGAGTG
CTTTTTTCTGAAACAGCCATCATGTATGTGTTCAGTGTGCAGCAAAAGTGGTTGGTTTGT
ATTTTTCCATTCATTACACAGAATATAAAAAGATGGGCTTCTAGGATTGAGCTTTGACAA
AATTAGTAATGTTTACTGCTTCATCAGGATGTTCTTAGGTGAAATGGCTATTTTTGCTTG
GTGTTGGAGGTTCTTGGGATTTCCCTGTTGGCTCAGACGGTAAAGAATCTGCCTGCAATG
CAGGAGACCCAGGTTTGATCCCTGGTTTGAGAAGATCCTTTGGAGAAGGGAATGGCAACC
CATTCCAGTATTTTTGCCTGGGAATTTCCATGGACAGAGGAGCCTGGAGGGCTGCAGTCC
ATGGAGTCACAAAGAGTAGGACGCATCTTGGGCACAAACCTATTACTCTGAAAATGTATA
AAGAGAAAGACAAGCATTTTCCCTACCTTCTTTGTATAAACATGTTTCATAATAACTGGA
TAGTTGATAAAAGTTCTTTACAGAAGAATTCCAATTCATTACAAATGCCCATGGAATGCT
GAATTTATGAAATCAACATGTTGTAACCTCTGTTGGTGGAGAAGGAAATGGCAACCCACT
CCAGTATTCATGCCTGGAGAATCCCATGGACAGAGGAGCCTGGCAGATTATGGTCCATTG
GGTAGCAGAGAGTCAGACACGGTTGAAGCAACTTAGCTTGGAACCCCTGTTGATAATGGA
TCTAGGCAATGATCATCAGTTGATGTTAAAACCTTATAGAAGGATCAGTGGAGGAACTTC
TTTATAATGAGTTAATTGTCACAGTCTGAACAGCCTATTAGATATAATATCTCAGAGATT
ACATGCTTCCTGCTGTGATGCAAGGCTGATTATACCACCATGAGGTTATTTTGCCAAAA
CAAATCAATAAAATTGAATCATGCTTCTTTAATTACCAGTTTAAAACAAAGCTGACAGAA
GTGCAAAGTATCATGAAGACACGTCAGGCAAATCTGGACTGTTAAACGTCCTGCAGACAA
ATAACCCAGCTTCTTAAAACATAAAGAGCATTAAAAAAGAGGATGGGCAAGCTGAGAGA
CCGTTAAAGACTGAGAAAGACTTGAGGAGGCAACAAGCACATGCAGTGTGTAGACCTTAT
TTGGACCTTGTTTTAAAGAAACCTACTATAAGAAACTTTTTTTTAGATAACAGGAAAAT
GTGAATATGAACTCAGTATTATATGATATTGAGGAACTGTTAATATCTAAGTGTGATAAT
GACCTTTTGATTACAGAAAAATAAAAATCCTGTTGCATTAGTGATGCTTAGTAAAGCATT
TTTGGGTAAAATGGATAATTTTTCCTCAAATTTGTTGTAAAATATTCCAAGATTAGAGAA
AGGGGTGGGGAGTTATGGAAGAAGAAAGATTGGCAAAATGTGGATAATTGTTGAAGCTGG
TTAATGGGTATATGGTGGTTTATTTTATGCTTATCTTTTTGAATATGTTTAAAATTTTC
CATAATAAGTTTTTAAAGAGATATTATAATCCATGGAAATAAGAAAAAGGGGAAAATTGC
ATCTGGAAGCATGTTCTTCCCTGTTATCCTAATGAATAAATAAGGAGAAAATAAAGCGTA
CAAGCTTGAGATTACTTACACAGTGAGCACTTATTTAATAAGAAAGCTCAAATTTTCTTT
GTAAGGGAGTCATAGGATAGGCTTTTGACGTGTGATGTTCTTTTGGCTCAGTTTTCTGTT
```

*FIG. 1S*

```
TTCCTTTTTTAAAGGAGACAAAAACACCCAGCCCGCATAAAGATTTCACTGTTGGTGTGG
ATTTCGTGATGTCACTAATTTTATTAAATTTGGGCACATAAAGGTGTAATTGATAATTGT
CCTACAGAAATAGGCTGTATTACTGTCACCGTCTTTTTGAAGATTCCCTTGTTAATATTT
TCTGGTAGCACAACAAATCAGAAGCTCTGGGCTGCGGAACTTCAGAAGACCATCTCCAGA
GACAACAAGTATGTGCTGCTGGCCTCTGAGCAGTTGGTGGGCGTCTGTCTGTTTGTTTTT
ATCAGACCACAGCACGCTCCCTTCATCAGGTGAGTAGACAGATGGCGCTCCGAAGGCTGC
CTCCTAACACCAGATAACCAAAAGGCCTGGCGTATTTTGGCTTCAGAGAAACACTGACG
CATGGTTCTTGTTTCTGAGTGTTCTTTTTTTTTTTTTTTAATTGAAGTGTAGTTGATTTA
TATGGACTTCCCAGGTGGCTCAGTGGTAAAGAATCCACCTGCTAATGCAGGAGACACAGG
AGACAGGGGTTCAGTCCCTGGGTCAGGAAGATCCTCTGGAGAAGGAAATGATAACCCACT
CCAGTATTCTTTCTTGGGAAATTCCATGGACAGAGGAGCCTGGCGGGCTACAGTCCATGG
GGTCGCAAAGAGTCGGACATGACTGTGCATGAACATGCATGATGGGTGATAGTTGATTTA
AATAGTGTTAGTTTCAAGTATACAACAAAGTGATCAGTTATACACTTGTGTGTGTGTGTG
TCTATCTTTTTAAGATTATTTTCCCTTATAGGTTATTACAAAAAAATAAGTATAGTTCTC
TGTGCTATATAGTAGGTCTTTGTTGGTTATCCATTCTATATGCCCTCTCACTCGCGCCTT
CCCTTTGGTAACCGTAAGTTTGTTTTCTGTGTCTGTGGGTCTGTTTCTGTCTTGTAAATA
AGTTCGTCTGTATCGCTAAGTAGTATTCCATTGTATTTACGTACCACATCTTCTTTATTC
ATTCATCTGTCAGCAGACATCTAAGTTGTTTCCATGTCTTGATATTGTGAATGGTGCTGC
AGTGAACATTGGGGTGCATGTGTTTTTTCAAATTATAGTTTTCTCCAGATATATCCCCAG
GAGTGGAACCCCTGTATCATGTGGTAACTCTTGTTTAAATATGTTCTTGATTAAAGAATT
GCTAGTAGTTTCTCTCCACTATTTCACAGGCTTCCCTACAAAATGCCCATGATGTATAGT
GTTGTAATTATGTAATAGACATTCTTCATTTCTTACACACGCAGAACTGTTGAAATTTCT
GATCTTGGATTTCAAATTCTTCCTTTTAAAGGGATGTTGCAGTTGATACTGTGAAAACTG
GAATGGGAGGCGCAACTGGAAATAAGGGAGCAGTTGCAATACGAATGCTGTTCCACACCA
CAAGCCTCTGCTTTGTCTGCAGCCACTTCGCTGCGGGACAATCCCAAGTCAAAGAACGAA
ATGATGATTTTGTAGAAATAGCGCGGAAGTTGAGTTTTCCAATGGTAAACTCTTGCTACT
TGTTTTCGAAAAGGAAGCTTTGGAACATATTTCAGTTCACCCCATATTCTATATCAGTTT
TTGAAAAGTTGGAATAACTCCTAGAAATGTCAGCAAATAGATAACTCCTTGTGTTATTAC
TGTGGGGTTAAATAAATCGAACCTGGCAGGGGTAAGGCAAAGAAAAAGTTGTAAAACATT
TTGTGAATTGATTGTTTGGAATTCTGTCTCTCTTCTTCCAGGGAAGGCTGCTCTTCTCCC
ATGACTATGTGTTTTGGTGTGGCGATTTCAACTACCGAATCGATCTCCCTAATGAGGAAG
TGAAAGAGCTTATCAGACAGCAAAACTGGGATTCTCTTATCGCAGGAGATCAGCTTATCA
ATCAGAAAAATGCTGGACAGGTATAGACATACCTAAGATACTTGCATTGGGAAGAAGGGG
ATGTCTGATTATGAAAACATGCTTTCCCTAAAGTTTTTTTTTTTTTTTTAACAATCTC
TTGGAGTCTATACTTAATAAGTATGTGCTAAGTTACTTCAGTCACGTCCTTCTTGTTGTG
ACGCTAGGAATGTAGCCCACCAGGCTCCTCTGTCCATGGGATTCTCCAGGCAAGAATGCT
CGAGTGGATTGTCATGCCCTTCTCCTGGGGATTTTCCAGACCCAGAGGTCAAACCTGGGT
CTGTTATGTTTCCTGCATTGGCTGATGGTTCTTCACACTAGCACCACTCAGGAAGCCTT
TACTAAGTATATATCTATAGTTTGCCTTCTCTTTTAAAAAAGGAAAAGGAAAGGAA
AACTTATAATAATTTCCAGGAGGAAAAGTATATCATGTCTCTATAAAATTCACCTTCAAG
TAGAAGAAGATTCTTTTTTTCTTTCAGCAGTAGCAAATTTAAGATCTTACTCATCAAGGC
TACTGCTGTTTGGCTCATAAGATCCTATGGTAATCTACTTTCATTTTTGTTACTTATTT
ATGGCCATGCTGTGTGATATGTGGGATCTTAGTTCCCTGACCAGGGATCGAACCTGCACC
TTGCCCTGCATTGGAAGCGCAGGCTCTTAACCACTGGACTACCAGAGAAGTCCTTGGAAG
AATTTATTTTAAAAAAATTTTTAGGAAGAGGTGATTGAGGCCACTTGATATAGTACCTTT
CTGATCATCAGACTTAAATTCTGATGGATACCATGTAACCTTCTTAGGCCCCAGTTCCTG
TTGAGAATAAGACATCACACAATGTGATTTCCAAAATCCCATACAGTTCTAAACGTTTGA
TACTGCTCAAAAGTCTGGTGGAAGTTCATCGTTCCAGTTTTTGTACTTTGTTACTCAGA
CATCAAGTGAGTGAGATGATAAAGCCCGCATCCTAGGTCATTTTGCCTTAAGCTCTGTTC
CATTCAGTTAGAAGTGTTCCTCAGAGGCACATAGATTTCACGAGTCTCTAGCACATAATA
GACATTTAGTGCATGACTGCCCGAATGAAAACAGAATGTTTTTGCCTTTTTGAAATAACT
```

FIG. 1T

```
TCCTTTATGTATGTTTATTTTAGATTTTTAGAGGATTTTTAGAAGGAAAAGTGACCTTTG
CTCCAACGTATAAATACGACTTGTTTTCTGATGACTACGACACTAGTGAAAAGTGCCGCA
CCCCTGCATGGACAGACCGTGTCCTCTGGAGAAGACGGAAGTGGCCTTTTGATAGATCAG
GTGGACATCGTCATTTAAATAAGTCAATGCAAATTTTACAAGGAAGAGGGGAATGATATA
AATGCCAAATAAGGCCAAGAGGACTACATTTTTTTTTCTCAGCATAGGTTATCTAGAAT
AAAATAAATATAATTCAAATATAAAACTTAAAAAAATTCTCAGACCTGCTTATAATAAAC
ACTTTGATTTTTCAATCTGTTTTCTTTCAGTGAAATAGTGTCATATAAAGAAAAGCAAGG
AAAAACATTTTTATGCAATTAACAACTGAATACTAAGTAAGATTTCTAACTGGAATAACT
CAAGTGGTTTTGCAAATATTTTGAACTGCTACTTGTCTGTTCAGTTATTTGTAAAACTCT
GGTCATGAAGTCTCAGAAGTAAAGGCTCATTGTAGTTTTAACTAAGTAAAGCATAATATG
ATGACCTCACCAAAAAACCCTGACTTAACAGAGTCTAGACTTCATGCCCATCAGCAAGTG
TGTCTGATGTCCCAGCCTCAGGCAACTGAAGCTAGTGAAATGAAGGATCTCCTGTGGTCT
GTCATGCTCAGGTGACTTCGCCTGTGTTCTGTTTTATTCTGACTGCAGCTGAAGATTTAG
ATCTCCTAAATGCTAGTTTTCAAGATGAAAGCAAAATCCTCTACACATGGACTCCTGGCA
CTTTGCTGCACTACGGAAGGGCTGAGCTGAAGACTTCTGACCATAGGTTTAAGCAATCTC
TGTATTTCTAATCATGCTTGAAATTTATTTGAAATACATCATTTCTGTAATGTTCCTAAC
ATGTCTCCATTCCTTCATGCTGAAGGCCTGTTGTTGCCCTGATCGATATTGATATATTTG
AAGTTGAAGCTGAAGAGAGGCAAAACATTTATAAAGAAGTAATTGCAGTTCAGGGTCCAC
CAGATGGTACGGTGTTGGTCTCAATCAAAAGCTCTTTACCAGAAAATAATTTTTTCAACG
ATGCTTTGATTGATGAGCTTTTACAGCAGTTTACAAATTTCGGTGAAGTTATACTCATAA
GGTGAGTAACGTAAAAAAAAAAGCAACTCATGATTCACAAATAATATCTTCTGTATTAA
AAGTTACCTTTCTTAGTATTTGACTAGTATGTGAGTATTTGTGGAAATTCCCTGGTAGCT
CAGTCAGTAAAGAATCTGCTTGCAGCGCCAGAGACCTGGCTTCAGTCCCTGGGTTGGGAA
GATCCCCTGGACAAGGAAATGGCAACCCTCTCCAGTATTCTTGCCTGGAAAATCCCATGG
ACAGAGGAACCTGGCGGGCTAAGTCCATGGGATTGCAATAGTCAGACATGATTTAGCAAG
TAAACCACCGTGAATATTTGTATCTTCAAACTAAAAGAAAATCATGCTATAGAAATATTA
TTCAAAAAACCCATGGGTTTTGAAACTGGACTCTCTGCTTAGAAAATTTAAAGTTGAGTA
GTGAAACTTCACGTGAACATCTGATGACAAAAATACGTGCACATTTAGATATGTTCTCTC
CAGATTTCTGTACACTATAACATGGAAGCCCTGTGGAAAAGTGAACATGTGATATTAGTA
TTTTAGTTTTTTGAGGAGTGATAGAAGTAAAGCAGAATGACTTTTCTGCCCTCCATTTAA
GACATTAGATGTTCTCAGTAATTTTAAGTGATTTGATTTCCGTCTGATGGAGGAGCGGCG
CTGCCCGGCACACAGTTAGGAGTCATCCTTCCCTGCCTTGGTTTCCGGCACTGACTTAAC
CATCTGCCTTTTGCAGAACCAGATGCCTCTTGCGTTGTTGAAATAAATGTTCTCTTCCCA
GTGTACAGCAGTTTTGACAAACTGAATAACATGTGTTTGAATTTCATAGGGAAGAGGTAC
TATTAAATTCCTTTCTGTGCTGTTTCATGTGTTTATTGAGGGATGTTTCATAGCTGTTTA
GTGGGCAAGTCTCTATACTGGGTGCTCTGGCAGACAGGGGAGGAATCGAAGATTCAGTTC
CTATTCGGAATCTAAGAAAGATAAGCGTGTGTGTAATGGCTTCCTTAGGTGTTTACCGGA
ACAGCCCACAGAATGAAGATGGCTTGGTTTCTTGCAGGGTGAGAAGCTTGCCTGAGAAGC
CTCCTCTCCTTTCTGAGAGTAAATGGGCAAATAGAGAAGAAATTATATTTAGACTTACCT
CAAATTGTTTGACAAAGATCTACCCTACAGGTTTAAAATGAAACAAAAAACCTCTAGAGA
TTTAAGACTCCAGCAAGTACATGGTGAAATTTCCCAATGACAGTAAGCGTTGCCAAGTAC
AGAAACACCGAACCACTGGGAGCATCATGTGGACTGTGTGAGTGGGCAGCACAGAGCAGT
TAAGTGTTCTTGCGAGCAAGTGTGAACTCTTGCTCAGAGTTTACAATACTTTTTCCAATG
ATAACAAGCATTTTGGGGAAAGCTTTTGGTTGCAATTTAACACTGTCAGGGGAGTGGGTA
ATTTTCCTTGGTTCTATTTCGACACAACAAAAATTTGAGGCGACGGATATTAAAGCCCTT
GGCGCATCACAGCTCTCGGATAGTATTACAGCTCCCTTGGTTTTATTTAGAAAATAAAGG
AAGATACATCCTTGAGGCATGAGGGCATGCCAACGCAAAAGACAGGACGAGAAAAGAGAA
AGCGAGCACTCTCTCTGGGTGAGAGAGAACCCATAGTGTACATAAGGAAGGAACGACTGA
CGCAGGGATAGGACCTTCCTGCCTTTTTTCTAGTCTCTAAAGAGCTTGGTGTTATTAGGT
AGTTAAGAATAGGAAAAGGAGTCCAGAATGATGGTGATTAAAAGACAAGGGAAAAGCTC
TTGAAAATAGGACAGAAGAAGGTCTGAGGACCGGAGTGAGGACCTCAGGTAGAACAAACA
```

FIG. 1U

```
GCACTCCTGGCTAGCCCCGTTTACGTAGGGCAGGCCCAGAGGGAGAAAAAAACATATAAA
AAGAGGAGCCAAAGGGCTGGGGGTCTCTCCCACGCGTGCACGCTCATTGTCTCTCTCTGT
CTCCCACGCTTGCTCGCTCTCTTTTCTCATCCCGTCTTTTGGGTCGGGTCAGCATGCCCT
CATGCCTCGAGGTTGTATCTTCCTTTATTTTCTAAATAAAACTGTGGGAGCTGTAACACT
GTCTGAGATCTGTGATGTGCCAAGGGCTTTAACGTCCATCACCTCAAATTTTTGTTGTGT
CGAGACAGAACCGAGGAAAATTACCCACTCCCCTGACAGTATTAAATTGCAACCAAAAGC
TTTCCCCAAAATGCTTGTTATTATTGGAAAAAGTATTGGTAACAGAACAAGTACTGGTAA
CAAAACAAGGGTAATGTTATGCTGACGTTATAAAACCATGTGGTACCTCCTAACCTAGAA
TATTCTGATTGTTCCACCTTAAGACCACCAAGGTAGAACAGACAGGGGAGACACTGAAAG
TAAAGAAGGACAGGAATACTGTCCCCTGTCACCTGTAGGCTAAACTGATCATCACCTTCA
GCTCTAGAATAAGCCAACTGTTAGGGAATGACTGAAGTCATCATATGTAAATTATATGTA
AATAAGAGATTTCCTGGAAATGTAGATGGGGCAGGCTACTTATATTAATTGGGGGGGAAG
TCTAGAATGCTTCTATCCTATTGAGTAAAAATAGGAAAAAAGTACAACACACATTTGGAG
TTCCGCAGGCCCATTCCTTCTGACAGACAGTTTTAGTAACACTGTATTGGGTTGACAAAA
AACATCGTTTGGGTTTCTCCATACCTTCCAAGGGGGGAACCTGAACTTTTTGGCCAACCC
AGTATCTAAAGGAATTTGAATGCTTTTAGGGAAAGAGAGCCCTCTCCTGGTCACCGCTGG
CCCTGCCGCTCTCAGGCTTGTATTTTTGTTTCCTAGCCTCTGTAAGTCCTTGCTCATCAG
TAATCATTGGACGAGTCTTTGGGCTGGTTATATCTGAGGTATTCATTACGTTTTTTTATT
GTTTGTTTTTCTCTTCCTTAAAGATTTGTGGAAGATAAAATGTGGGTTACGTTTTTAGAG
GGAAGCTCTGCCTTGAATGTTCTGAACCTGAATGGGAAAGAGGTAAAGTAGCATTTGTTG
AATCTAAACCATTCAGTGATTTAGTGTCTGAGGACTGTATTTTAAGATACATGCAGCAA
ATTATCTAAACGTGTTTCGAATATCTAGTTGCATGATGCCTCGGATTACCTAACATCCAA
CATCCTAATTATTTTTTAACTTTGACAATCTGAAAAACTAGAAGTAGTATGTCACGTCTG
TGTTAAGATTTCAATGGAGAGTTTTTCAATTAACTGGTCGTTTCATACTTCTCTGGCAAG
CTGTTTATGACCTCAGCCTGTGTTCCCTCGGGGTATTCATCTTTTGAAGCTTCCCTGAT
GTTAATTCCTTTTCATAATGTGCTGTACATGTTCTTCCCAGTTCGTCTTGTGACTTTGTT
GTTTTCACCGTATAGAAATTACTGATTTTTAAATTTAATTCTGCCTTTAATATCTTAAGC
TTTTCCTCCTCCCATGATGTCATTAATATTTAAGAGCAGCTCTCAATTTGGCATCCCTTG
TCAGCTCTTACTCCTTTTTTGAATATTTCTTTTGTCTTTCCCCTGGTCATTTTCCTTGTT
TAGTTTTTTTCCTCCCTTCTTTTTCAGCTCTGTCCCTCACCCTCAAGTCTGTGTTACACT
TCTAGAAAGTGCCCACCCTTAGCTCCCTTAAAAGATTTTCAAATTCTGAAAAAATAATG
TTTCTGGAGAACATTTTGAAAGTCAGACGTGTCCAAACCTCTCCTCTGTCTTTGTTATTA
CAGTTGTTTCAGCCCAGATCTTCTAGATACAAGTAGATCGATAGGAACTCTTCCATTTCA
GGGGAGAATCTGGAAAAAGTACAGTGTAAGCAGAGCAAACTTAAAGGATAACCTGCTTGA
GCATTTTTTTTCCAGCATCTAAATTTCTTCCTTTTCATTCAGTTCTGATCTCTGCCAAG
TGAATATTCTTGATGAAGTACATCTTAAGTGGCCATTGTAGTGATTGAGGCTTAAGAAGA
CTTGTTAGTATTCTTTGGTGAATGCATAACAAAGGTTGTTGACTTAAAAAAATAAATGGT
CCATGAAGCCTATTGACTTAAAAAAATAAATGGTCCAGAATCCTAGTTCTGACTTCAAAC
CTCAGCATGGACGCTAAATTCCTATTAAACACGACTGTACTGTTCAGGCCGGCAGCTGTC
AGCCTTTCAGACTGTGCCATGAAGAATTCTGATGTCAGTAGCATTTAAGGAAAGTATTT
TTAATATGACAGGACAATGTAAGTTGATTATAATACATTGATTATTTTAGACTATACTTT
TGTCTAAAAGCTCCTCAACTTTTAGGAACAGCAGTGTGCCAGTTTCACAGATACCAGTC
CTTGTGTTTTCAGAATGGTTAATTTTGTTGATTTAAAATGATCTTAGATTCTCTTAAGT
ATGCTTGTGACATTTGAAATGCTGAAAAGTCTAAATGAACAGGAAAGTATTTTAAGAATT
TTATACTGTCCTTTCTTTGATTGTCTCATGTGGATTAATTAATTAATTTAATTAATTAAT
CTGTGGATCAAAATTAAAGGAAGTATAAATTTATGTAGCAGAGTTTTCAGTGAATTTAGA
TCTGGCCCGGGAAAGATATTTACTGCAGCAAAGAAAACTTAAATTTGTGTGCATCCTAGA
AAAGAAGACCTGAGCTTAGCAGCAGTAGGCTGTTTTGTTTTGGCCACACTGTGTGGCCAA
ATCTCAGTTCTGAGGTCGAGGATTAAACCTGGACCATGGCAGTGATGGCATCACCAGCTC
AAGGGTCATGAGTTTGAGCAAACTCCGAGAGACAGTGAAGGACAGAAGAGCCTGGCATGC
TGCAGTCTATAGGGTCGCAAAGAGATGCATATGACTTAGCAACTGAACAACAGCAATGAC
```

FIG. 1V

```
AGTGAAAGCCTGGAGTCCTAACCACTAGGCCACCAGGAAGCTCCCTAACAGGTTTTTAAA
GGGAGGATTGGGGACATTTGAAACTAGGTGACAATACAATATATGTGAAATGATTGTGTT
GAATGAATCTGAGTTAAGCCTATACTATTGTTATAACTTAAACAGACACTTTATTCCAAG
ATACTTAATTTTCATGCCAATGAATTTTTAATTTTGTATCTCTTTTACTCAACCAGTTAC
TGGGTAGGACAATAACAATTACTTTAAAAAGTCCAGACTGGATCAAAACTTTGGAAGAAG
AAATGAGCTTAGAGAAAATCAACGTCCCCTTGCCATCATCAACCAGCTCCACCCTCCTAG
GTGAAGACGCGGAGGTCACGGCCGACTTCGATATGGAAGGTCTGCTCATGGAGCACATTG
ACTTCTATCCTTCTAGACAGGTTTCCTTCCCATCAGCAAAGTCTCAGTCTCCAAATCTGT
CCTTCTGTTTCTTCTTGTAACACTCAGAGAAGTATTAATCAGATTTGGTTTACATTGTAT
TGTGTGTTTTTTGCTTGTTACACAGACTTCAGATGTGTGTGCCCTTCTGCCATACAAAGG
TCAAGACCTTTACAATAGTTAGTTTATGTCCTTGTGTGATAAAAGCAGGAAGTGGTATTT
TTGGTGTGTGGTTTGGTTCCACTGATTGTAGTTAAAGTAGAAGAGTAGGAGTTCTGTGCA
GAAATGAGTTCAAAATATTTACAACCAAAGAGGATATATTTCAAAGTCATTTTAAAAATT
CTTAAAGTGGCTGGGAACACATTTGAAACTGAACCCACTCATGTAGATGTAATCATCTCA
AGTTTAAGAGTGGGCCAGGTTATCTTAATATAATAATTTCCTTAAATGTGATTAAGAAAT
GTATTTGCTTTTTAATGCTGTATCTGCTATATTATTTTAACATATTTTCCACTAAAATGC
ATACCTTAGTTTATAAAAGGGCAATATATCATATTGTGATATCCTGTACCTCTAGGTAAC
ACATTTAAGAGTTGAACACCTTAGAAGATCAGCTTGTTTTCATATTTCTCTGTTAATTTG
TTTGCTTGGTCCACACGTTTATGCACTTACCTTTTATGTGCCAGTTACATGCTAAGTGCT
GGAAATTCAACAGATGGCATCCTTGCCGTCCCTGAAGTCACAGCTCAGTGGGTGTTACCT
ACAAGTAGGCAGACGGTGACATCAACACACTCGTGAACGGTGCTGCTGTAGTTCTTGGGC
CTAACTTAGAGTTGGACAGTTAGGAGAATGTACCCAGAGAAATTGAAACTGAAAATCTGA
AGACTGAGTGAGAATCAGATTAAAGAGGATAGAGAGACATCACCAGGAAGAAGGAATGTG
CAGAGACCTAAGGGGACAAAAGGATCTAAGTAGATGATGCAGATGTGCTTGTGCAAGAGG
AAGGGAAGAAAGAACAAGAAGAGGAGTGGGTGTGGATGGAAGGTGAATTTCTTTTCTGTT
TTGTTTGAAGTGTTTGTTTATTTGGCTGCACTGGGTCTTAGTTGCAGCATGCAGGATCTT
TAGCATGCAGACCCTTAGTTGTGACATGTGGGATCTGGTTCCCTGACCAGGAATCGAACC
TGGGCCCGCTGCATTGGGAGCACGGAGTCTTAGCCACTGGACCAGCAGGGAATCCTGAGT
TTGGTTTTGAATGTGTTGAAGTTGTGGCATCTGTGGGGTGCATTGGGTCCAGAAGTAAGC
TGTGGGCATGTGGGCCTGGCACTCAGCAGAGAGCCCGGAGCTTTGATGATAGGTAAGGCC
CTGCATTTGGATTTGCTTGGCCAGAAACCTGATAGAGATGGGAGAGGACTTCCTGGGATG
GAACTGAAACGCAGACTTTGAAGGACAGGCAGAAGAAGGCCGCCCATAAAAGGAAAAGCA
GAAGAAACGACTAGAAATGTCAGAGAGCCAGGAGAATATAGTGCTTAAAGACCAAGTGAA
GAAAAGATGATAAGGAAAAATGATCTATAGCGTCCTCTGTCGCAGGGCGAGAAGAAGTGA
GCGCCACAGCTTGCCCTTTGGGCTTGGAACCAGGGGAGGAAGCTGTTGGTGACATTCAGG
AGAGTGATTTCAGTGGAGTGAAGAAGCCAGATGGTGGTAAATCGGGGTGTGGATGGAAGA
CGAGGAAGTGCAGAAAGTGTCTGTAGACAACTCTCGACAGAAGTGTGCCTGAGACGGGAG
AAAGAGAGATGAAGGCAGTTGCTCCCTGAAGTGTTGTTTTGAAGTGGAGACACTTGAGGA
GCTTAATCCTGATGGAAAGGGCTGATGCTGCTGGGGAGGGGCAGGGCAACCTGCACTGGG
CAGAACCCCACCCTTTCCACCCATAGATATGGTTAGGCTACAGCTGGGGGCAGATTGTT
GAAGAAAGGGGTTCCCACCTTAGAACTTCCTTTTCTCTGCGAAGTTTAAGGAGGCGGGCA
GCACACGGTTTCAGGAAGGTTGAGAAGGTTCAAGACAAAGCTCCTGAGAAGCAGTCAGAT
GGGGAGCCAGCCAGGAAACTGTGGGTTGGCCAGGAGGCCATGGGAGCCCAGATGAGGCTG
AAACCACAAGTTAACACGTGCAGTCTTTAAGACCACACGGTTATCTGTCTGCAGCACCCA
GCCGCCCGTCTGCGGTTATGGAGACATTAGACTGCAGAATTGACGCAGGGCAACGGAAG
AATAGTGCAGGAGGGGACCAGCTGCGGCAAGGAGCCAGAGGATGTGAAGACAGCTGCAGG
GACAGGTGCAAAATCCAGTAGGGGCCCAAAGAAGAGGGATCGAAGGCTTGGGTCCTGGTG
AAGTCAGAAGAGGGGAAAGAGTAGCCAAGGGCAAGACTGAGCCTGGAAGGCGGTCAGAGG
GAAGTGTTTGAGTTTATTGTTTCAGAGGCACTGCGGTTCCAAGGGGCATGAGTGTGGAGT
AGAGGAGCGCATCAGCAGGGAAAAGTGTCAGGTTGTTGGTGTGTTATCCACAGTGGCTTC
AGTGTCACCCAGAAAGATGGCGGGCCCAGCTTACTGTCTTGCTCTCTCCTTGGTCCTCG
```

*FIG. 1W*

```
ATGAATGGGTTCAAGTGACCAAAAAGGTGAAGGTGGGAGATTATGGCGGCAAACGTGGGT
TGAGGGCGTTACATAAATTCTGGAAGGCACAGCTTCCAGAAATAAAGAGGCCTTTTTGTT
CAGGGTTGGAAGATTAAAGTTTTGGAATTGGAATCAGGTGGCATGGGGCTCCCTGACGCC
ACTTCCCAACCCTGTGGAAAACGGAGGTGAGGAGACCTCGGGGAGAACCAACTCCTGCCT
GTTTAATTAAAGCACAGAGGATTACGTGTCAGGTAGGGGCGCCCAGGGCACCAAGTAGTG
AGGAGACTTCCAGGGGGAAGGGTGTGTGACTGTGTGTGCCATGAGGGGCAGGTCCATAGA
CCTAGCAGGCAGGTTTGGAGGGAGGGCAGTGAGCATCCGACTCAGCCAGCACTGAGAGCG
CTGCTCAGGGCGCATTGACAGCTGTGGAGTCAGCCCAGCCCCAGATGTTAGCCGCCACTG
GGCCTCCTGTTGCTCTGAGACAAGAGACTTTTTTTTTTTAATTATTATTATTAAACGT
GTTTATTTTAATTGAAAGATAATTGCTTGATAGTATTGTGCTGGTTTCTGCCAATATCG
GCATTAATCAGCCATACATATTACTATATCCCCTGTGACTGTCTTTTTTAAGTAATTTA
ATTAATTAATGGCTGTGGGCTGTGCTGGGTCTTGGTTGCTGCAGACAGGCTTTCTCTAGC
TGTGGTGAGCAGGGGCTACTCTCTGTGGTGCACAGGCTTCAGTATTTGTGGCATGTGG
GATCTTCCCAGACCAGGGATTGAACCCATGTCCATCTGCATTGGCAGACAGATTCTTCAC
CACTGGACCACCTGGGAAGCCCAGGGGACTATTTTAATTACTTTTTCTACGGTACGAGA
GCATTTGCACTAATTCTACTTGTATACATATAAACTCTTTATACATGCCCACATGCTTAA
CTTATACATGTTTGCAGTATCATCATGTTAAGGTGTTCATTTTATATATTTAACCCCTTA
AGCCTGGACTTGGGGGGCAGCAATCTCTGAGAAAGTTAACATCTGGTAATGTGGCCGACC
TTGCGTTTTCTCAGGTGATGTGGATGACTATAGTGCTGAGGTAGAGGAGATCCTTCCTCA
GCATCTCCAGCCGTCTTCCAGTTCTGGCCTTGGCACGTCCCCCGGTTCTTCACCCCGGAC
CAGTCCCTGCCAGTCACCTACCATATCGGAGGGGCCTGTGCCTTCCCTCCCAGTGAGACC
AAGTCGAGCTCCGTCCAGAACGCCCGGGCCCCCTGCTTCACAAAGTATGTGTTTTATTTC
AAGTTCTGTATGACTTCCCGGGCTGGTATGTTTGATTTAGATGGTTAAACCTCCGATGCC
TTCAGATGTCCTTTGGAGAACTATTTTGCTTAACTTTCACATCCATAGGCTAAAGTGTA
GCATGTTTTCTGTGCGTACAAAAGAGGAAACTTTGTAGATGGTTCCACCCTAAGTGAAGA
GGAGGGTCGTTGCTATCACTAGATGAGAACTTTACTTCATCCTTTTTCCATGTGGCAGGT
TTGTCCATGGCTTATCACTGACGATTTTTAAGCATTATGGTCAGAACCCGTAACTCTTTG
GGCTTAACTATCTGTACATTACCTGCATTATAATAGGAAGCAGAAAGAGACAAAACAAGT
ATTTTGAATTCAACTTGATAGTCATGACTCCTCCAAAGTCAGGTTTTTCTCTGGAAGTTG
TTACATCACACAGTTCAGTCACTGTTCCACACTAACCAGTACCCTTGAAAAATACCTTTT
ATTTCAGCAATTTCTCAAGCTCCCCCATGCTACTCTTAGAGGACCGTCTTTAAATAGTCA
CTGAGTTGTATCTGACTCTTTTGCGACCCCATGGATTATAGCCTGCCAGGCTCCTCTGTC
CATTGGATTTCCCAGGCAAGAATATGGGAGTGGGTTGCCATTTCCTTCTCCAGGAGATCT
TCCCGATTCAGGGATCAAACTTGCATCTCCTGCATTGGCAGCGGATTCTTTAGCACTGA
GCCACGAGGGAAGCCCTCAGAGGATGGCTTCCTTCAGTAAATTCAGGATAAGTCAAGGC
ATAAAGAAGAGGCTCTCTTTGCTTTTCTTCTCTCCTGGCCAGCAGATTGAATTGC
AAATGACCTAAGTCACACAGTACTTCATGCCATCTTGTTAGGGCCGCTCAGTAAATCCCC
TTTCAGTACCCGGGGCCTGGGTAAGAAGTCCAGAGAGTAACCTGATTGCTCCCGTAGTAC
CAAAGGGTAAGGTAATAGCACAGCTGCTTGTGTTACTGATACTAAAAATGTATGTCATTC
CTCTGTAGTACAAATTATTTGCTAAATAATTTATCATACGCCTATAGAAAGTACCTGTG
TGCTCGTCCCTTGGAACCTGATCCTCTTACCTAAGGTACTTTTTTCTGGTAGGTTCTCCT
GTTGACACTCTGCCGGCAACACAGCTGCAGCAGAAAGATTCTTCCCAGACCCTGGAACCC
AAGCGGCCTCCCCCTCCCCGCCCGGTTGCTCCTCCTGCACGTCCAGCTCCTCCACAACGA
CCACCTCCGCCTTCAGGTGACAAATCCTTGTATTTCCATCTCTGCTGGATTTCACCACTC
TGCTGAAAAATGTTTTGCATGTTTTGAAACACTCGCTTTTAGATTTTATCAGTTTTCTG
TCACTGGTGCTACTTCCTTAGTTAGCTTTTCTCTAACAAACGGCATAGGCGTGACAGAAC
AGCTAGATTCCTATAACATGTTTTCAGAGCTGGCCTCTTACAAGCGTGCAGGAAACATTT
GCTTTGTTTTTGCTAATTTGATGTGGTTGTACTGATTTCTGTAAAATGCATGATTATCTA
AAAATGAAAATTTTTAATGCATGATTAGAACTGAAGAACATACATCTTTCTGTTTACAGT
TTTATATATTTGTTTAAATGTTCTTTTAAAATAAGTATAGTCTTGTTTCTGCTAGAGGTA
TTTGCGTTACATAATAACTTTTTTATAGCACCAAGATATGAATATGTAGTCTCTACATGA
```

*FIG. 1X*

```
TATTTGACATCTTGGAAACTATAGTAAATCTTTGACATTTCAATTCTTTATTTAATGTCA
TTTCCTTTCTGCTGCATATTCCCTTATGAACTATAAGGGGCTAGGAGTCCTGCACCTGCT
AGAAAAGAGTTTGGAGGTAACCATTTATATTTGTTATAATATATGGATCTTGGTTCATTA
ATTTTTTTGGAGTTTGAGCTCTGTAACTTAGTGACATTTTAGGTTGCTTTGATGCAAGCC
AAAATGAATGACATTTATATGCCAACTTAAAAATAACTCCAAACTTTCATTATATTTCTG
GTAAAGATTAGAGCTTGATTTTATTAGTGAATATTATTAGAATTAAGAAGACCTTCCAT
TTCCCTGATAAACAGAGTTGAATTACTTAAGGCCTGATATACTTTTTATTAATAAATATA
GTCAATTCGGTTATAAAGATTAAATGAGTCAAACACAATGAAAATAGGTGGTTTCCCAAG
GATTTGATTATATTGGATTATATTAGAACTCTAGTACGTCTTGCCAGTAGCCTGTGAATT
AGCAAAATGTCCTAGGAATGCAGTTTAAAGTTATCATAATTATCTGAAATATAGCTTTCA
TTTTGCATGGCTTTATCATAATTTGTCATAACATTCATGCCTCATTTTTAAAATAGAAGA
ACAAGTCTCTGTTATATATTTCGATAAAGAAATTTTTCTTAACACATGGGTCACTTTTTG
TAGTTTACTTGTTTTACATGAAGACTCTTACAAAGCTCAACTAGAGGCGTACATTTGACA
AGTTTATTTAATCTAGTTCTCAAGAAAGGCTGAGGCAGAATGTCTCAGTCCCACAGAAGA
GCTGTTCCTCACCCAGTTCTAGTGTCCTTAGGGCTCACGTGCACAGGCAGCTGGTCTCTC
CCTGCTCCAGCTGCCTGAGCACGTCGCCAGCCGACTCACGCTGTCACAGAGTGGCTGCAC
CGTGTGCAGACTTGAACGACTTTGGGTAATTAGGGTAGCAAAGTTCTTTCAGCACCAAGC
TTCTGTAAGATACTACTGGAGGATAACTTTTCCACTAACTTAAAGACGACATTGATTTTT
TTCCCATTTCAGACTTGTGCTTTGATTTATAGCTTCATGGAAGATTTTATTTACCTTCCC
CTTTAATTAGGAAACCAATCTGTAGAAAATTTAAAGAAATTTGTGAAAAGCTATACATA
TTAGCTACTCAGTGACTTACTTAGTCTGATGTTTTTTAAAAATTGCTTCTCTTCGTAATT
CTTTTGTAGGCAGTCTTAGCAGCATATTTTTAACCCTATAAACCAGTAACTGCTTGAAG
GCAATAATCTGAAAGTAATTATAGTACTTTTAGAGTTCTTTTTTTTTTTTTAATAATGC
ATTGAAAATTACCTTCTAAGGGACTAACACAGGACTCATAGAGATTTAAAATGAAATTGG
AACTTCCAGACTTTTTTTTCCTTTATGACTGGCAAATATTGGAGCTTTTATTAGTGGTTT
AATTCTGAATATAAAAAATGAGATGATTAAAAAGCAAAGACTTTCATTATTTTCAAATTC
CCTACTGCTAGTGAAGAAGTGAAAGTGTTAAGTCACTCAGTTGTATCCCGACTCTTTGGA
ACCCCATGGTCCGTAGCCCACCAGTCTCCTCTGTCCATGGGATTCTCCAGGCAAGAATGC
TGGAGGGGGTTGCCATTTCTTCCTCCAGGGAATCCTCCCATGATGTCAGATATAAAAAGA
AAACTATTTTCTCCTTTCAATTCTAACTGAAGAAAGGGCAAGGATCAGGTTTGGGCCAGG
CATCTAGAGGCACTTTGGTTTATACAGATATCTTTGAAGAAATTTGAAGCAGTGAAAGAA
CTTTTTTTGCAAAAGGACATTTAACTCAGAAACTGTTTTGTGTGCCTGCCTTTCCCTCTG
TTCTATGGACCCTGAACAATACACAGCTTCTGTTCTCTCTAAAAAGGTGTTGGAGCCC
CTCCCAGTCCGGGGGTAGCTAGGCGAGAGATGGAAGGTAACAAGACGTTTGCATCCTAGA
AATGGATCTCTCGTTTTATTCCTAAATGTCAGCCCCTCCAGTGTTTAAAGACATACCAAA
TCTTTTCTTGGTCCAACTGTAAACTCCCCCTCCCCCTCCTTCTGTATATCTTGTAACTTC
ATATTTTTTCTCTTTTCATTCTGTGTTGTGTAGTTTCTGGTGGTTGTCCATTTACTTTCT
CTGCAATTCTTAATGTTGTTTTGAGCTGTTCTGTATATATATATTTCATATACACTTAAG
ATGTGAAATTAATGTGCAGTATTATTTTAAGAGGAATGCCTTCAAAAATTTTTTCAGAAT
AAGTCAAATGTTTAGAAATGTACTGTACTAACTCTGAAGTTTTAAAAATTAATAATTAAA
CCTTGTTAATTCAGTCCAAGGATATAGTATTTTTAATCAACTTCAGATAACATAAATAT
GCTGAGTAAATTTGCTTAAAAGGCTATTAAAACTGGAAGCCATTCATTAAGATTACAGTT
ATTAAAAGTCTGATGGGTTTCATATAACAATTACACATGAATTTCCTTTCAAAAGAAGA
AATCTGAGATGCTGACCTTAATAGGGTCTCCTACTCCTTTTGGCCCCAAAAGTAGTTTAT
TGCATTTCAGTCTTCTCCTACGTTTCGAATGAGTTTGAGCAGTATTTTAACACTGTCTTG
CATAAGGCAGATATTGTAATAAGTAGTGCCCGCCTTCTACCTTAATGATAGGGTCTTTCT
GTAGAAATCCGAAAGGTCTCGTAAGAGCCCCTGTCCGTACTGACGTCCACAGCATGAAGC
CCTGAACAGTGCTGTTTGGTGTCTTGTGTGACTCGGAAAGTGCGGGTCTGTTGGTCCTGG
AGCCGTGAGCCCACCAAGCTCTGGGAAGTAGTGGGGCCACGTCTTGTGACTGTTCCCCCA
AACTGACCATGTGTTTTCAGGGTTCATAGGAAAGAGCTCTGTTGGGAAAGTTACCTTCCA
AATGAGGTAGCAGACCAACTGCCAACTTGTCCCATAAATGTTACTCTCAATAGTCTAAAT
```

FIG. 1Y

```
TTTTCTCTTTTGGAGGTATTTTCTAAAGGGCTGATAATACCCTCCAGCATTTCTAAAGCA
GAATAGTTTGTTTTGTTTTTCTTTTTCCACCTCGTGCCCCATTTCTGCTGGTAATGAAA
CAGAACAGCTAGCTAATATTATATAATATGGCTTATTTACTTATAGATAATTTTTTTTC
CTTCCTGCTTCAAAGCACCCAAAAGCCCAGGAACGACCCGGAGAGATAATCTAGGTAAAC
ATTCGAATTCAGCTACTTAACCTTAAAGCTGGACCATGAATAGACAGTGTGGTATAAGTG
CATGTTTCTTGTTTCTTTCTTTAAAAACAAAGACCTGAGCTACATGGTGTGATGTCTTTG
TTCCAGGACGCAGCCAGCTTCCACCTCAAGCCGGACTGCCAGGCCCGGGACTTGCTGGAC
ACAGTGCAGCCAGACCGGTAGGCAGCGCCTCGCTTGCGAGCCAGGAGGTCTAGGTCCTGG
GTCCCAACTTGCTACTAATCAAATGTGTTACCCTGAAGAAATCACGGGCCCATTAAGACT
CCAATTTCCTCAATTCTAAATTGGGGGAATTAGACTTGATGCTCTTCAAGGTACCTTCGT
GTGTATGTGTGTGTGTGTGTGTGTGTGTTTTACTCTCTGAGGTGTGTGTGTGTGTGTGTG
TGTACTTGCTGAGTTGTGTCCGACTCTTTGCAACCCCATGGACTGTACCCCATCAGGCTC
CTATGTCTATGAAATTTCCCTGGTAAGATTACTGGAGTGGGTTGCCATTTCCTTCTCCAG
GGGATCTCCCCAACCTAGGGATCAAACCCGCTTCTCCTGCATTGAGAGGCAGATTCTTTA
CCACTGAGCCACCAGGCAGCCCCACCTTCAACTCAAATGGTATTCTAACATCCTCTTCAG
AAGTAAAAGCATCCTTCATTATTTGAATAAAAGTGGTATACTTAAGTGATTACAGTCACT
AAATAAATATCTTAGAATCTTGAAATATATGGGGAAGTGATGTACTAGGGCAATTTTTTA
TGACATTATCTGAGTAATGAAGTAAAGTCATTCTTCTATCAGAAAGGTTTTATTTTACTT
TTATTTCCTTTTTATTTGTCTTTGCCACACCTTGAGGCATGCGGGATCTTAGTTCCCCAA
ACAGGGATTGAACCCGCACTCCCTGCAGTGGAAGCACAAGTCTTAACTGCTGGACCACCA
GGGAAGTCCAGAAGGATTTTAAAATTAGATTTCAGGAACCCCAATGATGATAGTCTGTCA
ACTAAAACTAGTTCTAAAGGTTTAACCACAGGAGAGCAGATGGCATTGCAGGGTTTCACC
CTGCGTTGTAAGTCTGGTTTTCTGCGTGTTTATGTGTGTTTTGTTATACACAGAATTATT
CTATTATTCACCCACATGAACATTTTCTCTGAGACAGAACAAGTAATTCAAAGAAAAAAA
AAAAGAGAAACCAGTGTCAGTCAGGTGGAGCCTGGACTTATTGGGAGGCCACTGGCTGAA
TCCTGGGAACTGTGACTATACCTGGAGATGAAGAGACTTCTGCTAATGAAACTACTTCAA
GAGTCCAAGAAATTCTCATGAGATTTCTAAAACAGAGATATTTTGTTTTTTGTCTTGTAG
CCAACCTGAAGGACTTTTTCTATATATAATATTATGCTCCAAAGTAAAGTGTCTGTGGAA
TTTACCTAAAATAGCCATTATCCACTCCCCTGTTTTTTTAAAAAAGAAGTTGTTATTCAC
TGACTACACACTTCCCACAAAGTACTTTGCTTACTGAATATTGTAAGAATAGGGAAGGAA
AGTCAGGATTTTGTGTGATTACATTTATAACTTTTGCTTATGCATGGAATCTAGAAAGAT
GGTACTGCTGAACCTGTTTGCAGGGCAGCAGTGGAGATGCAGACACAGACAGCAGACTTG
TGGACGCAGCGGGGGCAGGAGAGGGTGGGACTAACTGAGAGAATACTATGCTGCTGCTGC
TGCTAAGTCGCTTCAGTCGTGTCCGACTCTGTGCAACCCCACAGACGGCAGCCTCCCAGG
CTCCCCCGTCCCTGGGATTCTCCAGGCAAGAACACTGGAGTGGGTTGCCATTTCCTTCTC
CAGTGCATGAAAGTGAAAAGTGAAAGTGAAGTCGCTCAGTCTTTTCAGACTCTTAGCGAC
CCCATGGACTGCAGCCTACCAGGCTCCTCCATCCATGGGATTTTGCAGGCAAGAGTACTG
GAGTGGGGTGCCATCGCCTTCTCCGAGAGAATACTATGGAAATGTATATTACCATATGTA
AAACAGATAGCAAGTGGGAATCGGGGAGCTCAACTCTGTGCTGTGTGACAATTTAGAAGC
CTGGGAGGGGGTACAAGAGGGAGGGGACATGTGTGTACCTGTAGGAGATTCAGGAGGGAG
GGGACCTCCATGTGGCTGATTCATATTGATGTATGGCAGAAGCCAACAAATATTGTAAAG
CAATTATCCTCCAATTTATACAAAAATAAGAAAAATGTACTGAGTGCTTAAAGCCTTCAG
CAAACATGTGAAGATAGAAAAGGACGTTATTTCCCTAGTGTATCTTCCAGCCTATGTATT
TCAGCACATTGAGTTAGCCATTCCAGAGTTTTTAACCTCTGTGTTTAATAAAGAAAAACA
GCCTCAGTGTAGTTTTTGGTAAGCCTCTTAGTTCCACAGTGTATGTCCCGCTCCACCTCC
TCATGACCTGTAAAATCGTCCCACTAAGGAGTATGATACAGGATAAAGAAAACGGGCCCT
GAGTTCGGCTCCTGGCTTTATTTTGTAACTCTGTGGCTTTGGGACAGTTGTATACATTTC
TTCATTTTCATTTAAATTAGAGATGATAAAATAATACCTTACCCCCAGGGCCATTTGGA
CATTGAAATGTAAATTCATACCCAGTGCTTAGTTAACACAGTGCGTGGCACATAGTAAAC
AGTGAAAATATAAAGGAAGATTTTTGAAGCTTAAGGAACAAAATTGGGTCATTTGTAGA
GATGTGGATGGACCTAGAGAGTATCATACAGAATGAAGTAAGTCAGAAAGAGAGAAACAG
```

*FIG. 1Z*

```
TATTGTGTATTAACCCATATATGTGGAATGTAGATAAATACTATAGATGATCTTATTTGC
AAACCAGTAATAGAGACACAGACATAGAGAACAAATGTGTGGATACCAAGGGGCAGGGGA
GGAATTGGGAGATTCGAGTTGACACATATATGTGTGTCTGTGTGTGTATACACACACACA
TATATATATTACTGATACTATGTATAAAATAGATAATTAATGAGAAACTACTGTATATAG
CACAGAGAGTTCTACTTAACGCACTGTGATGACCTGAATGGGAGGGAAATCCAAAAGGGA
GGAGATATATATATATATATATATATATATATGTATGCCTGATTCATTTTGCTGAAGA
GTAGAGACCAACACAACTTTGTAAAGTAACTATGCACCAATAAAAGTTAATCCTTAATAA
AAAAAAATGAAACTTATGATCATATGGCAATAAATAGAGCCATTAGAATGACAAAGAGGC
AGAGGAAATGATACAAGATGCACAGACAAAATATTTTCATCAAATCTTATCCGTTGCAGA
TAAGGTAAATGTCTCAGTGGTTTTCGTTTCCCATCTTTAGATTATTCCGCCCCGTGCTGG
AGTCATCAGCGCCCCCCAGAGCCACGCACGGGTGTCTGCTGGGAGACTGACTCCTGAAAG
CCAAAGCAAAACCTCAGAAGTACTGAAAGGTAGACCCGTAGTCAAAACAGCAGTGCCATT
CTGTATCCTTCCCTTCCACTTCTTTTCTTTTTCTTTCGCAATCTCTCACTTTATACAAC
TTGCTCAAATTCTTTCTCTCTCTTTTTTTTTTCCTGTCTTTCTGAATGCCATAATAA
AGGAGGCTACTGGGGGCTGAGACAGGGACTGGAATTTCCTACCATTTCCTGAAAGGAAGG
ATAAACTCAGTTTTCCAGAGAATGCCTAACATCTGGAAATTACTTTCTTTAGGGCCAGCT
CTTCTTCCCGAGCCCCTGAAGCCTCAGGCCGCCCTTCCTGTGCCGCCTTCTCTTGCGCCA
CCTTCTCTTGCGCCACCTGTTCAGAAGATGCAGGAGCCTCTCATCCCGGTGGCCGCACCT
CTGGCCCAGGCTGCCCTGCAGCCCAGCCTGGAAACGCCCCGCAGCCACCCCCTCGGAGC
AGGTCGTCCCACAGCTTGCCTTCTGAGCCTCCGGCGCAGCCGCAGGTAAGGCCTTCCAGC
GGGGAGAAAGATCATCTGGGTGTGTGTGTGTGTGTGTGTGTGTGCCTTTGCTTACA
TTTTGTTTTGTTTTTCCCTTTTTTTTTTTTTACTGAGGCATATTTGATGCTCTTGCTG
TAGTCTTTGAACATACTTATTTTAATTATTAGCTTTAGAAAAAACACCTAAGATTTGATT
TTTTAAAAAATTTTGTCATTTGCTAGTAATAACATGTTTAGATATGACTTCAACCAGTGA
ATGTCATTTGACCACTCAGACTCATCACACAACAAAAGCACGTTTGGCCGTTTGAGGGTT
TGGGTTTTTGTTTGTTTGTCCAACCTGTTGTCTAGATCACGGGTTCTCAGAGAGTGACC
CTAGATTAGGGCTCTTTCCCTAAAGGCTCTTTTCCCTAAAACTTCCAAGCGGCCCCCACG
CTGTTTACTTTGTTTAAAGAGTAGGTGATTTTTTGGTTTTTCTGTGTGTAATTTACTTT
GGATACTTAATTAGAGTGGACAGTAATAACTTAGTTTCTTTTTGTTCACAGCTATTAGAT
TAGTTTTGTCCTTTACCTCCTGGACAGAAAGGCAGTCAGGTCAATCCCTGGCCATTGGCA
GTAAATTTCCAATAATCCTATCTCTCCTGATGCTGCAGTTAGCTCTTTTCAGTGATGGAG
TCGGCACTGGGCTTCCTTGGGGATCTCTAACAGTTTCAGACACTACTGGATCCATTTAGA
TGTTTCAGGCATGCAGCAGCAGGCTTATTAACCAAAGTAAAAGCCATCAAAATAATGTTC
TCATGAGTATCACATAGAAAATAGTACCATTGCCTTGGTGGGTGGAAATCACAGGATCAC
AGGGACTTTTGTTATACCAGAGTGATCTCACATTGGAAAGCCTTCTGGTGTATATACACA
AAGTTGTTTCAACACAAGAATATTCATGCGAGTTGAATTGTTTTACTTGGAGGCTGTTTT
ACTTAGTTTTATTATATACATCTCAGTAAAATCATTAAAATAAGGTTTATCTTTAGTAT
AAGTTTATCTTTAGTATAAGGTTTATCTTTATATTTCTGTTGTCTAGCCTCACATTGAAT
TTTATCCAAAAGTTTTAACTTGAAAATGCCATCAAGGCCAAAGAACTGAAGTCTAAGTCT
GCTTTTATTTTGGAATAGTCTAAAATACAGAAATATTTACACTGGTGATGTCCCTTAAGCA
TGTTTATAATAATAGTTTGCATTTATTTTACAGATATGTGAATATGTCCAACTAATTGG
CAGAAGTTAGCAGTTTCTTATGCTTCTTCATAGTGAAAAAAGATTATAAAGTAAATATG
AATCTTGAAACAATATGAATAGTTAGCAAAGCACTTACTTATCAGACTATTGGTCACATT
TTTTAAAAGCTAAGACGGATATATAATTGAGAATAATGTTCTCTTAAGCTAATGAACAC
CAAAAGTATTATATAGTTGAGGATGCTGAAGATATATAGTAATTATAGAAGCCCTTCAA
ACAATAAGTGTCCATTATTTTCTCTTTGCCAATCTACTTTTAGTGCATGATGATTTTTTC
TTTTCATTTTCTTATAAGGTGTAGTATTTATTATTATTGTTTTTTAGTGTAATTGGAGGG
CAAGAAACTTTCAAAGAAGCCATCTTAAAGCTTTGTATTACACAGTTTTAGGACAGAAA
GTGATCATGATTTTCACAGTAAAGGTGAACCCTAATTCCTAAAACTCTATAAAATGTTCT
CAGTATTGAAAGTAGGTGTGGTACTCTGAACAACTTCAGAAGAACACACTGTCAAAGAAG
ATTGCAGTTCTCAGTAGAAAGTCATCTTGTGACACAGAGAGTACAGGATGAATATTCCGT
```

*FIG. 1AA*

```
GACTGCCATCTATCATTTTCTTAGGTCATTTTCCCCTGTTTTGCTTTCTGATTTTCATTG
GAATGGGTATGGTGATTTGCTGACGAAGCACAGCAAGCCTGTGCTTTCTGTGTGGTTTAG
TAGATTGTATTCTTGACTCTTACATTCTGCTCATCAAAACTGTGAAAGGTGTTTGTTATA
AGCCTTTCTTTGCCTCAGTCATTGATATCAAATCCCTCTACACATTACATACACAGACAC
ACTTTCCTGGAGAGTGGAGGTCTTGTTCACGTGTAGGCTGCCTTTGTGCAAGATCACAAA
GAGCTTAGTTTCCTCCTGGGAGCTTACAGAAAGATAGGGAGGCATTTTACCTTTTTTGCC
TTTTTCATTTTGAACCATAAAAATAATGCCTATTCAAAAAATAATGAACATCTAAAGTCT
TAAAAATTCTTCTATAATGGCTATAACTTGAAGAGGGTGAGTTAGTAAAATAACTCACAT
TTTGATATTTTGGTAATAATATGAAACAGTCTTAGAATTGAACTTAGTAGTTTTTACAAG
TCTTTATTAATTCTGCCAAAAATATACAAGGTATTTAAAACATAGACCCACACATGACCC
AGCTTTACTTGTTATTACTATTTAAATTATTTGATTCTATAATTCTATATAGAAAGATT
CTTCTAATTCAAGTGATTATATGTTATATATCCTTTAGAAAATGTAAAAATGCCCCACTT
ATCTGACTTTCAATGTCTTAGGCATCTGATTATCAGCTGAAAACCAGAAGTCAGGAATCC
AATGGGAAGTAAAGTAATAGCATCACAGCTATACTATTGGAGTGACAGCCGATAGTGAGG
GAAGAGGCCAAGTAGAAAATCTCAGGACTTCCCTGGCAGTCCAGTGGTTAAGACCCCGTG
CTCCCAATGCAGAGGGCATGCCTTCGATCCCTGGTCAGGGAACTAAGATCCAGCATGCTG
CGCAGCACAGCCAAAAAGAAAAAAAAAATCTCAGCTTTCTGGATCAATTTAATACCAT
CCCCTTGCATCTTAGTATAAACCCATTCCCAGTTTTTATCCAACTCTTACAAAACTAATG
CATCAGGATCATCAGGAAAGGTTAAATTCAGGAGTCTCATGTTTTGTAGTAACACATTTT
ATATAATATAAATATATAATAAATATATTATTTATAAAATAATTTACTATAGAATGGTGT
CTCTCGAATCTGTCTAAGTGAGTTATGGTATTTTAAAATAAGGTAAGCTTTAAATATTGG
GGAAGATTTGTTCAAACTGTTTCTTAAGAATACTGTAATTTTTTAAAGTACTGCTGTTAT
AGAAAGATTGTGATTTCATCTTTAGTATCACCCTTCAGAAAATTTGAGTGATAGATTAAT
AGAACAAGCCTGGATCCTGACCATGTTAAAATAAATACCAGTTTTCACTTTTCTGCAAAG
TGGTGCCATTTTGAACAATTTCTCTAATCATGATAAACCCATAGGCTGTCTTAAGGCTGT
GTCCTAACCTTCTTGGGCTGCCGTAACAAAATACCATGAACTGGGTGACTCAGGCAGTAG
AAATTTGTCTTCTCAAGTTCTGGAGGCTAGAAGCCCGAGATCAGGATGCCAGCATGGTTG
GGTTCTGCTGGGCCTCTTCTCCTGTGCCCACATGGCCTTTCCTTGGTGCTTGCACAAGG
GAAGAAAGAGCAAGCCCTCTGGTGTGTCTCCTACAAAGGGTGCTAGTTCCATCAAGAGGG
CCCACTCTCACGACCTCATCTAACCCCAGTCACCTCCCAGAGGCCACGTCTCCAAATACC
ATCACATAAGAAGGTTGGGGTTCAGCATACGAATCTGAGGGGACACAAACATTTCACCCA
TAGCCTGCTGAAAATACTTCAGTGCTCCAGTAATGTATTTGGAATATTATTTTGGAATG
ACTACTTTGAACTAGTTAGTAATCAACCTCAGATAAAATTAAATCCTGAGCCCTATTACA
GCAATACATTTTATTGTCTCTTGATCTTATACTGTGACCTGCAGGTCTCACTGCTGTTGG
ATTTTGTACATAATATAAAACTGAAAGTGTTTTGAATTGTTAGGGTTGCTGCTTGGTCTC
AGATTGTCCTCCTAACTCTTTCCCTTGATGTCTATGTTTCGTTTTCTCAAAG**CAGGAGCA
ACCATCAGGC**TAACAGGTATCGGATTATTTCTCAATCTTATATGTGCTTCTCATCTGTCT
TAGCACAGTAGATGTATGAATCTTTCGCTTCATACATCTAAATTCTCACCCATTTTTAAA
AACCACCTGTCCACATTAATAAATTCTGTTATCATACCATAAAACCTGCTTTTTTTCTTA
GTATTTTGAATTCTTAGGAACCATTTTAGTTATTCTTGCTAATGCTTTCCCATTTTGCTT
TTTTTTTTTACAAAAATTAACAAGACTAAAAAGTATAACTTTAAGAAGGTAAGCTTTAGA
TATATGAAAGTGTATTTGGCAAAACCAAATTGGTTCGTGGTTTAACAATGGCAAAATTA
TGTAAGTATAAAATTCAATTTTTTTCCTAGATTTCTTTTGGGAAATTAAAAAAACCCAAA
AAACTAGTAGCATGTAGATTATAACTGGAGGCACTAGGAGATTTTTTTTTTTGTTAAAGA
AGAATTGATGATTTACAAAAATGAAAATGAACATTATAGCAGGATTATTTAAGGGCCTTT
CCAACACCCTTTTCTGTAAAAAATACCATCATCATTAATGTCAAGTCATCATAAATACTG
CTTAGATATATAGAAATTCATTCTAATGTAATGAATGATGATGTGGCTCTCATAATTTCA
AATCTCATTGAGCAAAATGATCATGTTTCTGTTAAATTACCTTTAACTTATTTGAAAGA
AAAATTTGTTAATATATGAAAATAAAGATATTTAAATGTGCAACATTTATTTGGCAAAAG
CCTATTATTCTAAGCTGTACAAAGCATAAACTTCCTACCTATAATGTCTGTGTCATGGAC
TCTTTGTCTACCATGGGAGAATCGGGGCCCAGACCCACTCAAGTACTTCTGTTTTGTCAT
```

⌐⌐⌐⌐⌐⌐ Stop Codon

*FIG. 1AB*

```
ATGAATCGTAAATAACCCAGTCATTACTGGTAATGTGTAGCTAATTGTAATTTTACAGCA
TCTATAGTAAATTTGTCTCTCAAGTACTATAATACACTTAGAATACAGTTTAGAATTTAT
GACATGTCTGCTTTTTAATTTTGTTCAAATTTATTGTCATATTAAGTTTGAAGAAAAATA
AAACTTGTTTACTTAAAGTATACTATAGATTAGTTGAATAAAATAGATCCTAGAGAGTGA
TTCACGTAAGAAGTTATCCACACTGTTTCCTTTTGCAAATGAGCAGCCTTCCTTATTCTT
TTTTTTTTTTTGCCACTGCATGTGGCTTGTGGGGTCTCTGTTCCCTGACCAGGGGTTGAA
CCCAGGCCCTGGCAGTGAAAGCAGAGAGCCCTAATCACTGGATCGGAGGGGAATTAGCCT
TCCCTATTCTTAAGCACCAAGTTACTGTTTAAGAAGATGCAATTATGTTTTATTGGAGTT
TCCCAGGCAGCTCAGTGATAAAGAATCTGTCTGCTAAAGAAGAAGACACAGGTTCAATCC
TGGGTCAGGAATATTCCCTGGAGAAGGGAATGGCAACCCACTCCAGTTTTCTTACCTGGT
AAATCCCATGGACAGAGGAGCCTGGTGGGCTATAGTTTGTAGTCGTCTTGTGGGGTCACA
GAGTCAGATATGACTTAGAGACTAAAATAAGAACAGCAAAACAATGTTTTATTGAGACTG
CTGCTCTTTTTCTCAACATATCTTATGAATGTTTAGTTACTTGCTTTAACAATGACCTAA
ATTCATTTGGGTCATGCTGCATTTTGTACATTGCCAAGTCTCTAGCTAAGTAAAATTCTC
CCTCTCCTGTGCTTTTCTTACCTTTAATTTGGCATAAATATCCAAGTCACCCACCTAGTT
TTAACAATTATATAGAGTTTTTTTTTTTTTAATTAAAATGGAGTTCCTGATAAAGCTAG
CTACTTTTCTCGTACAGCCAGGCTTCAGTTCAATGTTTCCCTTAGGAAAGTAGCCTGTGC
CCGGTACCACAGCCGGGCTCCACTCCAGCCGGCTTCTTTGTGAACTGGGCACACAGGGCA
GACTTTTCATAACTGTGAAGTAGGTCTGACCCCTCCTCCTGCCAGTAACTGTTCACAGCT
AGCTCTGCCATGCATAGCTTTATTTTGGTTGAAGAATTACTATCCCAAATAGAAACAGGA
TTCCTCCCCCCACCACGCCATCCAGTTTAAAGAATCATTGCAGTTAGTTACAACCTATCT
AAAGATGAGGAAGGTCAATTAAAAAATATTTTCACATTCAGAATTTATTCTACAAAGGAG
AGCTGACGTTAAAAGGCAAAGAATGCTTTGAAAATTTTATTCTACAAGTGGAAAAGGAAA
TGATGCATTGTCTTCAGCTTATGAATATAGATATACTAATAAAATTATTATCCATAAAGT
TGAATTTCCATAGTAACATTAACTCTCAATGAAAATATATTTCAAAAAACAATGAAACCA
CATCATCATCACAGATGGGTGTTGGAAGTTTATTCATAGCGATTTAGCATAAACTTTGTA
TTGAATGTGAGTTTTTTAAGTTCATTTGATTATCTGATAGAACTGGGCATGAACCAAACT
CATCTGCTAATTCAGTGCAGTTCTCCATTTTACGTATCAATACTTGCATGGATGAAATAA
GTTGTATTTATAAAGAACTTATTTAGCAGAGAGTTTTAAAAAAAAAAAAATTTCATGG
TACTTGTTT*AACCACCAGAGTAACAGACTACAC*AAAGCTCCTTTTTTTATTTTTTGAGTA
TGTATACTTGACCCCTTCAGAATAAAGAATAATTGAGACAGGAAACAGGGGGGGCATTCA
AAGTAACCTTATTGCTTTTTGTTTGTTCTGATTATTCAGTGGGCTCTCTCTTTCCCAGGT
GAAAACAAACGGAGTCTCCGCCGTCAGACTGGACTCGCCATTAAAGAGTGACCCATTTGA
AGACTTGTCATTGAACCTGCTTGCTGTATCAAAGGCTCAGCCATCTGTTCACACCCCAAA
CCCAAGGGGGTTGACGCCGTTGCCTTCTGCAGCCCCAAGTAACACCAACACTCTGAGTTC
TGTAAGCTGCATGCCGACAATGCCTCCAATTCCAGCCCGGAGTAAATCCCAGGAAAACAC
GCGATGTTCCCCAAACCCATTCATCCCAAGCTCAAGCAGCA*CAAATCCTTTCACCGACAG*
GACCGCCGCTCCTGGAAACCCCTTTCGAGCTGAGTCTCAAGAATCAGAGGCCACTTCATG
GTTCTCCAAAGAAGAGCCTGTTGCTCCGAGTCCATTCTCTTCGCTGAGGCCTCTGGATCA
GAACAGTAGCAAGCCTTCATCCTCCCTGGATGGGTTTAAGGACAGTTTTGATCCACAGGG
CCTGTCTGCACTAACAGTCAGCAACCCCAAAGGATGGGTAACCTTCGAGGAAGAAGAGGA
CTTTGGTGTGACAGGGAAGTCAGGGTCCACTCGCCCAGACGTTTTCCTGGGTAAGCAGCT
GAGCTCGTCTCCTGGCTCCAAGGTGATGCTTGGTGATGACTGGGGTAGGAGTACCAATGT
GTCTCTCTGTGTGTTG
                                                Primer 2
            bSYNJ1-C3981T
            Primer 1
```

*FIG. 1AC*

\>ENSBTAT00000003984 cdna:KNOWN_protein_coding  (SEQ ID NO:1)
ATGGCGTTCAGCAAAGGATTTCGGATCTATCACAAATTGGATCCCCCACCTTTCAGCCTC
ATAGTGGAAACCAGGCATAAGGAAGAATGTCTCATGTTCGAGTCTGGGGCTGTAGCGGTG
CTCTCATCAGCAGAAAAGAGGCAATCAAGGGTACATACTCCAAAGTTCTAGATGCCTAT
GGACTTTTAGGTGTTTTACGATTAAATCTTGGTGATATTATGTTACATTATCTGGTCCTA
GTCACTGGATGTATGTCTGTTGGAAAAATTCAAGAATCTGAAGTTTTCCGAGTTACTTCC
ACTGAATTTATATCACTGCGAGTTGATTCTTCGGATGAGGATCGCATTTCGGAAGTGCGA
AAAGTTTTAAATTCAGGAAACTTTTATTTTGCATGGTCTGCATCCGGAGTCAGTTTGGAT
CTGAGTCTTAATGCCCACCGTAGCTTGCAAGAACACACAACTGACAATAGATTTTTCTGG
AATCAGTCTTTGCACTTGCATCTCAAGCACTACGGTGTGAATTGTGACGACTGGTTATTA
CGCCTCATGTGTGGGGGAGTAGAAATCAGAACAATTTATGCTGCTCATAAACAGGCAAAG
GCTTGCCTCATTTCCAGACTAAGCTGTGAACGAGCTGGGACCAGGTTTAACGTCCGGGGA
ACAAATGATGATGGTCACGTTGCCAATTTTGTAGAAACAGAACAGGTTGTGTACTTAGAT
GACTCTGTTTCTTCCTTCATACAAATCCGGGGATCTGTCCCATTGTTCTGGGAGCAGCCA
GGATTGCAGGTGGGATCTCATCGTGTCCGTATGTCAAGGGGATTTGAAGCCAATGCACCT
GCTTTTGACAGGCATTTTAGGACACTTAAGAATTTGTATGGTAAACAAATAATAGTAAAT
CTGCTTGGATCTAAGGAAGGTGAACATATGCTAAGTAAGGCTTTCCAGAGTCATCTGAAA
GCTTCTGAACATGCTGCTGATATCCAGATGGTGAATTTTGACTATCATCAAATGGTTAAA
GGAGGAAAGGCAGAAAAATTACATAGTGTTCTTAAACCTCAAGTCCAGAAGTTTCTGGAT
TATGGAATTTTTCATTTTGATGGAAGTGAAGTTCAAAGGTGCCAGAGTGGTACAGTTCGA
ACAAACTGCTTGGATTGTCTTGACAGAACAAATAGTGTGCAGGCATTCCTTGGTTTAGAG
ATGCTGACTAAACAGTTGGAAGCTCTTGGTTTAGCTGAAAAGCCTCAGTTGGTGACTCGC
TTTCAAGAAGTTTTTCGATCAATGTGGTCTGTGAATGGTGATTCAATCAGTAAGATTTAT
GCAGGAACTGGAGCCCTTGAAGGAAAGGCTAAGTTAAAAGATGGTGCTCGTTCAGTTAGT
AGAACAATTCAGAATAACTTCTTTGACAGCTCCAAGCAAGAAGCAATTGATGTTTTGCTC
CTGGGAAATACTCTAAATAGTGATTTAGCTGACAAAGCTCGAGCCCTTTTAACTACTGGA
AGTTTGCGTGTTTCTGAACAGACGTTACAGTCAGCATCTTCTAAAGTACTAAAGAGTATG
TGTGAGAATTTCTACAAGTATTCAAAGCCCAAGAAAATTCGAGTATGTGTGGGCACATGG
AACGTGAATGGCGGGAAGCAGTTTCGCAGCATAGCTTTTAAGAATCAGACCCTTACGGAC
TGGCTTCTTGATGCCCCCAAGTTAGCTGGCATCCAGGAGTTTCAAGATAAAAGAAGTAAA
CCAATGGATATATTTGCAATTGGTTTTGAGGAAATGGTAGAGCTGAATGCTGGAAACATT
GTGAATGCAAGCACAACAAATCAGAAGCTCTGGGCTGCGGAACTTCAGAAGACCATCTCC
AGAGACAACAAGTATGTGCTGCTGGCCTCTGAGCAGTTGGTGGGCGTCTGTCTGTTTGTT
TTTATCAGACCACAGCACGCTCCCTTCATCAGGGATGTTGCAGTTGATACTGTGAAAACT
GGAATGGGAGGCGCAACTGGAAATAAGGGAGCAGTTGCAATACGAATGCTGTTCCACACC
ACAAGCCTCTGCTTTGTCTGCAGCCACTTCGCTGCGGGACAATCCCAAGTCAAAGAACGA
AATGATGATTTTGTAGAAATAGCGCGGAAGTTGAGTTTTCCAATGGGAAGGCTGCTCTTC
TCCCATGACTATGTGTTTGGTGTGGCGATTTCAACTACCGAATCGATCTCCCTAATGAG
GAAGTGAAAGAGCTTATCAGACAGCAAAACTGGGATTCTCTTATCGCAGGAGATCAGCTT
ATCAATCAGAAAAATGCTGGACAGATTTTAGAGGATTTTAGAAGGAAAAGTGACCTTT
GCTCCAACGTATAAATACGACTTGTTTTCTGATGACTACGACACTAGTGAAAAGTGCCGC
ACCCCTGCATGGACAGACCGTGTCCTCTGGAGAAGACGGAAGTGGCCTTTTGATAGATCA
GCTGAAGATTTAGATCTCCTAAATGCTAGTTTTCAAGATGAAAGCAAAATCCTCTACACA
TGGACTCCTGGCACTTTGCTGCACTACGGAAGGGCTGAGCTGAAGACTTCTGACCATAGG
CCTGTTGTTGCCCTGATCGATATTGATATATTTGAAGTTGAAGCTGAAGAGAGGCAAAAC
ATTTATAAAGAAGTAATTGCAGTTCAGGGTCCACCAGATGGTACGGTGTTGGTCTCAATC
AAAAGCTCTTTACCAGAAAATAATTTTTTCAACGATGCTTTGATTGATGAGCTTTTACAG
CAGTTTACAAATTTCGGTGAAGTTATACTCATAAGATTTGTGGAAGATAAAATGTGGGTT
ACGTTTTAGAGGGAAGCTCTGCCTTGAATGTTCTGAACCTGAATGGGAAGAGTTACTG
GGTAGGACAATAACAATTACTTTAAAAAGTCCAGACTGGATCAAAACTTTGGAAGAAGAA

*FIG. 2A*

```
ATGAGCTTAGAGAAAATCAACGTCCCCTTGCCATCATCAACCAGCTCCACCCTCCTAGGT
GAAGACGCGGAGGTCACGGCCGACTTCGATATGGAAGGTGATGTGGATGACTATAGTGCT
GAGGTAGAGGAGATCCTTCCTCAGCATCTCCAGCCGTCTTCCAGTTCTGCCTTGGCACGT
CCCCCGGTTCTTCACCCCGGACCAGTCCCTGCCAGTCACCTACCATATCGGAGGGCCTG
CCTTCCCTCCCAGTGAGACCAAGTCGAGCTCCGTCCAGAACGCCCGGGCCCCCTGCTTCA
CAAAGTTCTCCTGTTGACACTCTGCCGGCAACACAGCTGCAGCAGAAAGATTCTTCCCAG
ACCCTGGAACCCAAGCGGCCTCCCCCTCCCCGCCCGGTTGCTCCTCCTGCACGTCCAGCT
CCTCCACAACGACCACCTCCGCCTTCAGGGGCTAGGAGTCCTGCACCTGCTAGAAAAGTT
TGGAGGCACCCAAAAGCCCAGGAACGACCCGGAGATAATCTAGGACGCAGCCAGCTTCCA
CCTCAAGCCGGACTGCCAGGCCCGGGACTTGCTGGACACAGTGCAGCCAGACCGATTATT
CCGCCCCGTGCTGGAGTCATCAGCGCCCCCAGAGCCACGCACGGGTGTCTGCTGGGAGA
CTGACTCCTGAAAGCCAAAGCAAAACCTCAGAAGTACTGAAAGGGCCAGCTCTTCTTCCC
GAGCCCCTGAAGCCTCAGGCCGCCCTTCCTGTGCCGCCTTCTCTTGCGCCACCTTCTCTT
GCGCCACCTGTTCAGAAGATGCAGGAGCCTCTCATCCCGGTGGCCGCACCTCTGGCCCAG
GCTGCCCTGCAGCCCAGCCTGGAAACGCCCCGCAGCCACCCCTCGGAGCAGGTCGTCC
CACAGCTTGCCTTCTGAGCCTCCGGCGCAGCCGCAGCAGGAGCAACCATCAGGGTAACAG
GTGAAAACAAACGGAGTCTCCGCCGTCAGACTGGACTCGCCATTAAAGAGTGACCCATTT
GAAGACTTGTCATTGAAC
```

FIG. 2B

FIG. 3

```
bta-let-7b microRNA              3´UUGGUGUGUUGGAuGAUGG*AGU5´
SEQ ID NO:11
bSYNJI mRNA with the C to U SNP 5´    ACGgAGUCU*CUGCCgUCA3´
SEQ ID NO:12 bta-let-7b microRNA              3´UUGGUGUGUUGGAuGAUGG*AGU5´
SEQ ID NO:11
bSYNJI mRNA without the SNP     5´    ACGgAGUCc*CUGCCgUCA3´
SEQ ID NO:13
```

FIG. 5

US 9,049,848 B1

SEQUENCE LISTING

```
<160> NUMBER OF SEQ ID NOS: 15

<210> SEQ ID NO 1
<211> LENGTH: 3978
<212> TYPE: DNA
<213> ORGANISM: Bos taurus

<400> SEQUENCE: 1
atggcgttca gcaaaggatt tcggatctat cacaaattgg atcccccacc tttcagcctc     60
atagtggaaa ccaggcataa ggaagaatgt ctcatgttcg agtctggggc tgtagcggtg    120
ctctcatcag cagaaaaaga ggcaatcaag ggtacatact ccaaagttct agatgcctat    180
ggacttttag gtgttttacg attaaatctt ggtgatatta tgttacatta tctggtccta    240
gtcactggat gtatgtctgt tggaaaaatt caagaatctg aagttttccg agttacttcc    300
actgaattta tatcactgcg agttgattct tcggatgagg atcgcatttc ggaagtgcga    360
aaagttttaa attcaggaaa cttttatttt gcatggtctg catccggagt cagtttggat    420
ctgagtctta atgcccaccg tagcttgcaa gaacacacaa ctgacaatag atttttctgg    480
aatcagtctt tgcacttgca tctcaagcac tacggtgtga attgtgacga ctggttatta    540
cgcctcatgt gtgggggagt agaaatcaga acaatttatg ctgctcataa acaggcaaag    600
gcttgcctca tttccagact aagctgtgaa cgagctggga ccaggtttaa cgtccgggga    660
acaaatgatg atggtcacgt tgccaatttt gtagaaacag aacaggttgt gtacttagat    720
gactctgttt cttccttcat acaaatccgg ggatctgtcc cattgttctg ggagcagcca    780
ggattgcagg tgggatctca tcgtgtccgt atgtcaaggg gatttgaagc caatgcacct    840
gcttttgaca ggcattttag gacacttaag aatttgtatg gtaaacaaat aatagtaaat    900
ctgcttggat ctaaggaagg tgaacatatg ctaagtaagg ctttccagag tcatctgaaa    960
gcttctgaac atgctgctga tatccagatg gtgaattttg actatcatca aatggttaaa   1020
ggaggaaagg cagaaaaatt acatagtgtt cttaaacctc aagtccagaa gtttctggat   1080
tatggaattt ttcattttga tggaagtgaa gttcaaaggt gccagagtgg tacagttcga   1140
acaaactgct tggattgtct tgacagaaca aatagtgtgc aggcattcct tggtttagag   1200
atgctgacta aacagttgga agctcttggt ttagctgaaa agcctcagtt ggtgactcgc   1260
tttcaagaag tttttcgatc aatgtggtct gtgaatggtg attcaatcag taagatttat   1320
gcaggaactg gagcccttga aggaaaggct aagttaaaag atggtgctcg ttcagttagt   1380
agaacaattc agaataactt ctttgacagc tccaagcaag aagcaattga tgttttgctc   1440
ctgggaaata ctctaaatag tgatttagct gacaaagctc gagccctttt aactactgga   1500
agtttgcgtg tttctgaaca gacgttacag tcagcatctt ctaaagtact aaagagtatg   1560
tgtgagaatt tctacaagta ttcaaagccc aagaaaattc gagtatgtgt gggcacatgg   1620
aacgtgaatg gcgggaagca gtttcgcagc atagctttta agaatcagac ccttacggac   1680
tggcttcttg atgcccccaa gttagctggc atccaggagt ttcaagataa aagaagtaaa   1740
```

-continued

```
ccaatggata tatttgcaat tggttttgag gaaatggtag agctgaatgc tggaaacatt    1800
gtgaatgcaa gcacaacaaa tcagaagctc tgggctgcgg aacttcagaa gaccatctcc    1860
agagacaaca agtatgtgct gctggcctct gagcagttgg tgggcgtctg tctgtttgtt    1920
tttatcagac cacagcacgc tcccttcatc agggatgttg cagttgatac tgtgaaaact    1980
ggaatgggag gcgcaactgg aaataaggga gcagttgcaa tacgaatgct gttccacacc    2040
acaagcctct gctttgtctg cagccacttc gctgcgggac aatcccaagt caaagaacga    2100
aatgatgatt ttgtagaaat agcgcggaag ttgagttttc aatgggaag gctgctcttc    2160
tcccatgact atgtgttttg gtgtggcgat ttcaactacc gaatcgatct ccctaatgag    2220
gaagtgaaag agcttatcag acagcaaaac tgggattctc ttatcgcagg agatcagctt    2280
atcaatcaga aaaatgctgg acagatttt agaggatttt tagaaggaaa agtgacccttt    2340
gctccaacgt ataaatacga cttgttttct gatgactacg acactagtga aaagtgccgc    2400
accccctgcat ggacagaccg tgtcctctgg agaagacgga agtggcctt tgatagatca    2460
gctgaagatt tagatctcct aaatgctagt tttcaagatg aaagcaaaat cctctacaca    2520
tggactcctg gcactttgct gcactacgga agggctgagc tgaagacttc tgaccatagg    2580
cctgttgttg ccctgatcga tattgatata tttgaagttg aagctgaaga gaggcaaaac    2640
atttataaag aagtaattgc agttcagggt ccaccagatg gtacggtgtt ggtctcaatc    2700
aaaagctctt taccagaaaa taattttttc aacgatgctt tgattgatga gcttttacag    2760
cagtttacaa atttcggtga agttatactc ataagatttg tggaagataa aatgtgggtt    2820
acgttttttag agggaagctc tgccttgaat gttctgaacc tgaatgggaa agagttactg    2880
ggtaggacaa taacaattac tttaaaaagt ccagactgga tcaaaacttt ggaagaagaa    2940
atgagcttag agaaaatcaa cgtccccttg ccatcatcaa ccagctccac cctcctaggt    3000
gaagacgcgg aggtcacggc cgacttcgat atggaaggtg atgtggatga ctatagtgct    3060
gaggtagagg agatccttcc tcagcatctc cagccgtctt ccagttctgc cttggcacgt    3120
cccccggttc ttcaccccgg accagtccct gccagtcacc taccatatcg gaggggcctg    3180
ccttccctcc cagtgagacc aagtcgagct ccgtccagaa cgcccgggcc ccctgcttca    3240
caaagttctc ctgttgacac tctgccggca acacagctgc agcagaaaga ttcttcccag    3300
accctggaac ccaagcggcc tcccctccc cgcccggttg ctcctcctgc acgtccagct    3360
cctccacaac gaccacctcc gccttcaggg gctaggagtc ctgcacctgc tagaaaagtt    3420
tggaggcacc caaaagccca ggaacgaccc ggagataatc taggacgcag ccagcttcca    3480
cctcaagccg gactgccagg cccgggactt gctggacaca gtgcagccag accgattatt    3540
ccgccccgtg ctggagtcat cagcgccccc cagagccacg cacgggtgtc tgctgggaga    3600
ctgactcctg aaagccaaag caaaaccttca gaagtactga aagggccagc tcttcttccc    3660
gagcccctga gcctcaggc cgcccttcct gtgccgcctt ctcttgcgcc accttctctt    3720
gcgccacctg ttcagaagat gcaggagcct ctcatcccgg tggccgcacc tctggcccag    3780
gctgccctgc agcccagcct ggaaacgccc ccgcagccac cccctcggag caggtcgtcc    3840
cacagcttgc cttctgagcc tccggcgcag ccgcagcagg agcaaccatc agggtaacag    3900
gtgaaaacaa acggagtctc tgccgtcaga ctggactcgc cattaaagag tgacccattt    3960
gaagacttgt cattgaac                                                  3978
```

<210> SEQ ID NO 2
<211> LENGTH: 88096

<212> TYPE: DNA
<213> ORGANISM: Bos taurus

<400> SEQUENCE: 2

```
ggcttgggct tgtgcggctt ctcttcaccg ccgctccccg ccccgggagc tcctgtggtg      60
tcggataatc ctttcccttc tctcactcct aaggagcttt gaatcagccc tgttcacctt     120
ccttcccacc ttcgtctcct ccccgcgcc cccagccca ggggatcggt ttgaagtttc       180
cgaatcgttt tccctttcaa acggcagtga gaaatcccga agcagaaagc tgataaacca    240
ctcccgagcg aaaatagact cattttttt tttcctttt ggtaaacaga aaggggaaac      300
tcatcttaac caaccgttc ttggaacttg gagtgatatg agaaccctgt cttgccttgc     360
tgtgagacca ctttccctct tgcttttcgg taaaaaatta agtgacgact tatcttttgg    420
aataaaccat tctgtccccg agctctctcc gcaccccctc cgctccaccc ccacccccc     480
cccccatcaa aacctagcag gggaggactt cggggtggct tgcagtcctt gctgcagaag    540
gaaacattag ctgtatttgc tttgcttgat tttcacaggg ctgcctccga agaaaggaga    600
atggcgttca gcaaaggatt tcggatctat cacaaattgg atcccccacc tttcagcctc    660
atagtggaaa ccaggcataa ggaagaatgt ctcatgttcg agtctggggc tgtagcggtg    720
ctctgtaagt cttctctctc aacccagctg atcaggatct gtttgcttgc aataattcag    780
attcaacctt ttttttttt tttttctttt tttcaaaaga agattctgat aaccccctca    840
ttgtatttca cctcacaggt catgctttta tttccttta accagacctt attgttttc     900
aaagttttct ttgcctgctg caggttttg atgagggtgg ggagagatgc cagtttgggt    960
acagattttt gctttcttgg gttctgctgc tgcttctaaa agtaaatctt tctttccaaa   1020
aaaatacagt tgcaatgtat agcatatcat gtaaacttgt aaaacagctt gcttgacatt   1080
tttgcagaat gaacagaatt tcttatacct gatatttgtt taatatttt ggaatatatt   1140
atgatgaggc tcttatattt tcattaagaa aattttaaac aacctttaaa atttcatgta   1200
aggtaggtgc ttgatttcat attggttaag aaattatttt gatagtttat tttaaagaaa   1260
aggactactg cagcacagga aaataatag attagtaagg tttgggttat tttgtgggca    1320
gatggatgag attaaaaata taaatattaa tttgaatatt acatttttta gtataagatt   1380
ttgacaggta acttcagttt gggattattt caaatgtgat tattgttaga ggctttcttg   1440
tgataactac ttgttctata ttatgttttt gctatgtagg atcaatttgg atattggtca   1500
tattttaaa agttaaaaat aacatttgaa aggcatactt acaactataa acccatgagc    1560
attaaagttt ctccagattt ggtagggaaa ggctgaagac tgtaatattt atatacagaa   1620
tattaacatg cagaatatta tgatcagtta aacctgatct taatactcaa aaataataaa   1680
attttaccct gattgtggac atagtgacat aatggaaaat cttaagcaaa gaacaaagta   1740
taagaaatac gtattttttg gtaaatacag taacatggtt ttagtgaaca ggaagaggtt   1800
atatgttttc taagaaacaa ttagtagcat gtgttacaat cagtcaggac ttagttcgtt   1860
tacattgtta tttatactta aatcaaccaa actgttgctt gctacagtgt taatttgcaa   1920
agtatgtttc tttgtactac aagtctcata ctgatgaatt ctatctagat caaagactgt   1980
ctatgggaa aaggtttgtc ttagcatatg aaacactttt cagctgcttg tgttttggtg    2040
gtttcctaat ttgtctaaat tctaaatgtt tctttaacgg tgattgttag taatactagg   2100
aagtcgaatt tctggctgca aagtatttat tacctatagg tcaggaagcc taaggataat   2160
cttaattcca aacctccagc agtcctcttt tatgccaaat aatggtttaa aaaaaaagt    2220
```

```
taactcccca gctatccatt ttggcattgc tggcagtgtg ctcagttgtg aatgactctt    2280
ttgtgacccc ttggactaga gcacccagg ctcttctgtc cttgtaattc tccaggcaaa    2340
aatactagag tgggttgcca tttcctactc cagggatct tccccaccca ggaattaaac    2400
ctgcatgtct tgtgtctcct gcattggcag gcttattctt taccactgcg tcatccagga    2460
agcccatttt ttaagttagc gttcatatta agaaaagaa tattaaaaac attgtcttta    2520
ctacttatta actctcttta ttttcattag ctttagactg tatatataag taatggtttt    2580
caggagaaga aaacttcgaa tgttgcctct ctctatagag ctcacataaa tggatattta    2640
attttctgag tatgtcatta gcttttctat tgtaaaattt aatatttaaa atattaatat    2700
ttaagagcta acagaccttt ttataaatca tttgacttgt aaaattgaca ttctagtctg    2760
aatgctacca agatgtgtac tgtgctgtag aatgttcatt tttaaaacct tcactttttt    2820
ttgaatacaa aaaaaaaaat gtacccaggg aattgtgctg ggaaaatact gacttgttct    2880
atttatcttc atctttctta gccctttgaa tttcagtgca tcttgcatgt taatctacca    2940
gaagaatctt ctaaaatcat ttttgatatt aacgaaaat gttacccat ttttcagtaa    3000 gagtaagttc aaactcctca gcctgtcaat tgaggccttc catcatttgg ccccacccca    3060
taattcactg ttgacctcct ttaagggaga ctggtgttac cttagcaccc tcccaaagta    3120
ttgttctttt tccagccctc atcatccttt cttcctggaa tgatggaatg cttttttcta    3180
tctttccagt caaagccagt cagttccagc ttcaggagtc ttcttcttc cagaagaatc    3240 tgccccaccc accccctcct tcttattctt gtctcttcct tccctgaatc ttgtgaactt    3300
tagtctttat cacaaggtga atgcttttttt tgtgctgcct tcattgctct ctgtatgctt    3360
gtatacagtg gtggaagtga tcctagcagg actcagcctt ctggtaccca agtttatga    3420 cttctattgg ctccagttgt ccagctctaa agtttaaaca gttagacatc ttaggccata    3480
catatcgtta aagattagtc acttactttt cttggcatag gccagaagtg ccatgagata    3540
cccaccatga aatgtcgtct ttccaattac tggcatacgt taaaaaatag ggtgcgagtg    3600
aaaatcagtt cctggatcct cttagggctt gggtatccac taatcagtcc agtcctgtct    3660
tcatgttgat aaaaatgtta aatcagtcct gatactacga cttaatcagt cagtgaacca    3720
gtgtctttca gctctggatg cacattacaa tttacaaata gtgatgcctg gctccagcc    3780 agaggttctg atataattag attgcgatga ctgtttctga gcatggttta tgtaggcttt    3840
cttatgatag attatggcat aacttttctg gcttgcagat tttatccaaa aatgaccatg    3900
tttccagaat tttaacgctg tcgttgtcta ctgtggggtc agaatggcac cccactccag    3960
tactcttgcc tggaaaatcc catggtgggc tacagtccat ggggtcgcaa agagttggac    4020
acaactgagc acacacacgt acatggcgtc agtaatgaat tttcttagaa ctcagcctga    4080
accaagtgcc gatgttcccg tagcactttc agtctacggg aacatcacag aacgggaaac    4140
ttgaagtttc tgtgtctcag tgctgcactc cttgagggaa aggcccagat ctcattgtaa    4200
tgtttgtatc cctagtgttt agttcagtat cttacctgta ttgcagaata aatgattatt    4260
aaataagtgg catgggggaa gacttaccta aactatatta tagtattctg tgttgaaagt    4320
gttgtacctt ttcgtataaa attgattctg tatcttttaa agaactgctg gttgaccaaa    4380
ttgctgattt aaaacacata tattaacatg ttgtttggat ttgttactga aaaattctgt    4440
tggaagtttt aactattagc attaactatt aaccacatca ttaaggtttt tctgaaatgc    4500
cagttaaaat ctgtgatgaa tgttgtttat aacttcataa gtacgattaa cagtttgttt    4560
taaaattact tttctatttta ggtagaaaaa cattttgtta tttctttcat tgcatgtatt    4620
```

```
taacaacctt ctgaaacatt cttagataat agttaatatg ctttttagta gcatgctcat    4680 tttagtgtt agtcgttttt taaaattacc agttcagaaa atatattcagt tgaactgaaa    4740 atttggtgtc tgtggagcag tgacccaggg tatcagctgt gactagtata ctgtgctgaa    4800
acagcataag cagcaagtgt gatggtcaac aagttataac actacatatt tcttcttgga    4860
actaatgtaa tgtagtaaga gataaaagaa gacatctgtc agttttgtgt ggagttcagt    4920
ttttctcctc tttatacggt tagacacatg aaaagaccat cacgagggaa ggacaagtag    4980
ccagtcagac agacagatgc ataaaatgca caggctatct tgttgttttt cagcccatct    5040
catgtttctg taaagggaaa taatttgctt tataattgta tcctaaatag aagatggagt    5100
aaagagaagg tcagcccaga ggaaatggag gatgatgctc aaaatagaat ttatgaatca    5160
cctgtttaaa agatggggat gtaaattgtt gatataaatt cctgactctt aaaggagag    5220 cttctgttct ttggtatcac atgctgatgt ggtaggaagg attaattgct tttatctgcc    5280
tagtggcaag attattttca ggccttaact ctggacatag ttttacccca ggctgttagt    5340
ctaagttttt tgtctacctc attttttttc cctctctttt gtcttatcat ggaaacatga    5400
gccataaaac tttaggacag tattctccag atctctgtca cagaacgtga agtgaaactg    5460
catactgtga aggagtcata attgccattt actgaaagtt actctgctag tccaacatta    5520
agctagaggt gcctaaactc tcttgtctca tggcatcttg gggtctcatt aagtttttaa    5580 cagcacccttt aagtcactgt tatgttcatt aagtagttag gtccaaataa taaacattta    5640
catcccaaca actttagtag ctgtttggaa aaaatgatgc caagaaattg aaaataattt    5700
actttgttcg taaataacca caattattta ctcaaagttt ggggtgcctg ctaagcactg    5760
aacagctttt caaaccttgg caccagattg aactgaacag caccacccctc attgcctgtt    5820 ccgcattgac tttggagtgg aagtgttttg ttttgttttg ttttttagtc agagaaacca    5880
ctgaaaactc agctgcccaa agatatgatg tcataaagga atgtactgca atcaaatgtt    5940
aaaaactcta aaccacccta gtgtaatagt ttgggcagtt cttagcatgt agtgagtatt    6000
tccgtgtttc cttccattta aaatatcctt catctctcct gggagtttgc tgaagtgtcc    6060
tggaccttct cagcatagag tttagactgt ggcactagac ttgctttatt tcattaaatt    6120
ctgtgggttg tacttttatc cccatttcga aaaagtggaa actgaggctt ggagagatta    6180
aataactact ccaatgacat agtccttagca tttgcttttt caccgtaatt attatttggg    6240
ctgctgttag ggtggtggtt attgtttggg gggttgagga atgaatagca aaaagacaag    6300
aatgcctata gaattttaaa gttgagtgaa atgggcagca ttttctaacg agggaagtgt    6360
taaacctgct gtgttttgcc tacaaattat tactatataa gggaaaaaac atggtttgat    6420
ttagcattag gtcattaaaa aaccaggttt ctttgccagg ccaagttaaa tgtcagcttt    6480
tagaattttg gatgacaact gtggtaggtg gtgataaaaa gcagtatccg tagttttttc    6540
ttttttttta attgccacat gctaccagtc accatgattg cccttagat aagttacagt    6600 gctttatctt ttttttaagaa aaaatttcaa gctgaaagaa gtgactttt tatagttgac    6660 ttttgctgca cagaaaaatg aattttagac ttgttagata cgactttatg ttagggttgc    6720
aaaatttcac ttttttttctg taaataattt ttggaatgtt catatttaat aaaaaagaaa    6780
gtaaatagca acttttaaat atcaatgctt aaaaaaagaa aattacccctt cctcctccat    6840 cctgggcagc agggttgttc agtggctcag tcgtgtctga ctctttgcga ccccatggac    6900
tgcagcacac caggcctccc tgtccttcac taactcccgg agtttgctca aactcgtgtt    6960
```

```
catcaagtca gtgatgccat ccaactgttt tgtcctctgt tgtccccttc tcttcctgcc   7020
ttcagtcttt cccatcgtca gggactttc  caatgattca tttcttctca tcagatggcc   7080
aaagtattgg agctgtagct tcagcatcag tcctttcaat gaacattcaa gactgatttc   7140
ctttactagc gactgctttg gtctccttgc cgtccaaggg actctcaaga gtcttctcca   7200
ataccacagt tcaaaagcat cagttctttt tttttttttt tttttaaagc atcagttctt   7260
tggtgctcag ctttctttat agtccaactc tcacatccat acatgactac tggaaaaacc   7320
atagctttga ctagatggac ctttgttggc aaagtaatgt ctctgctttt taaagtgctg   7380
tctaggtttg tcatagcttt tcttccaggg agcaagcatc ttaatttcac ggctgcagtc   7440
accatcagca gtgattttgg aacccaagaa aataaagtct gtcactattt cccttgtttc   7500
cccatctatt tgccatgaag tgatgggacc agatgccatg atcttaattt tgtaaatgtt   7560
gagttttaag ccagcttttt cactatcttt ttaccttcat caagaagccc tttagttcct   7620
ctttgctttc tgccataagg gtggtatcat ctgcctatct gagattattg atatttctcc   7680
ctgcaatctg gattccagct gtacttcatt cagtgcagca tttcacatga tgtattctgc   7740
atataagtta aataagcagg gtgactatat acaaccctga tatactcctt ttccaagttg   7800
gaaccagtcc gttgttccat atccagttct aactgttact tcttgacctc tatacagatt   7860
tctcaggagg cagatgaggt ggtctggttt tccattctct ttaagaattt tccacagttt   7920
gttgtgatcc acacaggcaa agactttagc agtcaataaa gcagaagtag atgttttct    7980 ggaattctct tacctttcct atggtctagt ggatgttggc agtttgaact ctggttcctc   8040
tgccttttct aaatccaact tgcacatctg gaagttcttg gtccacatac tgatgaagcc   8100
taggttatcc tgttgttata acataggact catagtagtt cctgggcttc ccaggtggct   8160
cagtggtaaa gaacccgcct cccagtactg gaaactcatg cttgattgct gggtcaggaa   8220
aatctcttgg agaaggaaat ggcagcccac tccagtattc ttgcatggga aatcccatgg   8280
gcttaggggc ctggagggct atagtacatg ggtttgcaaa gagtcagata ccactgagca   8340
actaaacaac aatagtaggt cctaagtgct ttcattttt  gccacttaag tttgctataa   8400
gaaaattaag ggtgaaggca aaatttctgt ctcactgaat agtaaagcct aattatgtga   8460
ccttttaaaa gaatatttat ttatttattt atttgactgc accagttctt agttatagca   8520
tgtggaatct agtttcccga ccagggattg aacctgggtc ccctgcattg ggagttcagt   8580
tttagccgct ggactaccag agaaatccta tgtctcagat tttctaaatt gtccttaaaa   8640
tatagcttaa tggtataaca ggatctagat ttgtcctccc actttatata ataacaacaa   8700
aacaaacaaa aaatgtgaaa cagttgtcag ctcttgaacc ataggcagca caagacactg   8760
atccctgaga gaagggaaac aaatgaggtg attcttgttt gtgggttgct gccttgagag   8820
tttccaggct acaatagcat caggaggaac ccagacaaag cctggcagtc tccccgaatt   8880
gagacagagt agggactttg gggaaactgg gcatctaga  gttctcagga ctgagtacca   8940
gcataaggat atctgcacag agctcctgag atgcatggtg ggttccacgt ggtccctcag   9000
ctgagttctg tttggtacca gtgtgagagg aagctaccaa gactgggaaa gaagcaccca   9060
aaaggagcca gcagaaaaat tcctggtgct cacccaggtc tgggaatagg tcatggtcca   9120
aacagccaga attgagaaag ctgtttggtt tgagcacccc gagagggta  tatattggtt   9180 cattagtggg cccaagttgc tctcaaccac atgctgctct ggtcctgccc aacaggcttc   9240
aaagcaacac ccaaagggat caaactgttt gcaactagtt tccaaatagc tcaactgtat   9300
cacagaacac agtttagcac tgttcacagg aacacaaagt gtatatacat atatccagca   9360
```

```
ttcaaccctg taaatttcac agtgtctggc attcaattaa aaattaccat gcatgcaaag   9420
aagcaagaaa atatgccaca taacgagaaa agtcaatctg tagaaacaga tgctcaaatt   9480
aataagaaca ttaaaacagc tattataaat atactccgta tgttcaggaa cacaagaaag   9540
aatgagcatg ttaaggagag gtatacaaaa tgtgaaagac ccaaatcaga cttctagaaa   9600
tgaaaacagc aatgtctgaa atgaaaaaaa tacactgata gggattaata gattagactg   9660
cagaataaat gaatgacaaa tttgaagatg caataataga caactcaaat gaaacatggg   9720
gaaaaagact taaatagata aacagaacat cagagggctg tgggaaaatc tcaagtggcc   9780
agatatatac acatgggctt ccctgatggc tcagctggtt aagaacctgc ctgccaatgc   9840
aggagacaca agaggtacag gtttgatccc tgggttggga acatcccctg gaggagggat   9900
tggcaatcca ctccagtatt cttgcctgga gaatcacatg gacagaggag catggcaggc   9960
tacagtccat ggggtcgcaa agaatcggat atgaatgaag tgactgagca cacacacatg  10020
tatatatagt tggaatccta aagggaggg gtggagccgg gaaatatttg aagaaattgt  10080
ggctgataat tttccaaagt tgatgaaaac tataaatcca cagatcctag aagctaaatg  10140
aaccataagc agaagaaaca tgaagagaaa gaactacaca tggtcaaatt gcttaaaacc  10200
agtgacagaa aaattctaaa aataatccaa gaaagaaaaa agacatatgt gtagaggaat  10260
gaagacacga atcatgatag acatttcttt agaagcaatt taacctggga cttccctggt  10320
ggtccagtgg ttaagacgcc acacttccag tgccgggaat gtggattaga tccctggatg  10380
agcggctaag atcccacatg ctgtgcagca tgactcaaaa aaagaaaaaa gaaacagtcc  10440
aacccagagg agaaagagct aggtctttaa tgagctgaaa tggaaaaaaa acagaagaat  10500
aatgaaaaaa aaaaaacaa aacaaaaccc aaaacctgtc catctagaat tctgtactcc  10560
atcacaaaga aaggtgatgt aaagactttt tagatgttca aaagccaaaa caaaatgagc  10620
taattatatg aatagcgatt tagattagta ttgcttttct ttatatctag tgccagtatt  10680
ttcagaaatt ctgagtttat aaagactgag tcagttttgt taattgtgta tatgtgtgtg  10740
tgtgttattt gcttagttgt gtccgattct ttgtgacccc atgtactgta gccctccagg  10800
ctcctctgtc tggaattttc caggcaagaa tactggagtg ggttgccatt tccttcaacg  10860
tgggaatctt cccgacccag ggatcaaacc caggtctcct gaattgcagg cagattattt  10920
gccacctgag cctccaggga agcccatttt gttacttagt tatgtttaaa ctctaaactt  10980
gaaagatgca gaaagagtgg aatggactta tgcagttggg gttagctttg taagtagagt  11040
gccagaagga ggtttatctg taaaaaattg tgtcttatgt tttgatggtg acacagttgc  11100
ttgagatttt taatagttgt taataagaat ttgtgtttta tctttttcca ctaaaatagg  11160
ttttgcctgt ttgcctataa tgtaagccat tgttatccct ctgtaatgtt ctacagtatg  11220
agcagagcat tcatgttggc atacatttcg tagccactga actaatagaa ttactgtgag  11280
tgcatttgga gagatgcatt aactctccct cgtcaactgg acactattta attactccca  11340
catttcaggt tgaaagactg tatgtgccct ttacactcct agatgattct gagataactt  11400
aagtcagtta aaagtaaaaa gagggacttc cctggtagtc cagtggttaa gaatttgtct  11460
accaatgcag gggatgaggg tttgattcct ggtcagggaa ctaaaatccc acatgcagta  11520
gggcaagtaa gcctgtgcac cgagactgga gagccagcca ctctagagcc cagcccatgc  11580
accgtaacaa gagcagcctg gcgccctgca ggccatgggg ttgcacagag ccggacgcga  11640
ctgagccact gaactgcgct gaagaccata ggatggggtt cccaggtggc tcagtggtaa  11700
```

-continued

```
agaatccgcc tgccaagcag cagacgtggg ttcgatccct aggtctggaa gatcccctga   11760
gaaggaaatg gcaacccatt ccagtattct tgcctgcaaa atcctgtgga cagagaagcc   11820
tggtgggcta cagtccatgg ggtcaccaaa gggttgtgga cacaacttag caactaaaca   11880
acagcaacag accataggat tactgtagtc tgttgactac cttactgaaa tgtagataaa   11940
caaagtcttt taatatcctg tggttcatat tctaagcata ggcaggatga atcatactat   12000
taagtaaatt cctagctgct ggtacattag tgctcgttag tggtctgtct tggtcagcgc   12060
tagggaagtg acgttggaga atggggtaga aatgtagtta ccagatgtgt agatgttaca   12120
acactgtgtg ggactgacac agagctgggt aaaataatta ctgattgtgg acggcacagt   12180
tgagatccaa cttttttaga ctgagaaaat ggattagaac ctgaaacatg aaaaatgcac   12240
tttccccttg tttaattttt gtgtccattc ctgaaccacg tgctgtgtgt gtagggccag   12300
caggactgct tgggttggac agatgattgg caacaggaga caactttgtg tagttgtctg   12360
agttcccata aagccgctac cagcaggatg ctacatagta aggaagggtt gatggccacc   12420
ttgaccactg tgttccttca aacctgctct tccttcagtc ttctttactc ggggagttgc   12480
cctccatccc cctggctgtt taaaccagaa cttaagaatc accctctacc cctccttcac   12540
tctggtttta cacattcact ccattaccaa atccagtcaa ctcaacctcc taatttcatt   12600
gagaatccat gcagtttacc atttcagctg gttttgcatc agtaatgcca ctgcattctt   12660
tttcatggac cattgtaatt gcctcaactg gtctccctgc ttccactctc cccacccaac   12720
tctgcagtgt ttttaaatat gcagtttact ttttttaatgt tttaaaagtt tgtttatttt   12780
gactgcgctg tgtcttttgtt gctgcgcctg ggtttcctct agttatagcg agcagggcct   12840
attttgttgc ggggcatggg ctctaggcgt gcaggcccag tgggcatggt gcatgggttt   12900
agctgtcctg tggcacttgg aatcttccta gcacagggaa cttttgaccc ctgcattggc   12960
aggtggattc ttagccactg gaccaccagg aaagtcctaa atacacaatt gagatcttat   13020
tcgcctgctc aatacccttc agtggttggc cactgaactt aaaatgcaga gtctttaaaa   13080
tggcctgcag tgaagtggag ccctgccccc ctcctcactc ttacactgta ctgtctcttg   13140
gtttctgtgt tccagccaca ttggcccttt tttaagttat gaatgtctca aattctttct   13200
ggtctcaggg tcttcacata tgctgttgct tctgctcaag atttttatttt taaaaataaa   13260 cttgttcaca catgtggaaa agtacataaa ccataaatgt tcaacttgat gacttattac   13320
agagtgaaca tattaatgtt gccactacca ggttgagaac tagaacatta ttgctggctc   13380
tcctttccaa ttattatctc catcatgata tgcagagatc ataactgcac gattgcttgc   13440
atcatagatt agttctgtct ggtttccaac ttaacataaa tgaaatcatt cagtaagtat   13500
tctcttgcac ccagcttctt tcattcagtg ttaaatatgg gagatcttgc ttgtgatagc   13560
gtatagcagt agtttattca tttttcattgc tatgtagtat tccattgtat gaacgttctg   13620
gtgttctgtt gacattggct ttatttttcaa tttttttctat tacagatgat tctagtatga   13680
acatccttct acatgtcttt cggtgcacat actttaatttt ctctgttgga tattcttagg   13740
aatgaaattt ctggttttag ggtatatgga tgttcctgga acactcttaa cctttactct   13800
tcagatacca actaaaaggt cacttccaca ggcaggcagg caggcaggcc tgcctccaac   13860
aaacaatttt aaattaggtt ctcttgctgc agtctattgg aactccatca ttgtgcttaa   13920
tataattttg cacttgtgtg attatataat gcctgtcttc ccaatggaag gtattagggc   13980
actgactttt tttattcctg gaatagacat tcagtcacaga cttattgcac caatgagtga   14040
aaggttattt tgaaatgtta ctaagattgg ggtgtataat ttatatagaa cactaatttg   14100
```

```
gacagtgggt tatctttcag ctaaaagttt agttatttaa tagtacaaag aaaaccattt    14160
tcttttcaaa taattttttt ctttatgtat gataaaattg aaagaggctt tcttgccagc    14220
tgcttacatg atcttaaatg aatcacttaa cctctagtct ttttcttctg gaatgagta     14280 gcttggcctg tagacctcga ggatcctctg acttgaggct ctctacatgc aaataagcca    14340
accacaaagt gcggtgcatg caacctcagg caaattgtga ttctaggcag ggtatgccga    14400
tttgtcatct tgttttcata ttcttaccgg cttttttcag cttggtcttc tgaatcagct    14460
aaggaaaggt gtctgttccc acctggaagg cttgagccac agtagaaggt tgaccttgga    14520
tggcaggatc ttaactgagt aatgtaatta tttagcttga agtattgtaa ttcatcagaa    14580
gttagaggaa tctacattta aatttaattc agaaatacca tggacgtttt taaagaaatg    14640 acatttttt tttttattac tcaaaaatgc ttcatttttt atttagtttt ctgactctgt     14700
gcttgtgctt tcaacacttt cacaacgatc ttctgctcct ctttaaggaa agcgtgcttg    14760
atcctgtcac ggacacattt agcacacatg gaaccaccat aggcttggct gacatgctta    14820
ttcattttag acaatctcat gagaacttta ggtttcacag cacgaacacc tctaagtcag    14880
cctgggcaca caccacatgc agattttggt tttttcccaa tctccttggt ataaaggtaa    14940
acaactgtat taccagggt tcgggacagc ctggttttgt tagaggctgt attgtaggac      15000
agcctacgat ggtatgtcag acgttgcacc atcctgaatg cctgtagctg ccatccccac    15060
aagaggaaaa aggaagtcct tgcaggttca agaaatgaca ttttaaatta tctgatgatc    15120
ttagatcata agatctaatt ttgcttcttt gggttcagat ggtggggtta ttagcaaggc    15180
gggtatgacc accatgtcac agttatcctg tttattaagc ctctatttag attcataact    15240
caggaaagtc aataaatagg tatatgattg ttttcatctg aatttctgta cctgatcttt    15300
ttttaaaatt tgtttatttt caattgacag ataattgctt tacagtatta tattggtttc    15360
tatcaaacat cagcctgaat gagccatagg tttacccatg tccctccca cttgagcatc      15420 tctcccacct ccctccccct gccacccttc taggttggta ctgagcccca gtttcagttc    15480
ctgagtcata cagcaaattc ccattggctc tctattttgc atatggtaac atatgttcca    15540
tgttactctc tccatatatc tcaacctctc cttcctcccc acagccatgt ccaccagtct    15600
gttctcaatg tctgtgtctc cattgctgct ctgcaaatag gttcatcagt actacctttc    15660
tagatcccat atatatgtgt tagtatacaa tatctccaaa taggaaaagg agtatgtcaa    15720
ggctgtatat tgtcaccctg cttatttaac ttatatgcag agtacatcat gagaaacgct    15780
ggactggcag aaacacaagc tggaatcaag attgccggga gaaatatcaa taaccctcaga   15840 tatgcagatg acaccaccct tatggcagaa agtgaagagg aactaaaaag tctcttgatg    15900
aaagtgaaaa aggagagtga aaagttggc ttaaagctca gcattcagaa aacgaagatc       15960
atggcaccca gtcccatcac ttcatggcaa atagatggga aaacagtgga aacagtgtca    16020
ctttattttt tggggctcca aaatcactac agatggtgac tgcagcaatg aaattaaaag    16080
atgcttactc cttggaagga aagttttgtc caacctagat agcatattca aaagcagaga    16140
cattactttg ccaacaaagg tccgtctagg caaggctatg gttttccag tggtcatgta      16200 tggatgtgag agttggactg tgaagaaggc tgaatgctga agaattgatg cttttggaat    16260
gtagtgttgg agaagactct tgagagtccc ttggactgca aggatagcca accagtccat    16320
tctgaaggag atcagccctg ggatttcttt ggaaggaatg atgctaaagc tgaaactcca    16380
gtactttggc cacctcatgt gaagagtttt ctcattggaa gagaccctga tgctgggagg    16440
```

```
gattgggggc aggaggagaa gggggatgac agaggatgag atggctggat ggcatcactg    16500
actcgatgga cgtgagtctg agtgaactcc gggagttggt gatggacagg gaggcctggt    16560
gtgctgtgat tcatggggtc acaaagagtc agacaggact gagcgactga actgaactga    16620
actgaactga tacaatattt gttttctgt gtacctgata ctatgtttca ttatttgcca     16680
taaattctca tttgaaaaga gaggtataac accagcaatg ctgagtaatg ccagtcacgt    16740
catatgacat agtaccataa aagtaagcca gtcgaacaga aaaggtgttg aatattgtga    16800
tagagaacaa ttggtaggtt aaattttgat agagaacaat tgatctattt atacactgag    16860
tgttttctgt agtctataaa gagatcaaag agtttataaa gctatatata ggtttatagc    16920
ttctattttc attattttcc tgtagcttaa ataggaaatg tagattaggc ctaccttcag    16980
acattaattt gttcaattca aaaactgtga acaccctca gagctaaaat aatgactaaa     17040
attgtaggat atcactagct catggctttg gtagttttaa atacttatta actacttctc    17100
cgatggtagg tgaaggcaac cttatgatct tccaactata actttgacag ggggctcccc    17160
tggtagctca gtgataaaga atttgcctgc aatacaggg gacacaagtt catccccgg      17220 tccaggaaga tcccacatgc tgtgggacaa ctaagtccat gtgccacaac tacgaggcca    17280
caaccactaa gtcacctggg aagccccatc agcataagaa ggactatttt ctatgagaaa    17340
tatgcaaaag atttatgaca gaatactagc aatatatttc atccttaaat attttttgga    17400
gagtatgtgc ttatagcaca tatttttattt tgctttaaat tcttttctgt gacctgattc    17460
ctgttcatat attcagtagg agtagaatcc tagggccttc agataatcaa tcctaatgat    17520
atgagattat acttaaaaat gtaactaaaa ttataaattt acactgaagg tagctcagtg    17580
ttctctggaa atgcacattt gtatttagag tgaagactaa gatttaaagc atgaatgaaa    17640
gatagtttca aacatgagaa gaaagttttt gcctttaaaa aaaaaaatta tttatttatg    17700
gccacatggc ttgtggaatc ttagttccct gacctgggat tgaacccatg cccgctgca     17760 ttggaagcac agaatcttaa ccactggacc accagggaag tcccaagttt ttcctttaa     17820 aataaggaaa ataagagtgg agttaacata ctgttgacgt ctgaagtgta atagcagtaa    17880
cttcagaagc cgggctctga cttgacttcc gtgcttaaag tgtgagctga agaggtgggg    17940
ccttcttact tcagctgaac tgctcaagat cctggctcag aaggacttgg aaaacaatgg    18000
gcttcttggc cattcattca tacctactgg tgtttagaaa ccagtcactt gtaaaaagga    18060
aggcttgact ttcctagcat ttcatttgtt aaatagcaac aacatgaaga ggaaagggga    18120 gaaaaaata cctcttacaa aaatcagtcc gttcccctca tggaaagcac agtggagaac     18180 cttttatca gcaaggcagc acttagggga gaatgagcgg cctgagcttc cgcacagcca     18240
ggcttcctgg actttgagct ctgctcctcc tctcactctg tgtcctccga gctctccgcc    18300
cctgctgcca tttcctgtgc tccatagcgt ggatcctggt ttgcagtcac ctaatggtgc    18360
ccatcttccc catctctact tcaccctca ccacagacat cacattcgaa aattgcctcc     18420
tttactgtga ggaattgtta aacttcaacg atgagggttt tcaaatgctg tcagtggtaa    18480
gatgtaatgt ttatcttctt tgcatatttt tttaaaacta acaaaccatt cccttttatg    18540
cccaaacctc ttttttttt tttggagtta agttttattt ggttcaaaat aaggactgca    18600
gcccaggaca cagtgcctca tatagttcag aagaaatgtt cctctcaatt tattattttt    18660
ttttctgtta gatgaaaatc tagtcagcag ctgcagtgtt cagaggcttg ggttaggtgg    18720
gtatcgtgtt gagatataag taagtaaaac ctagtttcta ttgctattag tagacaagag    18780
atttccttcc agccagagta ctcagggaaa actttaggaa gaaagcagca ttttttggtta   18840
```

```
ggtattgaaa ggtgatgggc ttccctggtg gctcagtggt aaagactgcc tgccagcgtg    18900
ggagaccggt tttgagcccc gatctgggaa gatcgcacat gctgaggaac agctaagcct    18960
gtgcgccacg tctgctgagc ctgtgctttg gagcctgcgg gtcgcagcta ctgagccagt    19020
gcacctggag cctgtgctcc acagcaagag aagtcacctc gatagaagcc tgcgcaccgc    19080
aactgcagag tggccccact caccccaact agaggaaagc cttcacagca acgaagaccc    19140
agcacagcca gatagatcaa tgactaacaa atattcagga tggaaagaac gctgtgaata    19200
aggaaaggga ggtgggggtg aagaacacgg agcctgtagg aggcaagcac attctggttt    19260
tggctgaagc tgggatgcga gggtagagtg ttaaggggac aagaaagatg gggatggact    19320
gagtaaattc gtgacaaatg ctgcgtttta tctaaaggtt atacacgtta ttttaaagcg    19380
ttatggcttt cctattttaa gtgatctctt tatagtagag attctcaaat tgttttctag    19440
aaattaaatt atcagagaaa tggaacaata atttagtcag gtccctccta attatatatt    19500
tctcagtatt tcatggagtt tcataaaata cgggagtctt ttttttcccc tcagttaaaa    19560
aaatacacat atgggaagga aataaaattg aattataagt aattatctta atgccattta    19620
gagatacaga cttcttaatt taggaatatg cacatgtatt tctaacagct attttttgctg    19680 gctacattaa aatgaaaaaa aaaacacatt aaataatgtt acatgtatgg aaaagttgaa    19740
gttcagcaca aaagaatttt cttttttctga actatttgac actattaagt tgctaacatg    19800
aggtaaacag ggtttatctg tttcccctaa atgctttatt ataatatttc ctagaaaggc    19860
attcttctgc ataactacca gataaccgtc aaaaaatgaa catggtacca gctgtccaat    19920
tctcagactc tatttagtt cattagctgt ccgaacaata tctttcatag caaaaagatc    19980
gagttgaatt gtgtatatta tatttagtta tcatgtctct ttagtatcct tagatgtgga    20040
gaagtttccc agtctttgac atttatgact ataaagtgtt atggctttg aaggcgaggg    20100 ccagttgttt ggtagaaatg tccctcactc agaatttgtc tgatggttct tcctgttcag    20160
agtcatgtgg tgttggcagg aatattacag aacagtgtgc ttttcatggt atcctgtcag    20220
ctgacacagt gttgacttgt cccatttact gttggtgttc actctgataa cttgtgttga    20280
tgtggtatct gccaggcgtc actggccagc tcttttttcc tttataatta ataagtgttt    20340
gaaggtgagg tactttgaga ctgtgtatga tcccattgct cttcaaactt aagtttatg    20400 ggtttattca gggatttata atcttttact cttaaaattt gtcttaaaat tgtcccaaat    20460
tttgccagaa gaagaagccc ctttaaggct ggcttctgta tttttgtgac gtgccttaat    20520
tgttctttga acacttgttt actttctggc acaaaaattt gttctagcct tgtcttgccc    20580
ctgctgttct cctggaatca gccatttctc cgtggagtcc tagttccttt tagtggagaa    20640
tgtattagaa agcaagatct gagtgctggc tgtgttgtct gttattgagc attgctgatc    20700
acaggtcctg tcaattgata gagtgaagga aaatgtataa gcgtgtatgt atatgcaagg    20760
gtctccccct ggctcagtgg tgaataatcc gcctgcaggg caggagacac aggaagtgag    20820
gattcgatcc ctggaaaatc ccctagagga ggaaatgtca acccactcca gtactcttag    20880
cagaaaatcc tgtggacaac ggagcctggt gggctatagt tcatggggttg caaagagtcg    20940 gacacgactg agcacaagtg ggtctatgta tttgaaagta taattatgcc cacccattc    21000 tgtctttgtc tgtctctcta gaaaactgag ttcacagtgg taactccagt tccgatcagc    21060
accacagcat ctttttctggt tttctctctg tgtttgtact gcccttttcc gacagtgaga    21120
aacctgctcc gtggttcttg gtcgtccccc tgtgtataac caaccactct cctgttgcca    21180
```

```
ctacagcctc atccacccca cgggtggctt ccttgcccca ctggggctct agcaccctgc   21240
ttggagcctc cgtccaacgc accgtgcctt ctctactctt tcaagctcca gcatcctttt   21300
gcaggccatt cccaccattc ctgggtggac accacccttc ttactccgct cagacttcat   21360
cacctcctgc ccgctgcccc tcccctcaaa tggagtcttt cttccccac ctgtggcttc    21420 aactccatga gcagggacac cttcttactc tccctggact cacagcctgc gaaggacctc   21480
cttccattct accccacacc tttgaagcat aaatgaaaca acagttaatc atctactgtc   21540
ctttagagta aagatattta agaaggaaac actaggtttt cttttataaa attggaagga   21600
tctagaggta aatgttcata tggttctgaa atcgccttca ccagttcact gaacataaat   21660
tactgaactc ctcctgggtg ccaggcactg agctagccca ccggggacag gccagtggat   21720
tagacaaagc cgcttcccte aagaagctgc cttctctgac tgttggagtg tagccagggt   21780
agtaaattag taacctccct aagcctgttc cctcctgtca aatatttgtc actctaaaaa   21840
ataatttaaa atttcattta atattttgag aagaaaccaa aaaattcctg gcagggaaaa   21900
tgacatctca tctattcttt gaatcatttt tctttccttt agcattattt tagttaagaa   21960
tatacacttt aatttaaatt gtgtatgttt gtgtgtgtgt cctgttccct gagtctcaga   22020
atataataca aaagcacaaa taactaaaca gtatgacatt tgttcacctg tttgaatcag   22080
gtgacagtct aatagatggg tcttctttgg gcctgaaaaa catggtagat tcatatattt   22140
ggagcacagt tattgaaaag gtaattatta tgcattatta gaagagagaa gattttgttg   22200
catggtaatt taagttataa aatgactttg tcttttctaa gggaaggtgt atgttagttg   22260
cttaggcatg tctgactctt tgcgacccca tgaactatag cctaccaggc tcctgtgtcc   22320
atgcgacttt ccaggcaaaa atactgaagt gggtggccat ttccttctcc agagggaaag   22380
tgacaactta acactaaaaa tatattttct ttttaaccct attactggta tttgaaccta   22440
aatggttggt gctaaaactg atagatatat ctggtaattt ctatattact gtactagtgg   22500
tagtgtttga aatgcatata acgtgtaaac tctagaatag aatttgccct ggaaaccatg   22560
ccttctatca tcagagagat aacaagcctc tctaaggttt gcttttgtac attttgtact   22620
tacaaggcaa gatgtgggag aaggggttcc tctattactt taaaattaaa aattgtgttg   22680
tgatattttc taacttggag aaggcgatgg cacccactc cagtactctt gcctggaaaa    22740
tcccatggac ggaggagcct ggtaggctgc agtccatggg gtcactaaga gtcggacacg   22800
actgagcgac ttccctttca cttttcactt tcatgcattg gagaaggaaa tggcaaccca   22860
ctccagtgtt cttgcctgga gaatcccagg gagcggggag cctggtgggc tgctgtctat   22920
ggggtcatac agagtcggac acgactgaag tgacttagca gcagcagcat tttctaactc   22980
tgttccttgt cattgaatgt taggagtaac ttctataaat atatagtgta acaaataata   23040
atgataggaa ctctaggaat gaagaatgaa attcacatcg ccataacttt aatggcttgg   23100
tgaaatcgtc ctcactccct aacttcatac aggtggtttg ataaaaataa aggcccaccg   23160
cagtaaagag catgctaaag aagtgtgaca tcatcaggtg gctgagtgag tgactcagtc   23220 ttttttttaat atttatttat ttatttggct gcatggggtc ttagttgcag cattccagat   23280
ctttagttgc ggcacgtgaa cttctggttg ccccacgtgg gatctagttc tctgaccagg   23340
aatcgaatgc cggccctctg cattgggagc ttaggagtct tagccactgg accaccgttc   23400
agtcttagcc tctgctgcca actagcagag cacagctcat tcgacagcag aagtgggata   23460
atcaggaaga agtctaaaag tcagtggtct gaaaagaggt gaggcaggca gggaagatga   23520
gctgtctgga gaaccctgga gacgagcttc gagacaaagg aaagagcttt aatgcagaat   23580
```

```
actatgggat attaggcaaa gcagtagact gagactatgg ccgttttgtt ggcaatagag    23640
atcaacagag aagactgtaa gaatctgctt acaagcgttt gtaaggtgga acacatgcat    23700
attgtcaaaa catattcaat actgtgattc tgtatcagaa tgtaatttat tagaatattt    23760
attagacttt gtaatatact gtattttatg tgcaaatctt tgagaaatga gagaagggaa    23820
aagtacaaga gataagagat aaataaggag tgagccagtc atctaagagg tgaactggga    23880 gctgtgggt aggctgtgga ttagggaggg cagtgaagaa ggaaagaact ggaaggaaa    23940 ggatggaatg aaaaagaggc tcctgtcttt ccagatttgt aggccttaga aggtcatatt    24000
tgctattgta cattgagata ctagctgtgg tttatgtttc tttggttctg tgtccagttt    24060
tcaataagtg tgtttgctaa gaactcggaa ggttttcctt taaagcttca ggatttgttt    24120 ttgtttttc tcaatagaat gaccatcaca gcctgtctaa gggaaattgt tctgtaggtt    24180
gtattcatta gtggatgaca ttaacttcat agcagaagaa ataaatccag acgaaggcca    24240
gactgacaat ttccctgtcc ctgtgcttga ctcatgtggt caagcattac cattaacttt    24300
cataatttaa gcgttagtag tcttccatgc gtcaagctct gttctaagtg tcaacgatta    24360
aagaatgaat aagacaagag ttccaccttc agggaacagg ttggctaatg agaaagacaa    24420
gtgatgaata tattttaaat gttttggcaa catgaagagg gagctctgtg aaattcttgt    24480
gcttagataa ataaaggttt caagaaagtg actttatgtc tttgtttttc taaggtgagt    24540
tcagttttgg ccagaggcaa aagttgggtc aagccttgca ggcagaaagc cagatcactg    24600
tgcaaaggca cagagatgta gaaagtgtgt ttgggcaaca gtgagcgtct catgtgactg    24660
gggcataagg tgcatgggct gtggagggaa ggggagcaat gaggactgaa gcagaaacgg    24720
tgggttgagg ctaaagtctg gaagagtctt tgttaagggg ttgggtgttg tcccgtaggg    24780
atatcaggac gcagtgtgtt cctggtatta agattagcta aacagatcag ggggacagcg    24840
aagaaaattc aaaagcaacc tccaaaagat aggaatatta ttaaagatag taagtacttc    24900
aggatcatta ggcgaggatg gattcatgaa ttgatggtgc tggaataact tgttacttct    24960
ttgggaaaaa ctattaaagt tactggttca aaaaaagatt ttatgcagta catttatgtt    25020
aagaatatca gacttagatt cagactttag attttttggtt gaaactctgg ctttatagct    25080
aaagcgaatc tggtgtttca ggtcctttt cttatactaa agcttttttt tttttttgt    25140 agcatcagca gaaaagagg caatcaaggg tacatactcc aaagttctag atgcctatgg    25200
acttttaggt gttttacgat taaatcttgg taagtattca atataattca atctgttttt    25260
tcatttctgt ttttgtaact ttgaagattt gatagacatt atttcataga ctctgtattt    25320
gatctgtgag tataatcatc tcttaacctt gagatggttg ttgcctgaaa agccatgcta    25380
catgctcatg ctctcatgat tctaaattcc agagacagca tcctgtctga acacttaag    25440 agatagtaac attgttagaa gagaaaaata agggcattgc ccccttttt ttttcttgct    25500 tcagtgcact taaggaaaga tgtcttagaa ccacacactg tttcccctgg tttgtggtgg    25560
aaaagatacc tgttttctac tcaaaacatc tcagcttgag cctgtatgcc attcagtgtc    25620
atcatgggct gcaaagtaac atttgtgatc accagttcta caacagtgtg actcagagtg    25680
tggcccacgg acaggttaca ctccatgaac tgttttgtta gtggtctgga tgagaaaaga    25740
agctggtgcg gtcatgcaaa tcaacacatg gcttccttca ttgataaagt cttactgtgg    25800
agaaaaaaaa agaagtcagc taaaccaaat agagaactta gtgaggcagt tttctcttct    25860
ggagcaagca cctgttctca ctaaactggt aactgaacta gtccatggat agtactttga    25920
```

```
ggagcactgg tcttgtcaaa tggagatatg ccattcgtta tgagtctgtc acacgtaaag    25980
cactgtgtgt gcgtgcgtgc tcactcactc agtcatgtcc gactctttgt gaccatgtgg    26040
actgtagccc accaggctct agtgtccata ggatttcagg caagaacact ggagtggctt    26100
gccatttcct cctccagggt atcttcccga ctcaggggtc aaacctgatt ctcttgcatc    26160
tcctgcattg gcaggcagat tctttaccac tgtgccacct gggagcactt aactagtatt    26220
gccctggatc atcctcacag tccaatgaga tttgctttaa tctcattttc tttttttatt    26280
tatttttggg ccaccctca tggcaggtgg gatcttagtt ccctgaccaa ggatcaaact     26340
tggatccctg cattggaagc agagtcttaa ccattggacc gccagggaag tcccttaatc    26400
ttatttctta aaggcaggat atctcatgtt gcatatgtta acacatgaag ttggttgatg    26460
taataagtag tggagaagcc aagatgcagg gcacttctgc ctatgtcaag cccccacatg    26520
ctcaaagtat accactgctg aattccacct tcatactcac tgcacaggat ttttgtcaaa    26580
attagatgaa aaaaattgct atgaaagttt tgtcagcca aatcacttta taaattgtta     26640
ccaaagactt tttcttcaca tagcagcaac agcagcagca gttcacattt aaatgccatt    26700
ttttcaacct tactgtttat gaaaaactct caattcattg tcttgtctga acttcttaca    26760
atcataaagg aaaggtaggg aagataacac ctacatttta aaaatttgat aaatctcaca    26820
tacttttaag tagaggaata atttcataaa tgtaagatta ttctgttaat gtttaaatgc    26880
ttcatcatac taaatgtatt taacaaggat tttttctccc aacttctgcc aaaatcttgt    26940
tgtgaactta aatgtgtcta tgataaattt aaaataacca cactgtcaga ttttaaaaga    27000
cagagacact agaagaaagt tggaagaaat tttgaatagc ttgtagaata ttggcacttc    27060
ccatcccatt aagtctttgg ttttttgcagg tgatattatg ttacattatc tggtcctagt    27120
cactggatgt atgtctgttg gaaaaattca agaatctgaa gttttccgag ttacttccac    27180
tgaatttata tcactgcgag ttgattcttc ggatgaggat cgcatttcgg aagtgcgaaa    27240
agttttaaat tcaggaaact tttatttgc atggtctgca tccggagtca gtttggatct     27300
gagtcttaat gcccaccgta gcttgcaaga acacacaact gacaatagat ttttctggtg    27360
agtttgtatt acgttttccc ttgtgatcac gtgcagtgca gccactggtg agctggaaca    27420
tggaaggcat aacagttatt tctagagtgg gcaacggtgg gcacggccag ttgagcacac    27480
cactctttac tgttgcggga tcctcagtgg agcatagcag atatctgcca tcgttttatt    27540
aaagtagtcc tgtgacgtga aacccattta ctcttcctga tctagacaga ccttccattg    27600
cagacatata tttaaaatat ttattttaa atcaggaagg aattaatcat aatagaattg     27660
tgttattcat atgtatggtt cttagtttga gatctcatct ctggccacat ttgcctttct    27720
aagcctacat tcccttattg ttttaattgg aaggttgtaa gtaaatgatt ttttttttat    27780
tcaagagcag ccgactacag ggaagtagta tgctggaatc aagtttagta ctgtaataaa    27840
atgggactta agtaggtaac tgccacatat ttcgggatta tgcatgaagg tgctgtatgg    27900
taagtatgcg ttaatggggc agcaggaccc acatgactgt aattggtatc gctttattgg    27960
aacagaccag atttccagta tagtcgttct cttgtccaca gtcagcattg ctgttgactt    28020
ttttccttaa cacaatggac aaattgtatt tcagttgttt acttacgtta taaggccaaa    28080
gtccaggact atgctcacag cttccctcag taattcagac tcggggttc cccactgtat      28140 actttctctc tctcccactt ccactatctg cctgaatggt cctggagaaa ggccctgggg    28200
atcagagggc tcaaagtcag caatgctagg actggaaact acatttagag caataacttg    28260
gtagcttgta gctcccatag aagtgtcttg gcccagagtg gcattgggga gccaagaagg    28320
```

```
cagagggaaa aggggctttg gagcgctgta tctggagact tggagcctag cggagggcga    28380
aaggatggcg gtggggaagg gagggcatag gagagatgag tcggcagtcc catctgctca    28440
tgtcaacccg gcacttctct gatggaagag acactgatgt ttctgaagaa gctgatggcg    28500
ttgcagctgg tcttagggca gctctcctta cctttcttcc ctctgctctt tctaacccca    28560
catttcttag attgagagag aaaagtttct ctgccgtaat caagtccagg caaatgcaga    28620
tgcattggct aaatgccag cagttaagaa tatcacaaag tttaatccgt gggataatt      28680
ctttatctt ttcattcagt tatgggtaga agtgggggcc aatttagata acagattgag      28740
gaggtttatg agctggaaac aggctgagca agaggaggc tgaaatgcta aaggtgagtt      28800
ttgctcactt tatagtcttt aaagctttgc taaggattag agtctggagc ttcactttgc    28860
atagaaaaag gaaagctttt agaattcatt atgccaaccc ttgcagcttt gtagaaatat    28920
ttcccaagat acagccaagt aagttctgta gccagagagt ggcaaacacc tatcccaaaa    28980
gcccatgtag ttttaatcca ttggggattt gaggctgctg ccagttgaga gtcaagtgta    29040
aacttaaata gaattaaaac agcaaggcat tgactgtgaa gaaaaacgaa aactgacagc    29100
agagggagaa attctatctg aacaaataca cggctcccac tgctatttaa atgggggaca    29160
atcagtctgt cctacctctg ctatgatctg ggcctcagct ttggtatctg gatgaactgg    29220
gtcacagcca gtttgagctt tgccagttca gatcaaggta gatattaagt aaagtgtgga    29280
aactgaagtc acgtttttaa attagtaata ttcatcggat ttaacgttat cccaagagta    29340
agcctactac tcactgactt tccagtctgc tttcttcagt ggataagaga ggctggggtt    29400
atatctggtt tatcaggatt acaagtggcc actacctgtt tactgtcccc tgcagcgtag    29460
cctgaagtgg tggggactgg aaagactgct ccaacagcat tgatgtagat tcttaacaac    29520
tctaagcttt caagaaaatg ctgtcacatt gtttttatac ctctttaaga aacaagatag    29580
tgcaaagcac ttaagatttc ctcttaaact ggtagtttga aaactcagag aaccaagctt    29640
caataattct agcaacttcc cttttgtaag gcgcctttat tatctgcaag tcccagagag    29700
gaagttttc tgcacaacag catatttac ttggtggtgg tttggtgagg cgttttggag       29760
gcctgtgttt ccaacctcca gccttccttt ggagaaggaa atggcaaccc actccagtac    29820
tcttgcctgg aaaatcccat ggacggagga gcctggtagg cttcagtcca tggggtcgcg    29880
aagagtcgga cacgactgag cgacttcact ttcacctttc actttgatgc attggagaag    29940
gaaatggcaa cccactccag tgttcttgcc tagagaatcc cagggatggg ggagcctggt    30000
gggcttccgt ctatggggtc gcacagagtc ggacacgact gaagcggctt agcagcagca    30060
gtggttccag cagagcccct gaggcaagca gagggatgtg aagatggcca gtgtagcagg    30120
tccccagccc ccatcccaac gttagccatg acaactccac ttttaatatg ttttctgatc    30180
atcaggtttc tgtgtgttca tttaaacaga actctctgcc ctaaaaagga ttgaaaagta    30240
ggccctctct gttacctaga gtatagaagt atttggagcg ctgggaaaac cctagacagg    30300
cattaatatg gtaattacta gctcatgtaa ctatttaaat ttaattaaaa tggagcctta    30360
taaaagtcaa gccttaagaa aatccatata tatatgaatt ccctggagtt gggtgtggaa    30420
acgcttttgg aacaagtggt aaatacatta tgaagaaaga cataacaaat ggggcccaaa    30480
ttctaaaaac gtagaatatg tgctgctttt gcatggccca ccgatcacac gtccaagggt    30540
ctctctgtct agccctatcc tccagtccct ggcacaatga atgtaagtgg gttgatttcc    30600
ctctggcgcc tctgaagtcc caggggcgct gtcttagaat gcatgttgtg ttgtgcagtg    30660
```

```
tgctgcctgt gctcatcgct cagtcacatc caactctttg tgacccaatg gactgcagtc    30720
catcaagctc ctatgtccat ggaatttttcc aggcaagaat actggagcgt gttggggagt    30780
gctcatcacg ctaatgcagt tctttctttt tctgttagga atcagtcttt gcacttgcat    30840
ctcaagcact acggtgtgaa ttgtgacgac tggttattac gcctcatgtg tgggggagta    30900
gaaatcagaa caatttatgc tgctcataaa caggcaaagg cttgcctcat ttccagacta    30960
agctgtgaac gagctgggac caggtttaac gtccggggaa caaatgatga tggtcacgtt    31020
gccaattttg tagaaacaga acaggtatat agtgttttat cttgcttaat cacaaagaac    31080
aattgcaaag cagatttta tttgattcag aactcatttt gacatctgta atgccatttt    31140
atggttgctc ttggctactt gtgagcctta agaaaggatc ctcaaaaaca agcttattta    31200
ggtatggctc tttgagtaag taacaatttg ttactaatca gcatgacatc atcagtgccc    31260
tatgttttag tattgaattg aaaatcttca gttacagagc tagacaactt aagaaaagtg    31320
ggttttaatg aaattaagtc aaactcaact cttaaaggta ggttgtgtac catctgaaag    31380
gagaagttac attattttg gctataacta tgtaattata aattcaggcc ttgccctcaa    31440
tccagttcaa gtcttcagat tagtttttaa aaattagaaa aagctaaaga aaataacaa    31500 aatgaattca aaaggaattt cttttttaaa agttgtaatg cttatgctta tattttcact    31560
atcggttaat gtttgtagaa ctatcactag ttgaaaaaaa ttcggcttat ttatggccta    31620
ttttgactat tttgttagga taatttgttt atgagagact ggtcaagaga tataactgtt    31680
agtagatttg tcttctgatg tagaggtaac aactttgtgg aagtatttta cccagtattt    31740
ttctctgtag gttgtgtact tagatgactc tgtttcttcc ttcatacaaa tccggggatc    31800
tgtcccattg ttctgggagc agccaggatt gcaggtatgt gttttgacat ttagtttttct    31860 ttcttttct cttcagaact tttcatattt tttaaacttt caggttagct tattagttcc    31920
tcggataatt ttgttactca gtctaataat gttacctgga tttataaata aatagtatac    31980
agaaattgtt tacaaatcct ggaattgtct tagttattct ttccttcagt gttcttcaa    32040 atatccatag gagtgcagct cccatatttc atattaaaat ttcaatgttt tcatggcgtg    32100 ttgatttttca aagtgtttct gtatttacta tcttcgtata taacaattta gcatctgtag    32160
gcagaaaaat gtagtagtta aaacaaagct tctgaaacta agcctctcaa tttgaatcct    32220
tatactgcta ggctgtgtga tctcaggcaa gtgatttaac cccttagtgt ccattttctt    32280
atctgtaaca tggtaatatt agtagttcct acttcttagt ttcttacaac ccttacctag    32340
ttctgaccgc cagaactagg taagggttag ctgaaatggc accccactcc agtattcttg    32400
tggggagaat cccagtccat gaggttgcaa agagttggac acagctgaat gtctgagcac    32460
gtttgttgtt attaatatat ctaggaattt cctggcatgg cagtcagtgg ttaggactcc    32520
atactttcac tactgagggc ccaggctaga tccctggtag gggaactaag attctgcaag    32580
ccatgcagtg tggccaaaaa aaaagagga acatatctgc tgatgaaatt ttactttgca    32640
gtttgtaatg acttgggact tgtcatcttg aacattgttc tctgttttgc tttctgatct    32700 tttcccccc aaactttcct tttgtttagt aaatgtctaa tctttaaaat gtaagatgtt    32760
tttttcacgt tagttcataa tattggattg cccatactag tgtgattttg catttttattt    32820 ttattcaaac atgtttagtc cctaaagtat aagttacatt catttgggc ttctgatata    32880 tactgcctag taaattctgt gcctcagtct atacttatga aaaaaatata caggaaaaag    32940
aaaattttgc cttcatttac tttcatttag ttcacagctg ggtctctctt acactctagg    33000
atggttattg tggagaaaaa ttgcacacca cttgaatctt ttcaataagg gagtttattc    33060
```

```
aagacaggct aagaattaac aaggattaac actggtgctg ctttgctaaa attcttgagt   33120
tcttgtcaac accagtttga gtcatgtggg tttcatcttt ggcattttgg cgtaacttat   33180
atagatatat ttcttcctgt gtctcccttta ggaaagaata ccaaccctac cccatttcta   33240
tttttgtgac cagagaaggg tgtttggaat atttgctcta agaaatttct aaaaccctgc   33300
tttgatggga ggtaaacgct tttggtttag agacaggcta gtgtaagaga ttcttctagt   33360
ctatttatag gccctctgtt ttactgcttt ctgtgttatt ttcttaagtt cagaattaca   33420
gtgtttgatt attcagtaat gttgggtcct gagtagttac atggagggat cctccttgga   33480
tgggacttcc tttcgacgtc cttctttgtt ctgtggcctg tccacacaga taatctgact   33540
ggataatgtc atttgattat gggccgacaa ctgtagattt gaaaattgtg cctttcttga   33600
tagagatagt aattttttgag acctcaagac agtccaacag ttctgccaaa tcatcactga   33660
gctggcctgt catcttgggt tgggttgagg gttgggtcag tggttctgag gtatttagct   33720
tagtagtttt taaagccaac ctttctttga ccagagatgg attagtttca tgagtatctt   33780
ttatcatttt ccccaccact ctaaaagagc agttaataga ggaatgaaaa taatagatac   33840
tgactttttg aaataaaaat accaaggccc taagttcatt tttgacttca agcggttgtt   33900
gggtgtcctg agtgttctta gggctggaat ttatttttcag ggctccttca agttagtcac   33960
ttagtgagct gtttcacttc agtggtcacg gacagtgagt ccttccttgg cagttgtccc   34020
ttgttctctc tcttttcctc catgatacat tcttctcagg ttcttgagct atttttaaagg   34080 aatcttttgag agtgatttta aaatgcagat tcatggcctc aacttcccat caactgaagt   34140
agaatttgtt ggagtagggc caaggaatct gcatttcaac caggtacccc accactcaga   34200
ttagagagct tggcggtagt ggatcctgct cagctgcttt tgcagcgcat ccagactgcc   34260
tgctccagcg gccaaccctg agccaagcaa ggcagccctg tgatgcttaa tcccagtgct   34320
gtctgaggtc ttggactttt cttttcattc ccacttctgt catcttggtt aaggtcttca   34380
tagttttttc ttgcctgaaa gattctcaga tttctaactg gtctcctccc atctttctgt   34440
tgtctaacca acgtattgct gtaagaattg tgaattgtag gtagtttttat atatgtgttg   34500 gggagcaagt aatagggaac aactacagcc attaccaaaa aacaaatatg agaaagcttg   34560
tatttttttt caccttcttg acagttaaga gtactagtgc aagatgaatg ttaatgaata   34620
aacaaaatgc aaagtattgg acttttagag agttagaggg caactacctg agatgactcc   34680
agagaaaaag tatgaacttt gtctgacgtt tctgccgcct aaaatgcaca aacgtgtctt   34740
ggagcacaca cctttcaaag cttaagattt tatacagtct attgtgtact aaaagtaaaa   34800
tgaaataaag atgtgacatt tggctaatca gtttcttact aagaaggaaa agctctaaag   34860
agagtccact gatttctcag gacagtcatt cagtcatctc ggcaggagag ggaatgctga   34920
atgaatgata atactgttaa ttcagtttgg gacatggatg agcatttaga gcttattttc   34980
tggttttatt tgtccaattg catgactgat ctggcacttc tcctccatgc cacctttaaa   35040
gtcacattat tcacagatga gccaggatga attctgggga accttgggcc cacagtctca   35100
gggaggtatt tacaagtgaa actcagggaa ataatctggt ctcactgttg tatttcttct   35160
tggcatcttt tgtatctctt gattctgcct catctctctc ccacttttcc tatatgagaa   35220
aagaaaaact gtagcaacac acagtaggta gttattttcc atcttgttta attcttataa   35280
cccaaatttc aaaatatgct gttgtttag ttgtgtgcct gagagattga cttggaaagt   35340 cttttttccag gaatggttat gggatctttg ggtgagagtg gagtgaatag ggtatttagc   35400
```

```
ataacagaga aaaaaaatat gtagccattg cacttgtcgg cagtctgaaa gagtagatgt    35460
tttggtcagg aggcctgtac tgtcatggga atcattttc ggaatgaatg atgttgctgt     35520
aagaggacag gtttcttcac ttgactgggt ttgttctttt gttgcacgaa tgacaatatc    35580
tgttgactta caaagggcac atatttagaa cgtaagacaa ggtaatgtat atgaaagcac    35640
tcttaaaaat atcttacata aataaaaatt cctgttttta cagtttacca gtttaccagt    35700
gttgcataat gctctaactt ctagtttttt ttttttttaa tgaggttgta ttttaaagaa    35760 taaaaggag aaaccccctag aacttatttt tttaagagaa tatcacaaat gacaattact    35820
gagcttacta ctgtgtgctt agcaaatgaa ttattacata gagtaaacaa tgctatttct    35880
ttcgtctgca tgttggcttt tggtacgatt aagcatattt ttcttatctt aggtgggatc    35940
tcatcgtgtc cgtatgtcaa ggggatttga agccaatgca cctgcttttg acaggtaaga    36000
ctgatgactt ttatatattg ctgtgagttt tgatgttgct aagcagtgag attagttgta    36060
tttactgctt catttcacct tttgggctct taagtaaaat ttcttcttga ctctgattta    36120
agtggaagac agtgacactc ttaggaattc taggagtgat ggcagtaagt gggtaggtct    36180
tgatgtcttg gccttaaaac tacctctgat gggtgtgtta ccaatatgg tggctattag     36240 ctacgtgaag ctagctcttg ggcatttgaa attgactagt ccagattgaa atatgttgta    36300
ggtatataat aggtcctgga tttcagacct agtgcaaaaa aaatgcaaaa tgccaatatt    36360
tgttttatat atcaattaca tgaactaaaa agcctcttga tgaaagtgaa agtggagagt    36420
gaaaaagttg gcttaaagct caacattcag aaaacaaaga tcatggcatc cagtctcatc    36480
acttcatggg aaatagatgg ggaaacagtg gaaacagtgt cagactttat tttttttgggc  36540 tccaaaatca ctgcagatgg tgactgcagc catgaaatta aaagacgctt actccttgga    36600
aggaaagtta tgaccaacct agatagcata ttgaaaagca gagacattac tttgctaaca    36660
aaagtctgtc tagtcaaggc tatggttttt tctctggtca tgtatggatg tgaaagttgg    36720
actgtgaaga aggctgagtg ctgaagaatt gatgcttttg aactgtggtg ttggagaaga    36780
ctcttgagag tcccttggac tgcaaggaga tccaaccagt ccattctgaa ggagatcagc    36840
cctgggattt ctttggaagg aatgatgcta aagctgaaac tccagtactt tggccccctc    36900
atgcgaagag ttgactcatt ggaaaagact ctgatgctgg gagggattga gggcaggagg    36960
agaaggggac gacagaggat gagatggctg gatggcatca ctgactcaat ggacgtgagt    37020
ctgagtgaac tccaggagtt ggtgatagac agggaagcct ggcgtgctgt gattcatgag    37080
gtcgcaaaga gtcggacacg actgagcgac tgaactgaac tgaacatgta gaaatgatac    37140
tttagttgta ttggattaaa taaaatatat gtaaattaat ttgaccttt ggtttttacc     37200 tttttaagtt gccttctgga aaattttaaa ttatatctgt gacttacgtt atatttcctg    37260
tggatgacat tgctctctag cctctggact gattagaagc tggagagact aaaggatcct    37320
ctgtggggcc tatttatctt aaggctggag ctgttcagga gctctgaatc cacacgagt     37380 aggcagtgtc ctcacatgtg aggtgcagcc tagtgccctc taccctcatt gccttgccaa    37440
cctagctgca tggctcctgg tttccatgtc cacccagcat tagcctcagg gtggagaggg    37500
ggccagatga ctctgaaagc cctagcatca gctcagtgca gttcagttgc tcagtcgtgt    37560
ccgactcttt gcgactgcat ggactgcagc acgccaggcc tccctgttca tcactaactc    37620
ctggagctta ttcaaaactca tgtccgttga gtcggtaatg ccatcaaacc atctcatctt    37680
ctgttgtccc cttctgctcc taccttcaat cattccccac atcaggatct tttccagtga    37740
gtcagttctt tgcatcaggt ggccaaagta caaggagttt cagcttcagc atcagtcctt    37800
```

```
ccaatgaata ttcaggactg atctccttta ggatggactg gttggatctc cttgcagtcc    37860
aagggactct caagagacta atggaaaaac caaagctttg actagacgga cttttgttgg    37920
caaagtaatg tctctgcttt ttaatatact gtctaggttg gtcataactt ttcttccaag    37980
gaggaagcat cttttaattt catggctgca gtcaaagtct gtcactgttt ccattgtttt    38040
cccatctatt tgccatgaag tgatggcaaa tagatgataa gttgataagt cagagagaaa    38100
attgcattaa ctgactttc acaaattcag agttttgatt ccacgtgaaa tggatttgta    38160
tatagttttg ccaatcctat gagtttaaaa tactgccatg taggtcctgg ttaaaagtgg    38220
gttcctgttt attgaaaaaa gttttgact tatcacttga catacgctta ctgcctttct    38280
acctttaaca ggcattttag gacacttaag aatttgtatg gtaaacaaat aatagtaaat    38340
ctgcttggat ctaaggaagg tgaacatatg ctaagtaagg cttccaggt aagtgatcat    38400 ttttttcctt ctgttctggc ccatggacac ctaggatagt attttaaaaa taatagtcaa    38460
attcttccag gaataagttc ttcctggaag aagattgaat acttgttgga accattagtt    38520 cttttgaaggc aggtaggcaa caatttaggg taatcttgct gaaattggga ttatagaacg    38580
cttttaaggc attgaccctg ttttctaatc tgcttattta tgtagtggag aagcagaaga    38640
ataccctcct cctaaaaaat gttcatcagt cactggcaga aagataccag gcagtttccc    38700
ccttcatctc ttcattgctt tggctagttc ctacaaacca tagtcactgt tttaaatcta    38760
tgaaattgtg aataaagcat ttgtatacac acaggacttc ttgtaccaat gaaagaaaat    38820
ttgagaattt cacataagta agaacctaaa gaaatgtctg acttctaaag aaaacatact    38880
tttcataaat atttattgga tcaataatga attgatataa attatagtgt tatataaggt    38940 tataaccta aacaaaatgg ctagaaaaca ttttctcacg ttaatgaagt ccaggattaa    39000
ttatttggct attttgtttg aatatcatta ataaacaagt tatactttag agagtgactt    39060
tttattataa gcttttaaaa catttgtata tattgaatga aggtataaaa atgaattctt    39120
caaattttga tgagcttttc cttagaagtc aattactttg ttttgagatt ctataataga    39180
tatagtcatt atatttttat ggtaaaaaat gaaatgctgg ttgttggaaa taacttttca    39240
ttttctaaac caaatgaaaa tgtgaagttc cctgatatta attatgtaag acctaactaa    39300
tctatctgga atagtatagg aggttttagg aaaaggatgc tgtaagatat tagcaagtaa    39360
tttttcattt tactgccaat ggcaatgaaa gaaagctttg tgaaattagt aagatttcaa    39420
gaacctgctt agattttcat ttaaaataaa agttccattt ataacattgt gttgatacaa    39480
tcatatttgg ttaacattta aatgaatatt tccatggtgg ctcaaacggt aaagagttca    39540
cctgcagtgc aggagacctg gttcaatccc tggatcggaa agttcccctg gagaagggaa    39600
tggctaccca cttcagtatt cttttctgga gaattccata gacgggagcc tggcgggcta    39660
cagtctatgg ggccgcaaag agtcagacac aactgagtga ctaacacttt cactttcctt    39720
ggcagtccag tgagtggtta agaatctgca gtttcactgc aagggcgtg ggtttgatcc    39780 ctgattgagg atagggggaga taggggatcc tgcctgccgg atctgtgatt tgcagccaaa    39840
aaaaaaaaac cgaagaagaa ttaaatgaat atttttatttt tattttcaga gtcatctgaa    39900
agcttctgaa catgctgctg atatccagat ggtgaatttt gactatcatc aaatggttaa    39960
aggaggaaag gcagaaaaat tacatagtgt tcttaaacct caagtccaga agtttctgga    40020
ttatggaatt tttcattttg atggaagtga agttcaaagg tttgacttct ctgttttcc    40080 ttttttttaa attggaactt ttctgtagtt atttaatttc tttattatac ttgattttaa    40140
```

```
gcttgttgtt cttctttcta atagtagctt acattactgg gcacgtgcta tgtgtgggtc   40200
aggtagtgca cttagtcttt acaattatta ataacaactg tagggatggg tcacactgga   40260
ggaagtgggg ggctgaaagc tgtcatcttc cccacgtcac gtaagtagaa agtgttagag   40320
ctcgaattca tctagctcca aatctcatgc tgctctttcg gaggctgttc catttctctc   40380
gtaaaattaa tgtcataata tttcttggcc tcagtaaaga ttatttaatg caaataaaag   40440
acatgggtta ttgtctgttc tgctatagaa ctgcgtggtt ataaatctga atgtgtgttt   40500
agctcctgac tactggcctc attaaaaata agtggatgtg gttgactgga gagctagtaa   40560
tagagagtgg acggcaaaat gttaacgctt atagaatctg gatggtgggt atatggatga   40620
tcactgtaaa attctttcat cttttttgtg tgtttgagaa ttatactaga gaattgaagt   40680
ggggagaaag tagatgctac atttaatca gcttaatttt tctcagtttg ttttagcttt   40740
tgttattttg gttttaaatt gcccatttag tttcactgaa tttgtttcag gtgccagagt   40800
ggtacagttc gaacaaactg cttggattgt cttgacagaa caaatagtgt gcaggcattc   40860
cttggtttag aggtaaaaaa atatgtgtat gtaacttaac gtcaaattcc tttttcagtg   40920
cttttgtgat atttatgttt ggcattaatt attttcaca aaatgaagtt aagcttcatt   40980
ttcacaaata aagtttgact tctccttctag ttttttttt tcaagtagtg tcccttttca   41040
tttaaatgtt tcctttatct gttctaaata cttctttag atagcttctg tttccttta   41100
ttgttcatta actttgcctc caaaaaaaaa aagcctgctg tttatactgt tttagtaatt   41160
gtctcgcctg cctgtctttt ggataggcaa aatatatata atatatatat atatatat    41220
attattctca gtattgtaat ttttaaaaaa taatttatt tatctatttt tggctgtgct   41280
gtgttttcat tgctgcgtgg gctcttttc tagttgtggc aagcagggc cactctgctg    41340
ttgcggtgct gggcttctca ttgcagtggc ctcttgttgc ggaacatggg ttccagcgtg   41400
ctcgggcatc agcagtcgca gctcccgggc tctagagcac aggctcaata gttgtggccc   41460
accagcttag ttgctccgca gcatgtgggc tcctcccaga ccaggggttg aacccgtgct   41520
tcctgcgttg gcaggtggat tctctagcac tgagccacca gggaaaccct tgatactgtc   41580
tttttaagac cttttggaat taaggaggat ctatttcac atgtacaacc ctatagaatt    41640
atattttaa caatctaaac cagtacagtt tacatagcat tttttaaaa attgctacaa    41700
aaaccaggat cagttgaaaa atgtcattgt tagaataaaa ctgaatgaga gccaacttct   41760
ctaacacact cttgtttaa aattttgtct ttagtactta cctatcaaac tcagtctaat    41820
ttaggcataa tctcaactat gtgacagact gtgtagcaat acttagattt cccaatcttg   41880
ccccttatgc agctgtcagg gtcataagac tatggtgggt cttcatttag ttctgtagga   41940
acttagcata gttctccaat actgtaaaac caggaataga aagtaaaagg ttcttatttc   42000
ctctagcaaa tgatcttaaa tttggctaga atattggtta attagttact ctgcagctga   42060
gattcattca gtctcaaaag gaaagtacca tgtatagaat ttcctactag aaaaatgtat   42120
ttttgatgta actagatttt actgctttgc cttttttgaa atctgttgtt gaggattatc   42180
attataattt agaaaatatg acagaagaaa agtgaaagca ggcatttgat tactgtggat   42240
tgagttttat gagatatctt gggtttatgt tgagttctct taagtggcta aagacattta   42300
gttagagtaa gcttgtgaaa cacttgaaca tcttcactga acatagaaca agtgttagtt   42360
ttcagaatct gtcttagtgg actacccact gtttgttatt aatattaggt gtgagagtac   42420
ttactcccct agtagcttga ctggttacaa aatatactgc aagtgtaagt aaaagcaaac   42480
tgcttgtagt gaaaaccagt tttgcccagt tctttgaaga aagaggagat gataaaggag   42540
```

```
aacctggagg cttgtttgct ttattctaca tgccagcaaa agaacagccc tggtgtaagt  42600
ctaggcaata ggattagacc cagtatagag ttttttaatat tatttttagtt tttgatccct  42660 gtgtaattat ggataatctc cataatatct ttatcttata gataagataa aaggaaacac  42720
aagtgggaag gagttaagta aaactacagg ggcatagact atgactggat tccaaataag  42780
agaaatagac tgggtaagga ttatacattg ctttgacttt gccagacttt aaggctaaga  42840
gtcattcaga gtaaagactt ctaaacacat atactgtgat gaaggaactg tggtagcccc  42900
aagatcctct cattcttcga atactgtgtt cccctagtt ctcccttatg tactttactg  42960
atacgaattc agtacattca gagctgtcat gactttattc agaaatatga cttatttaaa  43020
aattttgata tcaattcaag agcagctctg ctttttttcat aatctcctga ccttaattac  43080
ccaaacatat agaaccaaat gcaaaaatta aagaaagtta tttctataca ttttttaaata  43140 aagtatgtat attcctctgc tccagtgggt gctgttgcat aattattctt ttaggtgaac  43200
aagataaact agtctgattt ataggaactt tttttttttt tttttttctt attttggccc  43260
cacagcttgt gggatcttag atccccaacc aggaattaaa ctcaggcctt cggcagtgaa  43320
agcagggagt cctaaccact ggactgccag ggaattccct aaaggtttgg gacatttaa  43380 aaagcttaat atcatttaac cagaaaaagt tcttgttact acaaggattg aatactgtag  43440
gtggcattga tgtgatagtt actttagaaa ttggcatggg ggggaataac aaagcctagt  43500
aaacttgaat tttcagaatc cagacccaca acatcctgta acgataaatt tttggtttga  43560
ttctggtagt tcttaaaagg tcacatctta atggatgtat ttatatactt ataaaagttt  43620
cttttctgct attttagatg ctgactaaac agttggaagc tcttggttta gctgaaaagc  43680
ctcagttggt gactcgcttt caagaagttt ttcgatcaat gtggtctgtg aatggtgatt  43740
caatcagtaa gatttatgca ggaactggag cccttgaagg aaaggctaag gtagatctag  43800
attataaaag atcctctttt tttcttcttt aataaagctt taaatgaact cttttaagtt  43860
agtagttttt tttaaggtat ctattttaga attctgtttc atcatgtttt tatgtcctgt  43920
ttattacctc cttctctagt ggatactaat gactgaatgg atagttattt ccctaggttt  43980
gagaggtata ttatatatgt atgacatatt tagttgttta gtgataatct actaggctta  44040
catacgtatt acttacgatt tttttaatga ttttttcactt gcatatgtgt ttttaatttttt  44100 atactgttta ttttaatcag aaaatatgttt ttttttaagc ctttgctttg cctttttttat  44160 ttatttttttt tggtcacaca aggcagcatg tggaccttag ttccttggat cagggatcaa  44220
acccaggccc ctgcagtgaa agtgcagagt cttaaccacc agactgctat ggaattaccc  44280
aaaatatgtt tgtgtttttt taaattaggg ccgtctttgg tggcccagtg gttaagattc  44340
cacgcttcta gtgcagggg cgtggattcg atccttagtt ggggaactaa gatcccacag  44400
gctgcgcagc acaaccataa ttaaaacaaa agttcccgcc tccccaaatg ttactcttgc  44460
caagaaaggg tcttacccta cttgccttttg tgtcccagt gcttgccgca gcacatacag  44520
ttggatagat gggtgacaag cgccggatgg acagataaat cagtgggtac tttatgcaac  44580
accacctatg aacccagtgc tatcagggct gaagttttta ttcttttttct tatcttacct  44640 tgacaaggag gctatcaaaa tgtgcctttg caagtgtgag gtgtggacgt aattatgtat  44700
ctgtatgtca tcattacttt aatttgttgg tattatctac agactgcttc tgcttttagtg  44760 tttgtcccctt actgagggac tttgggtaca tacttgaaat attttttcatt atatccttaa  44820 atattgacct tttatggctt ctggattcag ctgaatttat taatgtacta caaccctaca  44880
```

```
atttctcaaa ttaccccagg aatagaaaca gagacattta ctacttgtat agtttcttac    44940
ttagtctctt cagtatagca gctgaatttc atcatctcaa gtcttctgtt ttccacttct    45000
tcctcttctg tgtctcataa aacgccatgc ctctgttcag aagtattggc cttagctgca    45060
aagttccttt tgttcaactc agaaataatt tgtattgaca tttacaaata tttacttctt    45120
aaatggtccc tgttttgaaa aacctgatgt tgttaaactt tcatgtattc ttttttaaat    45180
aaacaacata attcttgctt ttaaacctga ttctctacaa ctattgctta aaatattctt    45240
ttatgttctg cctctttgtt tctgcaattg actgtctatg tacagaggtt acatatattt    45300
tcagtgatct tttctaacaa actagatatg aaattttatg tattaaatat actagtctga    45360
attgacctga aatctaacat ctgaactgct cttctttttc ctttctctgg gttccttttg    45420
attaattgcc tgataatgtg aatggtgagt cccctttta aaataatgtt atttacattt    45480
gttttatgga aggaaataac attttaagc ctcaaatcct tgttatttct ttgaggaata    45540
aaaattacat attgcaaact aaagttttt tttaactttt ttttaaacag tcatcaaaat    45600
ctgtaagatt aaaatatctt tatggtaact aacacacctg agtgaagtaa acgttcacta    45660
gaagttataa tcagctctct cactgtagga attggcatgc agtttatatt tttatattta    45720
cataggcaaa atgagctaaa atagaaaact gtagtttcta tgttacaggc tagaccttca    45780
ctctcatgct cagttttgtt tctaactaat atcagttact tgggagcaat ctcagtttta    45840
ttctctgctg ttcgtgtgct ttggagtttt tctgagagtg cggacgtgca gtgtgtcctc    45900
ctctatctcc tctgcttctc cccacccgcc ccgtccaccc caggcctgac agtcacaatg    45960
ggagaagtga tctccttgcc ttgagtaagc acatttcagt ctgtttcctc tccagtaaac    46020
agttacacag gtttactgct ctggatgtca tcagtggatg cagctgtggc actgagcccc    46080
ttctgtctcc ctgcagtgct gtgatccaaa agaggaaagg aaacagtgac accttaatgt    46140
gacattttaa tgtgacagtt tgatattcag aatggaatga tgaggtcctt ttactacagt    46200
gaagtcgtat acaacttatc taaagtttca gaatacctat tgagtgaaaa caatgtagaa    46260
tgaaagtcca tgctttttc cccaacaggc tggaaagtta aagatggtg ctcgttcagt    46320 tagtagaaca attcagaata acttctttga cagctccaag caagaagcaa ttgatgttt    46380 gctcctggga aatactctaa atagtgattt agctgacaaa gctcgagccc ttttaactac    46440
tggaagtttg cgtggtaggc gtactttata ttttacttta tgttgtctgt attccttcta    46500
aaagtccaag aggtgaatgt aaacttattt acatatatac tttctagttt gaattgatta    46560
aaatagtttt ttgaaagaat ttctatcatt gtaatttct aaaattccat tctccaaagg    46620
aagtttgatt ctcctaaaat atttatagca ttagcagaat tattaagctg taaactgaag    46680
cccatgcatg ttttctttta tagattatga ttgagggggc aaatgattta aatattgcta    46740
actttattta aggcaagatt tcataaaata ttcaactagt actttcagta ttcagtaacc    46800
tagttatgta gaaagcattg ctttattgaa aaaaaacaat acctgttctg gttattttac    46860
taatcacaac cccagacgtt tctataactt ggtcttactt tttaagtgct gctgtttgaa    46920
taagctttaa atcatattaa taattttaaa atgttgctta ttattggaca ctgtcatccc    46980 caatttaat atttgacata aaatatatgc caggctttca gaatagctgt tgattttca    47040 ctgtgtttct ttaaaaccaa aagaatttga gctcatgtca gtgagcatat taagcaggat    47100
catgggaaaa ctcagtatac attgtataac ttattaaatt agactccctt aattttttt    47160 tttttctat tttagctttc cagcactctg aacattttt tttacttctg ttatccccca    47220 aaagaacccct ttcagttttc cctgttcaac taggagaaat tgttcctcaa ataacctcct    47280
```

```
catgggttat cacttgttat catggattct ttcagaattc tgcgtggtgc tgaaggtagt   47340
taattacatg tcagctcctc agggatctgt gagtagactg ggggactgaa atctactaaa   47400
gctctgaaca ccagaatctg atcatagcta ctgcttttaa cttcaggctt tcttccagca   47460
gtagacactg actcatttgc gtcttatcac ctctttccac ccgtgccttc tttgatatgg   47520
aggcattaat cagcaaccac tgaaagtaag ctattaaagg aaagagaagt gagggacctg   47580
aataattccc agacttgatc attagttttt tagtttcctg cacattttac tatgtgaaga   47640
acgtacccct aaaaaaacag tacagtcaat tctgctatag ctcttatttt aagaatgaga   47700
atttattcca acggggatgc tatgtcagga aaaattgtga gtataacgcc aattctgtag   47760
tagttcatgc atatttcact ggtggtagta gtgctagaga aatgcagaaa gctgtactca   47820
gcggaactga ggtggataga aatatacaaa acacacatat acatgtgcat ggacctctcc   47880
ctccctctgt tcaccaactg tgtgatgagc cagatcctcc catatctggt gtcacagctt   47940
actatctagt ttcggagaag ccttcttcca gcattcacaa ttgctcacaa gcacaggcat   48000
cttcctgctc atttataagc aaacctcaag tcttttttcaa gataaagtac catatgttag   48060
acgtatttgt ccattcctta accgtttaac atgtgtaggg ttctgctact gtttttatag   48120
caggttccta tcttggcaca tcattgctga agtgtttgaa tgttgtgccc aaacccaaat   48180
atttttgcca taaaccccat gcctgtggga atttatacca tcttgcatag ctggtcattg   48240
tgttggaatg tatgtgtttt tttaataact gaactgattg tacctgtcag ctggtgagtc   48300
ccaaaaaata ctccaaggtg tgcattaggg cagtatctgc aatatttcag tgtcctccag   48360
cctcttaggt tttcaggttc gtattctcag aagtatgtgc acttgcacac tcaacagaca   48420
tacatatggg accggcctgg aaagcaggcc tagaaccttc tgattgtgaa actctgcaca   48480
tcactatgtc cccgtaggat ttttcttaga tacagtgggt ttacatcagt tattgtcatt   48540
tattttatct ttggtatcct tcagccatca gaaaaaatgt catcaaacta aatcaaaaga   48600
aaaaaatgaa gctgtctgag aaggttttgt cataacactc gacttcaact gtaacttact   48660
gtgttactaa tgactctttg ttttcttctt gatgcatccg tagtttctga acagacgtta   48720
cagtcaggta cagtatagaa aatcaacctg tcaataaatg caacttttc tcaaattttt   48780 tttaaaaagc ggatgttgta tataaataga gccacaaata aatggaaact ttattttttcc   48840 ctctgattct gacaggataa attgatgctt tgttttaatc taagaaaaag aattttaagt   48900
ttgagaaaac agactacttc atttagaagg agctatgcca agctctttgt cttcttgtag   48960
caagtgctta atttcaatta aatatgggtc atctagtttt aattttactt ttacatttca   49020
gtgaacaaac attattagtg ttatattta cccctttattg ttgtttagtc actaagtcat   49080
gtctgactcc tttgcgaccc catggaccat agcccaccac gttcttctgt ccatggaatt   49140
tctcaggcaa gaatattgga gtgtgttgcc atgtcctcct ccagggatt tcccagctcg   49200 ggggttgaac ctgcatatcc tgcgttgtca ggaggattct ttaccactga gccaacaggg   49260
aagtcctgaa aaaacctag atgtgactct tacagattaa tgggaaatac tacctatgat   49320
gtttacaact actcaatagc acttgtcaca cacataacat tttaaaaag acattgactc   49380 attttctcat atggtgtgtg aaatattttc tgaaactgga agacctgcac taaaatatga   49440
tctgaaatct tttaaaaagc attaagattg ctagcaaagt tagaagagcc aagtgtgtaa   49500
gacctaaagg tcttattttt cttgtcattc cagttcttaa aaatctcata ccttcattct   49560
ctggacaagg tttatgatct tgtctttaaa cttgagtctg tggcaaaagg aactcttgcc   49620
```

```
agaaactttg ctgaaaagac atcttttctt cccttcactt aagatttggt atcacttaag    49680 attttttgttt cacttagtta tttttctgag tgtttttaaga cactgtaggt aagtttttga   49740
gaagatggag gaagagagca cttgtatttta tttttgaatt aacatcatga aatccgtttt   49800
ctgaaatgat atgatatttta ggaatggaca tctgtttgaa cagagacaca tttctttctg   49860
cacattaagg tgccaaccag ttttttttaaa aaagaataaa ctaggaatttt taaaactttt  49920 tattcccatt tataaactga ctttagtagc ttactcaatg tggtacatgg ttttcttcac   49980
acaattcatt gtatgtcttg ctgcatattt taagccatta aataattata gagcttgtgt    50040
tttcatgtag aaaggattgt agaagctgtt ttcatagtag taacactgtc agtgacttcg    50100
attagaaaga ccagtgttga tcagtagtaa tagagaagga ttctttatcc aagttcagcc    50160
aacattcagt taaccatatc aacaggccag aaaaacaatc tgctttcatt ccccccagac    50220
tcggtgcaag taatcagata acagactcag agatgtatac atgtgcccta ggaacagtga    50280
ggatgtgctt gtcacctgaa cctgcagttc ttttgtagga ttcacaagtc agactgttttt   50340 cattctaatc caaaaatgtt atcagccttt ttcactcatt ctttcacaag cttgcttgct    50400
gtaccttggt atccattcca aaaataataa ttaatatcat aataaaataa gatcacctgg    50460
tgagaggtga agatcatttt gatttccgtc tcctcttggc agttaaccac cctttttaagg   50520 gcatattctt tatcattatt aatggattga agtcctagga agtttctatt cactttaagt    50580
gccaggattt gacttaatct aagtgaaatg tggtttagaa ggcagaaagt taggtggaag    50640
ccaaaaagta ggtggagaag agagattgag gattcaaaat gtatttcatg tttattcatt    50700
taaccattgt ttactgaacg ctcagtatgt accgggagaa ggcagtggca ccccactcca    50760
gtactcttgc ctggaaaatc ccatggacag aggagcctgg taggctgcag tccgtggggt   50820
tgctaagagt cggacacaac tgagcgactt cccttttcact tttcactttc atgcattgga   50880
ggaggaaatg gcaacccact ccagtgttct tgcctggaga atcccaggga cggtggggcc    50940
tggtgggctg ccgtctatgg ggtcacagag tcggacatga ctgaagtgac ttagcagcaa    51000
gcagcagcag tatgtaccag gtgctcttct agtctggaga tattggagca aataaaatag    51060
accaaaactt ctatatagca cagggaactt gacttaatga tctgtggtgg ctcaaatggg    51120
aaggaaatcc aaaaaagagg ggatgtatgt atacatgtag ccgattccct ttgctgtaga    51180
gcagaaacgg acacaacatt atatagcgac tatcggggct tcctgtgtgg tgcagcagta    51240
aagaattcac ctgccattgc aggggcaca agagacacgg gttcgatccc taggtgagaa    51300
gatcccctgg aggagtaagt ggcaatgcgc tccagtattc tgcctggaaa attccatggg    51360
cagaggatcc tggtgggcta tggttgaaaa gagtcagacg tgactgagca catacactca    51420
cacatcccaa taaataaata aaatgaaagg atattcattc tgtatgtgtt agtcactcag    51480
tcatgttcta ctttgtgccc catggactgt agccctccag gctcctctgt ctgtggaatt    51540
ctccaggcaa gaatactaga gtgagttgcc atttcctact ccaggggatt ttcatgacct    51600
agggattgta cccgggtctc ctacatcgca ggcagattct ttactgtctg agccacagaa    51660
ctatcatatt atcaagcata tctacttctg gatatatatt tgcatactga agtgggtagc   51720
cattcccttt tccaggggat cttcttgatc cagggatcaa acccaggtct cctgcattgc   51780
aagcagattc ttttaccatc tgagctacca gggaagctcc attcattctg gttccctgc    51840 acaaaaaatg aaaatgagat caaccaacat ttctgcccttt gtggaacttc cattttcggt   51900
gaggggtgac agttaacagg ataaataaat aaaatgcata gtttgtacat ggtaataaat    51960
aaacaccata gagaaaagta aagcagggag gtgatatgga cagtaagaga cagaatgcac    52020
```

```
attttaataa gctgatcagg aaaagcctca cggcagagtt gatgcctgca agcggtgagg    52080
gaatagtgtt gcgagcagtg gaagcagcca gtgcagaggg ggtccagggc cagagcggtg    52140
agcgaacaag gtgggatggc agctgagggt agagaggcag ggcaggttgt ctggggtctt    52200
gtagaacatt ggtgaagacg gtgtcgcctg tgatctggga ggcttttagt aatggcttca    52260
ttctccagca tctcattatt gtccatgatt tgcgtttgtg tcagggagct gttttttcatc   52320 aagctacctg tgagtagtta gagtcctata tgtcatggtt cttgaacatc tttctttggg    52380
gaaaaataac ttatttttac tagcttccga atgaaagttg tctgtaagtc agttgctata    52440
ttccttaaaa tttgcagtct ctgattttgt gtatcataaa atgatgtact acttcactga    52500
aacagaactg ttttgcatgt tttatgttgc tgaattaatt ttgtaatagt ttttttttact   52560 tgggctgttg tacttcacgt agttgatatt ttcaaagtgt gttggttact tgcattgtgt    52620
tgggctctgt gttcaaggct tatctctttt gtgcctgtgc atgtatttga tgcttgtttg    52680
tgccaatgat ggtaattgta ctttctagcc atcatctctc agttatgaag atcaattttt    52740
gtaaatgttt tcacgcaccc aaaattttgt tgtatttttgt ttttaccagc atcttctaaa   52800
gtactaaaga gtatgtgtga gaatttctac aagtattcaa agcccaagaa aattcgagta    52860
tgtgtgggca catggaacgt gaatggcggg aagcagtttc gcagcatagc ttttaagaat    52920 cagacccctta cggactggct tcttgatgcc cccaagttag ctggcatcca ggagtttcaa    52980
ggttggcttc ttacaatatg gattaattaa ccctgactct gatgtattaa cctagaaaac    53040
aaatgcggcg cttcacaata tgcagtactt tataaaagaa acttctatat atacatttga    53100
agcccagcat tcttcttaga gatcaaatct cttcaaatct taggtcttct gtattcatag    53160
acctttctct actacttcat aggaacctat ggtaaagtga gaaatctttt tgttatttga    53220
ttctcagaca atgtaatcca tacatgagta gataactctt ttgtgtgtgg gtttgtgtat    53280
ttattttttt aagatgtgat ttttttttctc ctgtttttat tctttaaact gatgcatagc   53340
aaatttattt tgtgattaag aattttttcaa acctaatgta ttttgttttt caaatagagc    53400
cctttatttg ctaagataag aaatagggta ggtcatgagt aggttacaa aactcatttt    53460 gacatttatt gtccctgtaa cagaacaata ctgattcatc cttgtaaaaa ctcatcactg    53520
agtttgggta ctctaccacc aagctcttaa tagccagtac ttaagctgag gatgcttgta    53580
ttaagatttt taactagaat catggatttg aggactgttt gcttcaactt gaattccttt    53640
ttaaaatggt acacatttac caagtgttat ttatgaagga gatatgtata ggaaatactg    53700
tgagatacag atttttcttt tttagttgcc tttaatcagt cacaccttaa accctgggaa    53760 ttccctaaa cttttactaa aatgctgctt ttcattttac attgaaccta acttgaaatt     53820
gtagctgtag tattaatagt aataacaata ataagtaac agctaacact actattatga    53880
gtacttgaca tctattcatt taatcattat aacagaccta atacatagcc actcttagta    53940
tttcagtttt tagatgagga aactgagaca caggaagaga agtgacacgc ccaacgtcat    54000
gcagctggca gtgacagagc caggatttag ggatggacat ctggcagttt gattctggag    54060
ttgtgccgca ctgcactttg tgtgtgaact tgggcaagtt gcttagattt tccagagcct    54120
cagtttcctg tctgtaaata acaggcagat gtaatctgtc tcgtaaggtg tctgtagtaa    54180
aagagaagat tcacaggtaa gccttgcaca caatagcagt cagtgaatac tttacatttt    54240
ttattcctca gtatttgttc atagtatttta tataagctct ttctcttagc tatttgtccc    54300
gtttctgaat gcttgggcca cccaggctac cctgggcttg cttatctaaa gcagttctgt    54360
```

```
tctcttttgg taagccatgg gagagctaat ggctagaaga gaggggtctg aagccctgac  54420
ttcccatttt cctggattgc ttccacctag gaatttccaa attaaagtgt aaaattccct  54480
ctcagctgtt tgctctaatt tgagttggtt actcgcccac cttattgttt gtgctctttc  54540
tgaaaaattt cttggtggct aaaaaaggag gggatttatg tatacttagg gttgattcat  54600
gttgttgtac agcagaaacc aatacaacat tgtaaagcaa ttatcctcca attaaaaata  54660
aataatttaa aaaaatttta agtaattact tatccatttg gattcatctt ttagcctctg  54720
agaagcggct tgtttctctg ctgtccatgg ttcaaaccat aacaacagtt ctttcaaaaa  54780
tgatttctga aaggacttat cttcaagaat aatagtcttc aagaaaagca aacttaggtc  54840
acctaaatag aaattgaaag taattttgtc cccctcatgg ttttttgcct ttaatttgct  54900
tttggttaaa cttggaacac aaaaatggac ttgtatgaga tctgatgttc gtcttagttc  54960
tgttggggta gggaagttgc cgtttaacta aggccatctt ttaaaaggct ttcttggatg  55020
cttaatttta gataaaagaa gtaaaccaat ggatatattt gcaattggtt ttgaggaaat  55080
ggtagagctg aatgctggaa acattgtgaa tgcaaggtaa gccagccagg taacacacag  55140
ggaaactttc tagttgatga acatggggga caggtaacta agtacttact acaagcatag  55200
atagagataa tatatgtgaa ggtgcttttt aaactgtaat tcaaataata gttctcaaac  55260
ttttttggttt caggtctttc tacactctta aaaatgttga agatcttaaa gaacttttat  55320
ttatgtggtt ttatctcttg atacgtatca cattagaaat tagagacaaa aatttttaag  55380
cattcagttc atttaaaaat aataactcat tacatgttaa cataagtaac acattttttt  55440
tctgaaaagt aactattttc caaaacaaaa atttactaag aaggatggca tcaattgata  55500
gcttgcaaat ctgtttagtc tggtttaaga tggctgggtt ctcacatcta cctctgcatt  55560
agtctgtgta gtgtgttgtt ttgattgaaa tatatgaaga aaatcacata aatacgtagt  55620
tggaaaccaa atatttttag tagccttttt agattttttc ttctctgata atactcagca  55680
aatagtcatt tttggtggtt agttacagtg tggaatctga aaccatagtg atgaactttt  55740
tgtgctcaat tataccaaaa catcggtctg tcttttaccc gtgcgtgatt ttgacacgtc  55800
attcattagg catttggaac atagtagtag taaactaatt atgtagatct ttcagaatta  55860
tgtagatctt tcagattttg atacatgtca ttgtataata tcaaaacata atattggtta  55920
atttcatcac caaattaatt taatctcttc agcaaattct tcaactattg ggaagctgtc  55980
aagatcatag tagcaaatac aggtttatca aaattccccc ttttctttca aaatgtaaat  56040
tttattatta gaaatataca ccataggtca tgtcctttga aaacacaggc atggttgaaa  56100
acatgtttgc cggatagtct aaatttgaat aatcatagtg tgtctgtcac tagttcttcc  56160
aagtaaaaat tgtattctat aaaaaaagtg gcatttcagc tctgacctca gacttgagtg  56220
cttttttctg aaacagccat catgtatgtg ttcagtgtgc agcaaaagtg gttggtttgt  56280
atttttccat tcattacaca gaatataaaa agatgggctt ctaggattga gctttgacaa  56340
aattagtaat gtttactgct tcatcaggat gttcttaggt gaaatggcta ttttttgcttg  56400
gtgttggagg ttcttgggat ttccctgttg gctcagacgg taaagaatct gcctgcaatg  56460
caggagaccc aggtttgatc cctggtttga gaagatcctt tggagaaggg aatggcaacc  56520
cattccagta ttttttgcctg ggaatttcca tggacagagg agcctggagg gctgcagtcc  56580
atggagtcac aaagagtagg acgcatcttg ggcacaaacc tattactctg aaaatgtata  56640
aagagaaaga caagcatttt ccctaccttc tttgtataaa catgtttcat aataactgga  56700
tagttgataa aagttccttta cagaagaatt ccaattcatt acaaatgccc atggaatgct  56760
```

```
gaatttatga aatcaacatg ttgtaacctc tgttggtgga gaaggaaatg gcaacccact   56820
ccagtattca tgcctggaga atcccatgga cagaggagcc tggcagatta tggtccattg   56880
ggtagcagag agtcagacac ggttgaagca acttagcttg gaaccctgt tgataatgga    56940 tctaggcaat gatcatcagt tgatgttaaa accttataga aggatcagtg gaggaacttc   57000
tttataatga gttaattgtc acagtctgaa cagcctatta gatataatat ctcagagatt   57060
acatgcttcc tgctgtgatg caaggctgat tataccacca tgaggttatt tttgccaaaa   57120
caaatcaata aaattgaatc atgcttcttt aattaccagt ttaaaacaaa gctgacagaa   57180
gtgcaaagta tcatgaagac acgtcaggca atctggact gttaaacgtc ctgcagacaa     57240
ataacccagc ttcttaaaac ataaagagca ttaaaaaaga ggatggggca agctgagaga   57300
ccgttaaaga ctgagaaaga cttgaggagg caacaagcac atgcagtgtg tagaccttat   57360
ttggaccttg ttttaaagaa acctactata agaaactttt tttttagata acaggaaaat   57420
gtgaatatga actcagtatt atatgatatt gaggaactgt taatatctaa gtgtgataat   57480
gaccttttga ttacagaaaa ataaaaatcc tgttgcatta gtgatgctta gtaaagcatt   57540
tttgggtaaa atggataatt tttcctcaaa tttgttgtaa atattccaa gattagagaa     57600 aggggtgggg agttatggaa gaagaaagat tggcaaaatg tggataattg ttgaagctgg   57660
ttaatgggta tatggtggtt tattttatgc ttatcttttt tgaatatgtt taaaattttc   57720
cataataagt ttttaaagag atattataat ccatggaaat aagaaaaagg ggaaaattgc    57780
atctggaagc atgttcttcc ctgttatcct aatgaataaa taaggagaaa ataaagcgta   57840
caagcttgag attacttaca cagtgagcac ttatttaata agaaagctca aattttcttt   57900
gtaagggagt cataggatag gcttttgacg tgtgatgttc ttttggctca gttttctgtt   57960
ttcctttttt aaaggagaca aaaacaccca gcccgcataa agatttcact gttggtgtgg    58020
atttcgtgat gtcactaatt ttattaaatt tgggcacata aaggtgtaat tgataattgt   58080
cctacagaaa taggctgtat tactgtcacc gtcttttga agattccctt gttaatattt       58140
tctggtagca caacaaatca gaagctctgg gctgcggaac ttcagaagac catctccaga   58200
gacaacaagt atgtgctgct ggcctctgag cagttggtgg gcgtctgtct gtttgttttt   58260
atcagaccac agcacgctcc cttcatcagg tgagtagaca gatggcgctc cgaaggctgc   58320
ctcctaacac cagataacca aaaggcctgg cgtattttg gcttcagaga aacactgacg      58380
catggttctt gtttctgagt gttcttttt tttttttta attgaagtgt agttgattta        58440
tatggacttc ccaggtggct cagtggtaaa gaatccacct gctaatgcag gagacacagg    58500 agacagggt tcagtccctg ggtcaggaag atcctctgga gaaggaaatg ataacccact       58560
ccagtattct ttcttgggaa attccatgga cagaggagcc tggcgggcta cagtccatgg   58620
ggtcgcaaag agtcggacat gactgtgcat gaacatgcat gatgggtgat agttgattta   58680
aatagtgtta gttcaagta tacaacaaag tgatcagtta tacacttgtg tgtgtgtgtg      58740
tctatctttt taagattatt ttccttata ggttattaca aaaaataag tatagttctc         58800 tgtgctatat agtaggtctt tgttggttat ccattctata tgccctctca ctcgcgcctt    58860 cccttttggta accgtaagtt tgttttctgt gtctgtgggt ctgttctgt cttgtaaata    58920 agttcgtctg tatcgctaag tagtattcca ttgtatttac gtaccacatc ttctttattc   58980
attcatctgt cagcagacat ctaagttgtt tccatgtctt gatattgtga atggtgctgc   59040
agtgaacatt ggggtgcatg tgttttttca aattatagtt ttctccagat atatccccag   59100
```

```
gagtggaacc cctgtatcat gtggtaactc ttgtttaaat atgttcttga ttaaagaatt    59160
gctagtagtt tctctccact atttcacagg cttccctaca aaatgcccat gatgtatagt    59220
gttgtaatta tgtaatagac attcttcatt tcttacacac gcagaactgt tgaaatttct    59280
gatcttggat ttcaaattct tccttttaaa gggatgttgc agttgatact gtgaaaactg    59340
gaatgggagg cgcaactgga aataagggag cagttgcaat acgaatgctg ttccacacca    59400
caagcctctg ctttgtctgc agccacttcg ctgcgggaca atcccaagtc aaagaacgaa    59460
atgatgattt tgtagaaata gcgcggaagt tgagttttcc aatggtaaac tcttgctact    59520
tgttttcgaa aaggaagctt tggaacatat ttcagttcac cccatattct atatcagttt    59580
ttgaaaagtt ggaataactc ctagaaatgt cagcaaatag ataactcctt gtgttattac    59640
tgtggggtta aataaatcga acctggcagg ggtaaggcaa agaaaaagtt gtaaacatt    59700 ttgtgaattg attgtttgga attctgtctc tcttcttcca gggaaggctg ctcttctccc    59760
atgactatgt gttttggtgt ggcgatttca actaccgaat cgatctccct aatgaggaag    59820
tgaaagagct tatcagacag caaaactggg attctcttat cgcaggagat cagcttatca    59880
atcagaaaaa tgctggacag gtatagacat acctaagata cttgcattgg gaagaagggg    59940
atgtctgatt atgaaaacat gctttcccta agttttttt ttttttttt taacaatctc    60000 ttggagtcta tacttaataa gtatgtgcta agttacttca gtcacgtcct tcttgttgtg    60060
acgctaggaa tgtagcccac caggctcctc tgtccatggg attctccagg caagaatgct    60120
cgagtggatt gtcatgccct tctcctgggg attttccaga cccagaggtc aaacctgggt    60180
ctgttatgtt tcctgcattg gctgatgggt tcttcacact agcaccactc aggaagcctt    60240
tactaagtat atatatctat agtttgcctt ctctttttaa aaaaaggaaa aggaaggaa    60300 aacttataat aatttccagg aggaaaagta tatcatgtct ctataaaatt caccttcaag    60360
tagaagaaga ttcttttttt ctttcagcag tagcaaattt aagatcttac tcatcaaggc    60420
tactgctgtt tggctcataa gatcctatgg taatctactt tcattttttg ttacttattt    60480
atggccatgc tgtgtgatat gtgggatctt agttccctga ccagggatcg aacctgcacc    60540
ttgccctgca ttggaagcgc aggctcttaa ccactggact accagagaag tccttggaag    60600
aatttatttt aaaaaaattt ttaggaagag gtgattgagg ccacttgata tagtaccttt    60660
ctgatcatca gacttaaatt ctgatggata ccatgtaacc ttcttaggcc ccagttcctg    60720
ttgagaataa gacatcacac aatgtgattt ccaaaatccc atacagttct aaacgtttga    60780
tactgctcaa aagtctggtg gaagttcatc gttccagttt ttgtactttg tttactcaga    60840
catcaagtga gtgagatgat aaagcccgca tcctaggtca ttttgcctta agctctgttc    60900
cattcagtta gaagtgttcc tcagaggcac atagatttca cgagtctcta gcacataata    60960
gacatttagt gcatgactgc ccgaatgaaa acagaatgtt tttgcctttt tgaaataact    61020
tcctttatgt atgtttattt tagattttta gaggattttt agaaggaaaa gtgacctttg    61080
ctccaacgta taaatacgac ttgttttctg atgactacga cactagtgaa aagtgccgca    61140
cccctgcatg gacagaccgt gtcctctgga gaagacggaa gtggcctttt gatagatcag    61200
gtggacatcg tcatttaaat aagtcaatgc aaattttaca aggaagaggg gaatgatata    61260
aatgccaaat aaggccaaga ggactacatt ttttttttct cagcataggt tatctagaat    61320
aaaataaata taattcaaat ataaaactta aaaaattct cagacctgct tataataaac    61380
actttgattt ttcaatctgt tttctttcag tgaaatagtg tcatataaag aaaagcaagg    61440
aaaaacattt ttatgcaatt aacaactgaa tactaagtaa gatttctaac tggaataact    61500
```

```
caagtggttt tgcaaatatt ttgaactgct acttgtctgt tcagttattt gtaaaactct   61560
ggtcatgaag tctcagaagt aaaggctcat tgtagtttta actaagtaaa gcataatatg   61620
atgacctcac caaaaaaccc tgacttaaca gagtctagac ttcatgccca tcagcaagtg   61680
tgtctgatgt cccagcctca ggcaactgaa gctagtgaaa tgaaggatct cctgtggtct   61740
gtcatgctca ggtgacttcg cctgtgttct gttttattct gactgcagct gaagatttag   61800
atctcctaaa tgctagtttt caagatgaaa gcaaaatcct ctacacatgg actcctggca   61860
ctttgctgca ctacggaagg gctgagctga agacttctga ccataggttt aagcaatctc   61920
tgtatttcta atcatgcttg aaatttattt gaaatacatc atttctgtaa tgttcctaac   61980
atgtctccat tccttcatgc tgaaggcctg ttgttgccct gatcgatatt gatatatttg   62040
aagttgaagc tgaagagagg caaaacattt ataaagaagt aattgcagtt cagggtccac   62100
cagatggtac ggtgttggtc tcaatcaaaa gctctttacc agaaaataat ttttcaacg    62160 atgctttgat tgatgagctt ttacagcagt ttacaaattt cggtgaagtt atactcataa   62220
ggtgagtaac gtaaaaaaaa aaagcaactc atgattcaca aataatatct tctgtattaa   62280
aagttacctt tcttagtatt tgactagtat gtgagtattt gtggaaattc cctggtagct   62340
cagtcagtaa agaatctgct tgcagcgcca gagacctggc ttcagtccct gggttgggaa   62400
gatcccctgg acaaggaaat ggcaaccctc tccagtattc ttgcctggaa aatcccatgg   62460
acagaggaac ctggcgggct aagtccatgg gattgcaata gtcagacatg atttagcaag   62520
taaaccaccg tgaatatttg tatcttcaaa ctaaaagaaa atcatgctat agaaatatta   62580
ttcaaaaaac ccatgggttt tgaaactgga ctctctgctt agaaaattta agttgagta    62640 gtgaaacttc acgtgaacat ctgatgacaa aaatacgtgc acatttagat atgttctctc   62700
cagatttctg tacactataa catggaagcc ctgtggaaaa gtgaacatgt gatattagta   62760 ttttagttttt ttgaggagtg atagaagtaa agcagaatga cttttctgcc ctccatttaa   62820
gacattagat gttctcagta atttttaagtg atttgatttc cgtctgatgg aggagcggcg   62880
ctgcccggca cacagttagg agtcatcctt ccctgccttg gtttccggca ctgacttaac   62940
catctgcctt ttgcagaacc agatgcctct tgcgttgttg aaataaatgt tctcttccca   63000
gtgtacagca gttttgacaa actgaataac atgtgtttga atttcatagg gaagaggtac   63060
tattaaattc ctttctgtgc tgtttcatgt gtttattgag ggatgtttca tagctgttta   63120
gtgggcaagt ctctatactg ggtgctctgg cagacagggg aggaatcgaa gattcagttc   63180
ctattcggaa tctaagaaag ataagcgtgt gtgtaatggc ttccttaggt gtttaccgga   63240
acagcccaca gaatgaagat ggcttggttt cttgcagggt gagaagcttg cctgagaagc   63300
ctcctctcct ttctgagagt aaatgggcaa atagagaaga aattatattt agacttacct   63360
caaattgttt gacaaagatc taccctacag gtttaaaatg aaacaaaaaa cctctagaga   63420
tttaagactc cagcaagtac atggtgaaat tcccaatga cagtaagcgt tgccaagtac    63480
agaaacaccg aaccactggg agcatcatgt ggactgtgtg agtgggcagc acagagcagt   63540
taagtgttct tgcgagcaag tgtgaactct tgctcagagt ttacaatact tttcaatg     63600 ataacaagca ttttggggaa agcttttggt tgcaatttaa cactgtcagg ggagtgggta   63660
attttccttg gttctatttc gacacaacaa aaatttgagg cgacggatat taaagcccctt  63720 ggcgcatcac agctctcgga tagtattaca gctcccttgg ttttatttag aaaataaagg   63780
aagatacatc cttgaggcat gagggcatgc caacgcaaaa gacaggacga gaaaagagaa   63840
```

```
agcgagcact ctctctgggt gagagagaac ccatagtgta cataaggaag gaacgactga    63900
cgcagggata ggaccttcct gcctttttc  tagtctctaa agagcttggt gttattaggt    63960
agttaagaat aggaaaaagg agtccagaat gatggtgatt aaaagacaag ggaaaagctc    64020
ttgaaaatag gacagaagaa ggtctgagga ccggagtgag gacctcaggt agaacaaaca    64080
gcactcctgg ctagccccgt ttacgtaggg caggcccaga gggagaaaaa aacatataaa    64140
aagaggagcc aaagggctgg gggtctctcc cacgcgtgca cgctcattgt ctctctctgt    64200
ctcccacgct tgctcgctct cttttctcat cccgtctttt gggtcgggtc agcatgccct    64260
catgcctcga ggttgtatct tcctttattt tctaaataaa actgtgggag ctgtaacact    64320
gtctgagatc tgtgatgtgc caagggcttt aacgtccatc acctcaaatt tttgttgtgt    64380
cgagacagaa ccgaggaaaa ttacccactc ccctgacagt attaaattgc aaccaaaagc    64440
tttccccaaa atgcttgtta ttattggaaa aagtattggt aacagaacaa gtactggtaa    64500
caaaacaagg gtaatgttat gctgacgtta taaaaccatg tggtacctcc taacctagaa    64560
tattctgatt gttccacctt aagaccacca aggtagaaca gacaggggag acactgaaag    64620
taaagaagga caggaatact gtcccctgtc acctgtaggc taaactgatc atcaccttca    64680
gctctagaat aagccaactg ttagggaatg actgaagtca tcatatgtaa attatatgta    64740
aataagagat ttcctggaaa tgtagatggg gcaggctact tatattaatt gggggggaag    64800
tctagaatgc ttctatccta ttgagtaaaa ataggaaaaa agtacaacac acatttggag    64860
ttccgcaggc ccattccttc tgacagacag ttttagtaac actgtattgg gttgacaaaa    64920
aacatcgttt gggtttctcc ataccttcca aggggggaac ctgaactttt tggccaaccc    64980
agtatctaaa ggaatttgaa tgcttttagg gaaagagagc cctctcctgg tcaccgctgg    65040
ccctgccgct ctcaggcttg tatttttgtt tcctagcctc tgtaagtcct tgctcatcag    65100
taatcattgg acgagtcttt gggctggtta tatctgaggt attcattacg tttttttatt    65160
gtttgttttt ctcttcctta aagatttgtg gaagataaaa tgtgggttac gttttagag    65220
ggaagctctg ccttgaatgt tctgaacctg aatgggaaag aggtaaagta gcatttgttg    65280
aatctaaacc attcagtgat ttagtgtctg aggactgtat ttttaagata catgcagcaa    65340
attatctaaa cgtgtttcga atatctagtt gcatgatgcc tcggattacc taacatccaa    65400
catcctaatt attttttaac tttgacaatc tgaaaaacta gaagtagtat gtcacgtctg    65460
tgttaagatt tcaatggaga gttttcaat  taactggtcg tttcatactt ctctggcaag    65520
ctgtttatga cctcagcctg tgttcccctc ggggtattca tcttttgaag cttccctgat    65580
gttaattcct tttcataatg tgctgtacat gttcttccca gttcgtcttg tgactttgtt    65640
gttttcaccg tatagaaatt actgattttt aaatttaatt ctgcctttaa tatcttaagc    65700
ttttcctcct cccatgatgt cattaatatt taagagcagc tctcaatttg gcatcccttg    65760
tcagctctta ctcctttttt gaatatttct tttgtctttc ccctggtcat tttccttgtt    65820
tagttttttt cctcccttct ttttcagctc tgtccctcac cctcaagtct gtgttacact    65880
tctagaaagt gcccacccct agctccctta aaagattttc aaaattctga aaaataatg    65940
tttctggaga acattttgaa agtcagacgt gtccaaacct ctcctctgtc tttgttatta    66000
cagttgtttc agcccagatc ttctagatac aagtagatcg ataggaactc ttccatttca    66060
ggggagaatc tggaaaaagt acagtgtaag cagagcaaac ttaaaggata acctgcttga    66120
gcattttttt ttccagcatc taaatttctt ccttttcatt cagttctgat ctctgccaag    66180
tgaatattct tgatgaagta catcttaagt ggccattgta gtgattgagg cttaagaaga    66240
```

```
cttgttagta ttctttggtg aatgcataac aaaggttgtt gacttaaaaa aataaatggt  66300
ccatgaagcc tattgactta aaaaaataaa tggtccagaa tcctagttct gacttcaaac  66360
ctcagcatgg acgctaaatt cctattaaac acgactgtac tgttcaggcc ggcagctgtc  66420
agcctttcag actgtgccat gaaagaattc tgatgtcagt agcatttaag gaaagtattt  66480
ttaatatgac aggacaatgt aagttgatta taatacattg attattttag actatacttt  66540
tgtctaaaag ctcctcaact ttttaggaac agcagtgtgc cagtttcaca gataccagtc  66600
cttgtgtttt cagaatggtt aattttgtt gatttaaaat gatcttagat tctcttaagt  66660
atgcttgtga catttgaaat gctgaaaagt ctaaatgaac aggaaagtat ttaagaatt  66720 ttatactgtc ctttctttga ttgtctcatg tggattaatt aattaattta attaattaat  66780
ctgtggatca aaattaaagg aagtataaat ttatgtagca gagttttcag tgaatttaga  66840
tctggcccgg gaaagatatt tactgcagca agaaaacttt aaatttgtgt gcatcctaga  66900
aaagaagacc tgagcttagc agcagtaggc tgttttgttt tggccacact gtgtggccaa  66960
atctcagttc tgaggtcgag gattaaacct ggaccatggc agtgatggca tcaccagctc  67020
aagggtcatg agtttgagca aactccgaga gacagtgaag gacagaagag cctggcatgc  67080
tgcagtctat agggtcgcaa agagatgcat atgacttagc aactgaacaa cagcaatgac  67140
agtgaaagcc tggagtccta accactaggc caccaggaag ctccctaaca ggttttttaaa  67200 gggaggattg gggacatttg aaactaggtg acaatacaat atatgtgaaa tgattgtgtt  67260
gaatgaatct gagttaagcc tatactattg ttataactta aacagacact ttattccaag  67320
atacttaatt ttcatgccaa tgaattttta attttgtatc tcttttactc aaccagttac  67380
tgggtaggac aataacaatt actttaaaaa gtccagactg gatcaaaact ttggaagaag  67440
aaatgagctt agagaaaatc aacgtcccct tgccatcatc aaccagctcc accctcctag  67500
gtgaagacgc ggaggtcacg gccgacttcg atatggaagg tctgctcatg gagcacattg  67560
acttctatcc ttctagacag gtttccttcc catcagcaaa gtctcagtct ccaaatctgt  67620
ccttctgttt cttcttgtaa cactcagaga agtattaatc agatttggtt tacattgtat  67680
tgtgtgtttt tgcttgtta cacagacttc agatgtgtgt gcccttctgc catacaaagg  67740 tcaagaccctt tacaatagtt agtttatgtc cttgtgtgat aaaagcagga agtggtattt  67800
ttggtgtgtg gtttggttcc actgattgta gttaaagtag aagagtagga gttctgtgca  67860
gaaatgagtt caaaatattt acaaccaaag aggatatatt tcaaagtcat tttaaaaatt  67920
cttaaagtgg ctgggaacac atttgaaact gaacccactc atgtagatgt aatcatctca  67980
agtttaagag tgggccaggt tatcttaata taataatttc cttaaatgtg attaagaaat  68040
gtatttgctt tttaatgctg tatctgctat attattttaa catattttcc actaaaatgc  68100
ataccttagt ttataaaagg gcaatatatc atattgtgat atcctgtacc tctaggtaac  68160
acatttaaga gttgaacacc ttagaagatc agcttgtttt catatttctc tgttaatttg  68220
tttgcttggt ccacacgttt atgcacttac cttttatgtg ccagttacat gctaagtgct  68280
ggaaattcaa cagatggcat ccttgccgtc cctgaagtca cagctcagtg ggtgttacct  68340
acaagtaggc agacggtgac atcaacacac tcgtgaacgg tgctgctgta gttcttgggc  68400
ctaacttaga gttggacagt taggagaatg tacccagaga aattgaaact gaaaatctga  68460
agactgagtg agaatcagat taagaggat agagagacat caccaggaag aaggaatgtg  68520
cagagaccta aggggacaaa aggatctaag tagatgatgc agatgtgctt gtgcaagagg  68580
```

-continued

```
aagggaagaa agaacaagaa gaggagtggg tgtggatgga aggtgaattt cttttctgtt    68640
ttgtttgaag tgtttgttta tttggctgca ctgggtctta gttgcagcat gcaggatctt    68700
tagcatgcag acccttagtt gtgacatgtg ggatctggtt ccctgaccag gaatcgaacc    68760
tgggcccgct gcattgggag cacggagtct tagccactgg accagcaggg aatcctgagt    68820
ttggttttga atgtgttgaa gttgtggcat ctgtggggtg cattgggtcc agaagtaagc    68880
tgtgggcatg tgggcctggc actcagcaga gagcccggag cttttgatgat aggtaaggcc   68940
ctgcatttgg atttgcttgg ccagaaacct gatagagatg ggagaggact tcctgggatg    69000
gaactgaaac gcagactttg aaggacaggc agaagaaggc cgcccataaa aggaaaagca    69060
gaagaaacga ctagaaatgt cagagagcca ggagaatata gtgcttaaag accaagtgaa    69120
gaaaagatga taaggaaaaa tgatctatag cgtcctctgt cgcagggcga agaagtgaa     69180
gcgccacagc ttgcccttttg gcttggaac caggggagga agctgttggt gacattcagg    69240
agagtgattt cagtgagtg aagaagccag atggtggtaa atcggggtgt ggatggaaga     69300
cgaggaagtg cagaaagtgt ctgtagacaa ctctcgacag aagtgtgcct gagacgggag    69360
aaagagagat gaaggcagtt gctccctgaa gtgttgtttt gaagtggaga cacttgagga    69420
gcttaatcct gatggaaagg gctgatgctg ctggggaggg gcagggcaac ctgcactggg    69480
cagaaccccca ccctttccac ccatagatat ggttaggcta cagctggggg gcagattgtt    69540
gaagaaaggg gttcccacct tagaacttcc ttttctctgc gaagtttaag gaggcgggca    69600
gcacacggtt tcaggaaggt tgagaaggtt caagacaaag ctcctgagaa gcagtcagat    69660
ggggagccag ccaggaaact gtgggttggc caggaggcca tgggagccca gatgaggctg    69720
aaaccacaag ttaacacgtg cagtcttttaa gaccacacgg ttatctgtct gcagcaccca    69780
gccgcccgtc tgcggttatg gagacattag actgcagaat tgacgcaggg gcaacggaag    69840
aatagtgcag gagggaccca gctgcggcaa ggagccagag gatgtgaaga cagctgcagg    69900
gacaggtgca aaatccagta gggcccaaaa gaagagggat cgaaggcttg ggtcctggtg    69960
aagtcagaag aggggaaaga gtagccaagg gcaagactga gcctggaagg cggtcagagg    70020
gaagtgtttg agtttattgt ttcagaggca ctgcggttcc aaggggcatg agtgtggagt     70080
agaggagcgc atcagcaggg aaaagtgtca ggttgttggt gtgttatcca cagtggcttc    70140
agtgtcaccc agaaagatgg cggggcccag cttactgtct tgctctctcc ttggtcctcg    70200
atgaatgggt tcaagtgacc aaaaaggtga aggtgggaga ttatggcggc aaacgtgggt    70260
tgagggcgtt acataaattc tggaaggcac agcttccaga aataaagagg ccttttttgtt   70320
cagggttgga agattaaagt tttggaattg gaatcaggtg gcatgggggct ccctgacgcc   70380
acttcccaac cctgtggaaa acggaggtga ggagacctcg gggagaacca actcctgcct    70440
gtttaattaa agcacagagg attacgtgtc aggtaggggc gcccagggca ccaagtagtg    70500
aggagacttc caggggggaag ggtgtgtgac tgtgtgtgcc atgaggggca ggtccataga   70560
cctagcaggc aggtttggag ggagggcagt gagcatccga ctcagccagc actgagagcg    70620
ctgctcaggg cgcattgaca gctgtggagt cagcccagcc ccagatgtta gccgccactg    70680
ggcctcctgt tgctctgaga caagagactt ttttttttt taattattat tattaaacgt      70740
gtttattttt aattgaaaga taattgcttg atagtattgt gctggtttct gccaatatcg    70800
gcattaatca gccatacata ttactatatc ccctgtgact gtcttttttt aagtaattta    70860
attaattaat ggctgtgggc tgtgctgggt cttggttgct gcagacaggc tttctctagc    70920
tgtggtgagc agggggctact ctctctgtgg tgcacaggct tcagtatttg tggcatgtgg   70980
```

```
gatcttccca gaccagggat tgaacccatg tccatctgca ttggcagaca gattcttcac   71040
cactggacca cctgggaagc ccaggggact attttttaatt acttttttcta cggtacgaga   71100 gcatttgcac taattctact tgtatacata taaactcttt atacatgccc acatgcttaa   71160
cttatacatg tttgcagtat catcatgtta aggtgttcat tttatatatt taacccctta   71220
agcctggact tgggggggcag caatctctga gaaagttaac atctggtaat gtggccgacc   71280
ttgcgttttc tcaggtgatg tggatgacta tagtgctgag gtagaggaga tccttcctca   71340
gcatctccag ccgtcttcca gttctggcct tggcacgtcc cccggttctt caccccggac   71400
cagtccctgc cagtcaccta ccatatcgga ggggcctgtg ccttccctcc cagtgagacc   71460
aagtcgagct ccgtccagaa cgcccgggcc cctgcttca caaagtatgt gttttatttc   71520
aagttctgta tgacttcccg ggctggtatg tttgatttag atggttaaac ctccgatgcc   71580
ttcagatgtc ctttggagaa ctattttttgc ttaactttca catccatagg ctaaagtgta   71640
gcatgttttc tgtgcgtaca aaagaggaaa ctttgtagat ggttccaccc taagtgaaga   71700
ggagggtcgt tgctatcact agatgagaac tttacttcat ccttttttcca tgtggcaggt   71760 ttgtccatgg cttatcactg acgattttta agcattatgg tcagaacccg taactctttg   71820
ggcttaacta tctgtacatt acctgcatta aataggaag cagaaagaga caaacaagt   71880 atttgaatt caacttgata gtcatgactc ctccaaagtc aggttttttct ctggaagttg   71940 ttacatcaca cagttcagtc actgttccac actaaccagt accccttgaaa ataccctttt   72000 atttcagcaa tttctcaagc tcccccatgc tactcttaga ggaccgtctt taaatagtca   72060
ctgagttgta tctgactctt ttgcgacccc atggattata gcctgccagg ctcctctgtc   72120
cattggattt cccaggcaag aatatgggag tgggttgcca tttccttctc caggagatct   72180
tcccgattca gggatcaaac ttgcatctcc tgcattggca ggcggattct ttagcactga   72240
gccacgaggg aagccctcag aggatgggct tccttcagta aattcaggat aagtcaaggc   72300
ataaagagaa gaggctctct ttgcttttttc ttctctctcc tggccagcag attgaattgc   72360
aaatgaccta agtcacacag tacttcatgc catcttgtta gggccgctca gtaaatcccc   72420
tttcagtacc cggggcctgg gtaagaagtc cagagagtaa cctgattgct cccgtagtac   72480
caaagggtaa ggtaatagca cagctgcttg tgttactgat actaaaaatg tatgtcattc   72540
ctctgtagta caaattatttt tgctaaataa tttatcatac gcctatagaa agtacctgtg   72600
tgctcgtccc ttggaacctg atcctcttac ctaaggtact ttttttctggt aggttctcct   72660 gttgacactc tgccggcaac acagctgcag cagaaagatt cttcccagac cctgaaaccc   72720
aagcggcctc cccctccccg cccggttgct cctcctgcac gtccagctcc tccacaacga   72780
ccacctccgc cttcaggtga caaatccttg tatttccatc tctgctggat ttcaccactc   72840
tgctgaaaaa tgttttgcat gtttttgaaa cactcgcttt tagatttttat cagttttctg   72900 tcactggtgc tacttcctta gttagctttt ctctaacaaa cggcataggc gtgacagaac   72960
agctagattc ctataacatg ttttcagagc tggcctctta caagcgtgca ggaaacattt   73020 gctttgttttt tgctaatttg atgtggttgt actgatttct gtaaaatgca tgattatcta   73080
aaaatgaaaa tttttaatgc atgattagaa ctgaagaaca tacatctttc tgtttacagt   73140
tttatatatt tgtttaaatg ttcttttaaa ataagtatag tcttgtttct gctagaggta   73200
tttgcgttac ataataactt ttttttatagca ccaagatatg aatatgtagt ctctacatga   73260
tatttgacat cttggaaact atagtaaatc tttgacattt caattcttta tttaatgtca   73320
```

```
tttcctttct gctgcatatt cccttatgaa ctataagggg ctaggagtcc tgcacctgct    73380
agaaaagagt ttggaggtaa ccatttatat ttgttataat atatggatct tggttcatta    73440 attttttttgg agtttgagct ctgtaactta gtgacatttt aggttgcttt gatgcaagcc   73500
aaaatgaatg acatttatat gccaacttaa aaataactcc aaactttcat tatatttctg    73560
gtaaaagatt agagcttgat tttattagtg aatattatta gaattaagaa gaccttccat    73620
ttccctgata aacagagttg aattacttaa ggcctgatat acttttttatt aataaatata   73680 gtcaattcgg ttataaagat taaatgagtc aaacacaatg aaaataggtg gtttcccaag    73740
gatttgatta tattggatta tattagaact ctagtacgtc ttgccagtag cctgtgaatt    73800
agcaaaatgt cctaggaatg cagtttaaag ttatcataat tatctgaaat atagctttca    73860
ttttgcatgg ctttatcata atttgtcata acattcatgc ctcatttttta aaatagaaga   73920 acaagtctct gttatatatt tcgataaaga aattttttctt aacacatggg tcacttttttg  73980 tagtttactt gttttacatg aagactctta caaagctcaa ctagaggcgt acatttgaca    74040
agtttattta atctagttct caagaaaggc tgaggcagaa tgtctcagtc ccacagaaga    74100
gctgttcctc acccagttct agtgtcctta gggctcacgt gcacaggcag ctggtctctc    74160
cctgctccag ctgcctgagc acgtcgccag ccgactcacg ctgtcacaga gtggctgcac    74220
cgtgtgcaga cttgaacgac tttgggtaat tagggtagca aagttctttc agcaccaagc    74280
ttctgtaaga tactactgga ggataacttt tccactaact taaagacgac attgattttt    74340
ttcccatttc agacttgtgc tttgatttat agcttcatgg aagattttat ttaccttccc    74400
ctttaattag gaaaccaatc tgtagaaaaa tttaaagaaa tttgtgaaaa gctatacata    74460
ttagctactc agtgacttac ttagtctgat gttttttaaa aattgcttct cttcgtaatt    74520
cttttgtagg cagtcttagc agcatatttt ttaaccctat aaaccagtaa ctgcttgaag    74580
gcaataatct gaaagtaatt atagtacttt tagagttctt ttttttttttt ttaataatgc   74640 attgaaaatt accttctaag ggactaacac aggactcata gagatttaaa atgaaattgg    74700
aacttccaga cttttttttttc ctttatgact ggcaaatatt ggagctttta ttagtggttt  74760
aattctgaat ataaaaaatg agatgattaa aaagcaaaga ctttcattat tttcaaattc    74820
cctactgcta gtgaagaagt gaaagtgtta agtcactcag ttgtatcccg actctttgga    74880
accccatggt ccgtagccca ccagtctcct ctgtccatgg gattctccag gcaagaatgc    74940 tggaggggggt tgccatttct tcctccaggg aatcctccca tgatgtcaga tataaaaaga   75000
aaactatttt ctcctttcaa ttctaactga agaaagggca aggatcaggt ttgggccagg    75060
catctagagg cactttggtt tatacagata tctttgaaga aatttgaagc agtgaaagaa    75120 cttttttttgc aaaaggacat ttaactcaga aactgttttg tgtgcctgcc tttccctctg   75180
ttctatggac cctgaacaat acacagcttc tgttctctct ctaaaaaggt gttggagccc    75240
ctcccagtcc gggggtagct aggcgagaga tggaaggtaa caagacgttt gcatcctaga    75300
aatggatctc tcgtttttatt cctaaatgtc agcccctcca gtgtttaaag acataccaaa   75360
tcttttcttg gtccaactgt aaactccccc tccccctcct tctgtatatc ttgtaacttc    75420 atatttttttc tcttttcatt ctgtgttgtg tagtttctgg tggttgtcca tttactttct   75480
ctgcaattct taatgttgtt ttgagctgtt ctgtatatat atatttcata tacacttaag    75540
atgtgaaatt aatgtgcagt attatttttaa gaggaatgcc ttcaaaaatt ttttcagaat   75600
aagtcaaatg tttagaaatg tactgtacta actctgaagt tttaaaaatt aataattaaa    75660
ccttgttaat tcagtccaag gatatagtat tttttaatca acttcagata acataaatat    75720
```

```
gctgagtaaa tttgcttaaa aggctattaa aactggaagc cattcattaa gattacagtt    75780
attaaaagtc tgatgggttt catataacaa ttacacatga atttcctttc aaaaagaaga    75840
aatctgagat gctgaccttaa ataggtctc ctactccttt tggccccaaa agtagtttat    75900
tgcatttcag tcttctccta cgtttcgaat gagtttgagc agtattttaa cactgtcttg    75960
cataaggcag atattgtaat aagtagtgcc cgccttctac cttaatgata gggtcttct     76020 gtagaaatcc gaaggtctc gtaagagccc ctgtccgtac tgacgtccac agcatgaagc     76080
cctgaacagt gctgtttggt gtcttgtgtg actcggaaag tgcgggtctg ttggtcctgg    76140
agccgtgagc ccaccaagct ctgggaagta gtggggccac gtcttgtgac tgttccccca    76200
aactgaccat gtgttttcag ggttcatagg aaagagctct gttgggaaag ttaccttcca    76260
aatgaggtag cagaccaact gccaacttgt cccataaatg ttactctcaa tagtctaaat    76320
ttttctcttt tggaggtatt ttctaaaggg ctgataatac cctccagcat ttctaaagca    76380
gaatagtttg ttttgttttt cttttccac ctcgtgcccc catttctgct ggtaatgaaa     76440
cagaacagct agctaatatt ataatatg gcttatttac ttatagataa tttttttttc      76500
cttcctgctt caaagcaccc aaaagcccag gaacgacccg gagagataat ctaggtaaac    76560
attcgaattc agctacttaa ccttaaagct ggaccatgaa tagacagtgt ggtataagtg    76620
catgtttctt gtttctttct ttaaaaacaa agacctgagc tacatggtgt gatgtctttg    76680
ttccaggacg cagccagctt ccacctcaag ccggactgcc aggccgggga cttgctggac    76740
acagtgcagc cagaccggta ggcagcgcct cgcttgcgag ccaggaggtc taggtcctgg    76800
gtcccaactt gctactaatc aaatgtgtta ccctgaagaa atcacgggcc cattaagact    76860
ccaatttcct caattctaaa ttggggaat tagacttgat gctcttcaag gtaccttcgt     76920
gtgtatgtgt gtgtgtgtgt gtgtgtttt tactctctga ggtgtgtgtg tgtgtgtgtg     76980
tgtacttgct gagttgtgtc cgactctttg caacccatg gactgtaccc catcaggctc     77040
ctatgtctat gaaatttccc tggtaagatt actggagtgg gttgccattt ccttctccag    77100
gggatctccc caacctaggg atcaaacccg cttcctcctgc attgagaggc agattcttta   77160
ccactgagcc accaggcagc cccaccttca actcaaatgg tattctaaca tcctcttcag    77220
aagtaaaagc atccttcatt atttgaataa aagtggtata cttaagtgat tacagtcact    77280
aaataaatat cttagaatct tgaaatatat ggggaagtga tgtactaggg caattttta    77340 tgacattatc tgagtaatga agtaaagtca ttcttctatc agaaaggttt tattttactt    77400
ttatttcctt tttatttgtc tttgccacac cttgaggcat gcgggatctt agttccccaa    77460
acagggattg aacccgcact ccctgcagtg gaagcacaag tcttaactgc tggaccacca    77520
gggaagtcca gaaggatttt aaaattagat ttcaggaacc ccaatgatga tagtctgtca    77580
actaaaacta gttctaaagg tttaaccaca ggagagcaga tggcattgca gggtttcacc    77640
ctgcgttgta agtctggttt tctgcgtgtt tatgtgtgtt ttgttataca cagaattatt    77700
ctattattca cccacatgaa cattttctct gagacagaac aagtaattca agaaaaaaa     77760 aaaagagaaa ccagtgtcag tcaggtggag cctggactta ttgggaggcc actggctgaa    77820
tcctgggaac tgtgactata cctggagatg aagagacttc tgctaatgaa actacttcaa    77880
gagtccaaga aattctcatg agatttctaa aacagagata ttttgttttt tgtcttgtag    77940
ccaacctgaa ggactttttc tatatataat attatgctcc aaagtaaagt gtctgtggaa    78000
tttacctaaa atagccatta tccactcccc tgttttttta aaaagaagt tgttattcac     78060
```

```
tgactacaca cttcccacaa agtactttgc ttactgaata ttgtaagaat agggaaggaa    78120
agtcaggatt ttgtgtgatt acatttataa cttttgctta tgcatggaat ctagaaagat    78180
ggtactgctg aacctgtttg cagggcagca gtggagatgc agacacagac agcagacttg    78240
tggacgcagc gggggcagga gagggtggga ctaactgaga gaatactatg ctgctgctgc    78300
tgctaagtcg cttcagtcgt gtccgactct gtgcaacccc acagacggca gcctcccagg    78360
ctcccccgtc cctgggattc tccaggcaag aacactggag tgggttgcca tttccttctc    78420
cagtgcatga aagtgaaaag tgaaagtgaa gtcgctcagt cttttcagac tcttagcgac    78480
cccatggact gcagcctacc aggctcctcc atccatggga ttttgcaggc aagagtactg    78540
gagtggggtg ccatcgcctt ctccgagaga atactatgga aatgtatatt accatatgta    78600
aaacagatag caagtgggaa tcggggagct caactctgtg ctgtgtgaca atttagaagc    78660
ctgggagggg gtacaagagg gagggacat gtgtgtacct gtaggagatt caggagggag    78720
gggacctcca tgtggctgat tcatattgat gtatggcaga agccaacaaa tattgtaaag    78780
caattatcct ccaatttata caaaaataag aaaaatgtac tgagtgctta aagcttcag    78840
caaacatgtg aagatagaaa aggacgttat ttccctagtg tatcttccag cctatgtatt    78900
tcagcacatt gagttagcca ttccagagtt tttaacctct gtgtttaata aagaaaaaca    78960
gcctcagtgt agttttggt aagcctctta gttccacagt gtatgtcccg ctccacctcc    79020
tcatgacctg taaaatcgtc ccactaagga gtatgataca ggataaagaa aacgggccct    79080
gagttcggct cctggcttta ttttgtaact ctgtggcttt gggacagttg tatacatttc    79140
ttcattttca tttaaattag agatgataaa ataataccttt accccccagg gccatttgga    79200
cattgaaatg taaattcata cccagtgctt agttaacaca gtgcgtggca catagtaaac    79260
agtgaaaaat ataaggaag attttgaag cttaaggaac aaaattgggt catttgtaga    79320
gatgtggatg gacctagaga gtatcataca gaatgaagta agtcagaaag agagaaacag    79380
tattgtgtat taacccatat atgtggaatg tagataaata ctatagatga tcttatttgc    79440
aaaccagtaa tagagacaca gacatagaga acaaatgtgt ggataccaag gggcagggga    79500
ggaattggga gattcgagtt gacacatata tgtgtgtctg tgtgtgtata cacacacaca    79560
tatatatatt actgatacta tgtataaaat agataattaa tgagaaacta ctgtatatag    79620
cacagagagt tctacttaac gcactgtgat gacctgaatg ggagggaaat ccaaagggga    79680
ggagatatat atatatatat atatatatat atatgtatgc ctgattcatt ttgctgaaga    79740
gtagagacca acacaacttt gtaaagtaac tatgcaccaa taaagttaa tccttaataa    79800
aaaaaaatga aacttatgat catatggcaa taaatagagc cattagaatg acaaagaggc    79860
agaggaaatg atacaagatg cacagacaaa atatttcat caaatcttat ccgttgcaga    79920
taaggtaaat gtctcagtgg ttttcgtttc ccatctttag attattccgc cccgtgctgg    79980
agtcatcagc gccccccaga gccacgcacg ggtgtctgct gggagactga ctcctgaaag    80040
ccaaagcaaa acctcagaag tactgaaagg tagacccgta gtcaaaacag cagtgccatt    80100
ctgtatcctt cccttccact tcttttcttt tttctttcgc aatctctcac tttatacaac    80160
ttgctcaaat tctttctctc tctcttttt ttttcctgt ctttctgaat gccataataa    80220
aggaggctac tggggctga acagggact ggaatttcct accatttcct gaaaggaagg    80280
ataaactcag ttttccagag aatgcctaac atctggaaat tactttcttt agggccagct    80340
cttcttcccg agccctgaa gcctcaggcc gccttcctg tgccgccttc tcttgcgcca    80400
ccttctcttg cgccacctgt tcagaagatg caggagcctc tcatcccggt ggccgcacct    80460
```

```
ctggcccagg ctgccctgca gcccagcctg gaaacgcccc cgcagccacc ccctcggagc   80520
aggtcgtccc acagcttgcc ttctgagcct ccggcgcagc cgcaggtaag gccttccagc   80580
ggggagaaag atcatctggg tgtgtgtgtg tgtgtgtgtg tgtgtgtgcc tttgcttaca   80640
ttttgttttg ttttccctt tttttttttt tttactgagg catatttgat gctcttgctg    80700
tagtctttga acatacttat tttaattatt agctttagaa aaacaccta agatttgatt    80760 ttttaaaaaa ttttgtcatt tgctagtaat aacatgttta gatatgactt caaccagtga   80820
atgtcatttg accactcaga ctcatcacac aacaaaagca cgtttggccg tttgagggtt   80880 tgggttttt gtttgtttgt ccaacctgtt gtctagatca cgggttctca gagagtgacc    80940
ctagattagg gctctttccc taaaggctct tttccctaaa acttccaagc ggccccacg    81000 ctgtttactt tgtttaaaga gtaggtgatt ttttggttt ttctgtgtgt aatttactt     81060 ggatacttaa ttagagtgga cagtaataac ttagtttctt tttgttcaca gctattagat   81120
tagttttgtc cttacctcc tggacagaaa ggcagtcagg tcaatccctg gccattggca    81180
gtaaatttcc aataatccta tctctcctga tgctgcagtt agctcttttc agtgatggag   81240
tcggcactgg gcttccttgg ggatctctaa cagtttcaga cactactgga tccatttaga   81300
tgtttcaggc atgcagcagc aggcttatta accaaagtaa aagccatcaa ataatgttc    81360 tcatgagtat cacatagaaa atagtaccat tgccttggtg ggtggaaatc acaggatcac   81420
agggactttt gttataccag agtgatctca cattggaaag ccttctggtg tatatacaca   81480
aagttgtttc aacacaagaa tattcatgcg agttgaattg ttttacttgg aggctgtttt   81540
acttagtttt tattatatac atctcagtaa aatcattaaa ataaggttta tctttagtat   81600
aagtttatct ttagtataag gtttatcttt atatttctgt tgtctagcct cacattgaat   81660
tttatccaaa agttttaact tgaaaatgcc atcaaggcca agaactgaa gtctaagtct    81720 gcttttattt tggaatagtc taaaatacag aaatattaca ctggtgatgt cccttaagca   81780
tgtttataat aatagtttgc atttattttt acagatatgt gaatatgtcc aactaattgg   81840
cagaagttag cagtttctta tgcttcttca tagtgaaaaa aagattataa agtaaatatg   81900
aatcttgaaa caatatgaat agttagcaaa gcacttactt atcagactat tggtcacatt   81960
ttttaaaaag ctaagacgga tatataattg agaataatgt tctcttaagc taatgaacac   82020 caaaagtat tatatagttg aggatgctga agatatatag taattataga agcccttcaa    82080
acaataagtg tccattattt tctctttgcc aatctacttt tagtgcatga tgattttttc   82140
ttttcatttt cttataaggt gtagtattta ttattattgt tttttagtgt aattggaggg   82200
caagaaactt tcaaagaagc catcttaaag ctttgtatta ctacagtttt aggacagaaa   82260
gtgatcatga ttttcacagt aaaggtgaac cctaattcct aaaactctat aaaatgttct   82320
cagtattgaa agtaggtgtg gtactctgaa caacttcaga agaacacact gtcaaagaag   82380
attgcagttc tcagtagaaa gtcatcttgt gacacagaga gtacaggatg aatattccgt   82440
gactgccatc tatcattttc ttaggtcatt ttcccctgtt ttgctttctg attttcattg   82500
gaatgggtat ggtgatttgc tgacgaagca cagcaagcct gtgctttctg tgtggtttag   82560
tagattgtat tcttgactct tacattctgc tcatcaaaac tgtgaaaggt gtttgttata   82620 agccttctt tgcctcagtc attgatatca aatccctcta cacattacat acacagacac    82680
actttcctgg agagtggagg tcttgttcac gtgtaggctg cctttgtgca agatcacaaa   82740
gagcttagtt tcctcctggg agcttacaga aagataggga ggcattttac cttttttgcc   82800
```

```
tttttcattt tgaaccataa aaataatgcc tattcaaaaa ataatgaaca tctaaagtct    82860
taaaaattct tctataatgg ctataacttg aagagggtga gttagtaaaa taactcacat    82920
tttgatattt tggtaataat atgaaacagt cttagaattg aacttagtag tttttacaag    82980
tctttattaa ttctgccaaa aatatacaag gtatttaaaa catagaccca cacatgaccc    83040
agctttactt gttattacta tttaaattat ttgattctat aattctatat agaaaagatt    83100
cttctaattc aagtgattat atgttatata tcctttagaa aatgtaaaaa tgccccactt    83160
atctgacttt caatgtctta ggcatctgat tatcagctga aaaccagaag tcaggaatcc    83220
aatgggaagt aaagtaatag catcacagct atactattgg agtgacagcc gatagtgagg    83280
gaagaggcca agtagaaaat ctcaggactt ccctggcagt ccagtggtta agaccccgtg    83340
ctcccaatgc agagggcatg ccttcgatcc ctggtcaggg aactaagatc cagcatgctg    83400
cgcagcacag ccaaaaaaga aaaaaaaaaa tctcagcttt ctggatcaat ttaataccat    83460
ccccttgcat cttagtataa acccattccc agtttttatc caactcttac aaaactaatg    83520
catcaggatc atcaggaaag gttaaattca ggagtctcat gttttgtagt aacacatttt    83580
atataatata aatatataat aaatatatta tttataaaat aatttactat agaatggtgt    83640
ctctcgaatc tgtctaagtg agttatggta ttttaaaata aggtaagctt taaatattgg    83700
ggaagatttg ttcaaactgt ttcttaagaa tactgtaatt ttttaaagta ctgctgttat    83760
agaaagattg tgatttcatc tttagtatca cccttcagaa aatttgagtg atagattaat    83820
agaacaagcc tggatcctga ccatgttaaa ataaatacca gttttcactt ttctgcaaag    83880
tggtgccatt ttgaacaatt tctctaatca tgataaaccc ataggctgtc ttaaggctgt    83940
gtcctaacct tcttgggctg ccgtaacaaa ataccatgaa ctgggtgact caggcagtag    84000
aaatttgtct tctcaagttc tggaggctag aagcccgaga tcaggatgcc agcatggttg    84060
ggttctgctg gggcctcttc tcctgtgccc acatggcctt tccttggtgc ttgcacaagg    84120
gaagaaagag caagccctct ggtgtgtctc ctacaaaggg tgctagttcc atcaagaggg    84180
cccactctca cgacctcatc taaccccagt cacctcccag aggccacgtc tccaaatacc    84240
atcacataag aaggttgggg ttcagcatac gaatctgagg ggacacaaac atttcaccca    84300
tagcctgctg aaaatacttc agtgctccag taatgtattt ggaatattat ttttggaatg    84360
actactttga actagttagt aatcaacctc agataaaatt aaatcctgag ccctattaca    84420
gcaatacatt ttattgtctc ttgatcttat actgtgacct gcaggtctca ctgctgttgg    84480
attttgtaca taatataaaa ctgaaagtgt tttgaattgt tagggttgct gcttggtctc    84540
agattgtcct cctaactctt tcccttgatg tctatgtttc gttttctcaa agcaggagca    84600
accatcaggg taacaggtat cggattattt ctcaatctta tatgtgcttc tcatctgtct    84660
tagcacagta gatgtatgaa tctttcgctt catacatcta aattctcacc cattttaaa    84720 aaccacctgt ccacattaat aaattctgtt atcataccat aaaacctgct tttttcttta    84780 gtatttgaa ttcttaggaa ccatttagt tattcttgct aatgctttcc cattttgctt    84840 tttttttta caaaattaa caagactaaa aagtataact ttaagaaggt aagctttaga    84900
tatatgaaag tgtatttggc aaaaccaaat tggttcgtgg ttttaacaat ggcaaaatta    84960
tgtaagtata aaattcaatt ttttttcctag attctttttg ggaaattaaa aaacccaaa    85020 aaactagtag catgtagatt ataactggag gcactaggag atttttttt ttgttaaaga    85080 agaattgatt atttacaaaa atgaaaatga acattatagc aggattattt aagggccttt    85140
ccaacaccct tttctgtaaa aaataccatc atcattaatg tcaagtcatc ataaatactg    85200
```

```
cttagatata tagaaattca ttctaatgta atgaatgatg atgtggctct cataatttca   85260
aatctcattg agcaaaatga tcatgtttct gttaaattac ctttaactta ttttgaaaga   85320
aaaatttgtt aatatatgaa aataaagata tttaaatgtg caacatttat ttggcaaaag   85380
cctattattc taagctgtac aaagcataaa cttcctacct ataatgtctg tgtcatggac   85440
tctttgtcta ccatgggaga atcggggccc agacccactc aagtacttct gttttgtcat   85500
atgaatcgta ataacccag tcattactgg taatgtgtag ctaattgtaa ttttacagca    85560
tctatagtaa atttgtctct caagtactat aatacactta gaatacagtt tagaatttat   85620
gacatgtctg cttttaatt ttgttcaaat ttattgtcat attaagtttg aagaaaaata    85680
aaacttgttt acttaaagta tactatagat tagttgaata aaatagatcc tagagagtga   85740
ttcacgtaag aagttatcca cactgttcc ttttgcaaat gagcagcctt ccttattctt    85800
tttttttttt tgccactgca tgtggcttgt ggggtctctg ttccctgacc aggggttgaa   85860
cccaggccct ggcagtgaaa gcagagagcc ctaatcactg gatcggaggg gaattagcct   85920
tccctattct taagcaccaa gttactgttt aagaagatgc aattatgttt tattggagtt   85980
tcccaggcag ctcagtgata aagaatctgt ctgctaaaga agaagacaca ggttcaatcc   86040
tgggtcagga atattccctg gagaagggaa tgcaaccca ctccagtttt cttacctggt    86100
aaatcccatg gacagaggag cctggtgggc tatagtttgt agtcgtcttg tggggtcaca   86160
gagtcagata tgacttagag actaaaataa gaacagcaaa acaatgtttt attgagactg   86220
ctgctctttt tctcaacata tcttatgaat gtttagttac ttgctttaac aatgacctaa   86280
attcatttgg gtcatgctgc attttgtaca ttgccaagtc tctagctaag taaaattctc   86340
cctctcctgt gcttttctta cctttaattt ggcataaata tccaagtcac ccacctagtt   86400
ttaacaatta tatagagttt ttttttttt taattaaaat ggagttcctg ataaagctag     86460 ctactttct cgtacagcca ggcttcagtt caatgtttcc cttaggaaag tagcctgtgc     86520
ccggtaccac agccgggctc cactccagcc ggcttctttg tgaactgggc acacagggca   86580
gacttttcat aactgtgaag taggtctgac ccctcctcct gccagtaact gttcacagct   86640
agctctgcca tgcatagctt tatttggtt gaagaattac tatcccaaat agaaacagga    86700
ttcctccccc caccacgcca tccagtttaa agaatcattg cagttagtta caacctatct   86760
aaagatgagg aaggtcaatt aaaaaatatt ttcacattca gaatttattc tacaaaggag   86820
agctgacgtt aaaaggcaaa gaatgctttg aaaatttat tctacaagtg gaaaggaaa     86880 tgatgcattg tcttcagctt atgaatatag atatactaat aaaattatta tccataaagt   86940
tgaatttcca tagtaacatt aactctcaat gaaatatat ttcaaaaaac aatgaaacca    87000
catcatcatc acagatgggt gttggaagtt tattcatagc gatttagcat aaactttgta   87060
ttgaatgtga gttttttaag ttcatttgat tatctgatag aactgggcat gaaccaaact   87120
catctgctaa ttcagtgcag ttctccattt tacgtatcaa tacttgcatg gatgaaataa   87180
gttgtattta taaagaact tatttagcag agagtttaa aaaaaaaaa aatttcatgg      87240 tacttgttta accaccagag taacagacta cacaaagctc cttttttat ttttgagta     87300 tgtatacttg accccttcag aataaagaat aattgagaca ggaaacaggg ggggcattca   87360
aagtaacctt attgcttttt gtttgttctg attattcagt gggctctctc tttcccaggt   87420
gaaaacaaac ggagtctctg ccgtcagact ggactcgcca ttaaagagtg acccatttga   87480
agacttgtca ttgaacctgc ttgctgtatc aaaggctcag ccatctgttc acaccccaaa   87540
```

-continued

```
cccaaggggg ttgacgccgt tgccttctgc agccccaagt aacaccaaca ctctgagttc    87600
tgtaagctgc atgccgacaa tgcctccaat tccagcccgg agtaaatccc aggaaaacac    87660
gcgatgttcc ccaaacccat tcatcccaag ctcaagcagc acaaatcctt tcaccgacag    87720
gaccgccgct cctggaaacc cctttcgagc tgagtctcaa gaatcagagg ccacttcatg    87780
gttctccaaa gaagagcctg ttgctccgag tccattctct tcgctgaggc ctctggatca    87840
gaacagtagc aagccttcat cctccctgga tgggtttaag gacagttttg atccacaggg    87900
cctgtctgca ctaacagtca gcaaccccaa aggatgggta accttcgagg aagaagagga    87960
cttggtgtg acaggaagt cagggtccac tcgcccagac gttttcctgg gtaagcagct    88020
gagctcgtct cctggctcca aggtgatgct tggtgatgac tggggtagga gtaccaatgt    88080
gtctctctgt gtgttg                                                    88096
```

<210> SEQ ID NO 3
<211> LENGTH: 3978
<212> TYPE: DNA
<213> ORGANISM: Bos taurus

<400> SEQUENCE: 3

```
atggcgttca gcaaaggatt tcggatctat cacaaattgg atcccccacc tttcagcctc      60
atagtggaaa ccaggcataa ggaagaatgt ctcatgttcg agtctggggc tgtagcggtg     120
ctctcatcag cagaaaaaga ggcaatcaag ggtacatact ccaaagttct agatgcctat     180
ggacttttag gtgttttacg attaaatctt ggtgatatta tgttacatta tctggtccta     240
gtcactggat gtatgtctgt tggaaaaatt caagaatctg aagttttccg agttacttcc     300
actgaattta tatcactgcg agttgattct tcggatgagg atcgcatttc ggaagtgcga     360
aaagttttaa attcaggaaa cttttatttt gcatggtctg catccggagt cagtttggat     420
ctgagtctta atgcccaccg tagcttgcaa gaacacacaa ctgacaatag atttttctgg     480
aatcagtctt tgcacttgca tctcaagcac tacggtgtga attgtgacga ctggttatta     540
cgcctcatgt gtgggggagt agaaatcaga acaatttatg ctgctcataa acaggcaaag     600
gcttgcctca tttccagact aagctgtgaa cgagctggga ccaggtttaa cgtccgggga     660
acaaatgatg atggtcacgt tgccaatttt gtagaaacag aacaggttgt gtacttagat     720
gactctgttt cttccttcat acaaatccgg ggatctgtcc cattgttctg ggagcagcca     780
ggattgcagg tgggatctca tcgtgtccgt atgtcaaggg gatttgaagc caatgcacct     840
gcttttgaca ggcattttag gacacttaag aatttgtatg gtaaacaaat aatagtaaat     900
ctgcttggat ctaaggaagg tgaacatatg ctaagtaagg ctttccagag tcatctgaaa     960
gcttctgaac atgctgctga tatccagatg gtgaattttg actatcatca aatggttaaa    1020
ggaggaaagg cagaaaaatt acatagtgtt cttaaacctc aagtccagaa gtttctggat    1080
tatgaatttt tcatttttga tggaagtgaa gttcaaaggt gccagagtgg tacagttcga    1140
acaaactgct tggattgtct tgacagaaca aatagtgtgc aggcattcct tggtttagag    1200
atgctgacta aacagttgga agctcttggt ttagctgaaa agcctcagtt ggtgactcgc    1260
tttcaagaag tttttcgatc aatgtggtct gtgaatggtg attcaatcag taagatttat    1320
gcaggaactg agcccttgaa ggaaaggct aagttaaaag atggtgctcg ttcagttagt    1380
agaacaattc agaataactt ctttgacagc tccaagcaag aagcaattga tgttttgctc    1440
ctgggaaata ctctaaatag tgatttagct gacaaagctc gagccctttt aactactgga    1500
agtttgcgtg tttctgaaca gacgttacag tcagcatctt ctaaagtact aaagagtatg    1560
```

```
tgtgagaatt tctacaagta ttcaaagccc aagaaaattc gagtatgtgt gggcacatgg      1620
aacgtgaatg gcgggaagca gtttcgcagc atagctttta agaatcagac ccttacggac      1680
tggcttcttg atgccccaa gttagctggc atccaggagt ttcaagataa agaagtaaa        1740 ccaatggata tatttgcaat tggttttgag gaaatggtag agctgaatgc tggaaacatt      1800
gtgaatgcaa gcacaacaaa tcagaagctc tgggctgcgg aacttcagaa gaccatctcc      1860
agagacaaca agtatgtgct gctggcctct gagcagttgg tgggcgtctg tctgtttgtt      1920
tttatcagac cacagcacgc tcccttcatc agggatgttg cagttgatac tgtgaaaact      1980
ggaatgggag gcgcaactgg aaataaggga gcagttgcaa tacgaatgct gttccacacc      2040
acaagcctct gctttgtctg cagccacttc gctgcgggac aatcccaagt caagaacga       2100 aatgatgatt ttgtagaaat agcgcggaag ttgagttttc caatgggaag gctgctcttc      2160
tcccatgact atgtgttttg gtgtggcgat ttcaactacc gaatcgatct ccctaatgag      2220
gaagtgaaag agcttatcag acagcaaaac tgggattctc ttatcgcagg agatcagctt      2280
atcaatcaga aaaatgctgg acagattttt agaggatttt tagaaggaaa agtgaccttt      2340
gctccaacgt ataaatacga cttgttttct gatgactacg acactagtga aaagtgccgc      2400 accctgcat ggacagaccg tgtcctctgg agaagacgga agtggccttt tgatagatca       2460
gctgaagatt tagatctcct aaatgctagt tttcaagatg aaagcaaaat cctctacaca      2520
tggactcctg gcactttgct gcactacgga agggctgagc tgaagacttc tgaccatagg      2580
cctgttgttg ccctgatcga tattgatata tttgaagttg aagctgaaga gaggcaaaac      2640
atttataaag aagtaattgc agttcagggt ccaccagatg gtacggtgtt ggtctcaatc      2700
aaaagctctt taccgaaaaa taattttttc aacgatgctt tgattgatga gcttttacag      2760
cagtttacaa atttcggtga agttatactc ataagatttg tggaagataa aatgtgggtt      2820
acgtttttag agggaagctc tgccttgaat gttctgaacc tgaatgggaa agagttactg      2880
ggtaggacaa taacaattac tttaaaaagt ccagactgga tcaaaacttt ggaagaagaa      2940
atgagcttag agaaaatcaa cgtccccttg ccatcatcaa ccagctccac cctcctaggt      3000
gaagacgcgg aggtcacggc cgacttcgat atggaaggtg atgtgatga ctatagtgct       3060 gaggtagagg agatccttcc tcagcatctc cagccgtctt ccagttctgc cttggcacgt      3120
cccccggttc ttcaccccgg accagtccct gccagtcacc taccatatcg gagggggcctg    3180 ccttccctcc cagtgagacc aagtcgagct ccgtccagaa cgcccgggcc ccctgcttca     3240
caaagttctc ctgttgacac tctgccggca acacagctgc agcagaaaga ttcttcccag     3300
accctggaac ccaagcggcc tcccctccc cgccggttg ctcctcctgc acgtccagct        3360
cctccacaac gaccacctcc gccttcaggg gctaggagtc ctgcacctgc tagaaaagtt     3420
tggaggcacc caaaagccca ggaacgaccc ggagataatc taggacgcag ccagcttcca     3480
cctcaagccg gactgccagg cccgggactt gctggacaca gtgcagccag accgattatt     3540
ccgccccgtg ctggagtcat cagcgccccc cagagccacg cacgggtgtc tgctgggaga     3600
ctgactcctg aaagccaaag caaaaccctca gaagtactga aagggccagc tcttcttccc    3660
gagcccctga agcctcaggc cgcccttcct gtgccgcctt ctcttgcgcc accttctctt     3720
gcgccacctg ttcagaagat gcaggagcct ctcatcccgg tggccgcacc tctggcccag    3780
gctgccctgc agcccagcct ggaaacgccc ccgcagccac cccctcggag caggtcgtcc    3840
cacagcttgc cttctgagcc tccggcgcag ccgcagcagg agcaaccatc agggtaacag   3900
```

```
gtgaaaacaa acggagtctc cgccgtcaga ctggactcgc cattaaagag tgacccattt    3960
gaagacttgt cattgaac                                                  3978

<210> SEQ ID NO 4
<211> LENGTH: 88096
<212> TYPE: DNA
<213> ORGANISM: Bos taurus

<400> SEQUENCE: 4
ggcttgggct tgtgcggctt ctcttcaccg ccgctccccg ccccgggagc tcctgtggtg      60
tcggataatc ctttcccttc tctcactcct aaggagcttt gaatcagccc tgttcacctt     120
ccttcccacc ttcgtctcct cccccgcgcc ccccagccca ggggatcggt ttgaagtttc     180
cgaatcgttt tcccttttcaa acggcagtga gaaatcccga agcagaaagc tgataaacca     240
ctcccgagcg aaaatagact cattttttttt tttccttttt ggtaaacaga aaggggaaac     300
tcatcttaac caaaccgttc ttggaacttg gagtgatatg agaaccctgt cttgccttgc     360
tgtgagacca ctttccctct tgcttttcgg taaaaaatta agtgacgact tatcttttgg     420
aataaaccat tctgtccccg agctctctcc gcaccccctc cgctccaccc ccaccccccc     480 ccccatcaa aacctagcag gggaggactt cggggtggct tgcagtcctt gctgcagaag      540
gaaacattag ctgtatttgc tttgcttgat tttcacaggg ctgcctccga agaaaggaga     600
atggcgttca gcaaaggatt tcggatctat cacaaattgg atcccccacc tttcagcctc     660
atagtggaaa ccaggcataa ggaagaatgt ctcatgttcg agtctggggc tgtagcggtg     720
ctctgtaagt cttctctctc aacccagctg atcaggatct gtttgcttgc aataattcag     780
attcaacctt tttttttttt tttttcttt tttcaaaaga agattctgat aaccccctca      840
ttgtatttca cctcacaggt catgctttta tttccttta accagacctt attgtttttc      900
aaagttttct ttgcctgctg caggttttttg atgagggtgg ggagagatgc cagtttgggt     960
acagattttt gctttcttgg gttctgctgc tgcttctaaa agtaaatctt tctttccaaa    1020
aaaatacagt tgcaatgtat agcatatcat gtaaacttgt aaaacagctt gcttgacatt    1080
tttgcagaat gaacagaatt tcttatacct gatatttgtt taatattttt ggaatatatt    1140
atgatgaggc tcttatattt tcattaagaa aattttaaac aacctttaaa atttcatgta    1200
aggtaggtgc ttgatttcat attggttaag aaattatttt gatagtttat tttaaagaaa    1260
aggactactg cagcacagga aaaataatag attagtaagg tttgggttat tttgtgggca    1320
gatggatgag attaaaaata taaatattaa tttgaatatt acatttttta gtataagatt    1380
ttgacaggta acttcagttt gggattattt caaatgtgat tattgttaga ggctttcttg    1440
tgataactac ttgttctata ttatgttttt gctatgtagg atcaatttgg atattggtca    1500
tatttttaaa agttaaaaat aacatttgaa aggcatactt acaactataa acccatgagc    1560
attaaagttt ctccagattt ggtagggaaa ggctgaagac tgtaatattt atatacagaa    1620
tattaacatg cagaatatta tgatcagtta aacctgatct taatactcaa aaataataaa    1680 attttacccct gattgtggac atagtgacat aatggaaaat cttaagcaaa gaacaaagta    1740
taagaaatac gtatttttttg gtaaatacag taacatggtt ttagtgaaca ggaagaggtt    1800
atatgttttc taagaaacaa ttagtagcat gtgttacaat cagtcaggac ttagttcgtt    1860
tacattgtta tttatactta aatcaaccaa actgttgctt gctacagtgt taatttgcaa    1920
agtatgtttc tttgtactac aagtctcata ctgatgaatt ctatctagat caaagactgt    1980
ctatggggaa aaggtttgtc ttagcatatg aaacactttt cagctgcttg tgttttggtg    2040
```

```
gtttcctaat ttgtctaaat tctaaatgtt tctttaacgg tgattgttag taatactagg    2100
aagtcgaatt tctggctgca aagtatttat tacctatagg tcaggaagcc taaggataat    2160
cttaattcca aacctccagc agtcctcttt tatgccaaat aatggtttaa aaaaaaagt    2220 taactcccca gctatccatt ttggcattgc tggcagtgtg ctcagttgtg aatgactctt    2280
ttgtgacccc ttggactaga gcacccagg ctcttctgtc cttgtaattc tccaggcaaa    2340
aatactagag tgggttgcca tttcctactc cagggatct tccccaccca ggaattaaac    2400
ctgcatgtct tgtgtctcct gcattggcag gcttattctt taccactgcg tcatccagga    2460
agcccatttt ttaagttagc gttcatatta agaaaaagaa tattaaaaac attgtcttta    2520
ctacttatta actctcttta ttttcattag ctttagactg tatatataag taatggtttt    2580
caggagaaga aaacttcgaa tgttgcctct ctctatagag ctcacataaa tggatattta    2640
attttctgag tatgtcatta gcttttctat tgtaaaattt aatatttaaa atattaatat    2700
ttaagagcta acagaccttt ttataaatca tttgacttgt aaaattgaca ttctagtctg    2760
aatgctacca agatgtgtac tgtgctgtag aatgttcatt tttaaaacct tcactttttt    2820
ttgaatacaa aaaaaaaaat gtacccaggg aattgtgctg ggaaaatact gacttgttct    2880
atttatcttc atctttctta gcccttt gaa tttcagtgca tcttgcatgt taatctacca    2940
gaagaatctt ctaaaatcat ttttgatatt taacgaaaat gttaccccat ttttcagtaa    3000
gagtaagttc aaactcctca gcctgtcaat tgaggccttc catcatttgg ccccacccca    3060
taattcactg ttgacctcct ttaagggaga ctggtgttac cttagcaccc tcccaaagta    3120
ttgttctttt tccagccctc atcatccttt cttcctggaa tgatggaatg cttttttcta    3180
tctttccagt caaagccagt cagttccagc ttcaggagtc ttcttccttc cagaagaatc    3240
tgccccaccc accccctcct tcttattctt gtctcttcct tccctgaatc ttgtgaactt    3300
tagtctttat cacaaggtga atgctttttt tgtgctgcct tcattgctct ctgtatgctt    3360
gtatacagtg gtggaagtga tcctagcagg actcagcctt ctggtaccca aagtttatga    3420
cttctattgg ctccagttgt ccagctctaa agtttaaaca gttagacatc ttaggccata    3480
catatcgtta aagattagtc acttactttt cttggcatag gccagaagtg ccatgagata    3540
cccaccatga aatgtcgtct ttccaattac tggcatacgt taaaaaatag ggtgcgagtg    3600
aaaatcagtt cctggatcct cttagggctt gggtatccac taatcagtcc agtcctgtct    3660
tcatgttgat aaaaatgtta aatcagtcct gatactacga cttaatcagt cagtgaacca    3720 gtgtcttca gctctggatg cacattacaa tttacaaata gtgatgcctg ggctccagcc    3780
agaggttctg atataattag attgcgatga ctgtttctga gcatggttta tgtaggcttt    3840
cttatgatag attatggcat aacttttctg gcttgcagat tttatccaaa aatgaccatg    3900
tttccagaat tttaacgctg tcgttgtcta ctgtggggtc agaatggcac cccactccag    3960
tactcttgcc tggaaaatcc catggtgggc tacagtccat ggggtcgcaa agagttggac    4020
acaactgagc acacacacgt acatggcgtc agtaatgaat tttcttagaa ctcagcctga    4080
accaagtgcc gatgttcccg tagcacttc agtctacggg aacatcacag aacgggaaac    4140
ttgaagtttc tgtgtctcag tgctgcactc cttgagggaa aggcccagat tcattgtaa    4200 tgtttgtatc cctagtgttt agttcagtat cttacctgta ttgcagaata aatgattatt    4260
aaataagtgg catgggggaa gacttaccta aactatatta tagtattctg tgttgaaagt    4320
gttgtacctt ttcgtataaa attgattctg tatcttttaa agaactgctg gttgaccaaa    4380
```

```
ttgctgattt aaaacacata tattaacatg ttgtttggat ttgttactga aaaattctgt    4440
tggaagtttt aactattagc attaactatt aaccacatca ttaaggtttt tctgaaatgc    4500
cagttaaaat ctgtgatgaa tgttgtttat aacttcataa gtacgattaa cagtttgttt    4560
taaaattact tttctattta ggtagaaaaa cattttgtta tttctttcat tgcatgtatt    4620
taacaacctt ctgaaacatt cttagataat agttaatatg cttttagta gcatgctcat    4680 ttttagtgtt agtcgttttt taaaattacc agttcagaaa atattcagt tgaactgaaa    4740 atttggtgtc tgtggagcag tgacccaggg tatcagctgt gactagtata ctgtgctgaa    4800
acagcataag cagcaagtgt gatggtcaac aagttataac actacatatt tcttcttgga    4860
actaatgtaa tgtagtaaga gataaaagaa gacatctgtc agttttgtgt ggagttcagt    4920
ttttctcctc tttatacggt tagacacatg aaaagaccat cacgagggaa ggacaagtag    4980
ccagtcagac agacagatgc ataaaatgca caggctatct tgttgttttt cagcccatct    5040
catgtttctg taaagggaaa taatttgctt tataattgta tcctaaatag aagatggagt    5100
aaagagaagg tcagcccaga ggaaatggag gatgatgctc aaaatagaat ttatgaatca    5160
cctgtttaaa agatggggat gtaaattgtt gatataaatt cctgactctt aaaaggagag    5220
cttctgttct ttggtatcac atgctgatgt ggtaggaagg attaattgct tttatctgcc    5280
tagtggcaag attattttca ggccttaact ctggacatag ttttacccca ggctgttagt    5340
ctaagttttt tgtctacctc attttttttc cctctcttt gtcttatcat ggaaacatga    5400
gccataaaac tttaggacag tattctccag atctctgtca cagaacgtga agtgaaactg    5460
catactgtga aggagtcata attgccattt actgaaagtt actctgctag tccaacatta    5520
agctagaggt gcctaaactc tcttgtctca tggcatcttg gggtctcatt aagtttttaa    5580 cagcacccatt aagtcactgt tatgttcatt aagtagttag gtccaaataa taaacattta    5640
catcccaaca actttagtag ctgtttggaa aaaatgatgc caagaaattg aaaataattt    5700
actttgttcg taaataacca caattattta ctcaaagttt ggggtgcctg ctaagcactg    5760
aacagctttt caaaccttgg caccagattg aactgaacag caccaccctc attgcctgtt    5820
ccgcattgac tttggagtgg aagtgttttg ttttgttttg tttttagtc agagaaacca    5880 ctgaaaactc agctgcccaa agatatgatg tcataaagga atgtactgca atcaaatgtt    5940
aaaaactcta aaccacccta gtgtaatagt ttgggcagtt cttagcatgt agtgagtatt    6000
tccgtgtttc cttccattta aaatatcctt catctctcct gggagtttgc tgaagtgtcc    6060
tggaccttct cagcatagag tttagactgt ggcactagac ttgctttatt tcattaaatt    6120
ctgtgggttg tacttttatc cccatttcga aaaagtggaa actgaggctt ggagagatta    6180
aataactact ccaatgacat agtccttagca tttgcttttt caccgtaatt attatttggg    6240
ctgctgttag ggtggtggtt attgtttggg gggttgagga atgaatagca aaaagacaag    6300
aatgcctata gaattttaaa gttgagtgaa atgggcagca ttttctaacg agggaagtgt    6360
taaacctgct gtgttttgcc tacaaattat tactatataa gggaaaaaac atggtttgat    6420
ttagcattag gtcattaaaa aaccaggttt ctttgccagg ccaagttaaa tgtcagcttt    6480
tagaattttg gatgacaact gtggtaggtg gtgataaaaa gcagtatccg tagttttttc    6540
ttttttttta attgccacat gctaccagtc accatgattg ccctttagat aagttacagt    6600
gctttatctt tttttaagaa aaaatttcaa gctgaaagaa gtgacttttt tatagttgac    6660
ttttgctgca cagaaaaatg aatttttgac ttgttagata cgactttatg ttaggggttgc    6720 aaaatttcac ttttttttctg taaataattt ttggaatgtt catatttaat aaaaaagaaa    6780
```

```
gtaaatagca acttttaaat atcaatgctt aaaaaaagaa aattacccct cctcctccat    6840
cctgggcagc agggttgttc agtggctcag tcgtgtctga ctctttgcga ccccatggac    6900
tgcagcacac caggcctccc tgtccttcac taactcccgg agtttgctca aactcgtgtt    6960
catcaagtca gtgatgccat ccaactgttt tgtcctctgt tgtcccctic tcttcctgcc    7020
ttcagtcttt cccatcgtca gggacttttc caatgattca tttcttctca tcagatggcc    7080
aaagtattgg agctgtagct tcagcatcag tcctttcaat gaacattcaa gactgatttc    7140
ctttactagc gactgctttg gtctccttgc cgtccaaggg actctcaaga gtcttctcca    7200
ataccacagt tcaaaagcat cagttctttt ttttttttt tttttaaagc atcagttctt    7260
tggtgctcag ctttctttat agtccaactc tcacatccat acatgactac tggaaaaacc    7320
atagctttga ctagatggac ctttgttggc aaagtaatgt ctctgctttt taaagtgctg    7380
tctaggtttg tcatagcttt tcttccaggg agcaagcatc ttaatttcac ggctgcagtc    7440
accatcagca gtgattttgg aacccaagaa aataaagtct gtcactattt cccttgtttc    7500
cccatctatt tgccatgaag tgatgggacc agatgccatg atcttaattt tgtaaatgtt    7560
gagttttaag ccagcttttt cactatcttt ttaccttcat caagaagccc tttagttcct    7620
ctttgctttc tgccataagg gtggtatcat ctgcctatct gagattattg atatttctcc    7680
ctgcaatctg gattccagct gtacttcatt cagtgcagca tttcacatga tgtattctgc    7740
atataagtta aataagcagg gtgactatat acaaccctga tatactcctt ttccaagttg    7800
gaaccagtcc gttgttccat atccagttct aactgttact tcttgacctc tatacagatt    7860
tctcaggagg cagatgaggt ggtctggttt tccattctct ttaagaattt tccacagttt    7920
gttgtgatcc acacaggcaa agactttagc agtcaataaa gcagaagtag atgtttttct    7980
ggaattctct taccttttcct atggtctagt ggatgttggc agtttgaact ctggttcctc    8040
tgccttttct aaatccaact tgcacatctg gaagttcttg gtccacatac tgatgaagcc    8100
taggttatcc tgttgttata acatagggct catagtagtt cctgggcttc ccaggtggct    8160
cagtggtaaa gaacccgcct cccagtactg gaaactcatg cttgattgct gggtcaggaa    8220
aatctcttgg agaaggaaat ggcagcccac tccagtattc ttgcatggga aatcccatgg    8280
gcttaggggc ctggagggct atagtacatg ggtttgcaaa gagtcagata ccactgagca    8340
actaaacaac aatagtaggt cctaagtgct ttcattttt gccacttaag tttgctataa    8400
gaaaattaag ggtgaaggca aaatttctgt ctcactgaat agtaaagcct aattatgtga    8460
cctttttaaaa gaatatttat ttatttattt atttgactgc accagttctt agttatagca    8520
tgtggaatct agtttcccga ccagggattg aacctgggtc ccctgcattg ggagttcagt    8580
tttagccgct ggactaccag agaaatccta tgtctcagat tttctaaatt gtccttaaaa    8640
tatagcttaa tggtataaca ggatctagat ttgtcctccc actttatata ataacaacaa    8700
aacaaacaaa aaatgtgaaa cagttgtcag ctccttgaacc ataggcagca caagacactg    8760
atccctgaga gaagggaaac aaatgaggtg attcttgttt gtgggttgct gccttgagag    8820
tttccaggct acaatagcat caggaggaac ccagacaaag cctggcagtc tccccgaatt    8880
gagacagagt agggactttg gggaaactgg ggcatctaga gttctcagga ctgagtacca    8940
gcataaggat atctgcacag agctcctgag atgcatggtg ggttccacgt ggtccctcag    9000
ctgagttctg tttggtacca gtgtgagagg aagctaccaa gactgggaaa gaagcaccca    9060
aaaggagcca gcagaaaaat tcctggtgct cacccaggtc tgggaatagg tcatggtcca    9120
```

```
aacagccaga attgagaaag ctgtttggtt tgagcacccc gagagggta tatattggtt    9180 cattagtggg cccaagttgc tctcaaccac atgctgctct ggtcctgccc aacaggcttc    9240
aaagcaacac ccaaagggat caaactgttt gcaactagtt tccaaatagc tcaactgtat    9300
cacagaaacc agtttagcac tgttcacagg aacacaaagt gtatatacat atatccagca    9360
ttcaaccctg taaatttcac agtgtctggc attcaattaa aaattaccat gcatgcaaag    9420
aagcaagaaa atatgccaca taacgagaaa agtcaatctg tagaaacaga tgctcaaatt    9480
aataagaaca ttaaaacagc tattataaat atactccgta tgttcaggaa cacaagaaag    9540
aatgagcatg ttaaggagag gtatacaaaa tgtgaaagac ccaaatcaga cttctagaaa    9600
tgaaaacagc aatgtctgaa atgaaaaaaa tacactgata gggattaata gattagactg    9660
cagaataaat gaatgacaaa tttgaagatg caataataga caactcaaat gaaacatggg    9720
gaaaaagact taaatagata aacagaacat cagagggctg tgggaaaatc tcaagtggcc    9780
agatatatac acatgggctt ccctgatggc tcagctggtt aagaacctgc ctgccaatgc    9840
aggagacaca agaggtacag gtttgatccc tgggttggga acatccctg gaggagggat    9900 tggcaatcca ctccagtatt cttgcctgga gaatcacatg gacagaggag catggcaggc    9960
tacagtccat ggggtcgcaa agaatcggat atgaatgaag tgactgagca cacacacatg   10020
tatatatagt tggaatccta aaagggaggg gtggagccgg gaaatatttg aagaaattgt   10080
ggctgataat tttccaaagt tgatgaaaac tataaatcca cagatcctag aagctaaatg   10140
aaccataagc agaagaaaca tgaagagaaa gaactacaca tggtcaaatt gcttaaaacc   10200
agtgacagaa aaattctaaa aataatccaa gaaagaaaaa agacatatgt gtagaggaat   10260
gaagacacga atcatgatag acatttcttt agaagcaatt taacctggga cttccctggt   10320
ggtccagtgg ttaagacgcc acacttccag tgccgggaat gtggattaga tccctggatg   10380
agcggctaag atcccacatg ctgtgcagca tgactcaaaa aaagaaaaaa gaaacagtcc   10440
aacccagagg agaaagagct aggtctttaa tgagctgaaa tggaaaaaaa acagaagaat   10500
aatgaaaaaa aaaaaaacaa aacaaaaccc aaaacctgtc catctagaat tctgtactcc   10560
atcacaaaga aaggtgatgt aaagactttt tagatgttca aaagccaaaa caaaatgagc   10620
taattatatg aatagcgatt tagattagta ttgctttttct ttatatctag tgccagtatt   10680
ttcagaaatt ctgagtttat aaagactgag tcagttttgt taattgtgta tatgtgtgtg   10740
tgtgttattt gcttagttgt gtccgattct ttgtgacccc atgtactgta gccctccagg   10800
ctcctctgtc tggaattttc caggcaagaa tactggagtg ggttgccatt tccttcaacg   10860
tgggaatctt cccgacccag ggatcaaacc caggtctcct gaattgcagg cagattattt   10920
gccacctgag cctccaggga agcccatttt gttacttagt tatgtttaaa ctctaaactt   10980
gaaagatgca gaaagagtgg aatggactta tgcagttggg gttagctttg taagtagagt   11040 gccgaagga ggtttatctg taaaaaattg tgtcttatgt tttgatggtg acacagttgc   11100
ttgagatttt taatagttgt taataagaat ttgtgtttta tcttttcca ctaaaatagg   11160 ttttgcctgt ttgcctataa tgtaagccat tgttatccct ctgtaatgtt ctacagtatg   11220
agcagagcat tcatgttggc atacatttcg tagccactga actaatagaa ttactgtgag   11280
tgcatttgga gagatgcatt aactctccct cgtcaactgg acactattta attactccca   11340
catttcaggt tgaaagactg tatgtgccct ttacactcct agatgattct gagataactt   11400
aagtcagtta aaagtaaaaa gagggacttc cctggtagtc cagtggttaa gaatttgtct   11460
accaatgcag gggatgaggg tttgattcct ggtcaggaa ctaaaatccc acatgcagta   11520
```

```
gggcaagtaa gcctgtgcac cgagactgga gagccagcca ctctagagcc cagcccatgc   11580
accgtaacaa gagcagcctg gcgccctgca ggccatgggg ttgcacagag ccggacgcga   11640
ctgagccact gaactgcgct gaagaccata ggatggggtt cccaggtggc tcagtggtaa   11700
agaatccgcc tgccaagcag cagacgtggg ttcgatccct aggtctggaa gatcccctga   11760
gaaggaaatg gcaacccatt ccagtattct tgcctgcaaa atcctgtgga cagagaagcc   11820
tggtgggcta cagtccatgg ggtcaccaaa gggttgtgga cacaacttag caactaaaca   11880
acagcaacag accataggat tactgtagtc tgttgactac cttactgaaa tgtagataaa   11940
caaagtcttt taatatcctg tggttcatat tctaagcata ggcaggatga atcatactat   12000
taagtaaatt cctagctgct ggtacattag tgctcgttag tggtctgtct tggtcagcgc   12060
tagggaagtg acgttggaga atgggtaga aatgtagtta ccagatgtgt agatgttaca   12120
acactgtgtg ggactgacac agagctgggt aaaataatta ctgattgtgg acggcacagt   12180
tgagatccaa cttttttaga ctgagaaaat ggattagaac ctgaaacatg aaaaatgcac   12240
tttccccttg tttaattttt gtgtccattc ctgaaccacg tgctgtgtgt gtagggccag   12300
caggactgct tgggttggac agatgattgg caacaggaga caactttgtg tagttgtctg   12360
agttcccata aagccgctac cagcaggatg ctacatagta aggaagggtt gatggccacc   12420
ttgaccactg tgttccttca aacctgctct tccttcagtc ttcttactc ggggagttgc   12480 cctccatccc cctggctgtt taaaccagaa cttaagaatc accctctacc cctccttcac   12540 tctggttta cacattcact ccattaccaa atccagtcaa ctcaacctcc taatttcatt   12600
gagaatccat gcagtttacc atttcagctg gttttgcatc agtaatgcca ctgcattctt   12660
tttcatggac cattgtaatt gcctcaactg gtctccctgc ttccactctc cccacccaac   12720
tctgcagtgt ttttaaatat gcagtttact tttttaatgt tttaaaagtt tgtttatttt   12780
gactgcgctg tgtctttgtt gctgcgcctg ggtttcctct agttatacg agcagggcct   12840 attttgttgc ggggcatggg ctctaggcgt gcaggcccag tgggcatggt gcatgggttt   12900
agctgtcctg tggcacttgg aatcttccta gcacagggaa cttttgaccc ctgcattggc   12960
aggtggattc ttagccactg gaccaccagg aaagtcctaa atacacaatt gagatcttat   13020
tcgcctgctc aatacccttc agtggttggc cactgaactt aaaatgcaga gtctttaaaa   13080
tggcctgcag tgaagtggag ccctgccccc ctcctcactc ttacactgta ctgtctcttg   13140
gtttctgtgt tccagccaca ttggcccttt tttaagttat gaatgtctca aattctttct   13200
ggtctcaggg tcttcacata tgctgttgct tctgctcaag atttttatttt taaaaataaa   13260 cttgttcaca catgtggaaa agtacataaa ccataaatgt tcaacttgat gacttattac   13320
agagtgaaca tattaatgtt gccactacca ggttgagaac tagaacatta ttgctggctc   13380
tcctttccaa ttattatctc catcatgata tgcagagatc ataactgcac gattgcttgc   13440
atcatagatt agttctgtct ggtttccaac ttaacataaa tgaaatcatt cagtaagtat   13500
tctcttgcac ccagcttctt tcattcagtg ttaaatatgg gagatcttgc ttgtgatagc   13560
gtatagcagt agtttattca ttttcattgc tatgtagtat tccattgtat gaacgttctg   13620
gtgttctgtt gacattggct ttattttcaa ttttttctat tacagatgat tctagtatga   13680
acatccttct acatgtcttt cggtgcacat actttaattt ctctgttgga tattcttagg   13740
aatgaaattt ctggttttag ggtatatgga tgttcctgga acactcttaa cctttactct   13800
tcagatacca actaaaaggt cacttccaca ggcaggcagg caggcaggcc tgcctccaac   13860
```

-continued

```
aaacaattttt aaattaggtt ctcttgctgc agtctattgg aactccatca ttgtgcttaa   13920
tataattttg cacttgtgtg attatataat gcctgtcttc ccaatggaag gtattagggc   13980
actgactttt tttattcctg aatagacat  tcagtacaga cttattgcac caatgagtga   14040
aaggttattt tgaaatgtta ctaagattgg ggtgtataat ttatatagaa cactaatttg   14100
gacagtgggt tatctttcag ctaaaagttt agttatttaa tagtacaaag aaaaccattt   14160
tcttttcaaa taattttttt ctttatgtat gataaaattg aaagaggctt tcttgccagc   14220
tgcttacatg atcttaaatg aatcacttaa cctctagtct ttttcttctg gaaatgagta   14280
gcttggcctg tagacctcga ggatcctctg acttgaggct ctcacatgc  aaataagcca   14340
accacaaagt gcggtgcatg caacctcagg caaattgtga ttctaggcag ggtatgccga   14400
tttgtcatct tgttttcata ttcttaccgg cttttttcag cttggtcttc tgaatcagct   14460
aaggaaaggt gtctgttccc acctggaagg cttgagccac agtagaaggt tgaccttgga   14520
tggcaggatc ttaactgagt aatgtaatta tttagcttga agtattgtaa ttcatcagaa   14580
gttagaggaa tctacattta aatttaattc agaaatacca tggacgtttt taaagaaatg   14640
acatttttt  ttttattac  tcaaaaatgc ttcattttt  atttagtttt ctgactctgt   14700
gcttgtgctt tcaacacttt cacaacgatc ttctgctcct ctttaaggaa agcgtgcttg   14760
atcctgtcac ggacacattt agcacacatg gaaccaccat aggcttggct gacatgctta   14820
ttcattttag acaatctcat gagaacttta ggtttcacag cacgaacacc tctaagtcag   14880
cctgggcaca caccacatgc agattttggt ttttttccaa tctccttggt ataaaggtaa   14940
acaactgtat taccagggt  tcgggacagc ctggttttgt tagaggctgt attgtaggac   15000
agcctacgat ggtatgtcag acgttgcacc atcctgaatg cctgtagctg ccatccccac   15060
aagaggaaaa aggaagtcct tgcaggttca agaaatgaca ttttaaatta tctgatgatc   15120
ttagatcata agatctaatt ttgcttcttt gggttcagat ggtgggtta  ttagcaaggc   15180
gggtatgacc accatgtcac agttatcctg tttattaagc ctctatttag attcataact   15240
caggaaagtc aataaatagg tatatgattg ttttcatctg aatttctgta cctgatcttt   15300
ttttaaaatt tgtttatttt caattgacag ataattgctt tacagtatta tattggtttc   15360
tatcaaacat cagcctgaat gagccatagg tttacccatg tcccctccca cttgagcatc   15420
tctcccacct ccctccccct gccacccttc taggttggta ctgagcccca gtttcagttc   15480
ctgagtcata cagcaaattc ccattggctc tctattttgc atatggtaac atatgttcca   15540
tgttactctc tccatatatc tcaacctctc cttcctcccc acagccatgt ccaccagtct   15600
gttctcaatg tctgtgtctc cattgctgct ctgcaaatag gttcatcagt actacctttc   15660
tagatcccat atatatgtgt tagtatacaa tatctccaaa taggaaaagg agtatgtcaa   15720
ggctgtatat tgtcaccctg cttatttaac ttatatgcag agtacatcat gagaaacgct   15780
ggactggcag aaacacaagc tggaatcaag attgccggga gaaatatcaa taaccctcaga  15840
tatgcagatg acaccaccct tatggcagaa agtgaagagg aactaaaaag tctcttgatg   15900
aaagtgaaag aggagagtga aaaagttggc ttaaagctca gcattcagaa aacgaagatc   15960
atggcaccca gtcccatcac ttcatggcaa atagatggga aacagtggaa acagtgtca   16020
ctttattttt tggggctcca aaatcactac agatggtgac tgcagcaatg aaattaaaag   16080
atgcttactc cttggaagga aagttttgtc caacctagat agcatattca aaagcagaga   16140
cattactttg ccaacaaagg tccgtctagg caaggctatg gttttccag  tggtcatgta   16200
tggatgtgag agttggactg tgaagaaggc tgaatgctga agaattgatg cttttggaat   16260
```

```
gtagtgttgg agaagactct tgagagtccc ttggactgca aggatagcca accagtccat    16320
tctgaaggag atcagccctg ggatttcttt ggaaggaatg atgctaaagc tgaaactcca    16380
gtactttggc cacctcatgt gaagagtttt ctcattggaa agaccctga tgctgggagg     16440 gattggggc aggaggagaa gggggatgac agaggatgga atggctggat ggcatcactg     16500
actcgatgga cgtgagtctg agtgaactcc gggagttggt gatggacagg gaggcctggt    16560
gtgctgtgat tcatggggtc acaaagagtc agacaggact gagcgactga actgaactga    16620
actgaactga tacaatattt gttttctgt gtacctgata ctatgtttca ttatttgcca     16680
taaattctca tttgaaaaga gaggtataac accagcaatg ctgagtaatg ccagtcacgt    16740
catatgacat agtaccataa agtaagcca gtcgaacaga aaaggtgttg aatattgtga     16800
tagagaacaa ttggtaggtt aaatttgat agagaacaat tgatctattt atacactgag     16860
tgttttctgt agtctataaa gagatcaaag agtttataaa gctatatata ggtttatagc    16920
ttctattttc attattttcc tgtagcttaa ataggaaatg tagattaggc ctaccttcag    16980
acattaattt gttcaattca aaaactgtga aacaccctca gagctaaaat aatgactaaa    17040
attgtaggat atcactagct catggctttg gtagttttaa atacttatta actacttctc    17100
cgatggtagg tgaaggcaac cttatgatct tccaactata actttgacag ggggctcccc    17160
tggtagctca gtgataaaga atttgcctgc caatacaggg gacacaagtt acatccccgg    17220
tccaggaaga tcccacatgc tgtgggacaa ctaagtccat gtgccacaac tacgaggcca    17280
caaccactaa gtcacctggg aagccccatc agcataagaa ggactatttt ctatgagaaa    17340
tatgcaaaag atttatgaca gaatactagc aatatatttc atccttaaat attttttgga    17400
gagtatgtgc ttatagcaca tattttattt tgctttaaat tcttttctgt gacctgattc     17460
ctgttcatat attcagtagg agtagaatcc tagggccttc agataatcaa tcctaatgat    17520
atgagattat acttaaaaat gtaactaaaa ttataaattt acactgaagg tagctcagtg    17580
ttctctggaa atgcacattt gtatttagag tgaagactaa gatttaaagc atgaatgaaa    17640
gatagtttca aacatgagaa gaaagttttt gcctttaaaa aaaaaaatta tttatttatg    17700
gccacatggc ttgtggaatc ttagttccct gacctgggat tgaacccatg ccccgctgca    17760
ttggaagcac agaatcttaa ccactggacc accaggaag tcccaagttt ttccttttaa     17820
aataaggaaa ataagagtgg agttaacata ctgttgacgt ctgaagtgta atagcagtaa    17880
cttcagaagc cgggctctga cttgacttcc gtgcttaaag tgtgagctga agaggtgggg    17940
ccttcttact tcagctgaac tgctcaagat cctggctcag aaggacttgg aaaacaatgg    18000
gcttcttggc cattcattca tacctactgg tgtttagaaa ccagtcactt gtaaaaagga    18060
aggcttgact ttcctagcat ttcatttgtt aaatagcaac aacatgaaga ggaaagggga    18120 gaaaaaata cctcttacaa aaatcagtcc gttcccctca tggaaagcac agtggagaac    18180 cttttatca gcaaggcagc acttagggga gaatgagcgg cctgagcttc cgcacagcca    18240
ggcttcctgg actttgagct ctgctcctcc tctcactctg tgtcctccga gctctccgcc    18300
cctgctgcca tttcctgtgc tccatagcgt ggatcctggt ttgcagtcac ctaatggtgc    18360
ccatcttccc catctctact tcacccctca ccacagacat cacattcgaa aattgcctcc    18420
tttactgtga ggaattgtta aacttcaacg atgagggttt tcaaatgctg tcagtggtaa    18480
gatgtaatgt ttatcttctt tgcatatttt tttaaaacta acaaaccatt ccctttatg     18540 cccaaaccct ttttttttt tttggagtta agttttattt ggttcaaaat aaggactgca    18600
```

```
gcccaggaca cagtgcctca tatagttcag aagaaatgtt cctctcaatt tattattttt    18660 tttttctgtta gatgaaaatc tagtcagcag ctgcagtgtt cagaggcttg ggttaggtgg    18720
gtatcgtgtt gagatataag taagtaaaac ctagtttcta ttgctattag tagacaagag    18780
atttccttcc agccagagta ctcagggaaa actttaggaa gaaagcagca ttttttggtta   18840 ggtattgaaa ggtgatgggc ttccctggtg gctcagtggt aaagactgcc tgccagcgtg    18900
ggagaccggt tttgagcccc gatctgggaa gatcgcacat gctgaggaac agctaagcct    18960
gtgcgccacg tctgctgagc ctgtgctttg gagcctgcgg gtcgcagcta ctgagccagt    19020
gcacctggag cctgtgctcc acagcaagag aagtcacctc gatagaagcc tgcgcaccgc    19080
aactgcagag tggcccact caccccaact agaggaaagc cttcacagca acgaagaccc     19140
agcacagcca gatagatcaa tgactaacaa atattcagga tggaaagaac gctgtgaata    19200
aggaaaggga ggtgggggtg aagaacacgg agcctgtagg aggcaagcac attctggttt    19260
tggctgaagc tgggatgcga gggtagagtg ttaaggggac aagaaagatg gggatggact    19320
gagtaaattc gtgacaaatg ctgcgtttta tctaaaggtt atacacgtta ttttaaagcg    19380
ttatggcttt cctatttaa gtgatctctt tatagtagag attctcaaat tgttttctag      19440
aaattaaatt atcagagaaa tggaacaata atttagtcag gtccctccta attatatatt    19500
tctcagtatt tcatggagtt tcataaaata cgggagtctt ttttttcccc tcagttaaaa    19560
aaatacacat atgggaagga aataaaattg aattataagt aattatctta atgccattta    19620
gagatacaga cttcttaatt taggaatatg cacatgtatt tctaacagct attttttgctg   19680 gctacattaa aatgaaaaaa aaaacacatt aaataatgtt acatgtatgg aaaagttgaa    19740
gttcagcaca aaagaatttt cttttttctga actatttgac actattaagt tgctaacatg   19800
aggtaaacag ggtttatctg tttcccctaa atgctttatt ataatatttc ctagaaaggc    19860
attcttctgc ataactacca gataaccgtc aaaaaatgaa catggtacca gctgtccaat    19920
tctcagactc tattttagtt cattagctgt ccgaacaata tctttcatag caaaaagatc    19980
gagttgaatt gtgtatatta tatttagtta tcatgtctct ttagtatcct tagatgtgga    20040
gaagtttccc agtctttgac atttatgact ataaagtgtt atggcttttg aaggcgaggg    20100
ccagttgttt ggtagaaatg tccctcactc agaatttgtc tgatggttct tcctgttcag    20160
agtcatgtgg tgttggcagg aatattacag aacagtgtgc ttttcatggt atcctgtcag    20220
ctgacacagt gttgacttgt cccatttact gttggtgttc actctgataa cttgtgttga    20280
tgtggtatct gccaggcgtc actggccagc tcttttttcc tttataatta ataagtgttt    20340
gaaggtgagg tactttgaga ctgtgtatga tcccattgct cttcaaactt taagtttatg    20400
ggtttattca gggatttata atcttttact cttaaaattt gtcttaaaat tgtcccaaat    20460
tttgccagaa gaagaagccc ctttaaggct ggcttctgta ttttttgtgac gtgccttaat   20520 tgttctttga acacttgttt actttctggc acaaaaattt gttctagcct tgtcttgccc    20580
ctgctgttct cctggaatca gccatttctc cgtggagtcc tagttccttt tagtggagaa    20640
tgtattagaa agcaagatct gagtgctggc tgtgttgtct gttattgagc attgctgatc    20700
acaggtcctg tcaattgata gagtgaagga aaatgtataa gcgtgtatgt atatgcaagg    20760
gtctccccct ggctcagtgg tgaataatcc gcctgcaggg caggagacac aggaagtgag    20820
gattcgatcc ctggaaaatc ccctagagga ggaaatgtca acccactcca gtactcttag    20880
cagaaaatcc tgtggacaac ggagcctggt gggctatagt tcatgggttg caaagagtcg    20940
gacacgactg agcacaagtg ggtctatgta tttgaaagta taattatgcc cacccatttc    21000
```

```
tgtctttgtc tgtctctcta gaaaactgag ttcacagtgg taactccagt tccgatcagc   21060
accacagcat cttttctggt tttctctctg tgtttgtact gcccttttcc gacagtgaga   21120
aacctgctcc gtggttcttg gtcgtcccce tgtgtataac caaccactct cctgttgcca   21180
ctacagcctc atccaccca cgggtggctt ccttgcccca ctggggctct agcaccctgc   21240
ttggagcctc cgtccaacgc accgtgcctt ctctactctt tcaagctcca gcatccttt   21300 gcaggccatt cccaccattc ctgggtggac accacccttc ttactccgct cagacttcat   21360
cacctcctgc ccgctgcccc tcccctcaaa tggagtcttt cttccccac ctgtggcttc   21420 aactccatga gcaggacac cttcttactc tccctggact cacagcctgc gaaggacctc   21480
cttccattct accccacacc tttgaagcat aaatgaaaca acagttaatc atctactgtc   21540
ctttagagta aagatattta agaaggaaac actaggtttt ctttataaa attggaagga   21600 tctagaggta aatgttcata tggttctgaa atcgccttca ccagttcact gaacataaat   21660
tactgaactc ctcctgggtg ccaggcactg agctagccca ccggggacag gccagtggat   21720
tagacaaagc cgcttccctc aagaagctgc cttctctgac tgttggagtg tagccagggt   21780
agtaaattag taacctccct aagcctgttc cctcctgtca aatatttgtc actctaaaaa   21840
ataatttaaa atttcattta atattttgag aagaaaccaa aaaattcctg gcagggaaaa   21900
tgacatctca tctattcttt gaatcatttt tctttccttt agcattattt tagttaagaa   21960
tatacacttt aatttaaatt gtgtatgttt gtgtgtgtgt cctgttccct gagtctcaga   22020
atataataca aaagcacaaa taactaaaca gtatgacatt tgttcacctg tttgaatcag   22080
gtgacagtct aatagatggg tcttctttgg gcctgaaaaa catggtagat tcatatattt   22140
ggagcacagt tattgaaaag gtaattatta tgcattatta gaagagagaa gattttgttg   22200
catggtaatt taagttataa aatgactttg tcttttctaa gggaaggtgt atgttagttg   22260
cttaggcatg tctgactctt tgcgacccca tgaactatag cctaccaggc tcctgtgtcc   22320
atgcgacttt ccaggcaaaa atactgaagt gggtggccat ttccttctcc agagggaaag   22380
tgacaactta acactaaaaa tatattttct ttttaaccct attactggta tttgaaccta   22440
aatggttggt gctaaaactg atagatatat ctggtaattt ctatattact gtactagtgg   22500
tagtgtttga aatgcatata acgtgtaaac tctagaatag aatttgccct ggaaaccatg   22560
ccttctatca tcagagagat aacaagcctc tctaaggttt gcttttgtac attttgtact   22620
tacaaggcaa gatgtgggag aaggggttcc tctattactt taaaattaaa aattgtgttg   22680
tgatattttc taacttggag aaggcgatgg caccccactc cagtactctt gcctggaaaa   22740
tcccatggac ggaggagcct ggtaggctgc agtccatggg gtcactaaga gtcggacacg   22800
actgagcgac ttccctttca cttttcactt tcatgcattg gagaaggaaa tggcaaccca   22860
ctccagtgtt cttgcctgga gaatcccagg gagcgggag cctggtgggc tgctgtctat   22920
ggggtcatac agagtcggac acgactgaag tgacttagca gcagcagcat tttctaactc   22980
tgttccttgt cattgaatgt taggagtaac ttctataaat atatagtgta acaaataata   23040
atgataggaa ctctaggaat gaagaatgaa attcacatcg ccataacttt aatggcttgg   23100
tgaaatcgtc ctcactccct aacttcatac aggtggtttg ataaaaataa aggcccaccg   23160
cagtaaagag catgctaaag aagtgtgaca tcatcaggtg gctgagtgag tgactcagtc   23220 ttttttttaat atttatttat ttatttggct gcatggggtc ttagttgcag cattccagat   23280
ctttagttgc ggcacgtgaa cttctggttg ccccacgtgg gatctagttc tctgaccagg   23340
```

```
aatcgaatgc cggccctctg cattgggagc ttaggagtct tagccactgg accaccgttc   23400
agtcttagcc tctgctgcca actagcagag cacagctcat tcgacagcag aagtgggata   23460
atcaggaaga agtctaaaag tcagtggtct gaaaagaggt gaggcaggca gggaagatga   23520
gctgtctgga gaaccctgga gacgagcttc gagacaaagg aaagagcttt aatgcagaat   23580
actatgggat attaggcaaa gcagtagact gagactatgg ccgttttgtt ggcaatagag   23640
atcaacagag aagactgtaa gaatctgctt acaagcgttt gtaaggtgga acacatgcat   23700
attgtcaaaa catattcaat actgtgattc tgtatcagaa tgtaatttat tagaatattt   23760
attagacttt gtaatatact gtattttatg tgcaaatctt tgagaaatga gagaagggaa   23820
aagtacaaga gataagagat aaataaggag tgagccagtc atctaagagg tgaactggga   23880 gctgtgggt aggctgtgga ttagggaggg cagtgaagaa ggaaagaact ggaaaggaaa   23940
ggatggaatg aaaaagaggc tcctgtcttt ccagatttgt aggccttaga aggtcatatt   24000
tgctattgta cattgagata ctagctgtgg tttatgtttc tttggttctg tgtccagttt   24060
tcaataagtg tgtttgctaa gaactcggaa ggttttcctt taaagcttca ggatttgttt   24120
ttgttttttc tcaatagaat gaccatcaca gcctgtctaa gggaaattgt tctgtaggtt   24180
gtattcatta gtggatgaca ttaacttcat agcagaagaa ataaatccag acgaaggcca   24240
gactgacaat ttccctgtcc ctgtgcttga ctcatgtggt caagcattac cattaacttt   24300
cataatttaa gcgttagtag tcttccatgc gtcaagctct gttctaagtg tcaacgatta   24360
aagaatgaat aagacaagag ttccaccttc agggaacagg ttggctaatg agaaagacaa   24420
gtgatgaata tattttaaat gttttggcaa catgaagagg gagctctgtg aaattcttgt   24480
gcttagataa ataaaggttt caagaaagtg actttatgtc tttgttttc taaggtgagt    24540 tcagttttgg ccagaggcaa aagttgggtc aagccttgca ggcagaaagc cagatcactg   24600
tgcaaaggca cagagatgta gaaagtgtgt ttgggcaaca gtgagcgtct catgtgactg   24660
gggcataagg tgcatgggct gtggagggaa ggggagcaat gaggactgaa gcagaaacgg   24720
tgggttgagg ctaaagtctg gaagagtctt tgttaagggg ttgggtgttg tcccgtaggg   24780
atatcaggac gcagtgtgtt cctggtatta agattagcta aacagatcag ggggacagcg   24840
aagaaaattc aaaagcaacc tccaaaagat aggaatatta ttaaagatag taagtacttc   24900
aggatcatta ggcgaggatg gattcatgaa ttgatggtgc tggaataact tgttacttct   24960
ttgggaaaaa ctattaaagt tactggttca aaaaaagatt ttatgcagta catttatgtt   25020
aagaatatca gacttagatt cagactttag attttggtt gaaactctgg ctttatagct    25080
aaagcgaatc tggtgtttca ggtccttttt cttatactaa agctttttt ttttttttgt    25140 agcatcagca gaaaagagg caatcaaggg tacatactcc aaagttctag atgcctatgg    25200
acttttaggt gttttacgat taaatcttgg taagtattca atataattca atctgttttt   25260
tcatttctgt ttttgtaact ttgaagattt gatagacatt atttcataga ctctgtattt   25320
gatctgtgag tataatcatc tcttaacctt gagatggttg ttgcctgaaa agccatgcta   25380
catgctcatg ctctcatgat tctaaattcc agagacagca tcctgtctga acactttaag   25440
agatagtaac attgttagaa gagaaaaata agggcattgc cccctttttt ttttcttgct   25500
tcagtgcact taaggaaaga tgtcttagaa ccacacactg tttccctgg tttgtggtgg    25560 aaaagatacc tgttttctac tcaaaacatc tcagcttgag cctgtatgcc attcagtgtc   25620
atcatgggct gcaaagtaac atttgtgatc accagttcta caacagtgtg actcagagtg   25680
tggcccacgg acaggttaca ctccatgaac tgttttgtta gtggtctgga tgagaaaaga   25740
```

```
agctggtgcg gtcatgcaaa tcaacacatg gcttccttca ttgataaagt cttactgtgg   25800
agaaaaaaaa agaagtcagc taaaccaaat agagaactta gtgaggcagt tttctcttct   25860
ggagcaagca cctgttctca ctaaactggt aactgaacta gtccatggat agtactttga   25920
ggagcactgg tcttgtcaaa tggagatatg ccattcgtta tgagtctgtc acacgtaaag   25980
cactgtgtgt gcgtgcgtgc tcactcactc agtcatgtcc gactctttgt gaccatgtgg   26040
actgtagccc accaggctct agtgtccata ggatttcagg caagaacact ggagtggctt   26100
gccatttcct cctccagggt atcttcccga ctcaggggtc aaacctgatt ctcttgcatc   26160
tcctgcattg gcaggcagat tctttaccac tgtgccacct gggagcactt aactagtatt   26220
gccctggatc atcctcacag tccaatgaga tttgctttaa tctcattttc tttttttatt   26280
tattttttgg ccacccctca tggcaggtgg gatcttagtt ccctgaccaa ggatcaaact   26340
tggatccctg cattggaagc agagtcttaa ccattggacc gccagggaag tcccttaatc   26400
ttattttcta aaggcaggat atctcatgtt gcatatgtta acacatgaag ttggttgatg   26460
taataagtag tggagaagcc aagatgcagg gcacttctgc ctatgtcaag cccccacatg   26520
ctcaaagtat accactgctg aattccacct tcatactcac tgcacaggat ttttgtcaaa   26580
attagatgaa aaaaattgct atgaaagttt ttgtcagcca aatcacttta taaattgtta   26640
ccaaagactt tttcttcaca tagcagcaac agcagcagca gttcacattt aaatgccatt   26700
ttttcaacct tactgtttat gaaaaactct caattcattg tcttgtctga acttcttaca   26760
atcataaagg aaaggtaggg aagataacac ctacatttta aaaatttgat aaatctcaca   26820
tacttttaag tagaggaata atttcataaa tgtaagatta ttctgttaat gtttaaatgc   26880
ttcatcatac taaatgtatt taacaaggat ttttctccc aacttctgcc aaaatcttgt    26940
tgtgaactta aatgtgtcta tgataaattt aaaataacca cactgtcaga ttttaaaaga   27000
cagagacact agaagaaagt tggaagaaat tttgaatagc ttgtagaata ttggcacttc   27060
ccatcccatt aagtctttgg tttttgcagg tgatattatg ttacattatc tggtcctagt   27120
cactggatgt atgtctgttg gaaaaattca agaatctgaa gttttccgag ttacttccac   27180
tgaatttata tcactgcgag ttgattcttc ggatgaggat cgcatttcgg aagtgcgaaa   27240
agttttaaat tcaggaaact tttatttgc atggtctgca tccggagtca gtttggatct    27300
gagtcttaat gcccaccgta gcttgcaaga acacacaact gacaatagat ttttctggtg   27360
agtttgtatt acgttttccc ttgtgatcac gtgcagtgca gccactggtg agctggaaca   27420
tggaaggcat aacagttatt tctagagtgg gcaacggtgg gcacggccag ttgagcacac   27480
cactctttac tgttgcggga tcctcagtgg agcatagcag atatctgcca tcgttttatt   27540
aaagtagtcc tgtgacgtga aacccattta ctcttcctga tctagacaga ccttccattg   27600
cagacatata tttaaaatat ttattttaa atcaggaagg aattaatcat aatagaattg    27660
tgttattcat atgtatggtt cttagtttga gatctcatct ctggccacat ttgcctttct   27720
aagcctacat tcccttattg ttttaattgg aaggttgtaa gtaaatgatt ttttttttat   27780
tcaagagcag ccgactacag ggaagtagta tgctggaatc aagtttagta ctgtaataaa   27840
atgggactta agtaggtaac tgccacatat ttcgggatta tgcatgaagg tgctgtatgg   27900
taagtatgcg ttaatggggc agcaggaccc acatgactgt aattggtatc gctttattgg   27960
aacagaccag atttccagta tagtcgttct cttgtcccaca gtcagcattg ctgttgactt   28020
ttttccttaa cacaatggac aaattgtatt tcagttgttt acttacgtta taaggccaaa   28080
```

```
gtccaggact atgctcacag cttccctcag taattcagac tcgggggttc cccactgtat    28140
actttctctc tctcccactt ccactatctg cctgaatggt cctggagaaa ggccctgggg    28200
atcagagggc tcaaagtcag caatgctagg actggaaact acatttagag caataacttg    28260
gtagcttgta gctcccatag aagtgtcttg gcccagagtg gcattgggga gccaagaagg    28320
cagagggaaa aggggctttg gagcgctgta tctggagact tggagcctag cggagggcga    28380
aaggatggcg gtggggaagg gagggcatag gagagatgag tcgcagtcc catctgctca     28440 tgtcaacccg gcacttctct gatggaagag acactgatgt ttctgaagaa gctgatggcg    28500
ttgcagctgg tcttagggca gctctcctta ccttcttcc ctctgctctt tctaacccca     28560
catttcttag attgagagag aaaagtttct ctgccgtaat caagtccagg caaatgcaga    28620
tgcattggct aaatgccag cagttaagaa tatcacaaag tttaatccgt gggaataatt     28680
cttttatctt ttcattcagt tatgggtaga agtgggggcc aatttagata acagattgag    28740
gaggtttatg agctggaaac aggctgagca aagaggaggc tgaaatgcta aaggtgagtt    28800
ttgctcactt tatagtcttt aaagctttgc taaggattag agtctggagc ttcactttgc    28860
atagaaaaag gaaagctttt agaattcatt atgccaaccc ttgcagcttt gtagaaatat    28920
ttcccaagat acagccaagt aagttctgta gccagagagt ggcaaacacc tatcccaaaa    28980
gcccatgtag ttttaatcca ttggggattt gaggctgctg ccagttgaga gtcaagtgta    29040
aacttaaata gaattaaaac agcaaggcat tgactgtgaa gaaaaacgaa aactgacagc    29100
agagggagaa attctatctg aacaaataca cggctcccac tgctatttaa atgggggaca    29160
atcagtctgt cctacctctg ctatgatctg ggcctcagct ttggtatctg gatgaactgg    29220
gtcacagcca gtttgagctt tgccagttca gatcaaggta gatattaagt aaagtgtgga    29280
aactgaagtc acgtttttaa attagtaata ttcatcggat ttaacgttat cccaagagta    29340
agcctactac tcactgactt tccagtctgc tttcttcagt ggataagaga ggctggggtt    29400
atatctggtt tatcaggatt acaagtggcc actacctgtt tactgtcccc tgcagcgtag    29460
cctgaagtgg tggggactgg aaagactgct ccaacagcat tgatgtagat tcttaacaac    29520
tctaagcttc caagaaaatg ctgtcacatt gttttatac ctctttaaga aacaagatag     29580
tgcaaagcac ttaagatttc ctcttaaact ggtagtttga aaactcagag aaccaagctt    29640
caataattct agcaacttcc cttttgtaag gcgccttat tatctgcaag tcccagagag     29700 gaagttttc tgcacaacag catatttac ttggtggtgg tttggtgagg cgttttggag      29760
gcctgtgttt ccaacctcca gccttccttt ggagaaggaa atggcaaccc actccagtac    29820
tcttgcctgg aaaatcccat ggacggagga gcctggtagg cttcagtcca tggggtcgcg    29880
aagagtcgga cacgactgag cgacttcact ttcacctttc actttgatgc attggagaag    29940
gaaatggcaa cccactccag tgttcttgcc tagagaatcc cagggatggg ggagcctggt    30000
gggcttccgt ctatggggtc gcacagagtc ggacacgact gaagcggctt agcagcagca    30060
gtggttccag cagagcccct gaggcaagca gagggatgtg aagatggcca gtgtagcagg    30120
tccccagccc ccatcccaac gttagccatg acaactccac ttttaatatg ttttctgatc    30180
atcaggtttc tgtgtgttca tttaaacaga actctctgcc ctaaaaagga ttgaaaagta    30240
ggccctctct gttacctaga gtatagaagt atttggagcg ctgggaaaac cctagacagg    30300
cattaatatg gtaattacta gctcatgtaa ctatttaaat ttaattaaaa tggagcctta    30360
taaaagtcaa gccttaagaa aatccatata tatatgaatt ccctggagtt gggtgtggaa    30420
acgcttttgg aacaagtggt aaatacatta tgaagaaaga cataacaaat ggggcccaaa    30480
```

```
ttctaaaaac gtagaatatg tgctgctttt gcatggccca ccgatcacac gtccaagggt    30540
ctctctgtct agccctatcc tccagtccct ggcacaatga atgtaagtgg gttgatttcc    30600
ctctggcgcc tctgaagtcc caggggcgct gtcttagaat gcatgttgtg ttgtgcagtg    30660
tgctgcctgt gctcatcgct cagtcacatc caactctttg tgacccaatg gactgcagtc    30720
catcaagctc ctatgtccat ggaattttcc aggcaagaat actggagcgt gttggggagt    30780
gctcatcacg ctaatgcagt tctttctttt tctgttagga atcagtcttt gcacttgcat    30840
ctcaagcact acggtgtgaa ttgtgacgac tggttattac gcctcatgtg tggggagta    30900 gaaatcagaa caatttatgc tgctcataaa caggcaaagg cttgcctcat tccagacta    30960 agctgtgaac gagctgggac caggtttaac gtccgggaa caaatgatga tggtcacgtt    31020
gccaattttg tagaaacaga acaggtatat agtgttttat cttgcttaat cacaaagaac    31080
aattgcaaag cagatttta tttgattcag aactcatttt gacatctgta atgccatttt    31140
atggttgctc ttggctactt gtgagcctta agaaaggatc ctcaaaaaca agcttattta    31200
ggtatggctc tttgagtaag taacaatttg ttactaatca gcatgacatc atcagtgccc    31260
tatgttttag tattgaattg aaaatcttca gttacagagc tagacaactt aagaaaagtg    31320
ggttttaatg aaattaagtc aaactcaact cttaaaggta ggttgtgtac catctgaaag    31380
gagaagttac attatttttg gctataacta tgtaattata aattcaggcc ttgccctcaa    31440
tccagttcaa gtcttcagat tagtttttaa aaattagaaa aagctaaaga aaaataacaa    31500
aatgaattca aaaggaattt cttttttaaa agttgtaatg cttatgctta tattttcact    31560
atcggttaat gtttgtagaa ctatcactag ttgaaaaaaa ttcggcttat ttatggccta    31620
ttttgactat tttgttagga taattttgttt atgagagact ggtcaagaga tataactgtt    31680
agtagatttg tcttctgatg tagaggtaac aactttgtgg aagtattta cccagtattt    31740 ttctctgtag gttgtgtact tagatgactc tgtttcttcc ttcatacaaa tccggggatc    31800
tgtcccattg ttctgggagc agccaggatt gcaggtatgt gttttgacat ttagttttct    31860 ttcttttct cttcagaact tttcatattt tttaaacttt caggttagct tattagttcc    31920
tcggataatt ttgttactca gtctaataat gttacctgga tttataaata aatagtatac    31980
agaaattgtt tacaaatcct ggaattgtct tagttattct ttccttcagt gttctttcaa    32040
atatccatag gagtgcagct cccatatttc atattaaaat ttcaatgttt tcatggcgtg    32100
ttgattttca aagtgtttct gtatttacta tcttcgtata taacaattta gcatctgtag    32160
gcagaaaaat gtagtagtta aaacaaagct tctgaaacta agcctctcaa tttgaatcct    32220
tatactgcta ggctgtgtga tctcaggcaa gtgatttaac cccttagtgt ccattttctt    32280
atctgtaaca tggtaatatt agtagttcct acttcttagt ttcttacaac ccttacctag    32340
ttctgaccgc cagaactagg taagggttag ctgaaatggc accccactcc agtattcttg    32400
tggggagaat cccagtccat gaggttgcaa agagttggac acagctgaat gtctgagcac    32460
gtttgttgtt attaatatat ctaggaattt cctggcatgg cagtcagtgg ttaggactcc    32520
atactttcac tactgagggc ccaggctaga tccctggtag gggaactaag attctgcaag    32580
ccatgcagtg tggccaaaaa aaaaagagga acatatctgc tgatgaaatt ttactttgca    32640
gtttgtaatg acttgggact tgtcatcttg aacattgttc tctgttttgc tttctgatct    32700 tttcccccc aaactttcct tttgtttagt aaatgtctaa tctttaaaat gtaagatgtt    32760
tttttcacgt tagttcataa tattggattg cccatactag tgtgattttg cattttattt    32820
```

```
ttattcaaac atgtttagtc cctaaagtat aagttacatt cattttgggc ttctgatata   32880
tactgcctag taaattctgt gcctcagtct atactattga aaaaaatata caggaaaaag   32940
aaaattttgc cttcatttac tttcatttag ttcacagctg ggtctctctt acactctagg   33000
atggttattg tggagaaaaa ttgcacacca cttgaatctt ttcaataagg gagtttattc   33060
aagacaggct aagaattaac aaggattaac actggtgctg ctttgctaaa attcttgagt   33120
tcttgtcaac accagtttga gtcatgtggg tttcatcttt ggcattttgg cgtaacttat   33180
atagatatat ttcttcctgt gtctccctta ggaaagaata ccaaccctac cccatttcta   33240
tttttgtgac cagagaaggg tgtttggaat atttgctcta agaaatttct aaaaccctgc   33300
tttgatggga ggtaaacgct tttggtttag agacaggcta gtgtaagaga ttcttctagt   33360
ctatttatag gccctctgtt ttactgcttt ctgtgttatt ttcttaagtt cagaattaca   33420
gtgtttgatt attcagtaat gttgggtcct gagtagttac atggagggat cctccttgga   33480
tgggacttcc tttcgacgtc cttctttgtt ctgtggcctg tccacacaga taatctgact   33540
ggataatgtc atttgattat gggccgacaa ctgtagattt gaaaattgtg cctttcttga   33600
tagagatagt aattttttgag acctcaagac agtccaacag ttctgccaaa tcatcactga   33660
gctggcctgt catcttgggt tgggttgagg gttgggtcag tggttctgag gtatttagct   33720
tagtagtttt taaagccaac ctttctttga ccagagatgg attagtttca tgagtatctt   33780
ttatcatttt ccccaccact ctaaaagagc agttaataga ggaatgaaaa taatagatac   33840
tgacttttg aaataaaaat accaaggccc taagttcatt tttgacttca agcggttgtt   33900
gggtgtcctg agtgttctta gggctggaat ttattttcag ggctccttca agttagtcac   33960
ttagtgagct gtttcacttc agtggtcacg gacagtgagt ccttccttgg cagttgtccc   34020
ttgttctctc tcttttcctc catgatacat tcttctcagg ttcttgagct attttaaagg   34080
aatctttgag agtgattta aaatgcagat tcatggcctc aacttcccat caactgaagt   34140
agaatttgtt ggagtagggc caaggaatct gcatttcaac caggtacccc accactcaga   34200
ttagagagct tggcggtagt ggatcctgct cagctgcttt tgcagcgcat ccagactgcc   34260
tgctccagcg gccaaccctg agccaagcaa ggcagccctg tgatgcttaa tcccagtgct   34320
gtctgaggtc ttggactttt cttttcattc ccacttctgt catcttggtt aaggtcttca   34380
tagtttttc ttgcctgaaa gattctcaga tttctaactg gtctcctccc atctttctgt   34440
tgtctaacca acgtattgct gtaagaattg tgaattgtag gtagttttat atatgtgttg   34500
gggagcaagt aatagggaac aactacagcc attaccaaaa aacaaatatg agaaagcttg   34560
tattttttt caccttcttg acagttaaga gtactagtgc aagatgaatg ttaatgaata   34620
aacaaaatgc aaagtattgg acttttagag agttagaggg caactacctg agatgactcc   34680
agagaaaaag tatgaacttt gtctgacgtt tctgccgcct aaaatgcaca aacgtgtctt   34740
ggagcacaca cctttcaaag cttaagattt tatacagtct attgtgtact aaaagtaaaa   34800
tgaaataaag atgtgacatt tggctaatca gtttcttact aagaaggaaa agctctaaag   34860
agagtccact gatttctcag gacagtcatt cagtcatctc ggcaggagag ggaatgctga   34920
atgaatgata atactgttaa ttcagtttgg gacatggatg agcatttaga gcttattttc   34980
tggttttatt tgtccaattg catgactgat ctggcacttc tcctccatgc cacctttaaa   35040
gtcacattat tcacagatga gccaggatga attctgggga accttgggcc cacagtctca   35100
gggaggtatt tacaagtgaa actcagggaa ataatctggt ctcactgttg tatttcttct   35160
tggcatcttt tgtatctctt gattctgcct catctctctc ccacttttcc tatatgagaa   35220
```

```
aagaaaaact gtagcaacac acagtaggta gttattttcc atcttgttta attcttataa    35280
cccaaatttc aaaatatgct gttgttttag ttgtgtgcct gagagattga cttggaaagt    35340
cttttttccag gaatggttat gggatctttg ggtgagagtg gagtgaatag ggtatttagc   35400
ataacagaga aaaaaaatat gtagccattg cacttgtcgg cagtctgaaa gagtagatgt    35460
tttggtcagg aggcctgtac tgtcatggga atcattttc ggaatgaatg atgttgctgt     35520
aagaggacag gtttcttcac ttgactgggt ttgttctttt gttgcacgaa tgacaatatc    35580
tgttgactta caaagggcac atatttagaa cgtaagacaa ggtaatgtat atgaaagcac    35640
tcttaaaaat atcttacata aataaaaatt cctgttttta cagtttacca gtttaccagt    35700
gttgcataat gctctaactt ctagtttttt tttttttaa tgaggttgta ttttaaaaga     35760
taaaaaggag aaaccoctag aacttatttt tttaagagaa tatcacaaat gacaattact    35820
gagcttacta ctgtgtgctt agcaaatgaa ttattacata gagtaaacaa tgctatttct    35880
ttcgtctgca tgttggcttt tggtacgatt aagcatattt ttcttatctt aggtgggatc    35940
tcatcgtgtc cgtatgtcaa ggggatttga agccaatgca cctgcttttg acaggtaaga   36000
ctgatgactt tatatattg ctgtgagttt tgatgttgct aagcagtgag attagttgta     36060
tttactgctt catttcacct tttgggctct taagtaaaat ttcttcttga ctctgattta    36120
agtggaagac agtgacactc ttaggaattc taggagtgat ggcagtaagt gggtaggtct    36180
tgatgtcttg gccttaaaac tacctctgat gggtgtgtta tccaatatgg tggctattag    36240
ctacgtgaag ctagctcttg ggcatttgaa attgactagt ccagattgaa atatgttgta    36300
ggtatataat aggtcctgga tttcagacct agtgcaaaaa aaatgcaaaa tgccaatatt    36360
tgttttatat atcaattaca tgaactaaaa agcctcttga tgaaagtgaa agtggagagt    36420
gaaaaagttg gcttaaagct caacattcag aaaacaaaga tcatggcatc cagtctcatc    36480
acttcatggg aaatagatgg ggaaacagtg gaaacagtgt cagactttat ttttttgggc    36540
tccaaaatca ctgcagatgg tgactgcagc catgaaatta aaagacgctt actccttgga    36600
aggaaagtta tgaccaacct agatagcata ttgaaaagca gagacattac tttgctaaca    36660
aaagtctgtc tagtcaaggc tatggttttt tctctggtca tgtatggatg tgaaagttgg    36720
actgtgaaga aggctgagtg ctgaagaatt gatgcttttg aactgtggtg ttggagaaga    36780
ctcttgagag tcccttggac tgcaaggaga tccaaccagt ccattctgaa ggagatcagc    36840
cctgggattt cttttgaagg aatgatgcta aagctgaaac tccagtactt tggcccctc     36900
atgcgaagag ttgactcatt ggaaaagact ctgatgctgg gagggattga gggcaggagg    36960
agaagggac gacagaggat gagatggctg gatggcatca ctgactcaat ggacgtgagt     37020
ctgagtgaac tccaggagtt ggtgatagac agggaagcct ggcgtgctgt gattcatgag    37080
gtcgcaaaga gtcggacacg actgagcgac tgaactgaac tgaacatgta gaaatgatac    37140
tttagttgta ttggattaaa taaaatatat gtaaattaat ttgacctttt ggttttttacc   37200
tttttaagtt gccttctgga aaattttaaa ttatatctgt gacttacgtt atatttcctg    37260
tggatgacat tgctctctag cctctggact gattagaagc tggagagact aaaggatcct    37320
ctgtggggcc tatttatctt aaggctggag ctgttcagga gctctgaatc cacacggagt    37380
aggcagtgtc ctcacatgtg aggtgcagcc tagtgccctc taccctcatt gccttgccaa    37440
cctagctgca tggctcctgg tttccatgtc cacccagcat tagcctcagg gtggagaggg    37500
ggccagatga ctctgaaagc cctagcatca gctcagtgca gttcagttgc tcagtcgtgt    37560
```

```
ccgactcttt gcgactgcat ggactgcagc acgccaggcc tccctgttca tcactaactc   37620
ctggagctta ttcaaactca tgtccgttga gtcggtaatg ccatcaaacc atctcatctt   37680
ctgttgtccc cttctgctcc taccttcaat cattccccac atcaggatct tttccagtga   37740
gtcagttctt tgcatcaggt ggccaaagta caaggagttt cagcttcagc atcagtcctt   37800
ccaatgaata ttcaggactg atctccttta ggatggactg gttggatctc cttgcagtcc   37860
aagggactct caagagacta atggaaaaac caaagctttg actagacgga cttttgttgg   37920
caaagtaatg tctctgcttt taatatact gtctaggttg gtcataactt ttcttccaag    37980
gaggaagcat cttttaattt catggctgca gtcaaagtct gtcactgttt ccattgtttt   38040
cccatctatt tgccatgaag tgatggcaaa tagatgataa gttgataagt cagagagaaa   38100
attgcattaa ctgacttttc acaaattcag agttttgatt ccacgtgaaa tggatttgta   38160
tatagttttg ccaatcctat gagtttaaaa tactgccatg taggtcctgg ttaaaagtgg   38220
gttcctgttt attgaaaaaa gttttttgact tatcacttga catacgctta ctgcctttct   38280
acctttaaca ggcattttag gacacttaag aatttgtatg gtaaacaaat aatagtaaat   38340
ctgcttggat ctaaggaagg tgaacatatg ctaagtaagg cttttccaggt aagtgatcat   38400 ttttttcctt ctgttctggc ccatggacac ctaggatagt attttaaaaa taatagtcaa   38460
attcttccag gaataagttc ttcctggaag aagattgaat acttgttgga accattagtt   38520 cttttgaaggc aggtaggcaa caatttaggg taatcttgct gaaattggga ttatagaacg   38580
cttttaaggc attgaccctg ttttctaatc tgcttattta tgtagtggag aagcagaaga   38640
ataccctcct cctaaaaaat gttcatcagt cactggcaga aagataccag gcagtttccc   38700
ccttcatctc ttcattgctt tggctagttc ctacaaacca tagtcactgt tttaaatcta   38760
tgaaattgtg aataaagcat ttgtatacac acaggacttc ttgtaccaat gaaagaaaat   38820
ttgagaattt cacataagta agaacctaaa gaaatgtctg acttctaaag aaaacatact   38880
tttcataaat atttattgga tcaataatga attgatataa attatagtgt tatataaggt   38940
tataacctta aacaaaatgg ctagaaaaca ttttctcacg ttaatgaagt ccaggattaa   39000
ttatttggct attttgtttg aatatcatta ataaacaagt tatactttag agagtgactt   39060
tttattataa gcttttaaaa catttgtata tattgaatga aggtataaaa atgaattctt   39120
caaattttga tgagcttttc cttagaagtc aattactttg ttttgagatt ctataataga   39180
tatagtcatt atattttat ggtaaaaaat gaaatgctgg ttgttggaaa taacttttca    39240
ttttctaaac caaatgaaaa tgtgaagttc cctgatatta attatgtaag acctaactaa   39300
tctatctgga atagtatagg aggttttagg aaaaggatgc tgtaagatat tagcaagtaa   39360
tttttcattt tactgccaat ggcaatgaaa gaaagctttg tgaaattagt aagatttcaa   39420
gaacctgctt agattttcat ttaaaataaa agttccattt ataacattgt gttgatacaa   39480
tcatatttgg ttaacattta aatgaatatt tccatggtgg ctcaaacggt aaagagttca   39540
cctgcagtgc aggagacctg gttcaatccc tggatcggaa agttcccctg gagaagggaa   39600
tggctaccca cttcagtatt cttttctgga gaattccata gacgggagcc tggcgggcta   39660
cagtctatgg ggccgcaaag agtcagacac aactgagtga ctaacacttt cactttcctt   39720
ggcagtccag tgagtggtta agaatctgca gtttcactgc aaggggcgtg ggtttgatcc   39780
ctgattgagg atagggggaga taggggatcc tgcctgccgg atctgtgatt tgcagccaaa   39840
aaaaaaaaac cgaagaagaa ttaaatgaat attttatttt tattttcaga gtcatctgaa   39900
agcttctgaa catgctgctg atatccagat ggtgaatttt gactatcatc aaatggttaa   39960
```

```
aggaggaaag gcagaaaaat tacatagtgt tcttaaacct caagtccaga agtttctgga   40020
ttatggaatt tttcattttg atggaagtga agttcaaagg tttgacttct ctgttttttcc  40080 ttttttttaa attggaactt ttctgtagtt atttaatttc tttattatac ttgattttaa   40140
gcttgttgtt cttctttcta atagtagctt acattactgg gcacgtgcta tgtgtgggtc   40200
aggtagtgca cttagtcttt acaattatta ataacaactg tagggatggg tcacactgga   40260
ggaagtgggg ggctgaaagc tgtcatcttc cccacgtcac gtaagtagaa agtgttagag   40320
ctcgaattca tctagctcca aatctcatgc tgctctttcg gaggctgttc catttctctc   40380
gtaaaattaa tgtcataata tttcttggcc tcagtaaaga ttatttaatg caaataaaag   40440
acatgggtta ttgtctgttc tgctatagaa ctgcgtggtt ataaatctga atgtgtgttt   40500
agctcctgac tactggcctc attaaaaata agtggatgtg gttgactgga gagctagtaa   40560
tagagagtgg acggcaaaat gttaacgctt atagaatctg gatggtgggt atatggatga   40620
tcactgtaaa attctttcat cttttttgtg tgtttgagaa ttatactaga gaattgaagt   40680
ggggagaaag tagatgctac attttaatca gcttaatttt tctcagtttg ttttagcttt   40740
tgttattttg gttttaaatt gcccatttag tttcactgaa tttgtttcag gtgccagagt   40800
ggtacagttc gaacaaactg cttggattgt cttgacagaa caaatagtgt gcaggcattc   40860
cttggtttag aggtaaaaaa atatgtgtat gtaacttaac gtcaaattcc ttttcagtg    40920 cttttgtgat atttatgttt ggcattaatt attttcaca aaatgaagtt aagcttcatt    40980
ttcacaaata aagtttgact tctcttctag tttttttttt tcaagtagtg tcccttttca   41040
tttaaatgtt tccttatct gttctaaata ctttctttag atagcttctg tttcctttta    41100
ttgttcatta actttgcctc caaaaaaaaa aagcctgctg tttatactgt tttagtaatt   41160
gtctcgcctg cctgtctttt ggataggcaa aatatatata atatatatat atatatatat   41220
attattctca gtattgtaat ttttaaaaaa taattttatt tatctatttt tggctgtgct   41280
gtgttttcat tgctgcgtgg gctctttttc tagttgtggc aagcaggggc cactctgctg   41340
ttgcggtgct gggcttctca ttgcagtggc ctcttgttgc ggaacatggg ttccagcgtg   41400
ctcgggcatc agcagtcgca gctcccgggc tctagagcac aggctcaata gttgtggccc   41460
accagcttag ttgctccgca gcatgtgggc tcctcccaga ccaggggttg aacccgtgct   41520
tcctgcgttg gcaggtggat tctctagcac tgagccacca gggaacccct tgatactgtc   41580 ttttttaagac cttttggaat taaggaggat ctattttcac atgtacaacc ctatagaatt   41640
atatttttaa caatctaaac cagtacagtt tacatagcat tttttttaaaa attgctacaa  41700 aaaccaggat cagttgaaaa atgtcattgt tagaataaaa ctgaatgaga gccaacttct   41760
ctaacacact ctttgtttaa aattttgtct ttagtactta cctatcaaac tcagtctaat   41820
ttaggcataa tctcaactat gtgacagact gtgtagcaat acttagattt cccaatcttg   41880 cccttatgc agctgtcagg gtcataagac tatggtgggt cttcatttag ttctgtagga    41940
acttagcata gttctccaat actgtaaaac caggaataga aagtaaaagg ttcttatttc   42000
ctctagcaaa tgatcttaaa tttggctaga atattggtta attagttact ctgcagctga   42060
gattcattca gtctcaaaag gaaagtacca tgtatagaat ttcctactag aaaaatgtat   42120
ttttgatgta actagatttt actgctttgc ctttttttgaa atctgttgtt gaggattatc   42180
attataattt agaaaatatg acagaagaaa agtgaaagca ggcatttgat tactgtggat   42240
tgagttttat gagatatctt gggtttatgt tgagttctct taagtggcta aagacattta   42300
```

```
gttagagtaa gcttgtgaaa cacttgaaca tcttcactga acatagaaca agtgttagtt   42360
ttcagaatct gtcttagtgg actacccact gtttgttatt aatattaggt gtgagagtac   42420
ttactcccct agtagcttga ctggttacaa aatatactgc aagtgtaagt aaaagcaaac   42480
tgcttgtagt gaaaaccagt tttgcccagt tcttttgaaga aagaggagat gataaaggag   42540
aacctggagg cttgtttgct ttattctaca tgccagcaaa agaacagccc tggtgtaagt   42600
ctaggcaata ggattagacc cagtatagag tttttaatat tattttagtt tttgatccct   42660
gtgtaattat ggataatctc cataatatct ttatcttata gataagataa aaggaaacac   42720
aagtgggaag gagttaagta aaactacagg ggcatagact atgactggat tccaaataag   42780
agaaatagac tgggtaagga ttatacattg ctttgacttt gccagactt aaggctaaga    42840 gtcattcaga gtaaagactt ctaaacacat atactgtgat gaaggaactg tggtagcccc   42900
aagatcctct cattcttcga atactgtgtt cccctagtt ctcccttatg tactttactg    42960
atacgaattc agtacattca gagctgtcat gactttattc agaaatatga cttatttaaa   43020
aattttgata tcaattcaag agcagctctg cttttttcat aatctcctga ccttaattac   43080
ccaaacatat agaaccaaat gcaaaaatta agaaagtta tttctataca ttttaaaata    43140
aagtatgtat attcctctgc tccagtgggt gctgttgcat aattattctt ttaggtgaac   43200
aagataaact agtctgattt ataggaactt tttttttttt tttttttctt attttggccc   43260
cacagcttgt gggatcttag atccccaacc aggaattaaa ctcaggcctt cggcagtgaa   43320
agcagggagt cctaaccact ggactgccag ggaattccct aaaggtttgg gacattttaa   43380
aaagcttaat atcatttaac cagaaaaagt tcttgttact acaaggattg aatactgtag   43440
gtggcattga tgtgatagtt actttagaaa ttggcatggg ggggaataac aaagcctagt   43500
aaacttgaat tttcagaatc cagacccaca acatcctgta acgataaatt tttggtttga   43560
ttctggtagt tcttaaaagg tcacatctta atggatgtat ttatatactt ataaaagttt   43620
cttttctgct attttagatg ctgactaaac agttggaagc tcttggttta gctgaaaagc   43680
ctcagttggt gactcgcttt caagaagttt ttcgatcaat gtggtctgtg aatggtgatt   43740
caatcagtaa gatttatgca ggaactggag cccttgaagg aaaggctaag gtagatctag   43800
attataaaag atcctctttt tttcttcttt aataaagctt taaatgaact cttttaagtt   43860
agtagttttt tttaaggtat ctattttaga attctgtttc atcatgtttt tatgtcctgt   43920
ttattacctc cttctctagt ggatactaat gactgaatgg atagttattt ccctaggttt   43980
gagaggtata ttatatatgt atgacatatt tagttgttta gtgataatct actaggctta   44040
catacgtatt acttacgatt ttttttaatga tttttcactt gcatatgtgt tttaatttttt  44100 atactgttta tttaatcag aaatatgttt tttttaagc ctttgctttg cctttttat     44160 ttatttttt tggtcacaca aggcagcatg tggaccttag ttccttggat cagggatcaa    44220
acccaggccc ctgcagtgaa agtgcagagt cttaaccacc agactgctat ggaattaccc   44280
aaaatatgtt tgtgttttt taaattaggg ccgtctttgg tggcccagtg gttaagattc    44340
cacgcttcta gtgcagggg cgtggattcg atccttagtt ggggaactaa gatcccacag    44400
gctgcgcagc acaaccataa ttaaaacaaa agttcccgcc tccccaaatg ttactcttgc   44460
caagaaaggg tcttaccttta cttgccttg tgtccccagt gcttgccgca gcacatacag    44520
ttggatagat gggtgacaag cgccggatgg acagataaat cagtgggtac tttatgcaac   44580
accacctatg aacccagtgc tatcagggct gaagttttta ttcttttttct tatcttacct   44640 tgacaaggag gctatcaaaa tgtgcctttg caagtgtgag gtgtggacgt aattatgtat   44700
```

```
ctgtatgtca tcattacttt aatttgttgg tattatctac agactgcttc tgctttagtg   44760
tttgtccctt actgagggac tttgggtaca tacttgaaat atttttcatt atatccttaa   44820
atattgacct tttatggctt ctggattcag ctgaatttat taatgtacta caaccctaca   44880
atttctcaaa ttaccccagg aatagaaaca gagacattta ctacttgtat agtttcttac   44940
ttagtctctt cagtatagca gctgaatttc atcatctcaa gtcttctgtt ttccacttct   45000
tcctcttctg tgtctcataa aacgccatgc ctctgttcag aagtattggc cttagctgca   45060
aagttccttt tgttcaactc agaaataatt tgtattgaca tttacaaata tttacttctt   45120
aaatggtccc tgttttgaaa aacctgatgt tgttaaactt tcatgtattc ttttttaaat   45180
aaacaacata attcttgctt ttaaacctga ttctctacaa ctattgctta aaatattctt   45240
ttatgttctg cctctttgtt tctgcaattg actgtctatg tacagaggtt acatatattt   45300
tcagtgatct tttctaacaa actagatatg aaatttatg tattaaatat actagtctga   45360
attgacctga aatctaacat ctgaactgct ctttcttttc ctttctctgg gttccttttg   45420
attaattgcc tgataatgtg aatggtgagt ccccttttta aaataatgtt atttacattt   45480
gttttatgga aggaaataac attttttaagc ctcaaatcct tgttatttct ttgaggaata   45540
aaaattacat attgcaaact aaagttttt tttaactttt tttaaacag tcatcaaaat   45600 ctgtaagatt aaaatatctt tatggtaact aacacacctg agtgaagtaa acgttcacta   45660
gaagttataa tcagctctct cactgtagga attggcatgc agtttatatt tttatattta   45720
cataggcaaa atgagctaaa atagaaaact gtagtttcta tgttacaggc tagaccttca   45780
ctctcatgct cagttttgtt tctaactaat atcagttact tgggagcaat ctcagtttta   45840
ttctctgctg ttcgtgtgct ttggagtttt tctgagagtg cggacgtgca gtgtgtcctc   45900
ctctatctcc tctgcttctc cccacccgcc ccgtccaccc caggcctgac agtcacaatg   45960
ggagaagtga tctccttgcc ttgagtaagc acatttcagt ctgtttcctc tccagtaaac   46020
agttacacag gtttactgct ctggatgtca tcagtggatg cagctgtggc actgagcccc   46080
ttctgtctcc ctgcagtgct gtgatccaaa agaggaaagg aaacagtgac accttaatgt   46140
gacattttaa tgtgacagtt tgatattcag aatggaatga tgaggtcctt ttactacagt   46200
gaagtcgtat acaacttatc taaagtttca gaatacctat tgagtgaaaa caatgtagaa   46260
tgaaagtcca tgcttttttc cccaacaggc tggaaagtta aaagatggtg ctcgttcagt   46320
tagtagaaca attcagaata acttctttga cagctccaag caagaagcaa ttgatgtttt   46380
gctcctggga aatactctaa atagtgattt agctgacaaa gctcgagccc ttttaactac   46440
tggaagtttg cgtggtaggc gtactttata ttttacttta tgttgtctgt attccttcta   46500
aaagtccaag aggtgaatgt aaacttattt acatatatac tttctagttt gaattgatta   46560
aaatagtttt ttgaaagaat ttctatcatt gtaatttttct aaaattccat tctccaaagg   46620
aagtttgatt ctcctaaaat atttatagca ttagcagaat tattaagctg taaactgaag   46680
cccatgcatg ttttctttta tagattatga ttgaggggc aaatgattta aatattgcta   46740
actttattta aggcaagatt tcataaaata ttcaactagt actttcagta ttcagtaacc   46800
tagttatgta gaaagcattg ctttattgaa aaaaacaat acctgttctg gttattttac   46860
taatcacaac cccagacgtt tctataactt ggtcttactt tttaagtgct gctgtttgaa   46920
taagctttaa atcatattaa taattttaaa atgttgctta ttattggaca ctgtcatccc   46980 caatttttaat atttgacata aaatatatgc caggctttca gaatagctgt tgattttttca   47040
```

-continued

```
ctgtgtttct ttaaaaccaa aagaatttga gctcatgtca gtgagcatat taagcaggat   47100
catgggaaaa ctcagtatac attgtataac ttattaaatt agactccctt aatttttttt   47160 tttttctat tttagctttc cagcactctg aacatttttt tttacttctg ttatccccca   47220
aaagaaccct ttcagttttc cctgttcaac taggagaaat tgttcctcaa ataacctcct   47280
catgggttat cacttgttat catggattct ttcagaattc tgcgtggtgc tgaaggtagt   47340
taattacatg tcagctcctc agggatctgt gagtagactg ggggactgaa atctactaaa   47400
gctctgaaca ccagaatctg atcatagcta ctgcttttaa cttcaggctt tcttccagca   47460
gtagacactg actcatttgc gtcttatcac ctctttccac ccgtgccttc tttgatatgg   47520
aggcattaat cagcaaccac tgaaagtaag ctattaaagg aaagagaagt gagggacctg   47580
aataattccc agacttgatc attagttttt tagtttcctg cacattttac tatgtgaaga   47640
acgtacccct aaaaaaacag tacagtcaat tctgctatag ctcttatttt aagaatgaga   47700
atttattcca acgggatgc tatgtcagga aaaattgtga gtataacgcc aattctgtag   47760
tagttcatgc atatttcact ggtggtagta gtgctagaga aatgcagaaa gctgtactca   47820
gcggaactga ggtggataga aatatacaaa acacacatat acatgtgcat ggacctctcc   47880
ctccctctgt tcaccaactg tgtgatgagc cagatcctcc catatctggt gtcacagctt   47940
actatctagt ttcggagaag ccttcttcca gcattcacaa ttgctcacaa gcacaggcat   48000
cttcctgctc atttataagc aaacctcaag tcttttcaa gataaagtac catatgttag   48060
acgtatttgt ccattcctta accgtttaac atgtgtaggg ttctgctact gttttatag    48120 caggttccta tcttggcaca tcattgctga agtgtttgaa tgttgtgccc aaacccaaat   48180 attttgcca taaaccccat gcctgtggga atttatacca tcttgcatag ctggtcattg    48240
tgttggaatg tatgtgtttt tttaataact gaactgattg tacctgtcag ctggtgagtc   48300
ccaaaaaata ctccaaggtg tgcattaggg cagtatctgc aatatttcag tgtcctccag   48360
cctcttaggt tttcaggttc gtattctcag aagtatgtgc acttgcacac tcaacagaca   48420
tacatatggg accggcctgg aaagcaggcc tagaaccttc tgattgtgaa actctgcaca   48480
tcactatgtc cccgtaggat ttttcttaga tacagtgggt ttacatcagt tatttgtcatt  48540 tatttatct ttggtatcct tcagccatca gaaaaaatgt catcaaacta aatcaaaaga   48600 aaaaatgaa gctgtctgag aaggttttgt cataacactc gacttcaact gtaacttact   48660
gtgttactaa tgactctttg ttttcttctt gatgcatccg tagtttctga acagacgtta   48720
cagtcaggta cagtatagaa aatcaacctg tcaataaatg caacttttc tcaaatttttt  48780 tttaaaaagc ggatgttgta tataaataga gccacaaata aatggaaact ttatttttcc   48840
ctctgattct gacaggataa attgatgctt tgtttaatc taagaaaaag aattttaagt    48900
ttgagaaaac agactacttc atttagaagg agctatgcca agctctttgt cttcttgtag   48960
caagtgctta atttcaatta aatatgggtc atctagtttt aattttactt ttacatttca   49020
gtgaacaaac attattagtg ttatatttta ccctttattg ttgtttagtc actaagtcat   49080
gtctgactcc tttgcgaccc catggaccat agcccaccac gttcttctgt ccatggaatt   49140
tctcaggcaa gaatattgga gtgtgttgcc atgtcctcct ccaggggatt tcccagctcg   49200
ggggttgaac ctgcatatcc tgcgttgtca ggaggattct ttaccactga gccaacaggg   49260
aagtcctgaa aaaacctag atgtgactct tacagattaa tgggaaatac tacctatgat   49320
gtttacaact actcaatagc acttgtcaca cacataacat tttaaaaaag acattgactc   49380
attttctcat atggtgtgtg aaatattttc tgaaactgga agacctgcac taaaatatga   49440
```

```
tctgaaatct tttaaaaagc attaagattg ctagcaaagt tagaagagcc aagtgtgtaa    49500
gacctaaagg tcttattttt cttgtcattc cagttcttaa aaatctcata ccttcattct    49560
ctggacaagg tttatgatct tgtctttaaa cttgagtctg tggcaaaagg aactcttgcc    49620
agaaactttg ctgaaaagac atcttttctt cccttcactt aagatttggt atcacttaag    49680 attttttgttt cacttagtta tttttctgag tgttttaaga cactgtaggt aagttttga     49740 gaagatggag aagagagca cttgtattta tttttgaatt aacatcatga aatccgtttt     49800
ctgaaatgat atgatattta ggaatggaca tctgtttgaa cagagacaca tttctttctg    49860
cacattaagg tgccaaccag ttttttaaa aaagaataaa ctaggaattt taaaacttt     49920 tattcccatt tataaactga ctttagtagc ttactcaatg tggtacatgg ttttcttcac    49980
acaattcatt gtatgtcttg ctgcatattt taagccatta ataattata gagcttgtgt    50040 tttcatgtag aaaggattgt agaagctgtt ttcatagtag taacactgtc agtgacttcg    50100
attagaaaga ccagtgttga tcagtagtaa tagagaagga ttctttatcc aagttcagcc    50160
aacattcagt taaccatatc aacaggccag aaaaacaatc tgctttcatt cccccccagac   50220 tcggtgcaag taatcagata acagactcag agatgtatac atgtgcccta ggaacagtga    50280
ggatgtgctt gtcacctgaa cctgcagttc ttttgtagga ttcacaagtc agactgtttt    50340
cattctaatc caaaaatgtt atcagccttt ttcactcatt cttttcacaag cttgcttgct    50400 gtaccttggt atccattcca aaaataataa ttaatatcat aataaaataa gatcacctgg    50460
tgagaggtga agatcatttt gatttccgtc tcctcttggc agttaaccac cctttaagg     50520 gcatattctt tatcattatt aatggattga agtcctagga agtttctatt cactttaagt    50580
gccaggattt gacttaatct aagtgaaatg tggtttagaa ggcagaaagt taggtggaag    50640
ccaaaaagta ggtggagaag agagattgag gattcaaaat gtatttcatg tttattcatt    50700
taaccattgt ttactgaacg ctcagtatgt accgggagaa ggcagtggca ccccactcca    50760
gtactcttgc ctggaaaatc ccatggacag aggagcctgg taggctgcag tccgtggggt    50820
tgctaagagt cggacacaac tgagcgactt cccttcact tttcactttc atgcattgga    50880
ggaggaaatg gcaacccact ccagtgttct tgcctggaga atcccaggga cggtggggcc    50940
tggtgggctg ccgtctatgg ggtcacagag tcggacatga ctgaagtgac ttagcagcaa    51000
gcagcagcag tatgtaccag gtgctcttct agtctggaga tattggagca aataaaatag    51060
accaaaactt ctatatagca cagggaactt gacttaatga tctgtggtgg ctcaaatggg    51120
aaggaaatcc aaaaaagagg ggatgtatgt atacatgtag ccgattccct ttgctgtaga    51180
gcagaaacgg acacaacatt atatagcgac tatcggggct tcctgtgtgg tgcagcagta    51240
aagaattcac ctgccattgc aggggggcaca agagacacgg gttcgatccc taggtgagaa    51300
gatcccctgg aggagtaagt ggcaatgcgc tccagtattc tgcctggaaa attccatggg    51360
cagaggatcc tggtgggcta tggttgaaaa gagtcagacg tgactgagca catacactca    51420
cacatcccaa taaataaata aaatgaaagg atattcattc tgtatgtgtt agtcactcag    51480
tcatgttcta ctttgtgccc catggactgt agccctccag gctcctctgt ctgtggaatt    51540
ctccaggcaa gaatactaga gtgagttgcc atttcctact ccaggggatt ttcatgacct    51600
agggattgta cccgggtctc ctacatcgca ggcagattct ttactgtctg agccacagaa    51660
ctatcatatt atcaagcata tctacttctg gatatatatt tgcatactga agtgggtagc    51720
cattcccttt tccagggat cttcttgatc cagggatcaa acccaggtct cctgcattgc     51780
```

```
aagcagattc ttttaccatc tgagctacca gggaagctcc attcattctg gttccctgc    51840 acaaaaaatg aaaatgagat caaccaacat ttctgccctt gtggaacttc cattttcggt   51900
gaggggtgac agttaacagg ataaataaat aaaatgcata gtttgtacat ggtaataaat   51960
aaacaccata gagaaaagta aagcagggag gtgatatgga cagtaagaga cagaatgcac   52020
attttaataa gctgatcagg aaaagcctca cggcagagtt gatgcctgca agcggtgagg   52080
gaatagtgtt gcgagcagtg gaagcagcca gtgcagaggg ggtccagggc cagagcggtg   52140
agcgaacaag gtgggatggc agctgagggt agagaggcag ggcaggttgt ctggggtctt   52200
gtagaacatt ggtgaagacg gtgtcgcctg tgatctggga ggcttttagt aatggcttca   52260
ttctccagca tctcattatt gtccatgatt tgcgtttgtg tcagggagct gttttcatc    52320 aagctacctg tgagtagtta gagtcctata tgtcatggtt cttgaacatc tttctttggg   52380
gaaaaataac ttatttttac tagcttccga atgaaagttg tctgtaagtc agttgctata   52440
ttccttaaaa tttgcagtct ctgattttgt gtatcataaa atgatgtact acttcactga   52500
aacagaactg ttttgcatgt tttatgttgc tgaattaatt ttgtaatagt ttttttact    52560 tgggctgttg tacttcacgt agttgatatt ttcaaagtgt gttggttact tgcattgtgt   52620
tgggctctgt gttcaaggct tatctctttt gtgcctgtgc atgtatttga tgcttgtttg   52680
tgccaatgat ggtaattgta ctttctagcc atcatctctc agttatgaag atcaattttt   52740
gtaaatgttt tcacgcaccc aaaatttgt tgtattttgt tttaccagc atcttctaaa     52800 gtactaaaga gtatgtgtga gaatttctac aagtattcaa agcccaagaa aattcgagta   52860
tgtgtgggca catggaacgt gaatggcggg aagcagtttc gcagcatagc ttttaagaat   52920 cagacccta cggactggct tcttgatgcc cccaagttag ctggcatcca ggagtttcaa    52980
ggttggcttc ttacaatatg gattaattaa ccctgactct gatgtattaa cctagaaaac   53040
aaatgcggcg cttcacaata tgcagtactt tataaaagaa acttctatat atacatttga   53100
agcccagcat tcttcttaga gatcaaatct cttcaaatct taggtcttct gtattcatag   53160
acctttctct actacttcat aggaacctat ggtaaagtga gaaatctttt tgttatttga   53220
ttctcagaca atgtaatcca tacatgagta gataactctt ttgtgtgtgg gtttgtgtat   53280 ttatttttt aagatgtgat ttttttttctc ctgttttat tctttaaact gatgcatagc    53340
aaatttattt tgtgattaag aattttttcaa acctaatgta ttttgttttt caaatagagc   53400
cctttatttg ctaagataag aaatagggta ggtcatgagt aggtttacaa aactcatttt   53460
gacatttatt gtccctgtaa cagaacaata ctgattcatc cttgtaaaaa ctcatcactg   53520
agtttgggta ctctaccacc aagctcttaa tagccagtac ttaagctgag gatgcttgta   53580
ttaagatttt taactagaat catggatttg aggactgttt gcttcaactt gaattccttt   53640
ttaaaatggt acacatttac caagtgttat ttatgaagga gatatgtata ggaaatactg   53700
tgagatacag attttctttt tttagttgcc tttaatcagt cacaccttaa accctgggaa   53760
tttccctaaa cttttactaa aatgctgctt ttcattttac attgaaccta acttgaaatt   53820
gtagctgtag tattaatagt aataacaata ataaagtaac agctaacact actattatga   53880
gtacttgaca tctattcatt taatcattat aacagaccta atacatagcc actcttagta   53940
tttcagtttt tagatgagga aactgagaca caggaagaga agtgacacgc ccaacgtcat   54000
gcagctggca gtgacagagc caggatttag ggatggacat ctggcagttt gattctggag   54060
ttgtgccgca ctgcactttg tgtgtgaact tgggcaagtt gcttagattt tccagagcct   54120
cagtttcctg tctgtaaata acaggcagat gtaatctgtc tcgtaaggtg tctgtagtaa   54180
```

```
aagagaagat tcacaggtaa gccttgcaca caatagcagt cagtgaatac tttacatttt   54240
ttattcctca gtatttgttc atagtattta tataagctct ttctcttagc tatttgtccc   54300
gtttctgaat gcttgggcca cccaggctac cctgggcttg cttatctaaa gcagttctgt   54360
tctcttttgg taagccatgg gagagctaat ggctagaaga gaggggtctg aagccctgac   54420
ttcccatttt cctggattgc ttccacctag gaatttccaa attaaagtgt aaaattccct   54480
ctcagctgtt tgctctaatt tgagttggtt actcgcccac cttattgttt gtgctctttc   54540
tgaaaatttt cttggtggct aaaaaggag gggatttatg tatacttagg gttgattcat   54600
gttgttgtac agcagaaacc aatacaacat tgtaaagcaa ttatcctcca attaaaaata   54660
aataatttaa aaaaatttta agtaattact tatccatttg gattcatctt ttagcctctg   54720
agaagcggct tgtttctctg ctgtccatgg ttcaaaccat aacaacagtt ctttcaaaaa   54780
tgatttctga aaggacttat cttcaagaat aatagtcttc aagaaaagca aacttaggtc   54840
acctaaatag aaattgaaag taattttgtc cccctcatgg ttttttgcct ttaatttgct   54900
tttggttaaa cttggaacac aaaaatggac ttgtatgaga tctgatgttc gtcttagttc   54960
tgttggggta gggaagttgc cgtttaacta aggccatctt ttaaaaggct ttcttggatg   55020
cttaatttta gataaaagaa gtaaaccaat ggatatattt gcaattggtt ttgaggaaat   55080
ggtagagctg aatgctggaa acattgtgaa tgcaaggtaa gccagccagg taacacacag   55140
ggaaactttc tagttgatga acatggggga caggtaacta agtacttact acaagcatag   55200
atagagataa tatatgtgaa ggtgcttttt aaactgtaat tcaaataata gttctcaaac   55260
tttttggttt caggtctttc tacactctta aaaatgttga agatcttaaa gaactttttat   55320 ttatgtggtt ttatctcttg atacgtatca cattagaaat tagagacaaa aattttttaag   55380 cattcagttc atttaaaaat aataactcat tacatgttaa cataagtaac acatttttt   55440 tctgaaaagt aactattttc caaaacaaaa atttactaag aaggatggca tcaattgata   55500
gcttgcaaat ctgtttagtc tggtttaaga tggctgggtt ctcacatcta cctctgcatt   55560
agtctgtgta gtgtgttgtt ttgattgaaa tatatgaaga aaatcacata aatacgtagt   55620
tggaaaccaa aatattttag tagccttttt agattttttc ttctctgata atactcagca   55680
aatagtcatt tttggtggtt agttacagtg tggaatctga aaccatagtg atgaactttt   55740
tgtgctcaat tataccaaaa catcggtctg tcttttaccc gtgcgtgatt ttgacacgtc   55800
attcattagg catttggaac atagtagtag taaactaatt atgtagatct ttcagaatta   55860
tgtagatctt tcagattttg atacatgtca ttgtataata tcaaaacata atattggtta   55920
atttcatcac caaattaatt taatctcttc agcaaattct tcaactattg ggaagctgtc   55980
aagatcatag tagcaaatac aggttatcaa aaattccccc ttttctttca aaatgtaaat   56040
tttattatta gaaatataca ccataggtca tgtcctttga aaacacaggc atggttgaaa   56100
acatgtttgc cggatagtct aaatttgaat aatcatagtg tgtctgtcac tagttcttcc   56160
aagtaaaaat tgtattctat aaaaaagtg gcatttcagc tctgacctca gcttgagtg   56220 cttttttctg aaacagccat catgtatgtg ttcagtgtgc agcaaaagtg gttggtttgt   56280 attttccat tcattacaca gaatataaaa agatgggctt ctaggattga gctttgacaa   56340
aattagtaat gtttactgct tcatcaggat gttcttaggt gaaatggcta ttttttgcttg   56400 gtgttggagg ttcttgggat ttcctgttg gctcagacgg taaagaatct gcctgcaatg   56460
caggagaccc aggtttgatc cctggtttga gaagatcctt tggagaaggg aatggcaacc   56520
```

```
cattccagta tttttgcctg ggaatttcca tggacagagg agcctggagg gctgcagtcc    56580
atggagtcac aaagagtagg acgcatcttg ggcacaaacc tattactctg aaaatgtata    56640
aagagaaaga caagcatttt ccctaccttc tttgtataaa catgtttcat ataactgga     56700 tagttgataa aagttcttta cagaagaatt ccaattcatt acaaatgccc atggaatgct    56760
gaatttatga aatcaacatg ttgtaacctc tgttggtgga aaggaaatg gcaacccact     56820 ccagtattca tgcctggaga atcccatgga cagaggagcc tggcagatta tggtccattg    56880
ggtagcagag agtcagacac ggttgaagca acttagcttg gaacccctgt tgataatgga    56940
tctaggcaat gatcatcagt tgatgttaaa accttataga aggatcagtg gaggaacttc    57000
tttataatga gttaattgtc acagtctgaa cagcctatta gatataatat ctcagagatt    57060
acatgcttcc tgctgtgatg caaggctgat tataccacca tgaggttatt tttgccaaaa    57120
caaatcaata aaattgaatc atgcttcttt aattaccagt ttaaaacaaa gctgacagaa    57180
gtgcaaagta tcatgaagac acgtcaggca aatctggact gttaaacgtc ctgcagacaa    57240
ataacccagc ttcttaaaac ataaagagca ttaaaaaaga ggatggggca agctgagaga    57300
ccgttaaaga ctgagaaaga cttgaggagg caacaagcac atgcagtgtg tagaccttat    57360
ttggaccttg tttttaaagaa acctactata agaaactttt tttttagata acaggaaaat    57420
gtgaatatga actcagtatt atatgatatt gaggaactgt taatatctaa gtgtgataat    57480 gacctttga ttacagaaaa ataaaaatcc tgttgcatta gtgatgctta gtaaagcatt     57540
tttgggtaaa atggataatt tttcctcaaa tttgttgtaa aatattccaa gattagagaa    57600
aggggtgggg agtatggaa gaagaaagat tggcaaaatg tggataattg ttgaagctgg     57660
ttaatgggta tatggtggtt tatttatgc ttatctttt tgaatatgtt taaaattttc      57720
cataataagt ttttaaagag atattataat ccatggaaat aagaaaaagg ggaaaattgc    57780
atctggaagc atgttcttcc ctgttatcct aatgaataaa taaggagaaa ataaagcgta    57840
caagcttgag attacttaca cagtgagcac ttatttaata agaaagctca aattttcttt    57900
gtaagggagt cataggatag cttttgacg tgtgatgttc ttttggctca gttttctgtt     57960
ttcctttttt aaaggagaca aaaacaccca gcccgcataa agatttcact gttggtgtgg    58020
atttcgtgat gtcactaatt ttattaaatt tgggcacata aaggtgtaat tgataattgt    58080
cctacagaaa taggctgtat tactgtcacc gtcttttga agattccctt gttaatattt     58140
tctggtagca caacaaatca gaagctctgg gctgcggaac ttcagaagac catctccaga    58200
gacaacaagt atgtgctgct ggcctctgag cagttggtgg gcgtctgtct gtttgttttt    58260
atcagaccac agcacgctcc cttcatcagg tgagtagaca gatggcgctc cgaaggctgc    58320
ctcctaacac cagataacca aaaggcctgg cgtattttg gcttcagaga aacactgacg      58380
catggttctt gtttctgagt gttctttttt ttttttttta attgaagtgt agttgattta    58440 tatgacttc ccaggtggct cagtggtaaa gaatccacct gctaatgcag agacacagg      58500 agacagggt tcagtccctg ggtcaggaag atcctctgga gaaggaaatg ataacccact     58560
ccagtattct ttcttgggaa attccatgga cagaggagcc tggcgggcta cagtccatgg    58620
ggtcgcaaag agtcggacat gactgtgcat gaacatgcat gatgggtgat agttgattta    58680
aatagtgtta gtttcaagta tacaacaaag tgatcagtta tacacttgtg tgtgtgtgtg    58740
tctatctttt taagattatt ttcccttata ggttattaca aaaaaataag tatagttctc    58800
tgtgctatat agtaggtctt tgttggttat ccattctata tgccctctca ctcgcgcctt    58860
ccctttggta accgtaagtt tgttttctgt gtctgtgggt ctgtttctgt cttgtaaata    58920
```

```
agttcgtctg tatcgctaag tagtattcca ttgtatttac gtaccacatc ttctttattc    58980
attcatctgt cagcagacat ctaagttgtt tccatgtctt gatattgtga atggtgctgc    59040
agtgaacatt ggggtgcatg tgttttttca aattatagtt ttctccagat atatccccag    59100
gagtggaacc cctgtatcat gtggtaactc ttgtttaaat atgttcttga ttaaagaatt    59160
gctagtagtt tctctccact atttcacagg cttccctaca aaatgcccat gatgtatagt    59220
gttgtaatta tgtaatagac attcttcatt tcttacacac gcagaactgt tgaaatttct    59280
gatcttggat ttcaaattct tccttttaaa gggatgttgc agttgatact gtgaaaactg    59340
gaatgggagg cgcaactgga aataagggag cagttgcaat acgaatgctg ttccacacca    59400
caagcctctg ctttgtctgc agccacttcg ctgcgggaca atcccaagtc aaagaacgaa    59460
atgatgattt tgtagaaata gcgcggaagt tgagttttcc aatggtaaac tcttgctact    59520
tgttttcgaa aaggaagctt tggaacatat ttcagttcac cccatattct atatcagttt    59580
ttgaaaagtt ggaataactc ctagaaatgt cagcaaatag ataactcctt gtgttattac    59640
tgtggggtta aataaatcga acctggcagg ggtaaggcaa agaaaaagtt gtaaaacatt    59700
ttgtgaattg attgtttgga attctgtctc tcttcttcca gggaaggctg ctcttctccc    59760
atgactatgt gttttggtgt ggcgatttca actaccgaat cgatctccct aatgaggaag    59820
tgaaagagct tatcagacag caaaactggg attctcttat cgcaggagat cagcttatca    59880
atcagaaaaa tgctggacag gtatagacat acctaagata cttgcattgg gaagaagggg    59940
atgtctgatt atgaaaacat gctttcccta aagtttttt tttttttttt taacaatctc    60000
ttggagtcta tacttaataa gtatgtgcta agttacttca gtcacgtcct tcttgttgtg    60060
acgctaggaa tgtagcccac caggctcctc tgtccatggg attctccagg caagaatgct    60120
cgagtggatt gtcatgccct tctcctgggg attttccaga cccagaggtc aaacctgggt    60180
ctgttatgtt tcctgcattg gctgatgggt tcttcacact agcaccactc aggaagcctt    60240
tactaagtat atatatctat agtttgcctt ctcttttaa aaaaggaaa aggaaaggaa    60300 aacttataat aatttccagg aggaaaagta tatcatgtct ctataaaatt caccttcaag    60360
tagaagaaga ttcttttttt ctttcagcag tagcaaattt aagatcttac tcatcaaggc    60420
tactgctgtt tggctcataa gatcctatgg taatctactt tcattttttg ttacttattt    60480
atggccatgc tgtgtgatat gtgggatctt agttccctga ccagggatcg aacctgcacc    60540
ttgccctgca ttggaagcgc aggctcttaa ccactggact accagagaag tccttggaag    60600
aatttatttt aaaaaaattt ttaggaagag gtgattgagg ccactgata tagtaccttt    60660 ctgatcatca gacttaaatt ctgatggata ccatgtaacc ttcttaggcc ccagttcctg    60720
ttgagaataa gacatcacac aatgtgattt ccaaaatccc atacagttct aaacgtttga    60780
tactgctcaa aagtctggtg gaagttcatc gttccagttt ttgtactttg tttactcaga    60840
catcaagtga gtgagatgat aaagcccgca tcctaggtca tttgcctta agctctgttc    60900 cattcagtta gaagtgttcc tcagaggcac atagatttca cgagtctcta gcacataata    60960
gacatttagt gcatgactgc ccgaatgaaa acagaatgtt tttgcctttt tgaaataact    61020
tcctttatgt atgtttattt tagattttta gaggattttt agaaggaaaa gtgacctttg    61080
ctccaacgta taaatacgac ttgttttctg atgactacga cactagtgaa aagtgccgca    61140
cccctgcatg gacagaccgt gtcctctgga gaagacggaa gtggcctttt gatagatcag    61200
gtggacatcg tcatttaaat aagtcaatgc aaatttaca aggaagaggg gaatgatata    61260
```

```
aatgccaaat aaggccaaga ggactacatt ttttttttct cagcataggt tatctagaat    61320
aaaataaata taattcaaat ataaaactta aaaaaattct cagacctgct tataataaac    61380
actttgattt ttcaatctgt tttctttcag tgaaatagtg tcatataaag aaaagcaagg    61440
aaaaacattt ttatgcaatt aacaactgaa tactaagtaa gatttctaac tggataaact    61500
caagtggttt tgcaaatatt ttgaactgct acttgtctgt tcagttattt gtaaaactct    61560
ggtcatgaag tctcagaagt aaaggctcat tgtagtttta actaagtaaa gcataatatg    61620
atgacctcac caaaaaaccc tgacttaaca gagtctagac ttcatgccca tcagcaagtg    61680
tgtctgatgt cccagcctca ggcaactgaa gctagtgaaa tgaaggatct cctgtggtct    61740
gtcatgctca ggtgacttcg cctgtgttct gttttattct gactgcagct gaagatttag    61800
atctcctaaa tgctagtttt caagatgaaa gcaaaatcct ctacacatgg actcctggca    61860
ctttgctgca ctacggaagg gctgagctga agacttctga ccataggttt aagcaatctc    61920
tgtatttcta atcatgcttg aaatttattt gaaatacatc atttctgtaa tgttcctaac    61980
atgtctccat tccttcatgc tgaaggcctg ttgttgccct gatcgatatt gatatatttg    62040
aagttgaagc tgaagagagg caaaacattt ataagaagt aattgcagtt cagggtccac    62100
cagatggtac ggtgttggtc tcaatcaaaa gctctttacc agaaataat tttttcaacg    62160
atgctttgat tgatgagctt ttacagcagt ttacaaattt cggtgaagtt atactcataa    62220
ggtgagtaac gtaaaaaaaa aaagcaactc atgattcaca ataatatct tctgtattaa    62280
aagttacctt tcttagtatt tgactagtat gtgagtattt gtggaaattc cctggtagct    62340
cagtcagtaa agaatctgct tgcagcgcca gagacctggc ttcagtccct gggttgggaa    62400
gatcccctgg acaaggaaat ggcaaccctc tccagtattc ttgcctggaa aatcccatgg    62460
acagaggaac ctggcgggct aagtccatgg gattgcaata gtcagacatg atttagcaag    62520
taaaccaccg tgaatatttg tatcttcaaa ctaaagaaa atcatgctat agaaatatta    62580
ttcaaaaaac ccatgggttt tgaaactgga ctctctgctt agaaaattta aagttgagta    62640
gtgaaacttc acgtgaacat ctgatgacaa aaatacgtgc acatttagat atgttctctc    62700
cagatttctg tacactataa catggaagcc ctgtggaaaa gtgaacatgt gatattagta    62760
ttttagtttt ttgaggagtg atagaagtaa agcagaatga cttttctgcc ctccatttaa    62820
gacattagat gttctcagta atttaagtg atttgatttc cgtctgatgg aggagcggcg    62880
ctgcccggca cacagttagg agtcatcctt ccctgccttg gtttccggca ctgacttaac    62940
catctgcctt ttgcagaacc agatgcctct tgcgttgttg aaataaatgt tctcttccca    63000
gtgtacagca gttttgacaa actgaataac atgtgtttga atttcatagg gaagaggtac    63060
tattaaattc ctttctgtgc tgtttcatgt gtttattgag ggatgtttca tagctgttta    63120
gtgggcaagt ctctatactg ggtgctctgg cagacagggg aggaatcgaa gattcagttc    63180
ctattcggaa tctaagaaag ataagcgtgt gtgtaatggc ttccttaggt gtttaccgga    63240
acagcccaca gaatgaagat ggcttggttt cttgcagggt gagaagcttg cctgagaagc    63300
ctcctctcct ttctgagagt aaatgggcaa atagagaaga aattatattt agacttacct    63360
caaattgttt gacaaagatc taccctacag gtttaaaatg aaacaaaaaa cctctagaga    63420
tttaagactc cagcaagtac atggtgaaat ttcccaatga cagtaagcgt tgccaagtac    63480
agaaacaccg aaccactggg agcatcatgt ggactgtgtg agtgggcagc acagagcagt    63540
taagtgttct tgcgagcaag tgtgaactct tgctcagagt ttacaatact ttttccaatg    63600
ataacaagca ttttggggaa agcttttggt tgcaatttaa cactgtcagg ggagtgggta    63660
```

```
attttccttg gttctatttc gacacaacaa aaatttgagg cgacggatat taaagccctt  63720
ggcgcatcac agctctcgga tagtattaca gctcccttgg ttttatttag aaaataaagg  63780
aagatacatc cttgaggcat gagggcatgc caacgcaaaa gacaggacga gaaaagagaa  63840
agcgagcact ctctctgggt gagagagaac ccatagtgta cataaggaag gaacgactga  63900
cgcagggata ggaccttcct gcctttttc tagtctctaa agagcttggt gttattaggt  63960
agttaagaat aggaaaaagg agtccagaat gatggtgatt aaaagacaag ggaaaagctc  64020
ttgaaaatag gacagaagaa ggtctgagga ccggagtgag gacctcaggt agaacaaaca  64080
gcactcctgg ctagccccgt ttacgtaggg caggcccaga gggagaaaaa aacatataaa  64140
aagaggagcc aaagggctgg gggtctctcc cacgcgtgca cgctcattgt ctctctctgt  64200
ctcccacgct tgctcgctct cttttctcat cccgtctttt gggtcgggtc agcatgccct  64260
catgcctcga ggttgtatct tcctttattt tctaaataaa actgtgggag ctgtaacact  64320
gtctgagatc tgtgatgtgc caagggcttt aacgtccatc acctcaaatt tttgttgtgt  64380
cgagacagaa ccgaggaaaa ttacccactc ccctgacagt attaaattgc aaccaaaagc  64440
tttccccaaa atgcttgtta ttattggaaa aagtattggt aacagaacaa gtactggtaa  64500
caaaacaagg gtaatgttat gctgacgtta taaaaccatg tggtacctcc taacctagaa  64560
tattctgatt gttccacctt aagaccacca aggtagaaca gacaggggag acactgaaag  64620
taaagaagga caggaatact gtcccctgtc acctgtaggc taaactgatc atcaccttca  64680
gctctagaat aagccaactg ttagggaatg actgaagtca tcatatgtaa attatatgta  64740
aataagagat ttcctggaaa tgtagatggg gcaggctact tatattaatt gggggggaag  64800
tctagaatgc ttctatccta ttgagtaaaa ataggaaaaa agtacaacac acatttggag  64860
ttccgcaggc ccattccttc tgacagacag ttttagtaac actgtattgg gttgacaaaa  64920
aacatcgttt gggtttctcc ataccttcca aggggggaac ctgaactttt tggccaaccc  64980
agtatctaaa ggaatttgaa tgcttttagg gaaagagagc cctctcctgg tcaccgctgg  65040
ccctgccgct ctcaggcttg tattttttgtt tcctagcctc tgtaagtcct tgctcatcag  65100
taatcattgg acgagtcttt gggctggtta tatctgaggt attcattacg ttttttttatt  65160 gtttgttttt ctcttcctta aagatttgtg gaagataaaa tgtgggttac gttttagag  65220 ggaagctctg ccttgaatgt tctgaacctg aatgggaaag aggtaaagta gcatttgttg  65280
aatctaaacc attcagtgat ttagtgtctg aggactgtat ttttaagata catgcagcaa  65340
attatctaaa cgtgtttcga atatctagtt gcatgatgcc tcggattacc taacatccaa  65400
catcctaatt atttttaac tttgacaatc tgaaaaacta gaagtagtat gtcacgtctg  65460
tgttaagatt tcaatggaga gttttcaat taactggtcg tttcatactt ctctggcaag  65520
ctgtttatga cctcagcctg tgttcccctc ggggtattca tcttttgaag cttccctgat  65580
gttaattcct tttcataatg tgctgtacat gttcttccca gttcgtcttg tgactttgtt  65640
gttttcaccg tatagaaatt actgattttt aaatttaatt ctgcctttaa tatcttaagc  65700
ttttcctcct cccatgatgt cattaatatt taagagcagc tctcaatttg gcatcccttg  65760
tcagctctta ctccttttt gaatatttct tttgtctttc cctggtcat tttccttgtt  65820 tagttttttt cctcccttct ttttcagctc tgtccctcac cctcaagtct gtgttacact  65880
tctagaaagt gcccacccct agctccctta aaagattttc aaaattctga aaaataatg  65940 tttctggaga acatttgaa agtcagacgt gtccaaacct ctcctctgtc tttgttatta  66000
```

```
cagttgtttc agcccagatc ttctagatac aagtagatcg ataggaactc ttccatttca   66060
ggggagaatc tggaaaaagt acagtgtaag cagagcaaac ttaaaggata acctgcttga   66120
gcattttttt ttccagcatc taaatttctt ccttttcatt cagttctgat ctctgccaag   66180
tgaatattct tgatgaagta catcttaagt ggccattgta gtgattgagg cttaagaaga   66240
cttgttagta ttctttggtg aatgcataac aaaggttgtt gacttaaaaa aataaatggt   66300
ccatgaagcc tattgactta aaaaaataaa tggtccagaa tcctagttct gacttcaaac   66360
ctcagcatgg acgctaaatt cctattaaac acgactgtac tgttcaggcc ggcagctgtc   66420
agccttccag actgtgccat gaaagaattc tgatgtcagt agcatttaag gaaagtattt   66480
ttaatatgac aggacaatgt aagttgatta taatacattg attattttag actatacttt   66540
tgtctaaaag ctcctcaact ttttaggaac agcagtgtgc cagtttcaca gataccagtc   66600
cttgtgtttt cagaatggtt aattttgtt gatttaaaat gatcttagat tctcttaagt   66660
atgcttgtga catttgaaat gctgaaaagt ctaaatgaac aggaaagtat tttaagaatt   66720
ttatactgtc ctttctttga ttgtctcatg tggattaatt aattaattta attaattaat   66780
ctgtggatca aaattaaagg aagtataaat ttatgtagca gagttttcag tgaatttaga   66840
tctggcccgg gaaagatatt tactgcagca aagaaaactt aaatttgtgt gcatcctaga   66900
aaagaagacc tgagcttagc agcagtaggc tgttttgttt tggccacact gtgtggccaa   66960
atctcagttc tgaggtcgag gattaaacct ggaccatggc agtgatgcca tcaccagctc   67020
aagggtcatg agtttgagca aactccgaga gacagtgaag gacagaagag cctggcatgc   67080
tgcagtctat agggtcgcaa agagatgcat atgacttagc aactgaacaa cagcaatgac   67140
agtgaaagcc tggagtccta accactaggc caccaggaag ctccctaaca ggtttttaaa   67200
gggaggattg gggacatttg aaactaggtg acaatacaat atatgtgaaa tgattgtgtt   67260
gaatgaatct gagttaagcc tatactattg ttataactta aacagacact ttattccaag   67320
atacttaatt ttcatgccaa tgaattttta atttttgtatc tcttttactc aaccagttac   67380
tgggtaggac aataacaatt actttaaaaa gtccagactg gatcaaaact ttggaagaag   67440
aaatgagctt agagaaaatc aacgtccccct tgccatcatc aaccagctcc accctcctag   67500
gtgaagacgc ggaggtcacg gccgacttcg atatggaagg tctgctcatg gagcacattg   67560
acttctatcc ttctagacag gttttccttcc catcagcaaa gtctcagtct ccaaatctgt   67620
ccttctgttt cttcttgtaa cactcagaga agtattaatc agatttggtt tacattgtat   67680
tgtgtgtttt ttgcttgtta cacagacttc agatgtgtgt gcccttctgc catacaaagg   67740
tcaagacctt tacaatagtt agtttatgtc cttgtgtgat aaaagcagga agtggtatttt   67800 ttggtgtgtg gtttggttcc actgattgta gttaaagtag aagagtagga gttcgtgca   67860 gaaatgagtt caaaatatt acaaccaaag aggatatatt tcaaagtcat tttaaaaatt   67920
cttaaagtgg ctgggaacac atttgaaact gaacccactc atgtagatgt aatcatctca   67980
agtttaagag tgggccaggt tatcttaata taataattc cttaaatgtg attaagaaat   68040
gtatttgctt tttaatgctg tatctgctat attattttaa catattttcc actaaaatgc   68100
ataccttagt ttataaaagg gcaatatatc atattgtgat atcctgtacc tctaggtaac   68160
acatttaaga gttgaacacc ttagaagatc agcttgtttt catatttctc tgttaatttg   68220
tttgcttggt ccacacgttt atgcacttac ctttttatgtg ccagttacat gctaagtgct   68280
ggaaattcaa cagatggcat ccttgccgtc cctgaagtca cagctcagtg ggtgttacct   68340
acaagtaggc agacggtgac atcaacacac tcgtgaacgg tgctgctgta gttcttgggc   68400
```

```
ctaacttaga gttggacagt taggagaatg tacccagaga aattgaaact gaaaatctga    68460
agactgagtg agaatcagat taaagaggat agagagacat caccaggaag aaggaatgtg    68520
cagagaccta aggggacaaa aggatctaag tagatgatgc agatgtgctt gtgcaagagg    68580
aagggaagaa agaacaagaa gaggagtggg tgtggatgga aggtgaattt cttttctgtt    68640
ttgtttgaag tgtttgttta tttggctgca ctgggtctta gttgcagcat gcaggatctt    68700
tagcatgcag acccttagtt gtgacatgtg ggatctggtt ccctgaccag gaatcgaacc    68760
tgggcccgct gcattgggag cacggagtct tagccactgg accagcaggg aatcctgagt    68820
ttggttttga atgtgttgaa gttgtggcat ctgtggggtg cattgggtcc agaagtaagc    68880
tgtgggcatg tgggcctggc actcagcaga gagcccggag ctttgatgat aggtaaggcc    68940
ctgcatttgg atttgcttgg ccagaaacct gatagagatg ggagaggact tcctgggatg    69000
gaactgaaac gcagactttg aaggacaggc agaagaaggc cgcccataaa aggaaaagca    69060
gaagaaacga ctagaaatgt cagagagcca ggagaatata gtgcttaaag accaagtgaa    69120
gaaaagatga taaggaaaaa tgatctatag cgtcctctgt cgcagggcga aagaagtga    69180
gcgccacagc ttgcccttg gcttggaac caggggagga agctgttggt gacattcagg    69240
agagtgattt cagtggagtg aagaagccag atggtggtaa atcggggtgt ggatggaaga    69300
cgaggaagtg cagaaagtgt ctgtagacaa ctctcgacag aagtgtgcct gagacgggag    69360
aaagagagat gaaggcagtt gctccctgaa gtgttgtttt gaagtggaga cacttgagga    69420
gcttaatcct gatggaaagg gctgatgctg ctggggaggg gcagggcaac ctgcactggg    69480
cagaacccca cccttttccac ccatagatat ggttaggcta cagctggggg gcagattgtt    69540
gaagaaaggg gttcccacct tagaacttcc ttttctctgc gaagtttaag gaggcgggca    69600
gcacacggtt tcaggaaggt tgagaaggtt caagacaaag ctcctgagaa gcagtcagat    69660
ggggagccag ccaggaaact gtgggttggc caggaggcca tgggagccca gatgaggctg    69720
aaaccacaag ttaacacgtg cagtctttaa gaccacacgg ttatctgtct gcagcaccca    69780
gccgcccgtc tgcggttatg gagacattag actgcagaat tgacgcaggg gcaacggaag    69840
aatagtgcag gaggggacca gctgcggcaa ggagccagag gatgtgaaga cagctgcagg    69900
gacaggtgca aaatccagta gggggcccaaa gaagagggat cgaaggcttg ggtcctggtg    69960
aagtcagaag aggggaaaga gtagccaagg gcaagactga gcctgaaagg cggtcagagg    70020
gaagtgtttg agtttattgt ttcagaggca ctgcggttcc aaggggcatg agtgtggagt    70080
agaggagcgc atcagcaggg aaaagtgtca ggttgttggt gtgttatcca cagtggcttc    70140
agtgtcaccc agaaagatgg cggggcccag cttactgtct tgctctctcc ttggtcctcg    70200
atgaatgggt tcaagtgacc aaaaaggtga aggtgggaga ttatgcggc aaacgtgggt    70260
tgagggcgtt acataaattc tggaaggcac agcttccaga aataaagagg ccttttttgtt    70320
cagggttgga agattaaagt tttggaattg gaatcaggtg gcatgggget ccctgacgcc    70380
acttcccaac cctgtggaaa acggaggtga ggagacctcg gggagaacca actcctgcct    70440
gtttaattaa agcacagagg attacgtgtc aggtaggggc gcccagggca ccaagtagtg    70500
aggagacttc caggggaaag ggtgtgtgac tgtgtgtgcc atgaggggca ggtccataga    70560
cctagcaggc aggtttggag ggagggcagt gagcatccga ctcagccagc actgagagcg    70620
ctgctcaggg cgcattgaca gctgtggagt cagcccagcc ccagatgtta gccgccactg    70680
ggcctcctgt tgctctgaga caagagactt ttttttttt taattattat tattaaacgt    70740
```

-continued

```
gtttattttt aattgaaaga taattgcttg atagtattgt gctggtttct gccaatatcg    70800
gcattaatca gccatacata ttactatatc ccctgtgact gtctttttt aagtaattta    70860 attaattaat ggctgtgggc tgtgctgggt cttggttgct gcagacaggc tttctctagc    70920
tgtggtgagc agggctact ctctctgtgg tgcacaggct tcagtatttg tggcatgtgg    70980
gatcttccca gaccagggat tgaacccatg tccatctgca ttggcagaca gattcttcac    71040
cactggacca cctgggaagc caggggact atttttaatt acttttcta cggtacgaga    71100 gcatttgcac taattctact tgtatacata taaactcttt atacatgccc acatgcttaa    71160
cttatacatg tttgcagtat catcatgtta aggtgttcat tttatatatt taacccctta    71220
agcctggact tgggggcag caatctctga gaaagttaac atctggtaat gtggccgacc    71280
ttgcgttttc tcaggtgatg tggatgacta tagtgctgag gtagaggaga tccttcctca    71340
gcatctccag ccgtcttcca gttctggcct tggcacgtcc cccggttctt caccccggac    71400
cagtccctgc cagtcaccta ccatatcgga ggggcctgtg ccttccctcc cagtgagacc    71460
aagtcgagct ccgtccagaa cgcccgggcc ccctgcttca caaagtatgt gttttatttc    71520
aagttctgta tgacttcccg ggctggtatg tttgatttag atggttaaac ctccgatgcc    71580
ttcagatgtc ctttggagaa ctatttttgc ttaactttca catccatagg ctaaagtgta    71640
gcatgttttc tgtgcgtaca aaagaggaaa ctttgtagat ggttccaccc taagtgaaga    71700
ggagggtcgt tgctatcact agatgagaac tttacttcat cctttttcca tgtggcaggt    71760
ttgtccatgg cttatcactg acgatttta agcattatgg tcagaacccg taactctttg    71820
ggcttaacta tctgtacatt acctgcatta taataggaag cagaaagaga caaaacaagt    71880
attttgaatt caacttgata gtcatgactc ctccaaagtc aggttttct ctggaagttg    71940 ttacatcaca cagttcagtc actgttccac actaaccagt acccttgaaa ataccttt     72000 atttcagcaa tttctcaagc tcccccatgc tactcttaga ggaccgtctt taaatagtca    72060
ctgagttgta tctgactctt ttgcgacccc atggattata gctgccagg ctcctctgtc    72120 cattggattt cccaggcaag aatatgggag tgggttgcca tttccttctc caggagatct    72180
tcccgattca gggatcaaac ttgcatctcc tgcattggca ggcggattct ttagcactga    72240
gccacgaggg aagccctcag aggatgggct tccttcagta aattcaggat aagtcaaggc    72300
ataaagagaa gaggctctct ttgcttttc ttctctctcc tggccagcag attgaattgc    72360
aaatgaccta agtcacacag tacttcatgc catcttgtta gggccgctca gtaaatcccc    72420
tttcagtacc cggggcctgg gtaagaagtc cagagagtaa cctgattgct cccgtagtac    72480
caaagggtaa ggtaatagca cagctgcttg tgttactgat actaaaaatg tatgtcattc    72540
ctctgtagta caaattattt tgctaaataa tttatcatac gcctatagaa agtacctgtg    72600
tgctcgtccc ttggaacctg atcctcttac ctaaggtact ttttctggt aggttctcct    72660 gttgacactc tgccggcaac acagctgcag cagaaagatt cttcccagac cctgaaccc    72720 aagcggcctc ccctcccccg cccggttgct cctcctgcac gtccagctcc tccacaacga    72780
ccacctccgc cttcaggtga caaatccttg tatttccatc tctgctggat ttcaccactc    72840
tgctgaaaaa tgttttgcat gttttgaaa cactcgcttt tagatttat cagttttctg    72900 tcactggtgc tacttcctta gttagctttt ctctaacaaa cggcataggc gtgacagaac    72960
agctagattc ctataacatg ttttcagagc tggcctctta caagcgtgca ggaaacattt    73020
gctttgtttt tgctaatttg atgtggttgt actgatttct gtaaaatgca tgattatcta    73080
aaaatgaaaa tttttaatgc atgattagaa ctgaagaaca tacatctttc tgtttacagt    73140
```

```
tttatatatt tgtttaaatg ttcttttaaa ataagtatag tcttgtttct gctagaggta    73200
tttgcgttac ataataactt ttttatagca ccaagatatg aatatgtagt ctctacatga    73260
tatttgacat cttggaaact atagtaaatc tttgacattt caattcttta tttaatgtca    73320
tttcctttct gctgcatatt cccttatgaa ctataagggg ctaggagtcc tgcacctgct    73380
agaaaagagt ttggaggtaa ccatttatat ttgttataat atatggatct tggttcatta    73440
atttttttgg agtttgagct ctgtaactta gtgacatttt aggttgcttt gatgcaagcc    73500
aaaatgaatg acatttatat gccaacttaa aaataactcc aaactttcat tatatttctg    73560
gtaaaagatt agagcttgat tttattagtg aatattatta gaattaagaa gaccttccat    73620
ttccctgata aacagagttg aattacttaa ggcctgatat actttttatt aataaatata    73680
gtcaattcgg ttataaagat taaatgagtc aaacacaatg aaaataggtg gtttcccaag    73740
gatttgatta tattggatta tattagaact ctagtacgtc ttgccagtag cctgtgaatt    73800
agcaaaatgt cctaggaatg cagtttaaag ttatcataat tatctgaaat atagctttca    73860
ttttgcatgg ctttatcata atttgtcata acattcatgc ctcatttta aaatagaaga    73920 acaagtctct gttatatatt tcgataaaga aattttttctt aacacatggg tcactttttg    73980
tagtttactt gttttacatg aagactctta caaagctcaa ctagaggcgt acatttgaca    74040
agtttattta atctagttct caagaaaggc tgaggcagaa tgtctcagtc ccacagaaga    74100
gctgttcctc acccagttct agtgtcctta gggctcacgt gcacaggcag ctggtctctc    74160
cctgctccag ctgcctgagc acgtcgccag ccgactcacg ctgtcacaga gtggctgcac    74220
cgtgtgcaga cttgaacgac tttgggtaat tagggtagca aagttctttc agcaccaagc    74280
ttctgtaaga tactactgga ggataacttt tccactaact taaagacgac attgattttt    74340
ttcccatttc agacttgtgc tttgatttat agcttcatgg aagatttat ttaccttccc    74400 ctttaattag gaaaccaatc tgtagaaaaa tttaaagaaa tttgtgaaaa gctatacata    74460
ttagctactc agtgacttac ttagtctgat gttttttaaa aattgcttct cttcgtaatt    74520
cttttgtagg cagtcttagc agcatatttt ttaaccctat aaaccagtaa ctgcttgaag    74580
gcaataatct gaaagtaatt atagtacttt tagagttctt tttttttttt ttaataatgc    74640
attgaaaatt accttctaag ggactaacac aggactcata gagatttaaa atgaaattgg    74700
aacttccaga ctttttttc ctttatgact ggcaaatatt ggagctttta ttagtggttt    74760
aattctgaat ataaaaaatg agatgattaa aaagcaaaga ctttcattat tttcaaattc    74820
cctactgcta gtgaagaagt gaaagtgtta agtcactcag ttgtatcccg actctttgga    74880 acccccatggt ccgtagccca ccagtctcct ctgtccatgg gattctccag gcaagaatgc    74940
tggagggggt tgccatttct tcctccaggg aatcctccca tgatgtcaga tataaaaaga    75000
aaactatttt ctccttttcaa ttctaactga agaaagggca aggatcaggt ttgggccagg    75060
catctagagg cactttggtt tatacagata tcttttgaaga aatttgaagc agtgaaagaa    75120 cttttttttgc aaaaggacat ttaactcaga aactgttttg tgtgcctgcc tttccctctg    75180
ttctatggac cctgaacaat acacagcttc tgttctctct ctaaaaaggt gttggagccc    75240
ctcccagtcc gggggtagct aggcgagaga tggaaggtaa caagacgttt gcatcctaga    75300
aatggatctc tcgttttatt cctaaatgtc agcccctcca gtgtttaaag acataccaaa    75360
tcttttcttg gtccaactgt aaactccccc tccccctcct tctgtatatc ttgtaacttc    75420 atatttttc tcttttcatt ctgtgttgtg tagtttctgg tggttgtcca tttactttct    75480
```

```
ctgcaattct taatgttgtt ttgagctgtt ctgtatatat atatttcata tacacttaag   75540
atgtgaaatt aatgtgcagt attattttaa gaggaatgcc ttcaaaaatt ttttcagaat   75600
aagtcaaatg tttagaaatg tactgtacta actctgaagt tttaaaaatt aataattaaa   75660
ccttgttaat tcagtccaag gatatagtat tttttaatca acttcagata acataaaatat   75720 gctgagtaaa tttgcttaaa aggctattaa aactggaagc cattcattaa gattacagtt   75780
attaaaagtc tgatgggttt catataacaa ttacacatga atttcctttc aaaagaaga    75840 aatctgagat gctgaccttta ataggtctc ctactccttt tggccccaaa agtagtttat   75900
tgcatttcag tcttctccta cgtttcgaat gagtttgagc agtattttaa cactgtcttg   75960
cataaggcag atattgtaat aagtagtgcc cgccttctac cttaatgata gggtctttct   76020
gtagaaatcc gaaggtctc gtaagagccc ctgtccgtac tgacgtccac agcatgaagc   76080
cctgaacagt gctgtttggt gtcttgtgtg actcggaaag tgcgggtctg ttggtcctgg   76140
agccgtgagc ccaccaagct ctgggaagta gtggggccac gtcttgtgac tgttccccca   76200
aactgaccat gtgttttcag ggttcatagg aaagagctct gttgggaaag ttaccttcca   76260
aatgaggtag cagaccaact gccaacttgt cccataaatg ttactctcaa tagtctaaat   76320
ttttctcttt tggaggtatt ttctaaaggg ctgataatac cctccagcat ttctaaagca   76380
gaatagtttg ttttgttttt cttttttccac ctcgtgcccc catttctgct ggtaatgaaa   76440
cagaacagct agctaatatt ataaatatg gcttatttac ttatagataa ttttttttc    76500 cttcctgctt caaagcaccc aaaagcccag gaacgacccg gagagataat ctaggtaaac   76560
attcgaattc agctacttaa ccttaaagct ggaccatgaa tagacagtgt ggtataagtg   76620
catgtttctt gtttctttct ttaaaaacaa agacctgagc tacatggtgt gatgtctttg   76680
ttccaggacg cagccagctt ccacctcaag ccggactgcc aggcccggga cttgctggac   76740
acagtgcagc cagaccggta ggcagcgcct cgcttgcgag ccaggaggtc taggtcctgg   76800 gtcccaacttt gctactaatc aaatgtgtta ccctgaagaa atcacgggcc cattaagact   76860
ccaatttcct caattctaaa ttgggggaat tagacttgat gctcttcaag gtaccttcgt   76920
gtgtatgtgt gtgtgtgtgt gtgtgtgttt tactctctga ggtgtgtgtg tgtgtgtgtg   76980
tgtacttgct gagttgtgtc cgactcttttg caaccccatg gactgtaccc catcaggctc   77040
ctatgtctat gaaatttccc tggtaagatt actggagtgg gttgccattt ccttctccag   77100
gggatctccc caacctaggg atcaaacccg cttctcctgc attgagaggc agattcttta   77160
ccactgagcc accaggcagc cccacccttca actcaaatgg tattctaaca tcctcttcag   77220
aagtaaaagc atccttcatt atttgaataa aagtggtata cttaagtgat tacagtcact   77280 aaataaaatat cttagaatct tgaaatatat ggggaagtga tgtactaggg caatttttta   77340
tgacattatc tgagtaatga agtaaagtca ttcttctatc agaaaggttt tattttactt   77400
ttatttcctt tttatttgtc tttgccacac cttgaggcat gcgggatctt agttccccaa   77460
acagggattg aacccgcact ccctgcagtg gaagcacaag tcttaactgc tggaccacca   77520
gggaagtcca gaaggatttt aaaattagat ttcaggaacc ccaatgatga tagtctgtca   77580
actaaaacta gttctaaagg tttaaccaca ggagagcaga tggcattgca gggtttcacc   77640
ctgcgttgta agtctggttt tctgcgtgtt tatgtgtgtt ttgttataca cagaattatt   77700
ctattattca cccacatgaa catttctct  gagacagaac aagtaattca aagaaaaaaa   77760
aaaagagaaa ccagtgtcag tcaggtggag cctggactta ttgggaggcc actggctgaa   77820
tcctgggaac tgtgactata cctggagatg aagagacttc tgctaatgaa actacttcaa   77880
```

```
gagtccaaga aattctcatg agatttctaa aacagagata ttttgttttt tgtcttgtag  77940
ccaacctgaa ggacttttc tatatataat attatgctcc aaagtaaagt gtctgtggaa   78000
tttacctaaa atagccatta tccactcccc tgtttttta aaaagaagt tgttattcac    78060
tgactacaca cttcccacaa agtactttgc ttactgaata ttgtaagaat agggaaggaa  78120
agtcaggatt ttgtgtgatt acatttataa cttttgctta tgcatggaat ctagaaagat  78180
ggtactgctg aacctgtttg cagggcagca gtggagatgc agacacagac agcagacttg  78240
tggacgcagc gggggcagga gagggtggga ctaactgaga gaatactatg ctgctgctgc   78300
tgctaagtcg cttcagtcgt gtccgactct gtgcaacccc acagacggca gcctcccagg  78360
ctcccccgtc cctgggattc tccaggcaag aacactggag tgggttgcca tttccttctc  78420
cagtgcatga aagtgaaaag tgaaagtgaa gtcgctcagt cttttcagac tcttagcgac  78480
cccatggact gcagcctacc aggctcctcc atccatggga ttttgcaggc aagagtactg  78540
gagtggggtg ccatcgcctt ctccgagaga atactatgga aatgtatatt accatatgta  78600
aaacagatag caagtgggaa tcggggagct caactctgtg ctgtgtgaca atttagaagc  78660
ctggaggggg gtacaagagg gagggggacat gtgtgtacct gtaggagatt caggagggag  78720
gggacctcca tgtggctgat tcatattgat gtatggcaga agccaacaaa tattgtaaag  78780
caattatcct ccaatttata caaaaataag aaaaatgtac tgagtgctta aagccttcag  78840
caaacatgtg aagatagaaa aggacgttat ttccctagtg tatcttccag cctatgtatt  78900
tcagcacatt gagttagcca ttccagagtt tttaacctct gtgtttaata aagaaaaaca  78960
gcctcagtgt agttttggt aagcctctta gttccacagt gtatgtcccg ctccacctcc    79020
tcatgacctg taaaatcgtc ccactaagga gtatgataca ggataaagaa aacgggccct  79080
gagttcggct cctggcttta ttttgtaact ctgtggcttt gggacagttg tatacatttc   79140
ttcattttca tttaaattag agatgataaa ataatacctt accccccagg gccatttgga  79200
cattgaaatg taaattcata cccagtgctt agttaacaca gtgcgtggca catagtaaac  79260
agtgaaaaat ataaggaag attttttgaag cttaaggaac aaaattgggt catttgtaga    79320
gatgtggatg gacctagaga gtatcataca gaatgaagta agtcagaaag agagaaacag  79380
tattgtgtat taacccatat atgtggaatg tagataaata ctatagatga tcttatttgc   79440
aaaccagtaa tagagacaca gacatagaga acaaatgtgt ggataccaag gggcagggga  79500
ggaattggga gattcgagtt gacacatata tgtgtgtctg tgtgtgtata cacacacaca  79560
tatatatatt actgatacta tgtataaaat agataattaa tgagaaacta ctgtatatag  79620
cacagagagt tctacttaac gcactgtgat gacctgaatg ggagggaaat ccaaaaggga  79680
ggagatatat atatatatat atatatatat atatgtatgc ctgattcatt ttgctgaaga  79740
gtagagacca acacaacttt gtaaagtaac tatgcaccaa taaaagttaa tccttaataa  79800
aaaaaaatga aacttatgat catatggcaa taaatagagc cattagaatg acaaagaggc  79860
agaggaaatg atacaagatg cacagacaaa atattttcat caaatcttat ccgttgcaga  79920
taaggtaaat gtctcagtgg ttttcgtttc ccatctttag attattccgc cccgtgctgg  79980
agtcatcagc gccccccaga gccacgcacg ggtgtctgct gggagactga ctcctgaaag  80040
ccaaagcaaa acctcagaag tactgaaagg tagacccgta gtcaaaacag cagtgccatt  80100
ctgtatcctt cccttccact tctttttctt tttcttcgc aatctctcac tttatacaac   80160
ttgctcaaat tctttctctc tctctttttt tttttcctgt cttctgaat gccataataa   80220
```

```
aggaggctac tgggggctga gacagggact ggaatttcct accatttcct gaaaggaagg    80280
ataaactcag ttttccagag aatgcctaac atctggaaat tactttcttt agggccagct    80340
cttcttcccg agcccctgaa gcctcaggcc gcccttcctg tgccgccttc tcttgcgcca    80400
ccttctcttg cgccacctgt tcagaagatg caggagcctc tcatcccggt ggccgcacct    80460
ctggcccagg ctgccctgca gcccagcctg gaaacgcccc cgcagccacc ccctcggagc    80520
aggtcgtccc acagcttgcc ttctgagcct ccggcgcagc cgcaggtaag gcttccagc     80580 ggggagaaag atcatctggg tgtgtgtgtg tgtgtgtgtg tgtgtgtgcc tttgcttaca    80640
ttttgttttg tttttccctt tttttttttt tttactgagg catatttgat gctcttgctg    80700
tagtctttga acatacttat tttaattatt agctttagaa aaaacaccta agatttgatt    80760
ttttaaaaaa ttttgtcatt tgctagtaat aacatgttta gatatgactt caaccagtga    80820
atgtcatttg accactcaga ctcatcacac aacaaaagca cgtttggccg tttgagggtt    80880
tgggtttttt gtttgtttgt ccaacctgtt gtctagatca cgggttctca gagagtgacc    80940
ctagattagg gctctttccc taaaggctct tttccctaaa acttccaagc ggcccccacg    81000
ctgtttactt tgtttaaaga gtaggtgatt ttttggtttt ttctgtgtgt aatttacttt    81060
ggatacttaa ttagagtgga cagtaataac ttagtttctt tttgttcaca gctattagat    81120
tagttttgtc ctttacctcc tggacagaaa ggcagtcagg tcaatccctg gccattggca    81180
gtaaatttcc aataatccta tctctcctga tgctgcagtt agctcttttc agtgatggag    81240
tcggcactgg gcttccttgg ggatctctaa cagtttcaga cactactgga tccatttaga    81300
tgtttcaggc atgcagcagc aggcttatta accaaagtaa aagccatcaa aataatgttc    81360
tcatgagtat cacatagaaa atagtaccat tgccttggtg ggtggaaatc acaggatcac    81420
agggactttt gttataccag agtgatctca cattggaaag ccttctggtg tatatacaca    81480
aagttgtttc aacacaagaa tattcatgcg agttgaattg ttttacttgg aggctgtttt    81540
acttagtttt tattatatac atctcagtaa aatcattaaa ataaggttta tctttagtat    81600
aagtttatct ttagtataag gtttatcttt atatttctgt tgtctagcct cacattgaat    81660
tttatccaaa agttttaact tgaaaatgcc atcaaggcca aagaactgaa gtctaagtct    81720
gcttttattt tggaatagtc taaaatacag aaatattaca ctggtgatgt cccttaagca    81780
tgtttataat aatagtttgc atttattttt acagatatgt gaatatgtcc aactaattgg    81840
cagaagttag cagtttctta tgcttcttca tagtgaaaaa aagattataa agtaaatatg    81900
aatcttgaaa caatatgaat agttagcaaa gcacttactt atcagactat tggtcacatt    81960
ttttaaaaag ctaagacgga tatataattg agaataatgt tctcttaagc taatgaacac    82020
caaaaagtat tatatagttg aggatgctga agatatatag taattataga agcccttcaa    82080
acaataagtg tccattattt tctctttgcc aatctacttt tagtgcatga tgattttttc    82140
ttttcatttt cttataaggt gtagtattta ttattattgt tttttagtgt aattggaggg    82200
caagaaactt tcaaagaagc catcttaaag ctttgtatta ctacagtttt aggacagaaa    82260
gtgatcatga ttttcacagt aaaggtgaac cctaattcct aaaactctat aaaatgttct    82320
cagtattgaa agtaggtgtg gtactctgaa caacttcaga agaacacact gtcaaagaag    82380
attgcagttc tcagtagaaa gtcatcttgt gacacagaga gtacaggatg aatattccgt    82440
gactgccatc tatcattttc ttaggtcatt ttcccctgtt ttgctttctg attttcattg    82500
gaatgggtat ggtgatttgc tgacgaagca cagcaagcct gtgctttctg tgtggtttag    82560
tagattgtat tcttgactct tacattctgc tcatcaaaac tgtgaaaggt gtttgttata    82620
```

```
agcctttctt tgcctcagtc attgatatca aatccctcta cacattacat acacagacac  82680
actttcctgg agagtggagg tcttgttcac gtgtaggctg cctttgtgca agatcacaaa  82740
gagcttagtt tcctcctggg agcttacaga aagataggga ggcatttttac cttttttgcc  82800 tttttcattt tgaaccataa aaataatgcc tattcaaaaa ataatgaaca tctaaagtct  82860
taaaaattct tctataatgg ctataacttg aagagggtga gttagtaaaa taactcacat  82920
tttgatattt tggtaataat atgaaacagt cttagaattg aacttagtag tttttacaag  82980
tctttattaa ttctgccaaa aatatacaag gtatttaaaa catagaccca cacatgaccc  83040
agctttactt gttattacta tttaaattat ttgattctat aattctatat agaaaagatt  83100
cttctaattc aagtgattat atgttatata tcctttagaa aatgtaaaaa tgccccactt  83160
atctgacttt caatgtctta ggcatctgat tatcagctga aaaccagaag tcaggaatcc  83220
aatgggaagt aaagtaatag catcacagct atactattgg agtgacagcc gatagtgagg  83280
gaagaggcca agtagaaaat ctcaggactt ccctggcagt ccagtggtta agaccccgtg  83340
ctcccaatgc agagggcatg ccttcgatcc ctggtcaggg aactaagatc cagcatgctg  83400
cgcagcacag ccaaaaaaga aaaaaaaaaa tctcagcttt ctggatcaat ttaataccat  83460
ccccttgcat cttagtataa acccattccc agttttttatc caactcttac aaaactaatg  83520
catcaggatc atcaggaaag gttaaattca ggagtctcat gttttgtagt aacacatttt  83580
atataatata aatatataat aaatatatta tttataaaat aatttactat agaatggtgt  83640
ctctcgaatc tgtctaagtg agttatggta ttttaaaata aggtaagctt taaatattgg  83700
ggaagatttg ttcaaactgt tcttaagaaa tactgtaatt ttttaaagta ctgctgttat  83760
agaaagattg tgatttcatc tttagtatca cccttcagaa aatttgagtg atagattaat  83820
agaacaagcc tggatcctga ccatgttaaa ataaatacca gttttcactt ttctgcaaag  83880
tggtgccatt ttgaacaatt tctctaatca tgataaaccc ataggctgtc ttaaggctgt  83940
gtcctaacct tcttgggctg ccgtaacaaa ataccatgaa ctgggtgact caggcagtag  84000
aaatttgtct tctcaagttc tggaggctag aagcccgaga tcaggatgcc agcatggttg  84060
ggttctgctg gggcctcttc tcctgtgccc acatggcctt tccttggtgc ttgcacaagg  84120
gaagaaagag caagccctct ggtgtgtctc ctacaaaggg tgctagttcc atcaagaggg  84180
cccactctca cgacctcatc taaccccagt cacctcccag aggccacgtc tccaaatacc  84240
atcacataag aaggttgggg ttcagcatac gaatctgagg ggacacaaac atttcaccca  84300
tagcctgctg aaaatacttc agtgctccag taatgtattt ggaatattat ttttggaatg  84360
actactttga actagttagt aatcaacctc agataaaatt aaatcctgag ccctattaca  84420
gcaatacatt ttattgtctc ttgatcttat actgtgacct gcaggtctca ctgctgttgg  84480
attttgtaca taatataaaa ctgaaagtgt tttgaattgt tagggttgct gcttggtctc  84540
agattgtcct cctaactctt tcccttgatg tctatgtttc gttttctcaa agcaggagca  84600
accatcaggg taacaggtat cggattattt ctcaatctta tatgtgcttc tcatctgtct  84660
tagcacagta gatgtatgaa tctttcgctt catacatcta aattctcacc catttttaaa  84720
aaccacctgt ccacattaat aaaattctgtt atcataccat aaaaacctgct ttttttctta  84780 gtattttgaa ttcttaggaa ccattttagt tattcttgct aatgctttcc catttttgctt  84840 ttttttttta caaaaattaa caagactaaa aagtataact ttaagaaggt aagctttaga  84900
tatatgaaag tgtatttggc aaaaccaaat tggttcgtgg ttttaacaat ggcaaaatta  84960
```

```
tgtaagtata aaattcaatt tttttcctag atttcttttg ggaaattaaa aaaacccaaa   85020
aaactagtag catgtagatt ataactggag gcactaggag attttttttt ttgttaaaga   85080
agaattgatg atttacaaaa atgaaaatga acattatagc aggattattt aagggccttt   85140
ccaacaccct tttctgtaaa aaataccatc atcattaatg tcaagtcatc ataaatactg   85200
cttagatata tagaaattca ttctaatgta atgaatgatg atgtggctct cataatttca   85260
aatctcattg agcaaaatga tcatgttttct gttaaattac cttttaactta ttttgaaaga   85320 aaaatttgtt aatatatgaa aataaagata tttaaatgtg caacatttat ttggcaaaag   85380
cctattattc taagctgtac aaagcataaa cttcctacct ataatgtctg tgtcatggac   85440
tctttgtcta ccatgggaga atcggggccc agacccactc aagtacttct gttttgtcat   85500
atgaatcgta aataacccag tcattactgg taatgtgtag ctaattgtaa ttttacagca   85560
tctatagtaa atttgtctct caagtactat aatacactta gaatacagtt tagaatttat   85620
gacatgtctg cttttttaatt ttgttcaaat ttattgtcat attaagtttg aagaaaaata   85680
aaacttgttt acttaaagta tactatagat tagttgaata aaatagatcc tagagagtga   85740
ttcacgtaag aagttatcca cactgttttcc ttttgcaaat gagcagcctt ccttattctt   85800
tttttttttt tgccactgca tgtggcttgt ggggtctctg ttccctgacc aggggttgaa   85860
cccaggccct ggcagtgaaa gcagagagcc ctaatcactg gatcggaggg gaattagcct   85920
tccctattct taagcaccaa gttactgttt aagaagatgc aattatgttt tattggagtt   85980
tcccaggcag ctcagtgata aagaatctgt ctgctaaaga agaagacaca ggttcaatcc   86040
tgggtcagga atattccctg gagaagggaa tggcaaccca ctccagtttt cttacctggt   86100
aaatcccatg gacagaggag cctggtgggc tatagtttgt agtcgtcttg tggggtcaca   86160
gagtcagata tgacttagag actaaaataa gaacagcaaa acaatgtttt attgagactg   86220
ctgctctttt tctcaacata tcttatgaat gtttagttac ttgctttaac aatgacctaa   86280
attcatttgg gtcatgctgc attttgtaca ttgccaagtc tctagctaag taaaattctc   86340
cctctcctgt gcttttcttta cctttaatttt ggcataaata tccaagtcac ccacctagtt   86400
ttaacaatta tatagagttt ttttttttttt taattaaaat ggagttcctg ataaagctag   86460
ctacttttct cgtacagcca ggcttcagtt caatgtttcc cttaggaaag tagcctgtgc   86520
ccggtaccac agccgggctc cactccagcc ggcttctttg tgaactgggc acacagggca   86580
gacttttcat aactgtgaag taggtctgac ccctcctcct gccagtaact gttcacagct   86640
agctctgcca tgcatagctt tattttggtt gaagaattac tatcccaaat agaaacagga   86700
ttcctccccc caccacgcca tccagtttaa agaatcattg cagttagtta caacctatct   86760
aaagatgagg aaggtcaatt aaaaaatatt ttcacattca gaatttattc tacaaaggag   86820
agctgacgtt aaaaggcaaa gaatgctttg aaaatttat tctacaagtg gaaaaggaaa   86880
tgatgcattg tcttcagctt atgaatatag atatactaat aaaattatta tccataaagt   86940
tgaatttcca tagtaacatt aactctcaat gaaaatatat ttcaaaaaac aatgaaacca   87000
catcatcatc acagatgggt gttggaagtt tattcatagc gatttagcat aaactttgta   87060
ttgaatgtga gttttttaag ttcatttgat tatctgatag aactgggcat gaaccaaact   87120
catctgctaa ttcagtgcag ttctccattt tacgtatcaa tacttgcatg gatgaaataa   87180
gttgtattta taaagaaact tatttagcag agagttttaa aaaaaaaaaa aatttcatgg   87240
tacttgttta accaccagag taacagacta cacaaagctc cttttttttat ttttgagta   87300 tgtatacttg accccttcag aataaagaat aattgagaca ggaaacaggg ggggcattca   87360
```

```
aagtaacctt attgctttt gtttgttctg attattcagt gggctctctc tttcccaggt    87420
gaaaacaaac ggagtctccg ccgtcagact ggactcgcca ttaaagagtg acccatttga    87480
agacttgtca ttgaacctgc ttgctgtatc aaaggctcag ccatctgttc acccccaaa    87540
cccaaggggg ttgacgccgt tgccttctgc agccccaagt aacaccaaca ctctgagttc    87600
tgtaagctgc atgccgacaa tgcctccaat tccagcccgg agtaaatccc aggaaaacac    87660
gcgatgttcc ccaaacccat tcatcccaag ctcaagcagc acaaatcctt tcaccgacag    87720
gaccgccgct cctggaaacc ctttcgagc tgagtctcaa gaatcagagg ccacttcatg    87780
gttctccaaa gaagagcctg ttgctccgag tccattctct tcgctgaggc ctctggatca    87840
gaacagtagc aagccttcat cctccctgga tgggtttaag gacagttttg atccacaggg    87900
cctgtctgca ctaacagtca gcaaccccaa aggatgggta accttcgagg aagaaggaga    87960
ctttggtgtg acagggaagt cagggtccac tcgcccagac gttttcctgg gtaagcagct    88020
gagctcgtct cctggctcca aggtgatgct tggtgatgac tggggtagga gtaccaatgt    88080
gtctctctgt gtgttg    88096
```

```
<210> SEQ ID NO 5
<211> LENGTH: 24
<212> TYPE: DNA
<213> ORGANISM: Bos taurus

<400> SEQUENCE: 5
aaccaccaga gtaacagact acac    24

<210> SEQ ID NO 6
<211> LENGTH: 19
<212> TYPE: DNA
<213> ORGANISM: Bos taurus

<400> SEQUENCE: 6
ctgtcggtga aaggatttg    19

<210> SEQ ID NO 7
<211> LENGTH: 471
<212> TYPE: DNA
<213> ORGANISM: Bos taurus

<400> SEQUENCE: 7
aaccaccaga gtaacagact acacaaagct ccttttttta ttttttgagt atgtatactt    60
gaccccttca gaataaagaa taattgagac aggaaacagg gggggcattc aaagtaacct    120
tattgctttt tgtttgttct gattattcag tgggctctct ctttcccagg tgaaaacaaa    180
cggagtctct gccgtcagac tggactcgcc attaaagagt gacccatttg aagacttgtc    240
attgaacctg cttgctgtat caaaggctca gccatctgtt cacacccaa acccaagggg    300
gttgacgccg ttgccttctg cagccccaag taacaccaac actctgagtt ctgtaagctg    360
catgccgaca atgcctccaa ttccagcccg gagtaaatcc caggaaaaca cgcgatgttc    420
cccaaaccca ttcatcccaa gctcaagcag cacaaatcct ttcaccgaca g    471

<210> SEQ ID NO 8
<211> LENGTH: 471
<212> TYPE: DNA
<213> ORGANISM: Bos taurus

<400> SEQUENCE: 8
```

-continued

| | |
|---|---|
| aaccaccaga gtaacagact acacaaagct cctttttta tttttttgagt atgtatactt | 60 |
| gaccccttca gaataaagaa taattgagac aggaaacagg gggggcattc aaagtaacct | 120 |
| tattgctttt tgtttgttct gattattcag tgggctctct ctttcccagg tgaaaacaaa | 180 |
| cggagtctcc gccgtcagac tggactcgcc attaaagagt gacccatttg aagacttgtc | 240 |
| attgaacctg cttgctgtat caaaggctca gccatctgtt cacacccaa acccaagggg | 300 |
| gttgacgccg ttgccttctg cagcccaag taacaccaac actctgagtt ctgtaagctg | 360 |
| catgccgaca atgcctccaa ttccagcccg gagtaaatcc caggaaaaca cgcgatgttc | 420 |
| cccaaaccca ttcatcccaa gctcaagcag cacaaatcct ttcaccgaca g | 471 |

<210> SEQ ID NO 9
<211> LENGTH: 231
<212> TYPE: DNA
<213> ORGANISM: Bos taurus
<220> FEATURE:
<221> NAME/KEY: misc_feature
<222> LOCATION: (140)..(140)
<223> OTHER INFORMATION: y designates pyrimidine

<400> SEQUENCE: 9

| | |
|---|---|
| atgtatactt gaccccttca gaataaagaa taattgagac aggaaacagg gggggcattc | 60 |
| aaagtaacct tattgctttt tgtttgttct gattattcag tgggctctct ctttcccagg | 120 |
| tgaaaacaaa cggagtctcy gccgtcagac tggactcgcc attaaagagt gacccatttg | 180 |
| aagacttgtc attgaacctg cttgctgtat caaaggctca gccatctgtt c | 231 |

<210> SEQ ID NO 10
<211> LENGTH: 231
<212> TYPE: DNA
<213> ORGANISM: Bos taurus
<220> FEATURE:
<221> NAME/KEY: misc_feature
<222> LOCATION: (140)..(140)
<223> OTHER INFORMATION: y designates pyrimidine

<400> SEQUENCE: 10

| | |
|---|---|
| atgtatactt gaccccttca gaataaagaa taattgagac aggaaacagg gggggcattc | 60 |
| aaagtaacct tattgctttt tgtttgttct gattattcag tgggctctct ctttcccagg | 120 |
| tgaaaacaaa cggagtctcy gccgtcagac tggactcgcc attaaagagt gacccatttg | 180 |
| aagacttgtc attgaacctg cttgctgtat caaaggctca gccatctgtt c | 231 |

<210> SEQ ID NO 11
<211> LENGTH: 22
<212> TYPE: RNA
<213> ORGANISM: Bos taurus

<400> SEQUENCE: 11

| | |
|---|---|
| ugagguagua gguugugugg uu | 22 |

<210> SEQ ID NO 12
<211> LENGTH: 18
<212> TYPE: RNA
<213> ORGANISM: Bos taurus

<400> SEQUENCE: 12

| | |
|---|---|
| acggagucuc ugccguca | 18 |

<210> SEQ ID NO 13
<211> LENGTH: 18

```
<212> TYPE: RNA
<213> ORGANISM: Bos taurus

<400> SEQUENCE: 13
acggaguccc ugccguca                                             18

<210> SEQ ID NO 14
<211> LENGTH: 21
<212> TYPE: DNA
<213> ORGANISM: Bos taurus

<400> SEQUENCE: 14
ggaggtgtcc atccctgacg g                                         21

<210> SEQ ID NO 15
<211> LENGTH: 26
<212> TYPE: DNA
<213> ORGANISM: Bos taurus

<400> SEQUENCE: 15
aagaggttga agttcttgaa gatgca                                    26
```

INCREASED RESISTANCE TO ENTEROBACTERIACEAE IN BOVINES

CROSS-REFERENCE TO RELATED APPLICATIONS

This application claims priority under 35 U.S.C. §119 to provisional application Ser. No. 61/695,842 filed Aug. 31, 2012, herein incorporated by reference in its entirety.

FIELD OF THE INVENTION

The present invention relates to bovine subjects with increased resistance to bacteria belonging to the Enterobacteriaceae family. The invention also relates to methods of testing that identifies bovine subjects with increased resistance to Enterobacteriaceae. The invention also relates to molecular markers for identifying bovine subjects with increased resistance to Enterobacteriaceae. The invention also relates to identifying genetic loci, and mutations thereof, which contribute to heritable differences in resistance to Enterobacteriaceae in bovine subjects.

BACKGROUND OF THE INVENTION

The Bovini tribe of the Bovidae family occupy a unique and important role in human history. Members of this group have been domesticated since at least the early Neolithic period with modern cattle being the most prominent example. Members of this group provide valuable economic contributions including the production of meat, dairy products and leather. As of Jan. 1, 2011, the US Department of Agriculture estimated that the US inventory was 92.6 million head of cattle. In 2010, US farmers produced more than 26 billion pounds of beef valued at an estimated $37 billion. The USDA estimated that the retail equivalent value of the US beef industry in 2010 was $74 billion. The Bovini tribe, particularly cattle, are an important part of the American farm economy.

Disease can have a significant negative impact on herds resulting in large economic losses. Disease can cause premature culling of infected animals, increased veterinary costs, increased susceptibility to further disease, breeding problems, decreased milk production, decreased slaughter value, and decreased feed efficiency. Additionally, disease agents can enter into food supply when the animals are harvested and processed. This can cause expensive recalls of potentially contaminated food products. As such, the control of disease causing agents is of particular concern in the farming industry.

One class of disease causing agents is the Enterobacteriaceae family of Gram-negative bacteria. While some members of this family are harmless symbionts or commensals, serious and familiar pathogens such as *Salmonella, Escherichia coli, Yersinia, Klebsiella, Shigella, Proteus, Enterobacter, Serratia*, and *Citrobacter* are also included. Infections with these pathogenic bacteria can result in diseases such as diarrhea, pneumonia, sepsis, hemorrhagic colitis, and hemolytic-uremic syndrome.

In order to control outbreaks of disease, a number of preventative measures are employed. These measures include culling affected animals, manure management programs, sterilization of instruments, vaccination, and the use of antibiotics. While these approaches are effective at reducing the rate of infection, the techniques can result in additional issues. For example, the regular use of antibiotics in herds has resulted in pathogens which are resistant to common antibiotics—a phenomenon which increases the difficulty of treating the disease and which poses a larger health risk. As such, there is a need in the art for new and additional approaches to increase Bovini resistance to Enterobacteriaceae.

The inventors have developed a novel approach for increasing such resistance in bovine subjects. Specifically, the inventors have developed a method of increasing resistance to Enterobacteriaceae by identifying genetic traits (high-affinity microRNA-binding sites in 3' untranslated regions) that decrease the expression of bovine proteins interacting with Enterobacteriaceae, using the protein designated as Synaptojanin 1 as the paradigm.

It is an object of the present invention to provide the molecular basis for increasing the resistance of a bovine subject to Enterobacteriaceae.

It is a further object of the present invention to provide bovine subjects and herds of bovine subjects with increased resistance to Enterobacteriaceae.

It is a further object of the present invention to provide materials for artificial insemination of bovine subjects, specifically semen, which can be used to produce bovine subjects and herds of bovine subjects which exhibit increased resistance to Enterobacteriaceae.

It is a further object of the present invention to provide a genetic test for determining a bovine subject's likely resistance to Enterobacteriaceae.

It is yet another object of the invention to provide further information for understanding and changing a bovine subject's resistance to Enterobacteriaceae.

It is yet another object of the invention to use the above information to identify other mutations in linkage disequilibrium with or that are causative of differences in resistance to Enterobacteriaceae in specific lines, populations, or breeds of cattle.

Other objects will become apparent from the detailed description of the invention which follows.

BRIEF SUMMARY OF THE INVENTION

In its broadest aspect, the present invention provides bovine subjects and herds of bovine subjects with increased resistance to Enterobacteriaceae through decreased expression of Synaptojanin 1 and other bovine proteins that interact with Enterobacteriaceae.

According to the invention the inventors have discovered that decreased expression of Synaptojanin 1 increases resistance to Enterobacteriaceae infection. The inventors have also discovered a mutation in the SYNJ1 gene which is very closely linked to or, most likely, is the causal mutation of differences in Synaptojanin 1 expression and increased resistance to Enterobacteriaceae. The mutation is located in the 3' untranslated region of the gene and is NCBI dbSNP ss105143728, also known as bSYNJ1_C3981T. The inventors have further discovered that the decreased expression is likely caused by destabilization of the mRNA transcribed from the bSYNJ1 gene.

The information was used to create a genetic test for screening for the mutation in cattle or in prospective parental cattle for use in marker-assisted breeding. According to the invention, a SNP was identified that is predictive of increased resistance to Enterobacteriaceae. This provides a method of predicting, breeding, and selecting for beef with improved resistance to Enterobacteriaceae. The invention also includes a micro-array chip which is able to discern the presence of this marker for use in marker-assisted breeding.

The invention also provides novel coding sequence that relates to differences in resistance to Enterobacteriaceae and, based upon results across various cattle breeds and related species, is likely to be predictive in other species, breeds or lines of animals used for meat products. The mutant gene has been found to decrease expression of Synaptojanin 1. The mutant protein allows for the development of in vitro and in vivo models and agents to improve the resistance of bovine subjects to Enterobacteriaceae.

In another aspect of the invention, one may use the SYNJ1 gene to screen for other markers in linkage disequilibrium with the SNP of the invention to create further tests, to identify other potential Enterobacteriaceae resistance associated mutations in other species of meat animals, lines, populations, or breeds of the same.

BRIEF DESCRIPTION OF THE DRAWINGS

FIG. 1A-AC. Is a diagram showing the annotated genomic sequence of the SYNJ1 gene in domestic cattle (SEQ ID NO:2).

FIG. 2A-B. Is the full length cDNA of a SYNJ1 transcript from domestic cattle SEQ ID NO:1).

Figure 3:
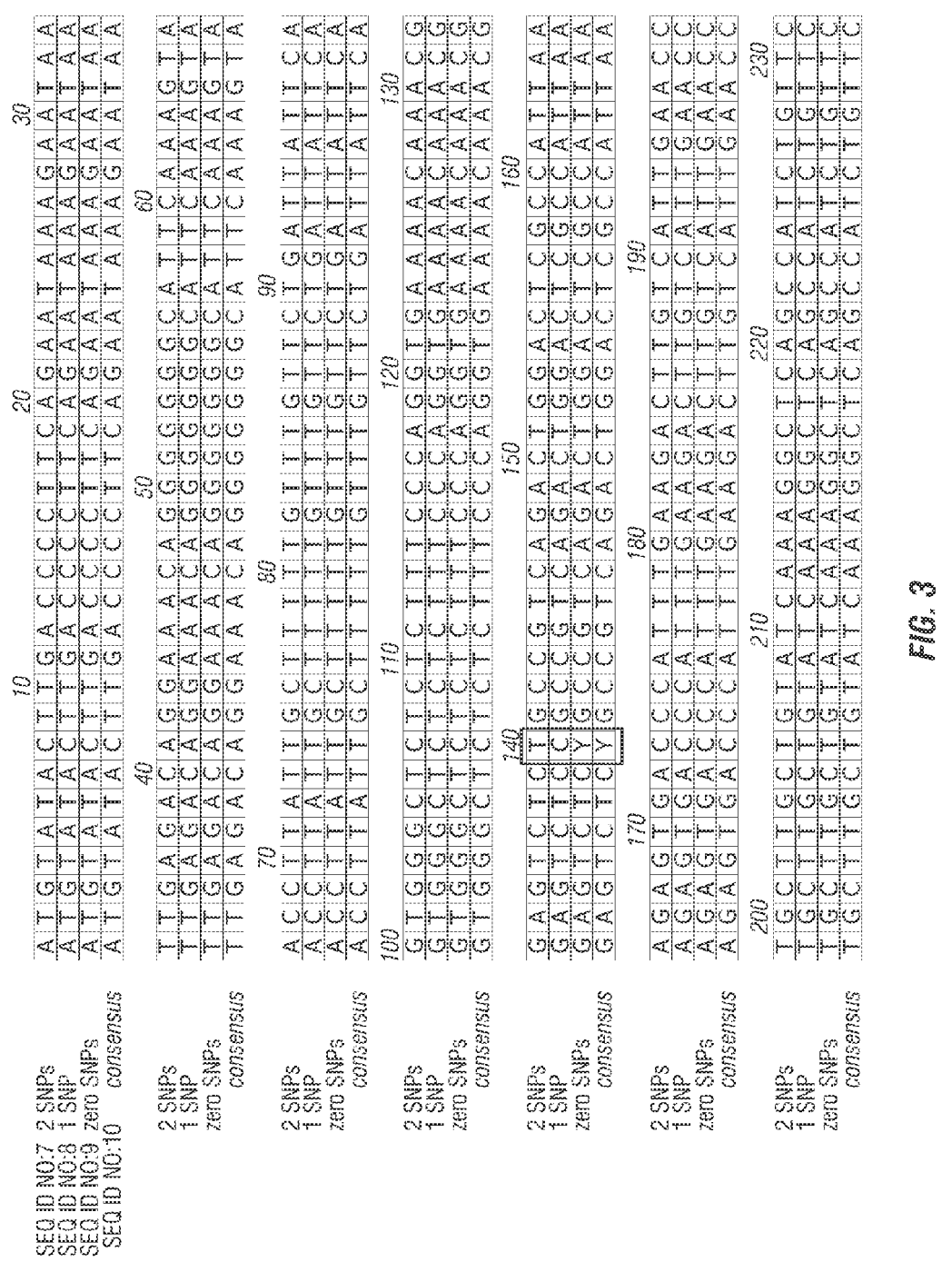

FIG. 3. Is a multiple sequence alignment between bovine subjects with zero copies of the mutant SYNJ1 allele (SEQ ID NO:9), one copy of the mutant SYNJ1 allele (SEQ ID NO:8), or two copies of the mutant SYNJ1 allele (SEQ ID NO:7).

FIG. 4. Is a photograph of an agarose gel electrophoretogram (following RT-PCR-based amplification of SYNJ1 mRNA) showing Synaptojanin 1 expression in wild-type, homozygous mutant, and heterozygous cattle.

FIG. 5. Is the proposed interaction between bta-let-7b miRNA (SEQ ID NO:11) and the mRNA from the mutant SYNJ1 variants (SEQ ID NO:12), with a depiction of the non-interaction between bta-let-7b miRNA and the wild-type SYNJ1 mRNA (SEQ ID NO:13).

FIG. 6. Is a graph showing the percentage of bovine leukocytes, of varying SYNJ1 genotypes, infected after challenge with invasive and non-invasive *Salmonella*.

FIG. 7. Is a graph of showing the percentage of leukocytes infected after challenging leukocytes of cattle with varying genotypes with 84 different serovars of *Salmonella*.

FIG. 8. Is a graph of clinical salmonellosis scores obtained after challenging cattle with varying SYNJ1 genotypes with invasive *Salmonella*.

FIG. 9. Is a graph showing the average percentage of *Salmonella* infected lymph nodes in cattle after challenging cattle with varying SYNJ1 genotypes with invasive *Salmonella*.

FIG. 10. Is a graph of measurements regarding the presence of *Salmonella* in intestinal contents and fecal matter of cattle after challenging cattle with varying SYNJ1 genotypes with commensal-type *Salmonella*.

FIG. 11. Is a graph of measurements of *E. coli* O157:H7 in recto-anal junction tissue of cattle after challenging cattle with varying SYNJ1 genotypes with *E. coli* O157:H7.

FIG. 12. Is a graph showing the percentage of leukocytes infected after challenging leukocytes of cattle with varying SYNJ1 genotypes with invasive and non-invasive *E. coli*.

FIG. 13. Is a graph showing the percentage of leukocytes infected after challenging leukocytes of cattle with varying SYNJ1 genotypes with invasive and non-invasive *Shigella dysentariae*.

FIG. 14. Is a graph showing the percentage of leukocytes infected after challenging leukocytes of cattle with varying SYNJ1 genotypes with invasive and non-invasive *Y. enterocolitica*.

FIG. 15. Is a graph showing the percentage of leukocytes infected after challenging leukocytes of cattle with varying SYNJ1 genotypes with invasive and non-invasive *Listeria monocytogenes*.

FIG. 16. Is a graph of showing the number of bacteria adhered per cell after challenging leukocytes of cattle with varying SYNJ1 genotypes with three different serotypes of Shiga toxin-producing *E. coli*.

FIG. 17. Is a graph of showing the number of bacteria adhered per cell after challenging leukocytes of bison and cattle with varying SYNJ1 genotypes with Shiga toxin-producing *E. coli*.

DETAILED DESCRIPTION OF THE INVENTION

One primary objective of the present invention is to enable the identification of animals with improved resistance to Enterobacteriaceae for use in breeding and selection. This is achieved by a method that detects the presence of a genetic marker in useful linkage disequilibrium with differences in Enterobacteriaceae resistance in a meat animal subject, using a bovine subject as the paradigm. More specifically, the genetic marker may be the bovine Synaptojanin 1 (SYNJ1) gene.

Definitions

Units, prefixes, and symbols may be denoted in their SI accepted form. Unless otherwise indicated, nucleic acids are written left to right in 5' to 3' orientation; amino acid sequences are written left to right in amino-terminal to carboxy-terminal orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant/algae, animal, and fungal mitochondria, the bacterium *Mycoplasma capricolum*, or the ciliate Macronucleus with read-through stop codons, may be used when the nucleic acid is expressed therein. When the nucleic acid is prepared or altered synthetically, advantage can be taken of known codon preferences of the intended host where the nucleic acid is to be expressed.

As used herein "full-length sequence" in reference to a specified polynucleotide or its encoded protein means having the entire amino acid sequence of, a native (nonsynthetic), endogenous, biologically active form of the specified protein. Methods to determine whether a sequence is full-length are well known in the art including such exemplary techniques as northern or western blots, primer extension, S 1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5'- and 3'-untranslated regions of mRNA aid in the identification of a polynucleotide as full-length. For example, the consensus Okazaki sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. "Host cell" also refers to eukaryotic cells that harbor infectious pathogens.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). "Introduced" can also mean the resulting aspect of a nucleotide polymorphism, as in "the SNP introduced a microRNA site into the 3'-untranslated region of a gene transcript".

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or, (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by nonnaturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses conservatively modified variants and known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning-A Laboratory Manual, 2nded., Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, conservatively modified variants, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to conservatively modified variants and to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of post-translation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant/algae promoter" is a promoter capable of initiating transcription in plant/algae cells whether or not its origin is a plant/algae cell. Exemplary plant/algae promoters include, but are not limited to, those that are obtained from plants/algae, plant viruses, and bacteria which comprise genes expressed in plant/algae cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue-specific". A "cell-type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "oligonucleotide" refers to short, single-stranded nucleic acids used for a variety of purposes in genetics and molecular biology. The strands of nucleic acids are chemically synthesized, usually to complement a given nucleotide sequence. Oligonucleotides are often utilized in applications such as DNA microarrays, PCR, DNA sequencing, and FISH. Oligonucleotides may also be used to probe for certain nucleotide sequences and are useful for finding genetic markers.

The term "selectively hybridizes" includes reference to hybridization, under stringent hybridization conditions, of a nucleic acid sequence to other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample. Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1,000 nucleotides in length, optionally less than 500 nucleotides in length.

Typically, stringent conditions will be those in which the salt concentration is less than about 1.5 M $Na^+$, typically about 0.01 to 1.0 M $Na^+$ concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1M NaCl, 1% SDS at 37° C., and a wash in <RTI 0.5× to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically the function of post-hybridization washes, the critical factors being the ionic strength and temperature of the final wash solution. For DNA/DNA hybrids, the $T_m$ can be approximated from the equation of Meinkoth and Wahl, Anal. Biochem., 138: 267-284 (1984): $T_m=81.5°$ C.$+16.6$ (log M)$+0.41$(% GC)$-0.61$(% form)$-500/$L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic animal, cell or tissue" includes reference to a animal which comprises within its genome a gene encoding a heterologous polynucleotide. Generally, the gene is stably integrated within the genome such that the expression of the polynucleotide is passed on to successive generations. The gene may be integrated into the genome alone or as part of a recombinant expression cassette. "Transgenic" is used herein to include any cell, cell line, tissue, or organ, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional breeding methods or by naturally occurring events such as random cross-fertilization, non recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a)"reference sequence", (b)"comparison window", (c) "sequence identity", and (d)"percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the GCG Wisconsin Genetics Software Package, Version 10 (available from Accelrys Inc., 9685 Scranton Road, San Diego, Calif., USA). The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215: 403-410 (1990); and, Altschul et al., Nucleic Acids Res. 25: 3389-3402 (1997).

Software for performing BLAST analyses is publicly available, e.g., through the National Center for Biotechnology Information www at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). One measure of similarity provided by the BLAST algorithm is the smallest sum probability (P(N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89: 10915).

Multiple alignment of the sequences can be performed using the CLUSTAL method of alignment (Higgins and Sharp (1989) CABIOS. 5: 151-153) with the default parameters (GAPPENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11-17 (1988) e. <RTI g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "bovine" refers to species which are part of the Bovini tribe of the Bovidae family. This includes the genera *Bubalus, Bos, Pseudoryx, Syncerus* and *Bison*. Members of the Bovini tribe include *Bos indicus, Bos taurus* (domestic cattle), *Bison bison* (American Bison), *Bubalus bubalis* (water buffalo) and *Bos mutus* (yaks). This includes domestic cattle of any breed. Thus, any of the various cow or ox species, whether male or female, are included in the term, and both adult and new-born animals are intended to be covered. The term does not denote a particular age. One example of a bovine subject is a member of the Holstein-Friesian cattle population.

The term "non-black" refers to a genotype of domestic cattle for the Melanocortin 1 Receptor (MCR1) gene. Non-black cattle are domestic cattle (*Bos Taurus* or *Bos indicus*) who contain no copies of the $E^D$ allele at the MCR1 locus. Specifically, these cattle bear nucleotide deletions in the coding regions of the MCR1 gene and these deletions lead to missense mutations, frame-shifts, or premature stop codons. Genetics tests for MCR1 genotype are commercially available throughout the industry and significant research has been done regarding MCR1 genotypes and its impact on various traits and traceability of products from domestic cattle (see e.g. Analysis of melanocortin 1 receptor (MC1R) gene polymorphisms in some cattle breeds, Russo et al, ITAL. J. ANIM. SCI. VOL. 6, 257-272, 2007). Additionally, PCR-based amplification and sequencing of the MCR1 gene can delineate black from non-black cattle. Furthermore, visual inspection of animals can be sufficient for declaration of the non-black phenotype, in the absence of a clear determination of the MCR1 deletion yielding the non-black phenotype. When used in conjunction with bovine (e.g., "non-black bovine subject") the combined term means all species which are members of the Bovini tribe except domestic cattle which contain one or more copies of the $E^D$ allele of the MCR1 locus, i.e., encoding intact MCR1 proteins that yield black pigmentation. An example of a non-black bovine is the Red Angus breed.

The term "genetic marker" refers to a variable nucleotide sequence (polymorphic) that is present in bovine genomic DNA on a chromosome and that is identifiable with specific oligonucleotides. Such a variable nucleotide sequence is distinguishable by nucleic acid amplification and observation of a difference in size or sequence of nucleotides due to the polymorphism. In useful embodiments, such genetic markers may be identified by several techniques known to those skilled in the art, and include typing of microsatellites or short tandem repeats (STR), restriction fragment length polymorphisms (RFLP), detection of deletion or insertion sites, and random amplified polymorphic DNA (RAPD) as well as the typing of single nucleotide polymorphism (SNP) by methods including restriction-fragment-length polymerase chain reaction, allele-specific oligomer hybridization, oligomer-specific ligation assays, mini-sequencing, direct sequencing, fluorescence-detected 5'-exonuclease assays, and hybridization with PNA and LNA probes, single nucleotide primer extension, and others. However, it will be appreciated that other genetic markers and techniques may be applied in accordance with the invention.

SEQ ID 1 is a mRNA sequence of the Synaptojanin 1 gene from *Bos taurus* containing the bSYNJ1_C3981T variant which exhibits increased resistance to Enterobacteriaceae. SEQ ID 2 is genomic DNA sequence showing the genomic sequence of Chromosome 1 of *Bos taurus* from 2108619 to 2196714 which contains the Synaptojanin 1 gene having the bSYNJ1_C3981T variant which exhibits increased resistance to Enterobacteriaceae. SEQ ID 3 is a mRNA sequence of the wild type Synaptojanin 1 gene from *Bos taurus*. SEQ ID 4 is genomic DNA sequence showing the genomic sequence of Chromosome 1 of *Bos taurus* from 2108619 to 2196714 which contains the wild type Synaptojanin 1 gene. SEQ ID 5 is the forward primer used in the experiments detailed below. SEQ ID 6 is the reverse primer used in the experiments detailed below. SEQ ID 7 is the sequence amplified using SEQ ID 5 and SEQ ID 6 when an individual has at least one copy of the bSYNJ1_C3981T variant which exhibits increased resistance to Enterobacteriaceae. SEQ ID 8 is the sequence amplified using SEQ ID 5 and SEQ ID 6 when an individual has at least one copy of the wild type bSYNJ1_C3981T variant. In individuals possessing one copy of each variant, both SEQ ID 7 and SEQ ID 8 will be amplified when the primers SEQ ID 5 and SEQ ID 6 are used.

The method according to the invention includes the provision of a sample of bovine genetic material. Such bovine genetic (DNA) material may be provided by any conventional method or means. The bovine DNA material may e.g. be extracted, isolated, and purified from blood (e.g., fresh or frozen), tissue samples (e.g., spleen or buccal smears), and hair samples containing follicular cells and semen.

As previously described, the method of the present invention further comprises a step of detecting in the genetic material the presence or absence of a genetic marker that is linked to increased resistance to Enterobacteriaceae or preferably is the causative mutation.

In order to detect if the genetic marker is present in the genetic material, standard methods well known to persons skilled in the art may be applied, e.g. by the use of nucleic acid amplification. In order to determine if the genetic marker is genetically linked to the Enterobacteriaceae resistance trait, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer program such as the MLINK program of the LINKAGE package (Lathrop et al., 1985). A lod score of greater than 3.0 is considered to be significant evidence for linkage between the genetic marker and the Enterobacteriaceae resistance trait or gene locus.

The synaptojanin family is a family of polyphosphoinositide phosphatases which serve a role as cytoskeletal-regulating proteins. Synaptojanins consist of three domains: a central inositol 5-phosphatase domain; an N-terminal Sac1-like inositol phosphatase domain; and a proline rich C-terminal domain. The first two domains interact with phosphatidylinositol (4,5)-bisphosphate ($PIP_2$) and phosphatidylinositol (3,4,5)-trisphosphate ($PIP_3$)—low-abundance membrane phospholipids which function in membrane trafficking, plasma membrane-cytoskeleton linkages, second messenger signaling, cell adhesion, cell motility and some other critical cellular processes. The C-terminal domain interacts with a number of proteins involved in vesicle endocytosis such as amphiphysin, endophilin, DAP160/intersectin, syndapin and Eps15.

The synaptojanin proteins appear to play an important function in endocytosis and, in particular, clathrin-mediated endocytosis. In this process, clathrin collects at a given location on the cell membrane and, in conjunction with other proteins, results in the formation of a coated pit on the inner surface of the cell membrane. The synaptojanin proteins are thought to attract clathrin which helps begin the vesicle endocytosis process.

In other species, Synaptojanin 1 is expressed as two major alternatively spliced isoforms. The smaller isoform is highly enriched in nerve terminals where it participates in clathrin-dependent synaptic vesicle recycling. The larger isoform includes a carboxy-terminal extension and is expressed in developing neurons as well as a variety of tissues. The carboxy terminus is capable of binding Eps 15, clathrin and AP-2, which are involved in receptor-mediated endocytosis.

Synaptojanin is vital for the host cell invasion of *Salmonella*. *Salmonella* injects a protein, designated as SopE, into the host cell during invasion of the host cell. SopE is physically homologous (based on amino acid alignments) to and thus mimics synaptojanin in regards to cytoskeletal rearrangements, a step necessary for *Salmonella* invasion into host cells. The deletion of SopE from *Salmonella* renders the microbe non-pathogenic and, as presented in this application, the absence of synaptojanin 1 renders the cell impervious to *Salmonella* invasion. Thus synaptojanin 1 is not absolutely required for host cell vitality.

In cattle, SYNJ1 is located on the forward strand of chromosome 1 and begins at approximately nucleobase number 2108619 and ends at approximately nucleobase number 2196714. SYNJ1 includes 35 exons. SNP ss105143728 occurs at nucleobase number 21 of exon 35. The genomic sequence encompassing SYNJ1 is included as FIG. 1. FIG. 1 also identifies the exons for the gene as well as SNP ss105143728 which is believed to be a mutation site responsible for different levels of resistance to Enterobacteriaceae. A number of other SNPs are known to be in close proximity to ss105143728, including rs110119682, rs134890864, and rs137729257. The region also includes STS sites BV10531 and BV104430 and UniSTS numbers 407157, 407120 and 42737.

FIG. 2 provides the mRNA encoded by SYNJ1 and indicates the location of ss105143728. ss105143728 can be detected through use of PCR, preferably with the use of 5'-AACCACCAGAGTAACAGACTACAC-3'(SEQ ID 5) as a forward primer and 5'-CTGTCGGTGAAAGGATTTG-3' (SEQ ID 6) as a reverse primer. The binding sites for these primers are identified on FIG. 1. A multiple sequence alignment amplicon derived from PCR using these primers is shown in FIG. 3 with individuals having one and two copies of the SNP as identified in the left margin, ss105143728 occurs at nucleotide 141 of the alignment. For those individuals which are homozygous for the "T" form of the SNP, expression of the SYNJ1 mRNA is greatly diminished (FIG. 4).

The "T" form of the SNP is believed to introduce a RNAi-based destabilization site in the SYNJ1 mRNA. Specifically, this mutation permits the binding of bta-let-7b microRNA (miRNA) to the mRNA transcript. As shown in FIG. 5, the wild-type allele contains a two base pair mismatch near the middle of the miRNA, this mismatch is sufficient to prevent binding. The mutation, however, changes the site to a single mismatch, which permits the miRNA to bind to the transcript.

The bta-let-7b miRNA is part of the lethal-7 (Let-7) microRNA family. Originally identified through developmental timing studies in *C. elegans*, Let-7 miRNAs have been found in a wide variety of species. Let-7 miRNAs begin as transcripts of several hundred nucleotides which are processed into hairpin structures of approximately 70 nucleotides before leaving the nucleus. In the cytoplasm, these structures are ultimately processed into the 22 nucleotide miRNAs—bta-let-7b has a mature sequence of UGAGGUAGUAGGUUGUGUGGUU (SEQ ID NO:11). The mature form of Let-7 members is highly conserved across species. In vertebrates, research has also shown that the sequences, expression timing and genomic clustering of the miRNAs are all conserved across species.

miRNAs are small RNAs which serve as post-transcriptional regulators. A miRNA typically functions by binding to target mRNAs resulting in translational repression, target degradation, and/or gene silencing. Different sets of miRNAs are expressed in different tissues and the miRNA composition may even change within a tissue at different time points. For animals, the miRNA typically binds in the 3' UTR of the target gene and upon binding trigger the RNA-induced targeting complex producing results such as those shown in FIG. 5.

As described below, at least one genetic marker may be linked to a gene causing the differences in Enterobacteriaceae resistance. Thus, in one embodiment, at least one genetic marker is located in exon 35 of SYNJ1 and is genetically linked to the differences in Enterobacteriaceae resistance.

It will be appreciated that, in order to detect the specific allele present in a bovine subject of associated with Enterobacteriaceae resistance, more than one genetic marker may be applied in accordance with the invention. Thus, at least one marker can be a combination of two or more genetic markers that are shown to be informative whereby the accuracy of the test can be increased.

Genetic markers of the present invention can be made using different methodologies known to those skilled in the art. Thus, it will be understood that, with the knowledge presented herein and the nucleotide sequences of the bovine SYNJ1 gene, which are known and publically available that additional markers in this gene may be identified and used according to the invention.

Genotyping is based on the analysis of genomic DNA that can be provided by using standard DNA extraction methods as described herein. When the genomic DNA is isolated and purified, nucleic acid amplification (e.g., polymerase chain reaction) can be used to amplify the region of the DNA corresponding to each genetic marker to be used in the analysis for detecting the presence in a bovine subject of a genetic marker associated with Enterobacteriaceae resistance.

In another embodiment, the invention comprises a method for identifying genetic markers for Enterobacteriaceae resistance in general—specifically variant genes containing high-affinity microRNA sites that repress gene synthesis. For example, the invention comprises a method that identifies variant non-SYNJ1 genes containing a high-affinity 3'UTR microRNA binding site (bta-let-7b and the like) that decreases the synthesis of a gene functionally-related to SYNJ1 (e.g., one of the other 33 genes encoding an Enterobacteriaceae interactome protein), thus conferring resistance to Enterobacteriaceae. Enterobacteriacea interactome proteins include: spectrin, adducing, B-catenein, T-plastin, Exo70, cytokeratin-8, cytokeratin-18, Cdc42, Rac1, Arp2/3, Rab7, RILP, dynein, dynactin, RhoA, TassC, Hook3, vimentin, 14-3-3, PipB2, Rab9, SKIP, kinesin-1, desmoplakin, caprin-1, TIP60, plakoglobin, filamin, VCP, RhoC, JUP, OSBP, and profilin.

Once a major effect gene has been identified, it is expected that other variations present in the same gene, allele or in sequences in useful linkage disequilibrium therewith may be used to identify similar effects on these traits without undue experimentation. The identification of other such genetic variation, once a major effect gene has been discovered, represents no more than routine screening and optimization of parameters well known to those of skill in the art and is intended to be within the scope of this invention. This can include other lines, breeds, or even other meat animals.

The present invention provides a method of genotyping an animal comprising a polynucleotide of the present invention. Genotyping provides a means of distinguishing homologs of a chromosome pair and can be used to differentiate segregants in an animal population. Molecular marker methods can be used for phylogenetic studies, characterizing genetic relationships among animal species, identifying crosses or somatic hybrids, localizing chromosomal segments affecting monogenic traits, map based cloning, and the study of quantitative inheritance. The particular method of genotyping in the present invention may employ any number of molecular marker analytic techniques described hereinafter.

In the present invention, the nucleic acid probes may be employed for molecular marker mapping of nuclear genomes which hybridize, under selective hybridization conditions, to the variant polynucleotide of the present invention. In preferred embodiments, the probes are selected from polynucleotides of the present invention. Typically, these probes are cDNA probes or restriction enzyme treated (e.g., PST I) genomic clones. The length of the probes is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

The method of detecting an RFLP comprises the steps of (a) digesting genomic DNA with a restriction enzyme; (b) hybridizing a nucleic acid probe, under selective hybridization conditions, to a sequence of a polynucleotide of the present invention of the genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNAse protection assays; 4) allele-specific oligonucleotides (ASOs); 5) the use of proteins which recognize nucleotide mismatches, such as the *E. coli* mutS protein; and 6) allele-specific PCR, e.g., mismatch PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The following is a general overview of techniques that can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds that are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W.H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the major effect gene of the invention as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA, which is then used as the amplification template, so that the PCR indirectly amplifies a specific population of RNA transcripts. See, e.g., Sambrook, supra, Kawasaki et al., Chapter 8 in *PCR Technology*, (1992) supra, and Berg et al., *Hum. Genet.* 85:655-658 (1990).

PCR Amplification

The most common means for amplification is the polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocyte from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 µL) in a buffer of 50 mM Tris-HCl (pH 8.3), 50 mM KCl, 1.5 mM $MgCl_2$, 0.5% Tween 20, 0.5% NP40 supplemented with 100 µg/mL of proteinase K. After incubating at 56° C. for 2 hr., the cells are heated to 95° C. for 10 min to inactivate the proteinase K and immediately moved to wet ice (snap-cool). If gross aggregates are present, another cycle of digestion in the same buffer should be undertaken. Ten µL of this extract is then used for amplification.

When extracting DNA from tissues, e.g., chorionic villus cells, tail snips, or confluent cultured cells, the amount of the above mentioned buffer with proteinase K may vary according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions in very small numbers of cells (1,000-5,000) derived from individual colonies from bone marrow and peripheral blood cultures. The cells in the sample are suspended in 20 µL of PCR lysis buffer [10 mM Tris-HCl (pH 8.3), 50 mM KCl, 2.5 mM $MgCl_2$, 0.1 mg/mL gelatin, 0.45% NP40, 0.45% Tween 20] and frozen until use. When PCR is to be performed, 0.6 µL of proteinase K (2 mg/mL) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 mL of lysis buffer (10 mM Tris-HCl, 400 mM NaCl, 2 mM $Na_2EDTA$, pH 8.2). Fifty µL of a 20 mg/mL solution of proteinase K and 150 µL of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µL of the 20 mg/mL proteinase K solution is mixed in the solution and incubated for another night at 37° C.

on a gently rocking or rotating platform. Following adequate digestion, 1 mL of a 6M NaCl solution is added to the sample and vigorously mixed. The resulting solution is centrifuged for 15 minutes at 3,000 rpm. The pellet contains the precipitated cellular proteins, while the supernatant contains the DNA. The supernatant is removed to a 15 mL tube that contains 4 mL of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), DNeasy Blood & Tissue Kit (Qiagen Inc, Valencia, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm, with the absorbance at 260 nm between 1 and 1.8 times that of the absorbance at 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 90° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63-67; and Radding, 1982, *Ann. Rev. Genetics* 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region using RT-PCR. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, $T_4$ DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology, supra.*

Allele Specific PCR

Allele-specific PCR differentiates between target regions differing in the presence of absence of a variation or polymorphism. PCR amplification primers are chosen that bind only to certain alleles of the target sequence. This method is described by Gibbs, *Nucleic Acid Res.* 17:12427-2448 (1989).

Allele Specific Oligonucleotide Screening Methods

Further diagnostic screening methods employ the allele-specific oligonucleotide (ASO) screening methods, as described by Saiki et al., *Nature* 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency they will bind to both polymorphic forms of the allele, but at high stringency, bind to the allele to which they correspond. Alternatively, stringency conditions can be devised in which an essentially binary response is obtained, i.e., an ASO corresponding to a variant form of the target gene will hybridize to that allele, and not to the wild type allele.

Ligase Mediated Allele Detection Method

Target regions of a test subject's DNA can be compared with target regions in unaffected and affected family members by ligase-mediated allele detection. See Landegren et al., *Science* 241:107-1080 (1988). Ligase may also be used to detect point mutations in the ligation amplification reaction described in Wu et al., *Genomics* 4:560-569 (1989). The ligation amplification reaction (LAR) utilizes amplification of specific DNA sequence using sequential rounds of template dependent ligation as described in Wu, supra, and Barany, *Proc. Nat. Acad. Sci.* 88:189-193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_m$). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for *DNA Amplification*, W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527 (1986), and Myers et al., in *Genomic Analysis, A Practical Approach*, K. Davies Ed. IRL Press Limited, Oxford, pp. 95-139 (1988), the contents of which are hereby incorporated by reference. The electrophoresis system is maintained at a temperature slightly below the $T_m$ of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high $T_m$ values.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at an particular locus can be differentiated using single-strand conformation polymorphism analysis, which identifies base differences by alteration in electrophoretic migration of single stranded PCR products, as described in Orita et al., *Proc. Nat. Acad. Sci.* 85:2766-2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212-222 (1991). In another method, differences between target sequences can be detected by enzymatic cleavage of mismatched base pairs, as described in Nelson et al., *Nature Genetics* 4:11-18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with polymorphisms.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5'nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e., there is a mismatch of some form; the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology at www.twt.com.

Non-PCR Based DNA Diagnostics

The identification of a DNA sequence linked to an allele sequence can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with $^{32}$P or $^{35}$S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a bovine chromosome where one of the major effect genes resides, and thus defining a genetic marker linked to one of the major effect genes, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to one embodiment of the invention, polymorphisms in a major effect gene has been identified which have an association with Enterobacteriaceae resistance. The presence or absence of the markers, in one embodiment may be assayed by PCR RFLP analysis using if needed, restriction endonucleases, and amplification primers which may be designed using analogous human, pig or other of the sequences due to the high homology in the region surrounding the polymorphisms, or may be designed using known sequences (for example, human) as exemplified in GenBank or even designed from sequences obtained from linkage data from closely surrounding genes based upon the teachings and references herein. The sequences surrounding the polymorphism will facilitate the development of alternate PCR tests in which a primer of about 4-30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), *Short Protocols in Molecular Biology*, Fourth Edition, John Wiley and Sons 1999. The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate animal DNA, genetically type individual animals, and detect genetic differences in animals. In particular, a sample of animal genomic DNA may be evaluated by reference to one or more controls to determine if a polymorphism in one of the sequences is present. Preferably, RFLP analysis is performed with respect to the animal's sequences, and the results are compared with a control. The control is the result of a RFLP analysis of one or both of the sequences of a different animal where the polymorphism of the animal gene is known. Similarly, the genotype of an animal may be determined by obtaining a sample of its genomic DNA, conducting RFLP analysis of the gene in the DNA, and comparing the results with a control. Again, the control is the result of RFLP analysis of one of the sequences of a different animal. The results genetically type the animal by specifying the polymorphism(s) in its gene. Finally, genetic differences among animals can be detected by obtaining samples of the genomic DNA from at least two animals, identifying the presence or absence of a polymorphism in one of the nucleotide sequences, and comparing the results.

These assays are useful for identifying the genetic markers relating to increased resistance to Enterobacteriaceae, as discussed above, for identifying other polymorphisms in the same genes or alleles that may be correlated with other characteristics, and for the general scientific analysis of animal genotypes and phenotypes.

One of skill in the art, once a polymorphism has been identified and a correlation to a particular trait established will understand that there are many ways to genotype animals for this polymorphism. The design of such alternative tests merely represents optimization of parameters known to those of skill in the art and is intended to be within the scope of this invention as fully described herein.

In accordance with the present invention there may be employed conventional molecular biology, microbiology, and recombinant DNA techniques within the skill of the art. Such techniques are explained fully in the literature. See, e.g., Maniatis, Fritsch & Sambrook, *Molecular Cloning: A Laboratory Manual* (1982); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription and Translation* (B. D. Hames & S. J. Higgins eds. (1984)); *Animal Cell Culture* (R. I. Freshney, ed. (1986)); *Immobilized Cells And Enzymes* (IRL Press, (1986)); B. Perbal, *A Practical Guide To Molecular Cloning*, (1984).

Creation of Transgenic Animals

Transgenic animals are animals which have had genetic material artificially inserted into the genome. Typically, this material is present as either an extrachromosomal element (e.g., cosmid) or is stably integrated into the chromosomal DNA of the organism in at least a subset of cells. Preferably, this includes stable integration into the germline cells. Typically, a chimeric animal (chimera) is produced where only a subset of the somatic cells possess the desired transgene. These chimeras are then used for further breeding to generate the ultimate transgenic animal.

A transgenic animal can be a knock-out having a partial or complete loss of function of the target gene. A knock-out of SYNJ1 means that SYNJ1 gene expression is undetectable or insignificant. This can be accomplished through a variety of means including: introduction of a disruption of the coding sequence (e.g., insertion of one or more stop codons and/or insertion of a DNA fragment), deletion of coding sequence, substitution of stop codons for coding sequence, chromosomal deletion of all or part of the native gene may be induced (including deletions of the non-coding regions, particularly the promoter region, 3' regulatory sequences, enhancers, or deletions of gene that activate expression of 5-HT6 genes), and/or introduction of an anti-sense construct that blocks expression of the native genes (for example, see Li and Cohen (1996) Cell 85:319-329). "Knock-outs" also include conditional knockouts, for example where alteration of the target gene occurs upon exposure of the animal to a substance that promotes target gene alteration, introduction of an enzyme that promotes recombination at the target gene site (e.g., Cre in the Cre-lox system), or other method for directing the target gene alteration postnatally.

For embryonic stem (ES) cells, an ES cell line may be employed, or embryonic cells may be obtained freshly from a host. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting progeny are screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

Reducing the Activity and/or Level of SYNJ1

Methods are also provided to reduce or eliminate the activity of an SYNJ1 by transforming a eukaryotic cell with an expression cassette that expresses a polynucleotide that inhibits the expression of Synaptojanin 1. The polynucleotide may inhibit the expression of the SYNJ1 directly, by preventing transcription or translation of Synaptojanin 1 mRNA, or indirectly, by encoding a polypeptide that inhibits the transcription or translation of an SYNJ1 gene encoding an SYNJ1. Methods for inhibiting or eliminating the expression of a gene in a eukaryotic cell are well known in the art, and any such method may be used in the present invention to inhibit the expression of the SYNJ1. Many methods may be used to reduce or eliminate the activity of an Synaptojanin 1 polypeptide. In addition, more than one method may be used to reduce the activity of a single SYNJ1.

1. Polynucleotide-Based Methods:

In some embodiments of the present invention, eukaryotic cells are transfected with an expression cassette that is capable of expressing a polynucleotide that inhibits the expression of an Synaptojanin 1 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one Synaptojanin 1 polypeptide is an expression cassette capable of producing an RNA molecule that inhibits the transcription and/or translation of at least one Synaptojanin 1 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of an Synaptojanin 1 polypeptide include sense Suppression/Co-suppression, where an expression cassette is designed to express an RNA molecule corresponding to all or part of a messenger RNA encoding a Synaptojanin 1 polypeptide in the "sense" orientation and over expression of the RNA molecule can result in reduced expression of the native gene; Antisense Suppression where the expression cassette is designed to express an RNA molecule complementary to all or part of a messenger RNA encoding the Synaptojanin 1 polypeptide and over expression of the antisense RNA molecule can result in reduced expression of the native gene; Double-Stranded RNA Interference, where a sense RNA molecule like that described above for cosuppression and an antisense RNA molecule that is fully or partially complementary to the sense RNA molecule are expressed in the same cell, resulting in inhibition of the expression of the corresponding endogenous messenger RNA, Hairpin RNA Interference and Intron-Containing Hairpin RNA Interference, where the expression cassette is designed to express an RNA molecule that hybridizes with itself to form a hairpin structure that comprises a single-stranded loop region and a base-paired stem, Small Interfering RNA or Micro RNA, where the expression cassette is designed to express an RNA molecule that is modeled on an endogenous miRNA gene.

2. Polypeptide-Based Inhibition of Gene Expression

In one embodiment, the polynucleotide encodes a zinc finger protein that binds to a gene encoding SYNJ1, resulting in reduced expression of the gene. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication Nos. 2003/0037355; each of which is herein incorporated by reference.

3. Polypeptide-Based Inhibition of Protein Activity

In some embodiments of the invention, the polynucleotide encodes an antibody that binds to at least one SYNJ1 gene and reduces the activity of the Synaptojanin 1 polypeptide. The expression of antibodies in eukaryotic cells and the inhibition of molecular pathways by expression and binding of antibodies to proteins in cells are well known in the art. See, for example, Conrad and Sonnewald, (2003) *Nature Biotech.* 21:35-36, incorporated herein by reference.

4. Gene Disruption

In some embodiments of the present invention, the activity of an ACC synthase polypeptide is reduced or eliminated by disrupting the gene encoding the ACC synthase polypeptide. The gene encoding the ACC synthase polypeptide may be disrupted by any method known in the art. For example, in one embodiment, the gene is disrupted by transposon tagging. In another embodiment, the gene is disrupted by mutagenizing plants using random or targeted mutagenesis, and selecting for plants that have reduced SYNJ1 activity.

Development of siRNAs

MicroRNAs (miRNAs) are small non-coding RNAs which negatively regulate protein-coding genes primarily by decreasing stability of RNA transcripts. Decreased stability is typically accomplished through the binding of the miRNA to the target transcript. These binding sites preferentially reside in the 3' UTRs of the genes, however, they can occur throughout the entire transcript. Generally, miRNA binding sites are well conserved. Some genes which are heavily expressed (e.g., housekeeping genes) have smaller 3' UTR regions which may reduce the likelihood of binding to miRNAs. Genes with a 3' UTR longer than 4 kB are less affected by miRNA. Other factors influence the selection and effectiveness of miRNAs. For example, many miRNAs are known to regulate genes involved in cell development processes. Another example is that miRNAs appear to preferentially target genes with high CpG promoters. Also, as highly expressed genes transcribe a large number of mRNAs, the miRNA regulation of those mRNAs can be different from those of weakly expressed genes, although current analyses disagree on whether miRNAs affect highly expressed genes more or less than medium or lowly expressed genes.

Potential miRNAs can be screened using high throughput experiments using microarrays or proteomics. Examples of these high-throughput systems are described in: Lim L P, et al. Nature 2005, 433:769-773; Grimson A, et al., Mol Cell 2007, 27:91-105; Selbach M, Schwanhausser B, et al., Nature 2008, 455:58-63; Baek D, Villén J, et al., Nature 2008, 455:64-71.

All of these references are incorporated by reference as if set forth fully herein. A well designed and effective miRNA will reduce expression by approximately 50%, 60%, 70%, 80%, 90% and/or 100% depending on site selection and other factors listed above. It is well within the skill in the art to design miRNAs which will bind to a target transcript and screen the same for determining effectiveness of the miRNA.

Creation of Microarrays

Microarrays are used to perform large parallel analysis of various biological and chemical samples. A microarray is an array of spots of samples (probes) which are immobilized at specified positions on a substrate. Each spot contains chemical or biological material which is capable of interacting with certain target molecules (such as a DNA sample). In order to use a microarray, it is flooded with a solution containing target molecules. For DNA/RNA applications, the probes are short oligonucleotides which are complimentary to target DNA/RNA samples. When the samples are labeled using fluorescent or radioactive labels, the microarray can be scanned to determine which spots interact with the target. The polynucleotides in the target hybridize with the spots that contain complimentary probe polynucleotides. The presence of hybridized target molecules is then detected by a microarray reader which reports the position and intensity of the label emissions. The identity of the probes which hybridize with the target can be determined by mapping the reported location to records indicating which probe was placed in the reported location.

Microarrays are typically fabricated using one of two techniques: photolithography and robotic spotting. Detailed instructions for using photolithography can be found in U.S. Pat. Nos. 5,445,934 and 5,744,305 which are both incorporated by reference as if set forth fully herein. The photolithographic technique takes approaches used in the design of integrated circuits and applies them in this biological context. While this technique has very high initial costs, it can be used to mass produce arrays at a low incremental cost. Robot spotting techniques are provided in U.S. Pat. No. 5,807,522 which is incorporated by reference as if set forth fully herein. This technique uses a robot to place the probes on the substrate. Techniques used include the use of a pin, capillaries, and inkjet technology. Depending on the technology used, the probes can be manufactured on the substrate or can be manufactured off site and then placed on the substrate. Robotic technology has a lower startup cost but can take time to create a single array. Additionally, the incremental cost per array is higher.

The design of the microarray probe sets has been discussed in detail and commercial software is readily available to perform this task. One such program is explained in Xu, Bioinformatics 2002 Vol. 18, Pages 1432-1437.

Once the data is captured, a number of software programs are available to perform analysis on the resulting data. An example of such software is the TM4 suite of tools available at www.tm4.org.

Selective Breeding Techniques

In order to increase the frequency of the mutant SYNJ1 allele, it is desirable to use selective breeding to increase the frequency of the allele within a herd. By increasing the frequency of the allele, the herd will exhibit greater average resistance to Enterobacteriaceae infection.

Selective breeding is the preferential breeding of animals with desired traits in order to increase the prevalence of the trait within the breeding herd. Before starting with selective breeding, a desired goal should be identified. Such goal may be to increase the prevalence of only one trait, or multiple traits of interest may be selected for at the same time. In the event that multiple traits are subject to selection, it is generally desirable to create measure of genetic fitness, a number which represents the overall performance of the animal across the desired traits. Typically, the closer the animal is to the identified goal, the higher the genetic measure.

Once the goals have been identified, selection and mating are used to produce animals which more closely approximate the ultimate goal. Using positive associative mating, animals are mated to other animals with similar genetic scores. In selecting breeding pairs, inbreeding should be below approximately 10%. Practically speaking, this means that animals should not be bred with their half-sisters or closer relation. Depending on the size and genetic variation of the herd, animals with low scores can be removed from the breeding program altogether. This removes undesirable traits from the breeding herd and results in an increase in the percentage of cattle possessing the desirable traits.

Marker assisted selection is one such form of selection where a marker is used for indirect selection of a phenotypic trait of interest. In this case, markers associated with decreased Synaptojanin 1 expression and/or increased resistance to Enterobacteriaceae infection. Markers in linkage disequilibrium with the trait of interest are identified. Preferably, markers are selected which are close to the gene of interest (typically less than 5 centiMorgans in distance). For greater accuracy, more than one such marker may be used. Once the markers have been identified, genetic samples are taken from members of the herd. These samples are screened for the presence of the genetic markers which are linked to the desired trait. Herd members possessing the markers are preferentially mated with other herd members possessing the markers. Through repeated cycles of this selective breeding, the number of herd members possessing the desired alleles increases. If repeated for enough cycles, eventually all members of the herd will be homozygous for the alleles which result in the desired trait.

Marker-assisted introgression, also known as introgressive hybridization, is the movement of a target gene or genes from one breed or species (the donor species) into the gene pool of another breed or species (the recipient species) by the repeated backcrossing of a hybrid with one of its parent breeds or species. Marker-assisted introgression programs are based on tandem selection in a multigenerational backcrossing program, in which a genetic fitness score based on the presence of donor breed alleles at or around the target gene is used in the first selection step (foreground selection), followed by background selection on a genetic fitness score based on presence or absence of recipient alleles at markers spread over the genome, on phenotype, or an index of the two. With each repeated round of backcrossing, the amount of non-target genes from the donor line is decreased. As such, depending on the permissible amount of donor genetic material, backcrossing can be conducted for 2, 3, 4, 5, 6, 7, 8, 9, 10, 11, 12, 13, 14, 15, 16, 17, 18, 19, 20 or more generations. Detailed procedures for performing introgression are well known in the art and are discussed in Frisch M, Melchinger A E, Genetics. 2005 June; 170(2):909-17 which is incorporated by reference in its entirety as if set forth fully herein. Although tandem selection has been implicit to gene introgression programs, the selection on an index of molecular score and phenotypic information in these programs should be considered, especially for quantitative traits, unless the gene has a very large effect. Although this could result in selection of some parents that do not carry the target allele, overall response is expected to be greater. In particular, if multiple genes or QTL regions must be introgressed simultaneously, the requirement that selected parents carry the target allele for all QTL is infeasible in livestock and not necessary for successful introgression.

Introgression typically makes use of cross-breeding. In cross-breeding two distinct parental types (e.g., closely related species, sub-species or breeds) are mated, or crossed, to produce a first filial generation (F1). The F1 progeny may then be backcrossed to the members of the recipient line using the process outlined above. Alternatively, the F1 progeny may be mated to each other to produce a second filial generation (F2). The F2 progeny are then screened and those possessing the target gene are selected for backcrossing as described above.

The invention also includes novel nucleotide and protein sequences which are associated with increased resistance to Enterobacteriaceae infection. This molecular information can be used in a variety of methods for studying the effects of, the causes of, and possibly the prevention of such infections both in vitro and in vivo.

In another embodiment, the invention comprises a method for identifying a genetic marker increased resistance to Enterobacteriaceae in a particular line, strain, breed, population or animal. Based upon the highly conserved nature of this gene among different animals and the location of the polymorphisms within these highly conserved regions, is it expected that with no more than routine testing as described herein this marker can be applied to different animal species to select increased resistance to Enterobacteriaceae based on the teachings herein. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons using the default parameters.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, CABIOS 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information world wide web at hcbi.nlm.nih.gov/.

It is also possible to establish linkage between specific alleles of alternative DNA markers and alleles of DNA markers known to be associated with a particular gene (e.g. the SYNJ1 gene discussed herein), which have previously been shown to be associated with a particular trait. Thus, in the present situation, taking the SYNJ1 gene, it would be possible, at least in the short term, to select for animals likely to exhibit increased resistance to Enterobacteriaceae, indirectly, by selecting for certain alleles of a SYNJ1 associated marker through the selection of specific alleles of alternative chromosome markers. As used herein the term "genetic marker" shall include not only the polymorphism disclosed by any means of assaying for the protein changes associated with the polymorphism, be also linked markers, use of microsatellites, or even other means of assaying for the causative protein changes indicated by the marker and the use of the same to influence the resistance to Enterobacteriaceae tendencies of an animal.

Example 1

The objective of this study was to evaluate the impact of bSYNJ1_C3981T on resistance to Enterobacteriaceae. Specifically, leukocytes from cattle were challenged with *Salmonella typhimurium* and then screened to determine whether the leukocytes were resistant to infection. The cattle (n=1, 313) were classified into four groups based on a combination of MCR1 genotypes and the presence of bSYNJ1_C3981T. The four groups were:

(1) homozygous "C" for bSYNJ1_C3981T ("wild type") with any genotype for MCR1 (n=486);
(2) heterozygous bSYNJ1_C3981T with any genotype for MCR1 (n=352);
(3) homozygous "T" for bSYNJ1_C3981T ("mutant") with at least one copy of the $E^D$ allele (n=238); and
(4) homozygous mutant bSYNJ1_C3981T and zero copies of the $E^D$ allele, i.e., non-black cattle (n=237).

Figure 6:
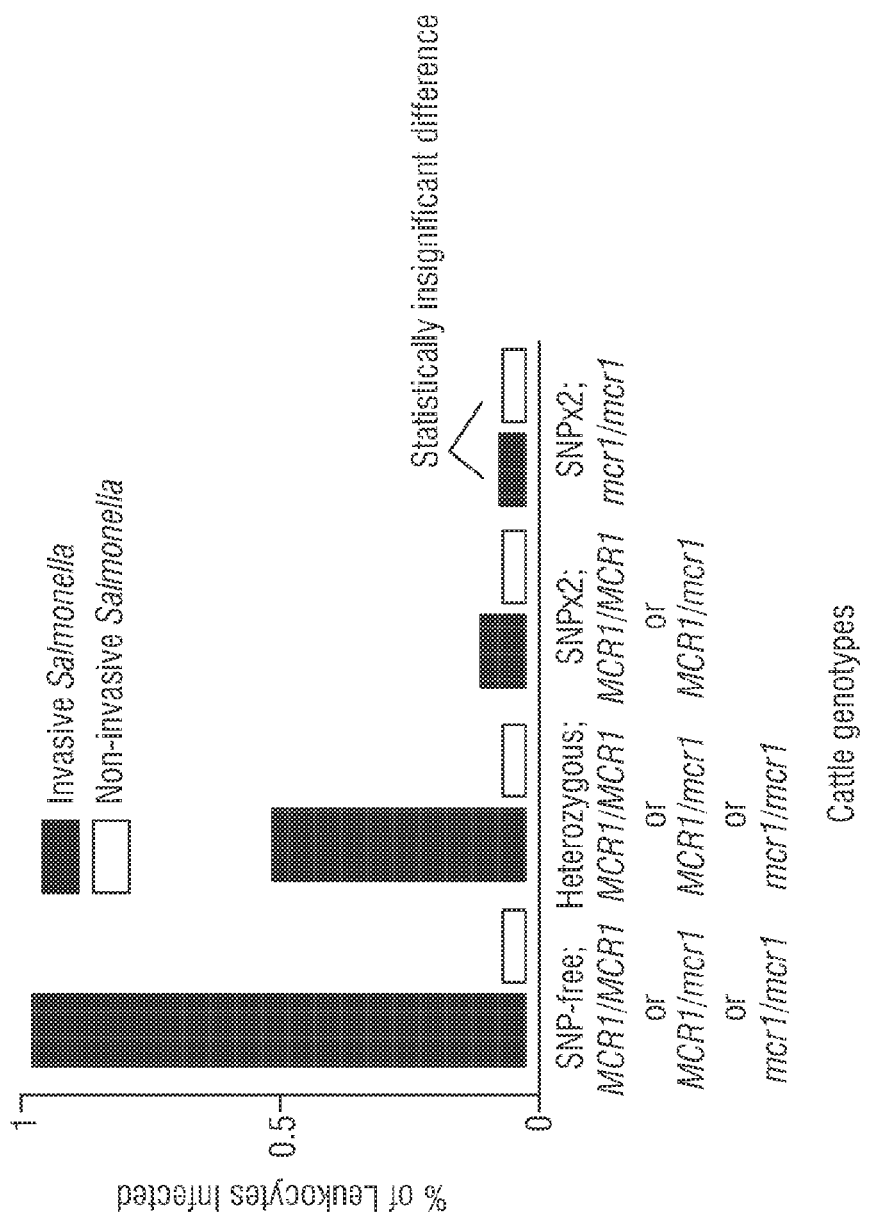

Group 1 exhibited 1.07%±0.07 of *Salmonella*-infected leukocytes, group 2 exhibited 0.53%±0.11, group 3 exhibited 0.14%±0.02 and group 4 exhibited 0.055%±0.01 when challenged with the invasive variant. Group 1 exhibited 0.04%±0.01 of *Salmonella*-infected leukocytes, group 2 exhibited 0.05%±0.01, group 3 exhibited 0.03%±0.01 and group 4 exhibited 0.05%±0.02 when challenged with the non-invasive variant. The results are summarized in FIG. 6. As demonstrated by the data, cattle possessing at least one copy of the mutant bSYNJ1_C3981T allele exhibited greater resistance than those without a copy. Homozygous mutants exhibited even greater resistance and non-black homozygous mutants were statistically indistinguishable from the negative control group. Based on this data, the mutant phenotype demonstrates significant decreases in susceptibility to Enterobacteriaceae infection.

Materials and Methods

Animals and Sample Collection.

A total of 710 black or black-influenced cattle (cattle containing at least one $E^D$ allele of the MCR1 locus) were used in this study. This included 449 purebred Black&White Holsteins, 195 purebred and Angus crosses, 39 purebred Piedmontese, and 30 purebred Simmental cattle. A total of 603 non-black cattle were also used in the study, including 133 purebred Braunvieh, 117 purebred Red Angus, 71 purebred Piedmontese, 58 purebred Red Simmental, 55 purebred Limousine, 35 purebred Shorthorn, 30 purebred Tarentaise, 27 purebred Pinzgauer, 25 purebred Charolais, and 3 purebred Hereford. The cattle were raised at various locations in the U.S. Leukocytes were collected from peripheral whole blood samples by density gradient centrifugation.

Enterobacteriaceae Resistance Analysis.

The isolated leukocytes were incubated with either infective *Salmonella typhimurium* or a non-infective variant (BJ68 described in Penheiter et al. 1998) using a multiplicity of infection equal to 100. After incubation for one hour, gentamicin (50 µg/mL) was applied to kill extracellular *Salmonella*. The leukocytes were then lysed and the lysates were plated on *Salmonella*-selective media (XLD) and incubated overnight. The percentage of *Salmonella*-infected leukocytes was then calculated by 100(number of *Salmonella* recovered from cells/number of leukocytes).

DNA Polymorphisms Identification.

Genomic DNA samples were isolated by proteinase K digestion followed by extraction as per the DNEasy kit from Qiagen. Primers were designed to amplify a segment within exon 35 of SYNJ1-5'-AACCACCAGAGTAA CAGACTACAC-3' (SEQ ID NO:5) as the forward primer and 5'-CTGTCGGTGAAAGGATTTG-3' (SEQ ID NO:6) as the reverse primer. The PCR reaction mixture contained 50-100 ng of genomic DNA, 1.5 mM $MgCl_2$, 4 µM of each primer, 0.2 mM of dNTP mixture, 2 µl DMSO, and 1 U of DNA polymerase at a final volume of 50 µL. The PCR reactions were performed in a DNA engine thermal cycler (Bio-Rad) with the following protocol: 94° C. for 2 min, followed by 40 cycles of 95° C. for 12 s, 55° C. for 30 s, and 72° C. for 30 s, with a final extension step at 72° C. for 10 min. The DNA sequence of PCR amplicons were determined with ABI 3730 DNA Analyzer (Applied Biosystems Inc.).

Genotyping.

The genotypes of the MCR1 locus were determined by PCR-based direct sequencing of the MCR1 gene using the PCR protocol described for SYNJ1 and the following primers: forward, 5'-GGAGGTGTCCATCCCTGACGG-3' (SEQ ID NO:14); and reverse, 5'-AAGAGGTTGAAGTTCTTGAAGATGCA-3' (SEQ ID NO:15).

Statistical Analysis.

Statistical differences, or lack thereof, were determined using an analysis of variance with Scheffe's F test for multiple comparisons (SAS software). $p<0.05$ indicates a statistical difference.

Example 2

The objective of this study was to evaluate resistance to Enterobacteriaceae through challenge with a number of different *Salmonella* strains. Specifically, the following bovine-associated serovars obtained from National Veterinary Services Laboratories (Ames, Iowa) were used (some serovars are represented by multiple isolates):

| | | | |
|---|---|---|---|
| S. agbeni | S. clackamas | S. heidelberg | S. rubislaw |
| S. agona | S. claibonei | S. indiana | S. saintpaul |
| S. alachua | S. cubana | S. infantis | S. schwarzengrund |
| S. albany | S. daressalaam | S. java | S. sendai |
| S. amager | S. decatur | S. javiana | S. senftenberg |
| S. amsterdam | S. derby | S. kentucky | S. stanley |
| S. anatum | S. djarkarta | S. litchfield | S. stanleyville |
| S. arizona | S. drypool | S. lohbruegge | S. tennessee |

-continued

| | | | |
|---|---|---|---|
| S. atlanta | S. dublin | S. mbandaka | S. thompson |
| S. balboa | S. dublin | S. meleagridis | S. tuebingen |
| S. binza | S. dublin | S. miami | S. typhimurium |
| S. blockley | S. dugbe | S. midway | S. typhimurium |
| S. bornum | S. duisburg | S. mississippi | S. typhimurium |
| S. braenderup | S. eastbourne | S. montevideo | S. typhimurium |
| S. brandenberg | S. emek | S. muenchen | S. typhimurium |
| S. brazos | S. enteritidis | S. newport | S. typhimurium |
| S. bredeney | S. enteritidis | S. newport | S. typhimurium |
| S. california | S. give | S. newport | S. wien |
| S. chester | S. hadar | S. ohio | S. worthington |
| S. choleraesuis | S. haifa | S. oranienburg | S. yovokome |
| S. christiansborg | S. hartford | S. panama | S. zanzibar |

Figure 7:
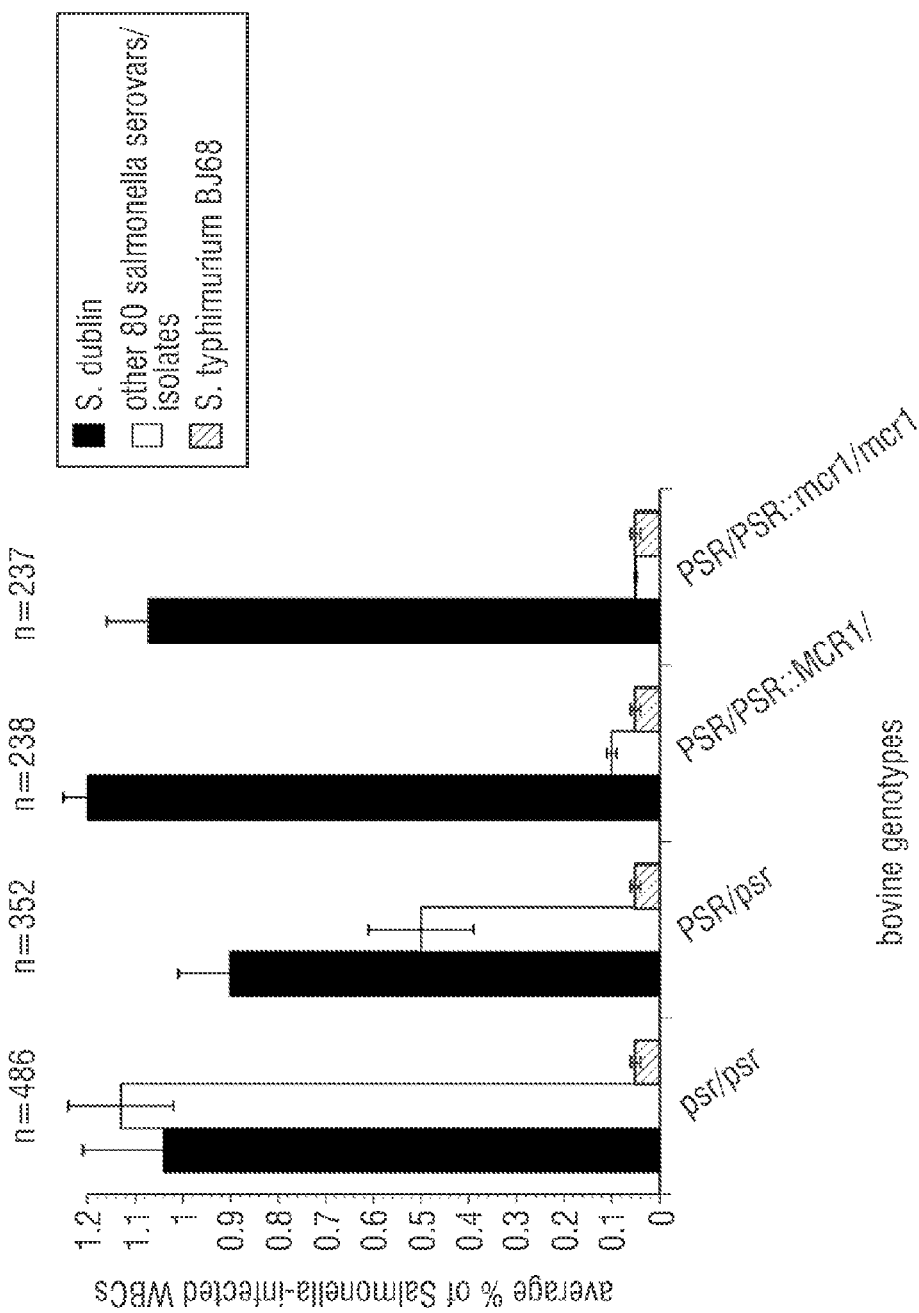

The study used the same population of cattle as Example 1, leukocytes were collected in the same manner and were exposed to the various serovars using the same protocol. Genotyping, data collection and statistical analysis were also performed using the same methods. Cattle possessing the bSYNJ1_C3981T allele exhibited resistance to infection by all serovars of *Salmonella* except *S. Dublin*. As such, the data for all serovars except *S. Dublin* were pooled. For *S. Dublin*, group 1 exhibited 1.02%±0.09 of *Salmonella*-infected leukocytes, group 2 exhibited 0.9%±0.11, group 3 exhibited 1.2%±0.03 and group 4 exhibited 1.08%±0.07. For the pooled results, group 1 exhibited 1.12%±0.1 of *Salmonella*-infected leukocytes, group 2 exhibited 0.52%±0.1, group 3 exhibited 0.1%±0.01 and group 4 exhibited 0.05%±0.005. For the negative control group 1 exhibited 0.07%±0.01 of *Salmonella*-infected leukocytes, group 2 exhibited 0.06%±0.02, group 3 exhibited 0.05%±0.01 and group 4 exhibited 0.05%±0.01. These results are summarized in FIG. 7.

Table 1 below shows the average percent infectivity (the number in parentheses) representing Group Four cattle (two copies of the bSYNJ1_C3981T allele and zero copies of the $E^D$ allele) for each strain tested.

Again, cattle possessing at least one copy of the mutant bSYNJ1_C3981T allele exhibited greater resistance than those without a copy of this allele. Homozygous mutants exhibited even greater resistance and non-black homozygous mutants were maximally resistant since *Salmonella* infectivity of their leukocytes was statistically indistinguishable from that observed in the negative control group. Based on this data, the bSYNJ1_C3981T allele confers a significant decrease in susceptibility to Enterobacteriaceae infection with *Salmonella* serving as the paradigm.

Example 3

In light of the in vitro resistance to Enterobacteriaceae infection, the inventors also tested resistance in vivo. In this study, animals were orally challenged with either $10^9$ or $10^{10}$ CFUs/kg of *Salmonella* newport using the protocols established by Dr. Carlson [Carlson et al., Inf. Immun. 2007]. The same genotype groupings were used as in Examples 1 and 2. With the exception of group 4, 25 animals per group were used in the experiment. Group 4 was represented by 30 animals. Five group 4 animals received the $10^{10}$ CFUs/kg dose, the rest of the animals received the lower dose. The breakdown of breeds within the low dose cohorts is shown in the table below:

| Genotype | Breed 1 | Breed 2 | Breed 3 | Breed 4 | Breed 5 |
|---|---|---|---|---|---|
| Group (1) zero bSYNJ1_C3981 T alleles | Red and Black Angus (n = 9) | Holstein- both colors (n = 9) | Pied- montese (n = 4) | Braunvieh (n = 3) | |
| Group (2) one bSYNJ1_C3981 T allele | Red and Black Angus (n = 8) | Holstein- both colors (n = 7) | Pied- montese (n = 5) | Braunvieh (n = 4) | Black Sim- mental (n = 1) |

| | | | | | |
|---|---|---|---|---|---|
| S. Agbeni (0.011) | S. Brazos (0.013) | S. Dublin (1.04) | S. Java (0.01) | S. Os (0.01) | S. Typhimurium (0.017) |
| S. Agona (0.012) | S. Bredeney (0.012) | S. Dublin (1.12) | S. Javiana (0.012) | S. Panama (0.012) | S. Typhimurium (0.02) |
| S. Alachua (0.01) | S. California (0.01) | S. Dugbe (0.011) | S. Kentucky (0.011) | S. Pullorum- non-infective control (0.009) | S. Typhimurium (0.01) |
| S. Albany (0.009) | S. Chester (0.005) | S. Duisburg (0.01) | S. Litchfield (0.014) | S. Rubislaw (0.013) | S. Typhimurium (0.013) |
| S. Amager (0.011) | S. Choleraesuis (0.011) | S. Eastbourne (0.008) | S. Lohbruegge (0.008) | S. Saintpaul (0.018) | S. Typhimurium (0.01) |
| S. Amsterdam (0.013) | S. Christiansborg (0.007) | S. Emek (0.012) | S. Mbandaka (0.014) | S. Schwarzengrund (0.011) | S. Wien (0.01) |
| S. Anatum (0.017) | S. Clackamas (0.01) | S. Enteritidis (0.015) | S. Meleagridis (0.007) | S. Sendai (0.009) | S. Worthington (0.012) |
| S. Arizona (0.012) | S. Claibonei (0.012) | S. Gallinarum-noninfective control (0.09) | S. Miami (0.01) | S. Senftenberg-noninfective control (0.008) | S. Yovokome (0.002) |
| S. Atlanta (0.008) | S. Cubana (0.008) | S. Give (0.011) | S. Midway (0.011) | S. Stanley (0.014) | S. Zanzibar (0.012) |
| S. Balboa (0.014) | S. Daressalaam (0.009) | S. Hadar (0.01) | S. Mississippi (0.01) | S. Stanleyville (0.012) | |
| S. Binza (0.01) | S. Decatur (0.01) | S. Haifa (0.008) | S. Montevideo (0.014) | S. Tennessee (0.013) | |
| S. Blockley (0.011) | S. Derby (0.012) | S. Hartford (0.013) | S. Muenchen (0.013) | S. Thompson (0.011) | |
| S. Bornum (0.015) | S. Djarkarta (0.014) | S. Heidelberg (0.01) | S. Newport (0.017) | S. Tuebingen (0.008) | |
| S. Braenderup (0.015) | S. Drypool (0.011) | S. Indiana (0.007) | S. Ohio (0.009) | S. Typhisuis (0.007) | |
| S. Brandenberg (0.009) | S. Dublin (0.93) | S. Infantis (0.013) | S. Oranienburg (0.01) | S. Typhimurium (0.015) | |

-continued

| Genotype | Breed 1 | Breed 2 | Breed 3 | Breed 4 | Breed 5 |
|---|---|---|---|---|---|
| Group (3) two bSYNJ1_C3981 T alleles, at least one $E^D$ allele | Black Angus (n = 12) | Black & White Holstein (n = 11) | Black Simmental (n = 1) | Black Piedmontese (n = 1) | |
| Group (4) two bSYNJ1_C3981 T allele, zero $E^D$ alleles | Red Angus (n = 6) | Red Simmental (n = 6) | Piedmontese (n = 6) | Braunvieh (n = 6) | Red & White Holstein (n = 1) |

The cattle were clinically scored each day, blood was drawn and fecal samples were also taken daily. Blood was screened for *Salmonella* DNA using PCR targeting the sipB gene Carlson et al., Mol Cell Probes, 1999. Blood and feces were screened for viable *Salmonella* using selective media (XLD). Clinical scores were established using the following scoring scale:

0 no *Salmonella* DNA in blood, no *Salmonella* in feces or blood, and no clinical signs of disease
1 *Salmonella* DNA in blood, no *Salmonella* in feces or blood, and no clinical signs of disease
2 *Salmonella* DNA in blood, *Salmonella* in feces, no *Salmonella* in blood, and no clinical signs of disease
3 *Salmonella* DNA in blood, *Salmonella* in feces, *Salmonella* in blood, and no clinical signs of disease
4 *Salmonella* DNA in blood, *Salmonella* in feces, *Salmonella* in blood, clinical signs of disease
5 Animals euthanized because either: rectal temperatures>104.5° F.; dehydration>6%; recumbency; or, two or more dyspneic events per minute.

Figure 8:
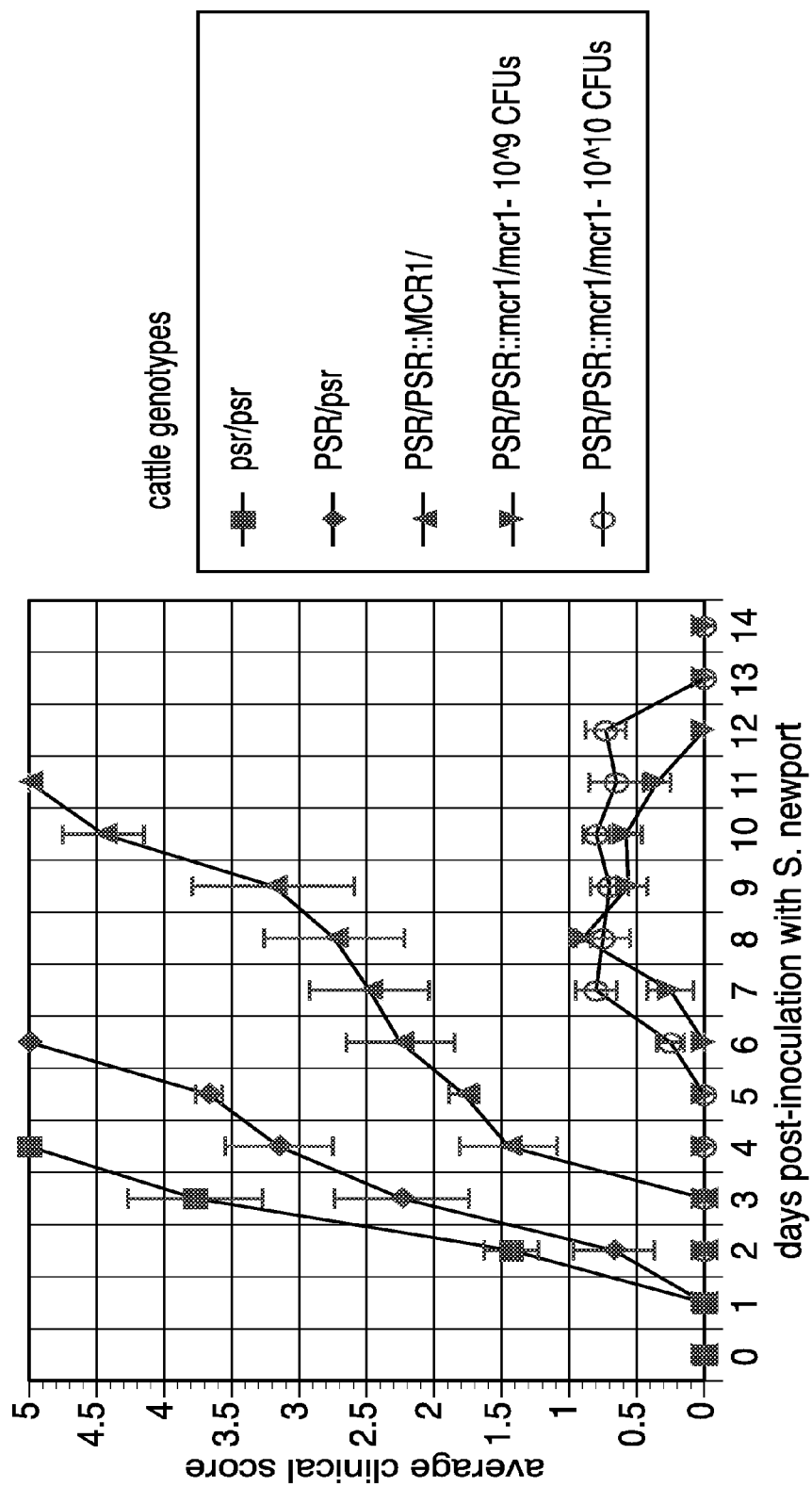
Figure 9:
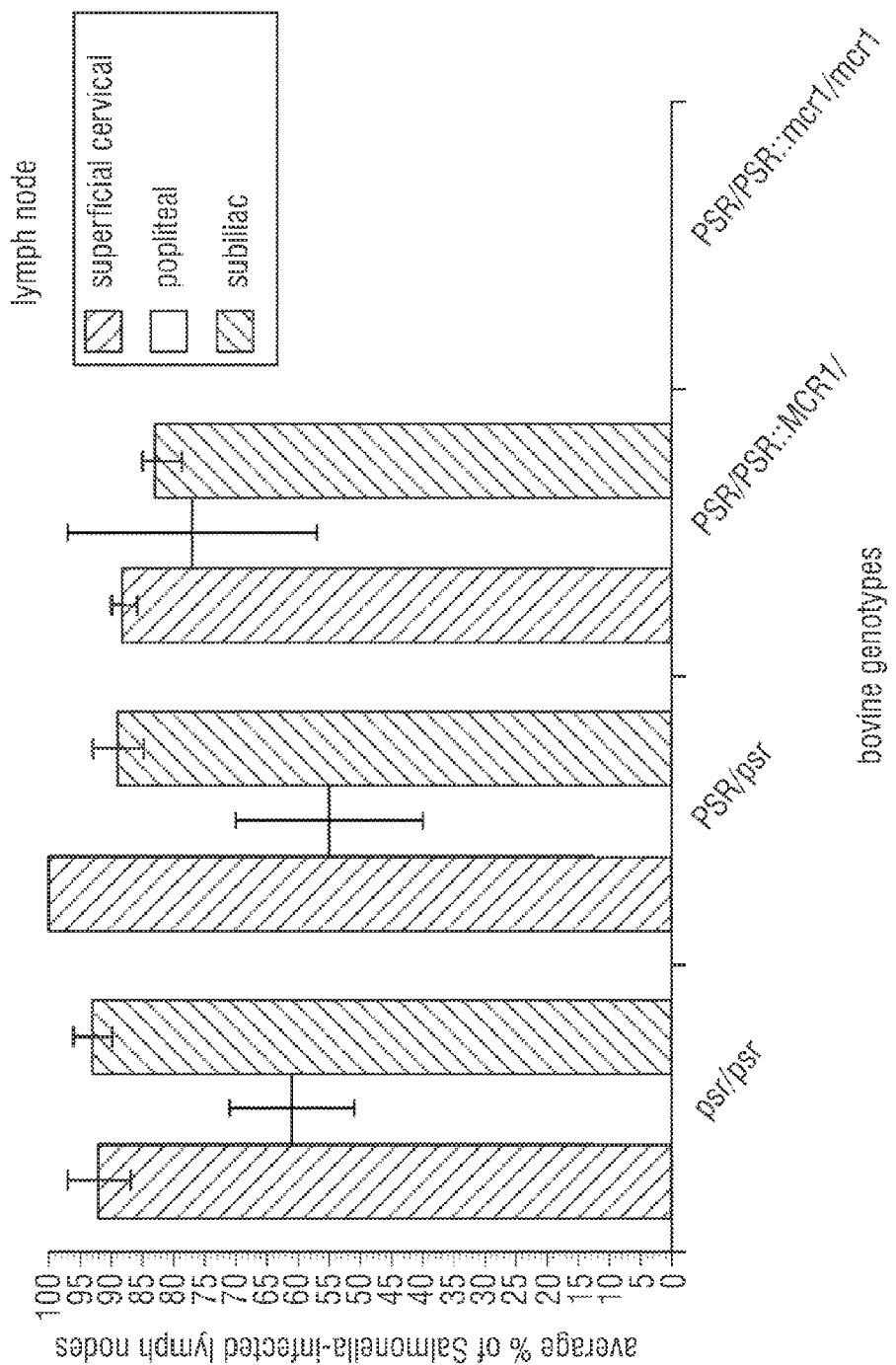
Figure 10:
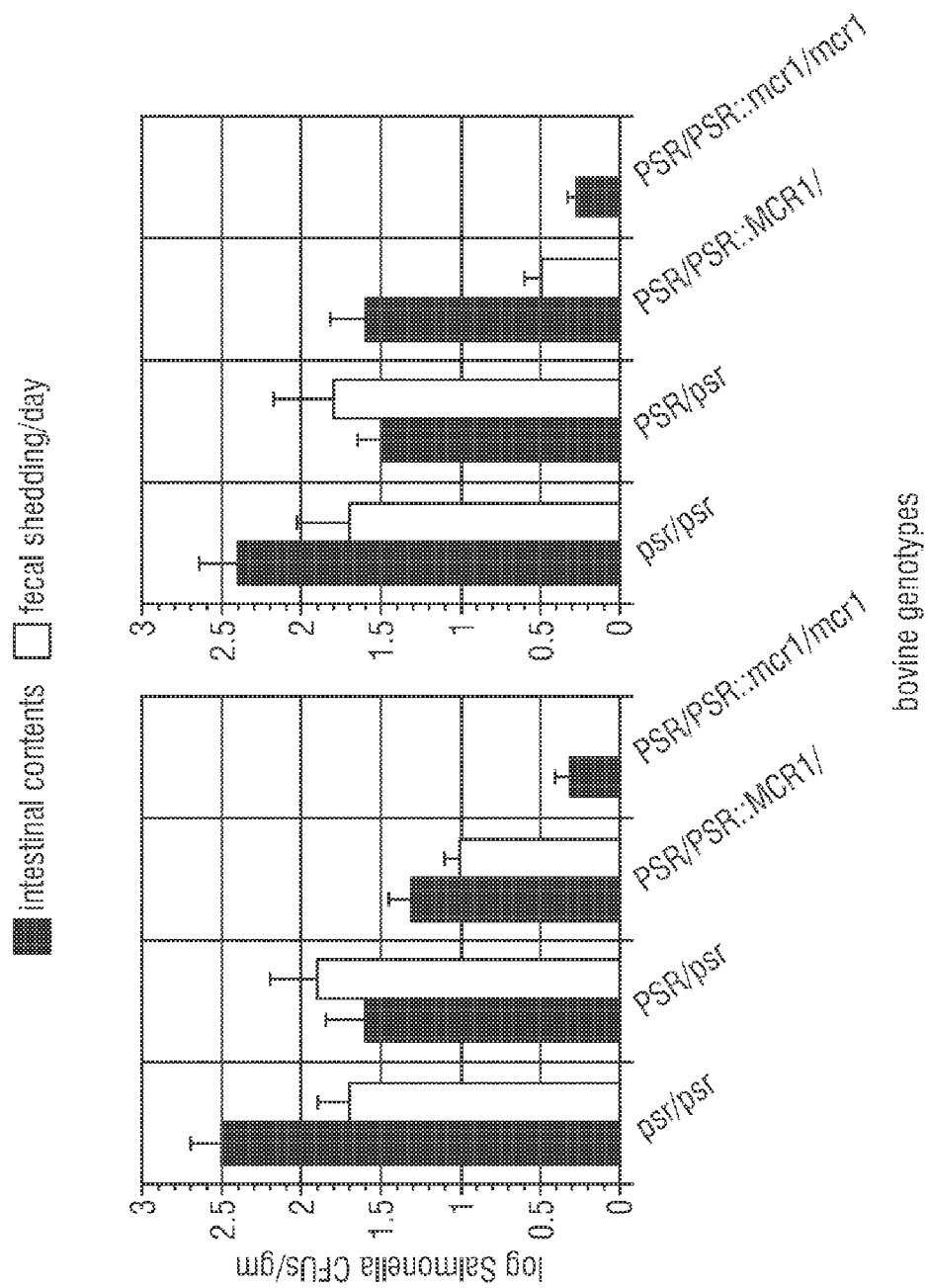

The results of the study are summarized in FIG. 8. With the exception of group 4 animals receiving the higher dose (which was a 5 animal cohort), each line represents 25 animals. The datapoints represent the mean±sem on a given day for the respective genotype/dose cohort. As shown in the figure, for group 2 animals possessing one bSYNJ1_C3981T allele, infection progressed slightly slower and extended animal life by approximately two days. For group 3 animals (black cattle homozygous for the bSYNJ1_C3981T allele), infection progressed even more slowly extending animal life by approximately seven days. Group 4 animals exhibited strong resistance to infection—even when challenged by the higher dose—showing only *Salmonella* DNA in the blood, a phenomenon which ultimately returned to baseline (clinical score of 0) by day 12 (lower dose) or 13 (higher dose). Again, this data shows that the bSYNJ1_C3981T allele confers increased resistance to Enterobacteriaceae infection especially in the non-black cattle with two mutant alleles.

Example 4

The impact of the resistant phenotype on lymph node infiltration of Enterobacteriaceae was also evaluated in vivo. Each genotype group was represented by 20 cattle using the breed breakdown shown in the table below:

| Genotype | Breed 1 | Breed 2 | Breed 3 | Breed 4 |
|---|---|---|---|---|
| Group (1) zero bSYNJ1_C3981T alleles | Red and Black Angus (n = 10) | Holstein- both colors (n = 10) | | |
| Group (2) one bSYNJ1_C3981T allele | Red and Black Angus (n = 15) | Piedmontese (n = 5) | Braunvieh (n = 1) | |
| Group (3) two bSYNJ1_C3981T alleles, at least one $E^D$ allele | Black Angus (n = 19) | Black Simmental (n = 1) | | |
| Group (4) two bSYNJ1_C3981T alleles, zero $E^D$ alleles | Red Angus (n = 8) | Red Simmental (n = 4) | Piedmontese (n = 4) | Braunvieh (n = 4) |

Cattle were challenged with $10^5$ CFUs/kg of both *Salmonella anatum* and Montevideo. At 14 days post-challenge the animals were euthanized. After euthanization, the superficial cervical, subiliac, and popliteal lymph nodes were bilaterally collected. Following decontamination of the surface of the lymph nodes, the collected nodes were subjected to selective qualitative culture of *Salmonella* using the techniques described above. The percentage of *Salmonella*-infected lymph nodes was calculated using the techniques described above and the values were averaged for each group.

The results are summarized in FIG. 9. Each data point represents the average±sem for lymph nodes obtained from each group (n=40 for each genotype, two lymph nodes per animals times 20 animals). As shown by the data, Groups 1-3 showed statistically indistinguishable levels of infiltration. Group 4, however, demonstrated no infiltration whatsoever. This data also confirms that non-black animals homozygous for the bSYNJ1_C3981T allele exhibit increased resistance to Enterobacteriaceae infection, with *Salmonella* serving as the paradigm.

Example 5

The impact of the resistant phenotype on intestinal colonization and fecal shedding of Enterobacteriaceae, particularly *Salmonella*, was also evaluated in vivo. Each genotype group was represented by 10 cattle using the breed breakdown shown in the table below:

| Genotype | Breed 1 | Breed 2 |
|---|---|---|
| Group (1) zero bSYNJ1_C3981T alleles | Red and Black Angus (n = 5) | Holstein- both colors (n = 5) |
| Group (2) one bSYNJ1_C3981T allele | Red and Black Angus (n = 10) | |
| Group (3) two bSYNJ1_C3981T alleles, at least one $E^D$ allele | Black Angus (n = 10) | |
| Group (4) two bSYNJ1_C3981T alleles,, zero $E^D$ alleles | Red Angus (n = 5) | Red Simmental (n = 5) |

Cattle were orally challenged with $10^5$-$10^6$ CFUs/kg of *Salmonella hadar* (panel A) or *S. infantis* (panel B). Each day, feces were collected and subjected to selective culture and *Salmonella* enumerations as described previously. At seven days post-inoculation, cattle were euthanized and intestinal contents (n=3 per animal) were collected and subjected to selective culture and *Salmonella* enumerations also as previously described.

The results of the study are presented in FIG. 10 where each bar represents five animals. Data points represent the mean±sem for each genotype. As shown in the figures, Groups 1-3 showed statistically indistinguishable levels in the intestinal contents and fecal material. Group 4, however, demonstrated no shedding and significantly decreased levels in the intestinal contents. This data also confirms that mutant individuals exhibit increased resistance to Enterobacteriaceae infection with *Salmonella* serving as the paradigm.

Example 6

The impact of the resistant phenotype on intestinal colonization and fecal shedding of Enterobacteriaceae, particularly *E. coli*, was also evaluated in vivo. Each genotype group was represented by 10 cattle using the breed breakdown shown in the table below:

| Genotype | Breed 1 | Breed 2 |
| --- | --- | --- |
| zero bSYNJ1_C3981T alleles | Red and Black Angus (n = 5) | Holstein- both colors (n = 5) |
| one bSYNJ1_C3981T allele | Red and Black Angus (n = 10) | |
| two bSYNJ1_C3981T alleles, at least one $E^D$ allele | Black Angus (n = 10) | |
| two bSYNJ1_C3981T alleles, zero $E^D$ alleles | Red Angus (n = 5) | Red Simmental (n = 5) |

Cattle were orally challenged with $10^{11}$ CFUs/kg of *E. coli* O157:H7 using the techniques described above. At 14 days post-challenge, cattle were euthanized and recto-anal junctions (n=3 per animal) were surgically collected and subjected to selective enumeration of *E. coli* O157:H7 using selective media as per Sharma et al. (Vaccine 2011).

Figure 11:
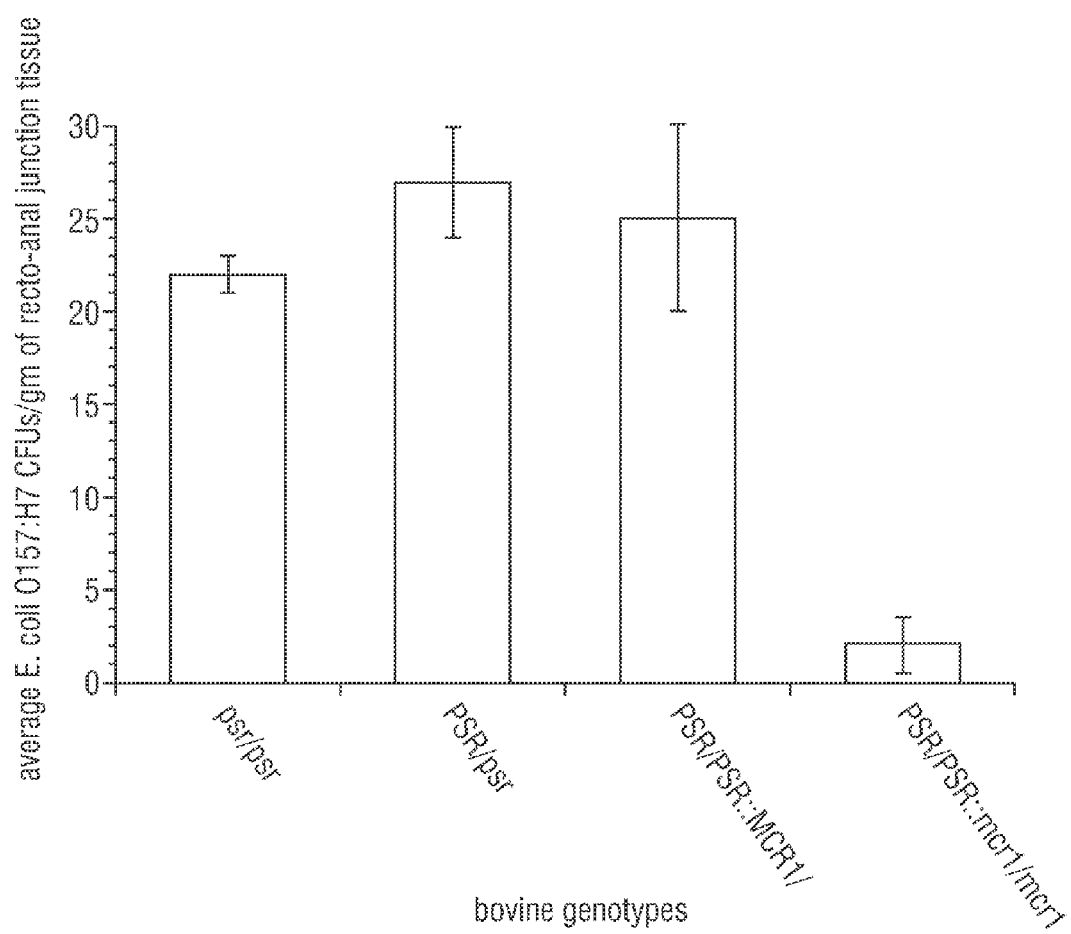
Figure 12:
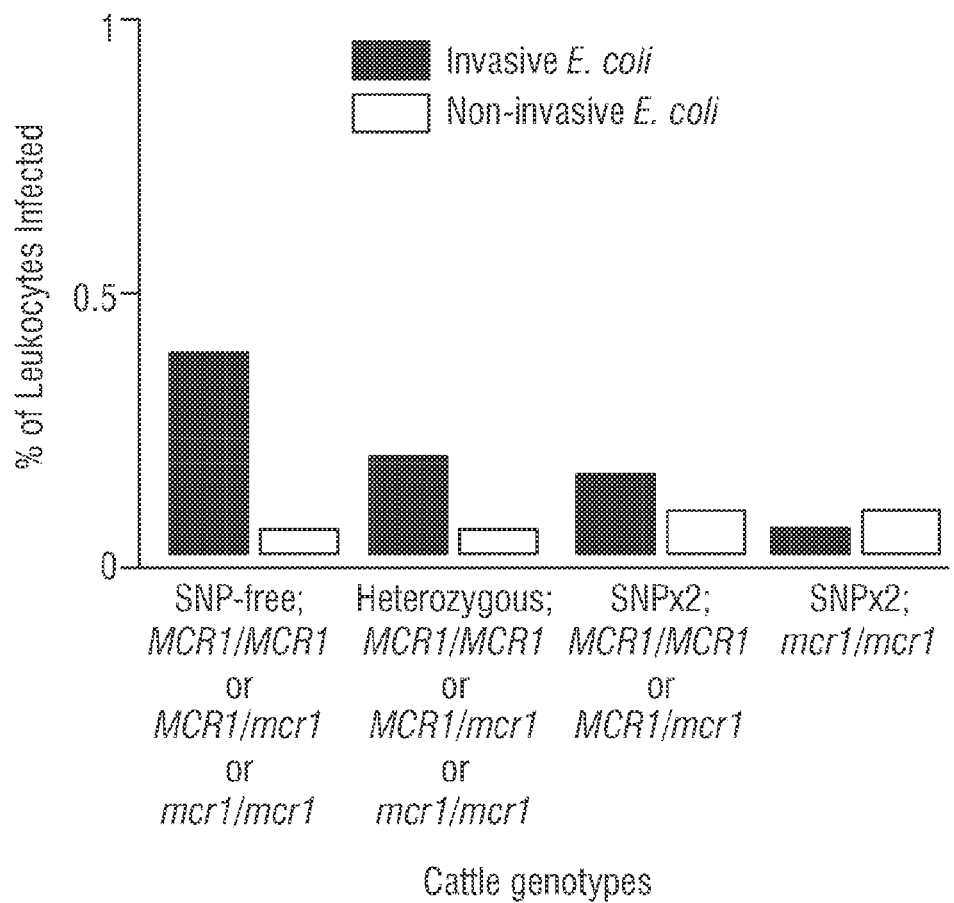
Figure 13:
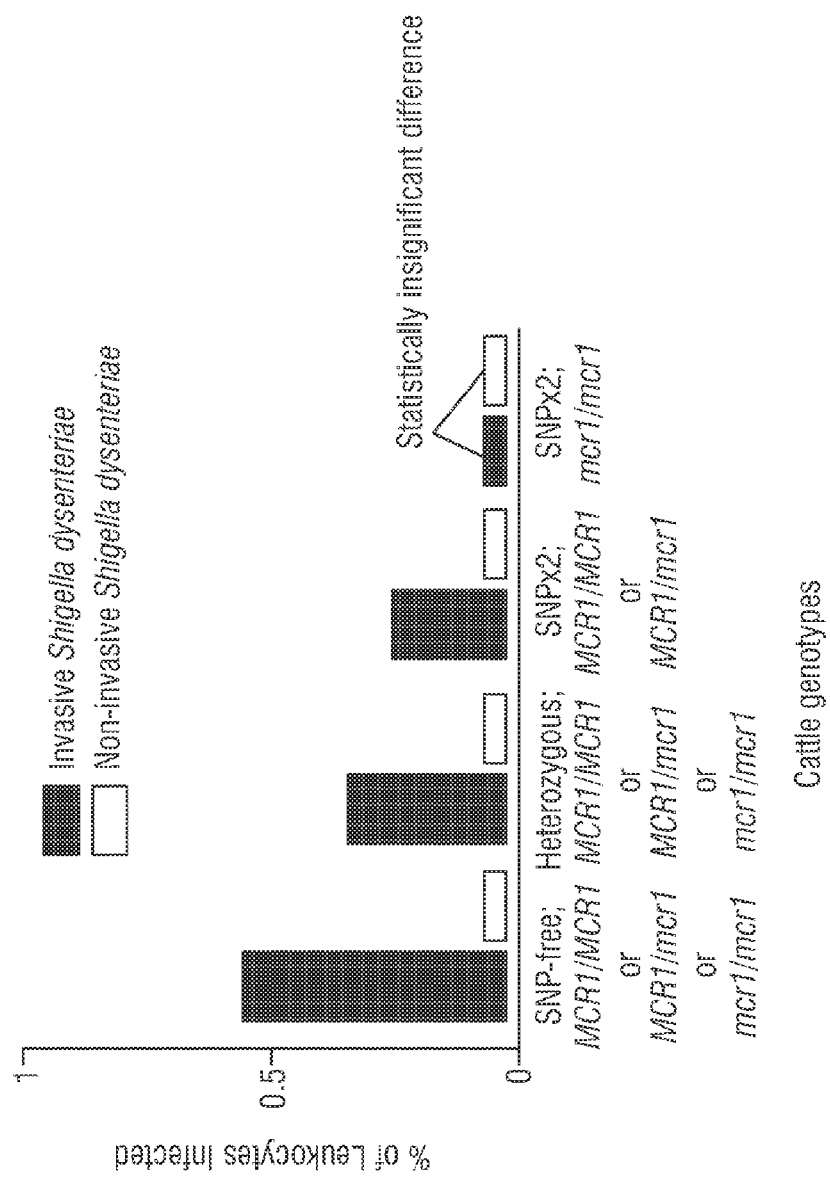
Figure 14:
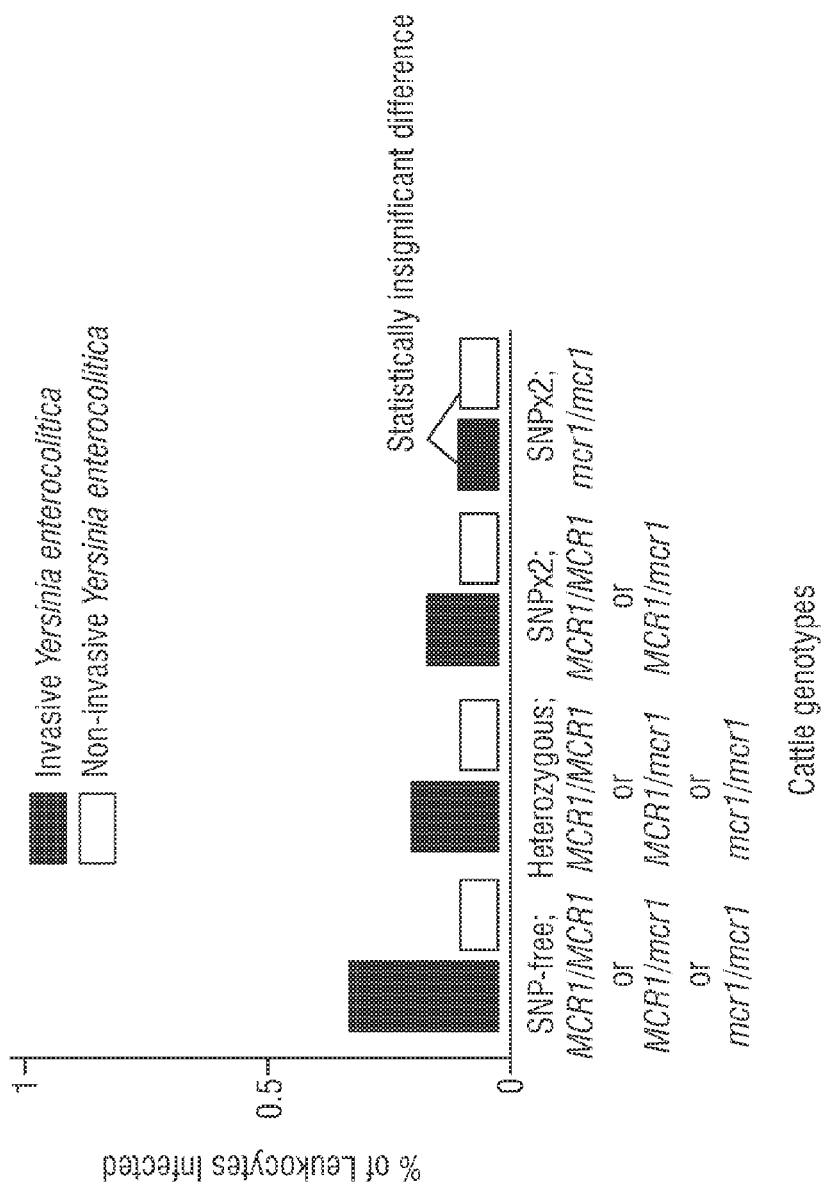
Figure 15:
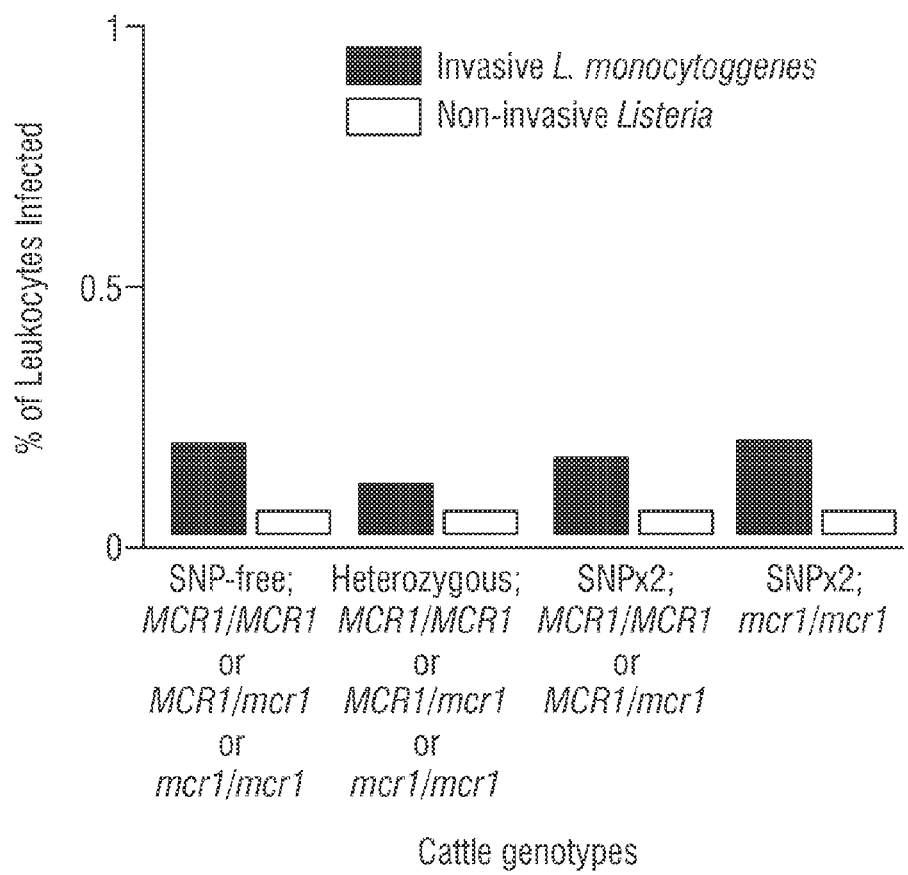
Figure 16:
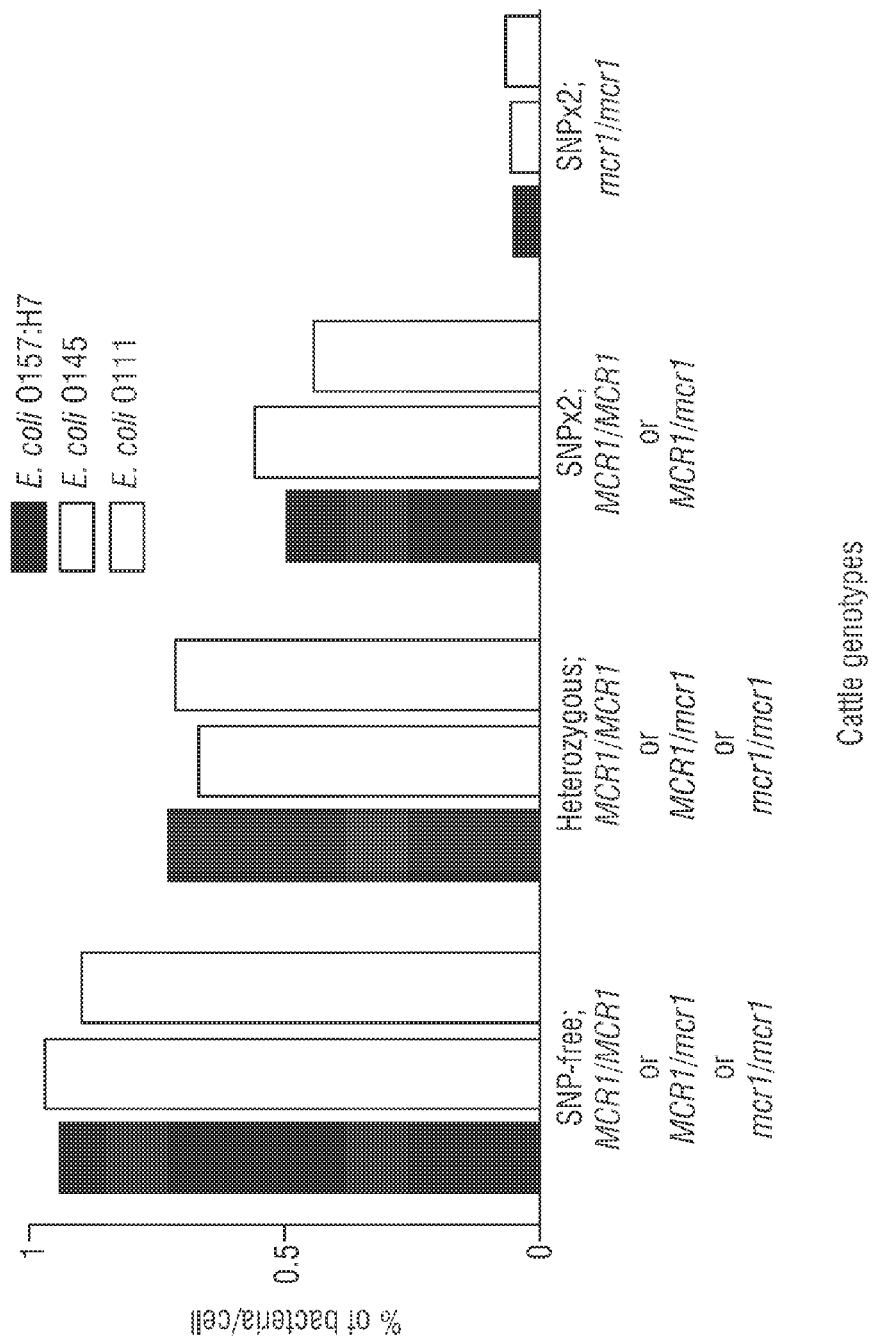
Figure 17:
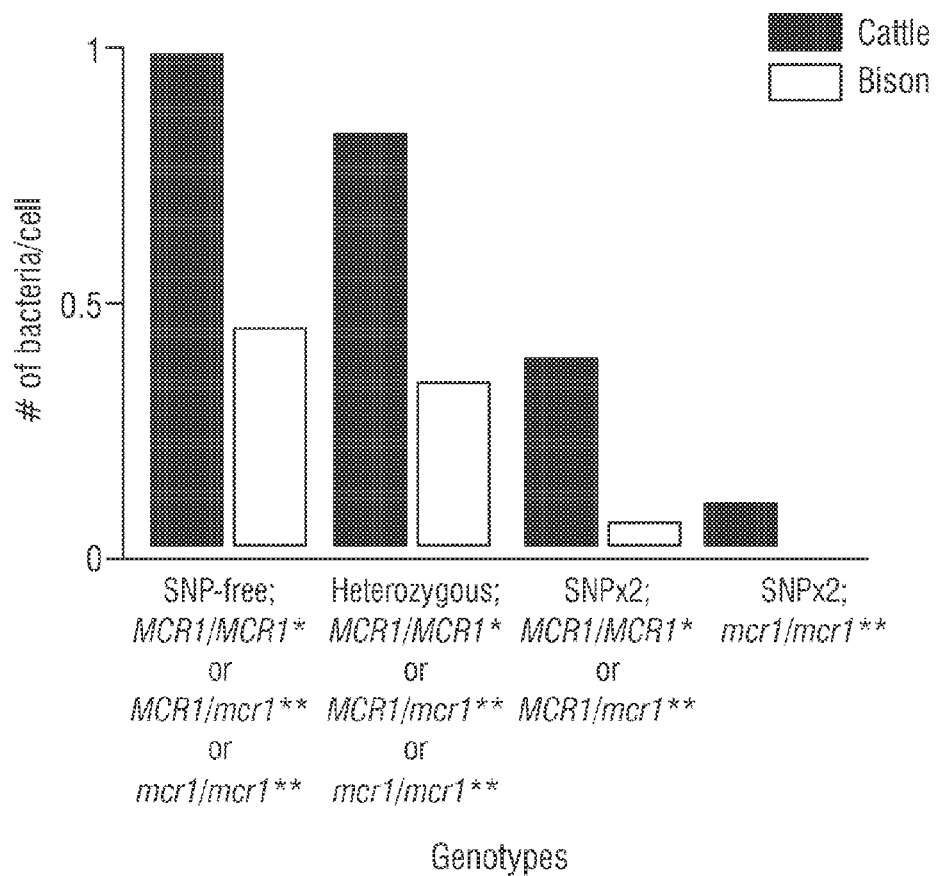

The results of the study are presented in FIG. 11. Each bar represents 10 animals. Data points represent the mean±sem for each genotype (n=30; three samples per animal times 10 animals). Group 1 exhibited 22 CFU/gm±2, group 2 exhibited 27 CFU/gm±4, group 3 exhibited 25 CFU/gm±6 and group 4 exhibited 2 CFU/gm±1.5 Again, groups 1-3 were statistically indistinguishable and group 4 exhibited significant decreases in the presence of *E. coli* at the recto-anal junction. This data also confirms that the bSYNJ1_C3981T allele confers resistance to Enterobacteriaceae infection, with *Salmonella* serving as the paradigm.

Example 7

The ability to extrapolate the results to other Enterobacteriaceae family members was tested in the following study. Specifically, the procedures described in Example 1 were repeated with enteroinvasive *E. coli*, *Yersinia enterocolitica*, *Shigella dysenteriae* and *Listeria monocytogenes* (a non-Enterobacteriaceae). Invasive and non-invasive variants of each bacteria were used.

For enteroinvasive *E. coli, Group* 1 exhibited 0.38%±0.06 infected leukocytes, group 2 exhibited 0.25%±0.04, group 3 exhibited 0.22%±0.04 and group 4 exhibited 0.1%±0.01 when challenged with the enteroinvasive *E. coli*. Group 1 exhibited 0.05%±0.01 of *E. coli*-infected leukocytes, group 2 exhibited 0.05%±0.01, group 3 exhibited 0.1%±0.02 and group 4 exhibited 0.18%±0.06 when challenged with the non-invasive variant. This data is presented in FIG. 12.

For *Shigella dysenteriae*, Group 1 exhibited 0.55%±0.1 infected leukocytes, group 2 exhibited 0.35%±0.05, group 3 exhibited 0.25%±0.04 and group 4 exhibited 0.05%±0.01 when challenged with the invasive *S. dysenteriae*. Group 1 exhibited 0.06%±0.01 of *Shigella*-infected leukocytes, group 2 exhibited 0.04%±0.006, group 3 exhibited 0.05%±0.01 and group 4 exhibited 0.04%±0.01 when challenged with the non-invasive variant. This data is presented in FIG. 13.

For *Yersinia enterocolitica, Group* 1 exhibited 0.36%±0.012 infected leukocytes, group 2 exhibited 0.2%±0.04, group 3 exhibited 0.18%±0.05 and group 4 exhibited 0.08%±0.01 when challenged with the invasive *Y. enterocolitica*. Group 1 exhibited 0.07%±0.01 of *Yersinia*-infected leukocytes, group 2 exhibited 0.07%±0.01, group 3 exhibited 0.06%±0.005 and group 4 exhibited 0.05%±0.01 when challenged with the non-invasive variant. This data is presented in FIG. 14.

For the non-Enterobacteriaceae bacteria *Listeria monocytogenes, Group* 1 exhibited 0.15%±0.1 infected leukocytes, group 2 exhibited 0.1%±0.01, group 3 exhibited 0.14%±0.1 and group 4 exhibited 0.17%±0.05 when challenged with the invasive *L. monocytogenes*. Group 1 exhibited 0.05%±0.03 of *Listeria*-infected leukocytes, group 2 exhibited 0.04%±0.01, group 3 exhibited 0.05%±0.002 and group 4 exhibited 0.05%±0.01 when challenged with the non-invasive variant. This data is presented in FIG. 15.

As demonstrated by the data, similar results were observed for all three non-*Salmonella* members of the Enterobacteriaceae family. Heterozygous individuals (Group 2) exhibited lower infection than homozygous wild-type individuals (Group 1). Black individuals homozygous for bSYNJ1_C3981T (Group 3) exhibit even lower infection levels and non-black animals homozygous for bSYNJ1_C3981T exhibit infection levels which are statistically indistinguishable from the negative control. These results differ in the non-Enterobacteriaceae data set (i.e., *Listeria*). In that data set, infection levels were statistically indistinguishable across all groups. Based on this data, the resistant phenotype demonstrates significant decreases in susceptibility to Enterobacteriaceae infection, however, this resistance does not translate to resistance to infection with a non-Enterobacteriaceae pathogen.

Example 8

Further research was conducted regarding resistance to non-O157:H7 *E. coli* that produce Shiga toxin like O157:H7. In this study, bacteria (*E. coli* O157:H7; O145; and O111) were soaked in fluoroscene isothocynate and then incubated with leukocytes. After 1 hour of incubation, leukocytes were microscopically visualized for adherent and fluorescent bacteria. The results from the study are summarized in FIG. 16. Heterozygous individuals (Group 2) exhibited lower infection than homozygous wild-type individuals (Group 1). Black animals homozygous for bSYNJ1_C3981T (Group 3) exhibit even lower adherence levels and non-black animals homozygous for bSYNJ1_C3981T exhibit the lowest adherence levels. Again, these data demonstrate that the bSYNJ1_C3981T allele confers resistance to Enterobacteriaceae infection with *E. coli* serving as the paradigm.

Example 9

The ability to expand these findings to other bovines was tested using bison. Bison are all homozygous $E^D$ at the MCR1 locus. As such, genotypically Bison mirror Groups 1-3 from the previous cattle studies. In the present study, the method of Example 1 was repeated using *E. coli* O157:H7 using Bison and cattle. The data from the study is summarized in FIG. 17. The results again mirror those found in the previous studies. Specifically, Bison possessing at least one copy of the mutant bSYNJ1_C3981T allele exhibited greater resistance than those without a copy. Homozygous mutants exhibited even greater resistance. Based on this data, the resistant phenotype demonstrates significant decreases in susceptibility to Enterobacteriaceae infection in bovines outside of the *Bos* genus, with *E. coli* O157:H7 serving as the paradigm.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention as described in the appended claims.

What is claimed is:

1. A method for producing a bovine subject with increased resistance to Enterobacteriaceae infection comprising:
   a) obtaining samples of genetic material from a bovine donor subjects, the sample comprising a bSynj1 gene;
   b) probing the samples with an oligonucleotide which selectively hybridizes to a genetic marker sequence for a polymorphism in the bSynj1 gene, said genetic marker linked to Enterobacteriaceae resistance, wherein the polymorphism is a single nucleotide polymorphism occurring at nucleobase number 21 of exon 35, as determined by reference to nucleotide 190 of SEQ ID NO:8;
   c) identifying samples which contain the genetic marker and selecting those bovine donor subjects for introgression;
   d) introgressing the polymorphism in the bSynj1 gene into a recipient breed which is non-resistant or exhibits less resistance to Enterobacteriaceae infection.

2. The method according to claim 1, wherein the introgressing comprises:
   a) providing F2 animals derived from selective breeding, the selective breeding including a first cross between one or more animals from the donor breed and one or more animals from the recipient breed to yield a heterozygous F1 generation;
   b) breeding two or more animals from the F1 generation to yield a segregating F2 generation;
   c) backcrossing F2 animals with animals from the recipient breed line to yield BC1 F1 generation animals, the F2 animals having one or more molecular markers for a polymorphism in the bSynj1 gene;
   d) identifying BC1 F1 animals having one or more molecular markers for a polymorphism in the bSynj1 gene.

3. The method according to claim 2, further comprising performing additional backcrosses and selections based upon the presence of one or more markers in each animal selected for backcrossing.

4. The method of claim 1 wherein the donor breed is a member of a group selected from domestic cattle, American Bison, water buffalo, and yaks.

5. The method of claim 1 wherein the donor breed is a non-black domestic animal of the *Bos* genus.

6. The method of claim 1 wherein the recipient breed is a member of a group selected from domestic cattle, American Bison, water buffalo, and yaks.

7. The method of claim 1 wherein the polymorphism introduces an RNAi-based destabilization site into SYNJ1 mRNA, permitting miRNA to bind to the transcript.

8. The method of claim 7 wherein said miRNA reduces SYNJ1 transcription by at least 50%.

9. The method of claim 7 wherein said miRNA reduces SYNJ1 translation by at least 80%.

10. The method of claim 1 wherein the polymorphism is located in the 3' UTR of the SYNJ1 gene.

11. The method of claim 7 wherein the polymorphism is bSYNJ1_C3981T.

* * * * *